(12) United States Patent
Levy et al.

(10) Patent No.: US 8,697,647 B2
(45) Date of Patent: Apr. 15, 2014

(54) HYBRID POLYPEPTIDES WITH SELECTABLE PROPERTIES

(76) Inventors: Odile Esther Levy, San Diego, CA (US); Michael R. Hanley, Corte Madera, CA (US); Carolyn M. Jodka, Encinitas, CA (US); Diana Y. Lewis, San Diego, CA (US); Christopher J. Soares, La Jolla, CA (US); Soumitra S. Ghosh, San Diego, CA (US); Lawrence J. D'Souza, San Diego, CA (US); David G. Parkes, Del Mar, CA (US); Christine M. Mack, Camarillo, CA (US)

( * ) Notice: Subject to any disclaimer, the term of this patent is extended or adjusted under 35 U.S.C. 154(b) by 0 days.

(21) Appl. No.: 13/323,608

(22) Filed: Dec. 12, 2011

(65) Prior Publication Data

US 2012/0253023 A1    Oct. 4, 2012

Related U.S. Application Data

(63) Continuation of application No. 11/206,903, filed on Aug. 17, 2005, now Pat. No. 8,076,288, which is a continuation-in-part of application No. 11/201,664, filed on Aug. 11, 2005, now abandoned, which is a continuation-in-part of application No. 11/055,093, filed on Feb. 11, 2005, now abandoned.

(60) Provisional application No. 60/543,407, filed on Feb. 11, 2004.

(51) Int. Cl.
*A61K 38/00* (2006.01)
*A61K 38/26* (2006.01)

(52) U.S. Cl.
USPC .............................. 514/7.2; 514/6.8; 514/6.9

(58) Field of Classification Search
None
See application file for complete search history.

(56) References Cited

U.S. PATENT DOCUMENTS

| | | |
|---|---|---|
| 4,397,780 A | 8/1983 | Orlowski et al. |
| 4,401,593 A | 8/1983 | Orlowski et al. |
| 4,414,149 A | 11/1983 | Orlowski et al. |
| 4,444,981 A | 4/1984 | Goudie |
| 4,495,097 A | 1/1985 | Orlowski et al. |
| 4,497,731 A | 2/1985 | Orlowski et al. |
| 4,537,716 A | 8/1985 | Orlowski et al. |
| 4,597,900 A | 7/1986 | Orlowski et al. |
| 4,604,238 A | 8/1986 | Orlowski et al. |
| 4,606,856 A | 8/1986 | Seyler et al. |
| 4,652,627 A | 3/1987 | Kempe et al. |
| 4,687,839 A | 8/1987 | Kempe |
| 4,697,002 A | 9/1987 | Kempe |
| 5,118,666 A | 6/1992 | Habener |
| 5,188,666 A | 2/1993 | Boccardo |
| 5,234,906 A | 8/1993 | Young et al. |
| 5,424,286 A | 6/1995 | Eng |
| 5,512,549 A | 4/1996 | Chen et al. |
| 5,521,283 A | 5/1996 | DiMarchi et al. |
| 5,532,336 A | 7/1996 | DiMarchi et al. |
| 5,545,618 A | 8/1996 | Buckley et al. |
| 5,604,203 A | 2/1997 | Balasubramaniam |
| 5,686,511 A | 11/1997 | Bobo |
| 5,739,106 A | 4/1998 | Rink et al. |
| 5,789,379 A | 8/1998 | Drucker et al. |
| 5,824,778 A | 10/1998 | Ishikawa et al. |
| 5,824,784 A | 10/1998 | Kinstler et al. |
| 5,998,367 A | 12/1999 | Gaeta et al. |
| 6,184,201 B1 | 2/2001 | Drucker et al. |
| 6,506,724 B1 | 1/2003 | Hiles et al. |
| 6,528,486 B1 | 3/2003 | Larsen et al. |
| 6,558,952 B1 | 5/2003 | Parikh et al. |
| 6,593,295 B2 | 7/2003 | Bridon et al. |
| 6,747,006 B2 | 6/2004 | Efendic |
| 2002/0141985 A1 | 10/2002 | Pittner et al. |
| 2003/0026812 A1 | 2/2003 | Duft et al. |
| 2004/0053370 A1 | 3/2004 | Glaesner et al. |
| 2004/0115135 A1 | 6/2004 | Quay |
| 2004/0209803 A1 | 10/2004 | Baron et al. |
| 2004/0228846 A1 | 11/2004 | Pang et al. |
| 2006/0135747 A1 | 6/2006 | Levy et al. |

FOREIGN PATENT DOCUMENTS

| | | |
|---|---|---|
| EA | 4791 B1 | 8/2004 |
| EP | 1421950 A1 | 5/2004 |
| EP | 2330125 A3 | 8/2006 |
| EP | 1718665 A2 | 11/2006 |
| WO | 91/08220 A1 | 6/1991 |
| WO | 9111457 A1 | 8/1991 |
| WO | 94/22467 A1 | 10/1994 |
| WO | 9519785 A1 | 7/1995 |
| WO | 9605309 A2 | 2/1996 |
| WO | 96/22308 A2 | 7/1996 |

(Continued)

OTHER PUBLICATIONS

Reda et al., Obes. Res. 10: 1087-1091, 2002.*
Szayna et al., Endocr. 141: 1936-1941, 2000.*
Or Bhaysar et al., Phys. Behavior, 64: 557-561, 1998.*
Ashraf, et al., "Soldid phase synthesis of peptide dimers and trimers linked through an N-terminallysine residue", Tetrahedron Letters, 2003,44: pp. 9115-9119.
Gonzales-Muniz (In J Pept Protein Res., 1991; 37: 331-40-abstract only).
Bray, et al., "Afferent signals regulating food intake", Proceedings of the Nutrition Society, 2000; 59: pp. 373-384.
Mezna, Mokdad, eta/., Biochem. Soc. Trans. 25:450S (1997): Calcium Mobilizing Actions of Chimeric Hormone-Mastoparan Peptides.

(Continued)

*Primary Examiner* — Gyan Chandra
(74) *Attorney, Agent, or Firm* — Kilpatrick Townsend & Stockton LLP

(57) ABSTRACT

The present invention relates generally to novel, selectable hybrid polypeptides useful as agents for the treatment and prevention of metabolic diseases and disorders which can be alleviated by control plasma glucose levels, insulin levels, and/or insulin secretion, such as diabetes and diabetes-related conditions. Such conditions and disorders include, but are not limited to, hypertension, dyslipidemia, cardiovascular disease, eating disorders, insulin-resistance, obesity, and diabetes mellitus of any kind, including type 1, type 2, and gestational diabetes.

20 Claims, 9 Drawing Sheets

(56) References Cited

FOREIGN PATENT DOCUMENTS

| WO | 96/31526 | | 10/1996 |
|---|---|---|---|
| WO | 96/40196 | A1 | 12/1996 |
| WO | 9702004 | A2 | 1/1997 |
| WO | 9715322 | A1 | 5/1997 |
| WO | 97/26321 | | 7/1997 |
| WO | 9727286 | A1 | 7/1997 |
| WO | 9731621 | A1 | 9/1997 |
| WO | 9805351 | A1 | 2/1998 |
| WO | 9812224 | A1 | 3/1998 |
| WO | 9818486 | A1 | 5/1998 |
| WO | 98/28427 | A1 | 7/1998 |
| WO | 9830231 | A1 | 7/1998 |
| WO | 9836763 | A1 | 8/1998 |
| WO | 9848831 | A1 | 11/1998 |
| WO | 9855139 | A1 | 12/1998 |
| WO | 9907404 | A1 | 2/1999 |
| WO | 9925727 | A2 | 5/1999 |
| WO | 9925728 | A1 | 5/1999 |
| WO | 00/73331 | A2 | 12/2000 |
| WO | 01/04156 | A1 | 1/2001 |
| WO | 01/44284 | A2 | 6/2001 |
| WO | 01/51078 | A1 | 7/2001 |
| WO | 02/46227 | | 6/2002 |
| WO | 02/47712 | A2 | 6/2002 |
| WO | 03/011892 | A2 | 2/2003 |
| WO | 03/022304 | A1 | 3/2003 |
| WO | 03/026591 | A2 | 4/2003 |
| WO | 03/057235 | A2 | 7/2003 |
| WO | WO 03/059934 | * | 7/2003 |
| WO | 2004/037195 | A2 | 5/2004 |
| WO | 2004/039832 | A2 | 5/2004 |
| WO | 2004/056313 | A2 | 7/2004 |
| WO | 2004/103390 | A1 | 12/2004 |
| WO | 2005/000222 | | 1/2005 |
| WO | 2005/077072 | A2 | 8/2005 |
| WO | 2005/077094 | A2 | 8/2005 |
| WO | 2006/066024 | A2 | 6/2006 |
| WO | 2006/083254 | A1 | 8/2006 |
| WO | 2006/086769 | | 8/2006 |
| WO | 2007022123 | | 2/2007 |
| WO | 2007/055728 | A1 | 5/2007 |

OTHER PUBLICATIONS

Tatemoto, Kuzahiko, et al "Neuropeptide Y: Complete Amino Acid Sequence of the Brain Peptide" Proc Natl Acad Sci (1982) 5485-5489, 79(18).
Bark, Peer, "Powers and Pitfalls in Sequence Analysis: The 70% Hurdle." Genome Research, 10:398-400, 2000.
Bark, Peer, "Go hunting in sequence databases but watch outfor traps." Trends in Genetics, vol. 12. No. 10. pp. 425-427, 1996.
Brenner, S.E., "Errors in genome annotation." Trends in Genetics, vol. 15. No. 4. pp. 132-133, 1999.
Doerks, Tobias, Protein annotation: detective work for function prediction. Trends in Genetics, vol. 14. No. 6. pp. 248-250, 1998.
Ngo, Thomas J., "Computational Complexity, Protein Structure Prediction and the Levinthal Paradox." In Merz and Le Grand (Eds.) the Protein Folding Problem and Tertiary Structure Predication, Birkhauser Boston, pp. 492-495, 1992.
Skolnick, Jeffrey et al., "From genes to protein structure and function: novel applications of computational approaches in the genomic era." Tibtech, vol. 18. No. 1. pp. 248-250, 1998.
Smith, Temple F. et al., "The challenges of genome sequence annotation or The devil is in the details". Nature Biotechnology, vol. 15. pp. 1222-1223, 1997.
Wells, J.A., "Additivity of Mutational Effects in Proteins." Biochemistry, vol. 29. No. 37. pp. 8509-8517, 1990.
Weigle, David S., et al "Recombinant ob Protein Reduces Feeding and Body Weight in the ob/ob Mouse", J Clin D Invest (1995) 2065-2070, 96.
Wimalawansa, Sunil J., et al "Amylin, Calcitonin Gene-Related Peptide, Calcitonin, and Adrenomedullin: A Peptide Superfamily", Crit Rev Neurobiol (1997) 167-239, 11 (2-3).

Zhang, L. et al., "Preparation of Functionally Active Cell-permeable Peptides by Single-step Ligation of Two Peptides Modules." Proc. Natl. Acad. Sci. USA, vol. 95, pp. 9184-9189, Aug. 1998, Biochemistry.
Halford, Jason, et al. "The Pyschopharmacology of Appetite: Targets for Potential Anti-Obesity Agents," Curr. Med. Chern.—Central Nervous System Agents, 2003. 3, 283-310.
Montrose-Rafizadeh, C., et al "High Potency Antagonists of the Pancreatic Glucagon-like Peptide 1 Receptor", The Journal of Biological Chemistry (1997) vol. 272, No. 24, 21201-21206.
Batterham, "Gut hormone PYY 3-36 physiologically inhibits.food intakes." Nature vol. 418, Aug. 2002.
Cabrele, C. et al., "Y-receptor affinity modulation by the design of pancreatic polypeptide/neuropeptide Y chimera led to Y5-receptor ligands with picomolar affinity." Peptides 22 (2001) 365-378.
Cabrele, C. et al., "Aia31-Aib32: Identification of the Key Motif for High Affinity and Selectivity of Neuropeptide Y at the Y5-Receptor." Biochemistry 2002, 41, 8043-8049.
Halford, J. et al., "The Psychopharmacology of Appetite: Targets for Potential Anti-Obesity Agents." Curr. Med. Chern.—Central Nervous System Agents, 2003, 3, 283-310.
Koda, J. et al., "Amylin Concentrations and Glucose Control." The Lancet, vol. 339: May 9, 1992, 1179.
Krstnansky, J. et al., "C-Terminal Modifications of Neuropeptide Y and its Analogs Leading to Selectivity for the Mouse Brain Receptor over the Porcine Spleen Receptor." Neuropeptides (1990) 17, 117-120.
Malts, D., et al., "Influence of TASP-V, a novel neuropeptide Y (NPY) Y2 agonist, on nasal and bronchial responses evoked by histamine in anaesthetized pigs and in humans." British Journal of Pharmacology (1990) 126, 989-996.
Andreu, David, et al "Shortened Cecropin A-Melittin Hybrids", FEBS (1992) 190-194, 296 (2).
Aponte, Gregory W., et al "Meal-Induced Peptide Tyrosine Tyrosine Inhibition of Pancreatic Secretion in the Rat", FASEB J. (1989) 1949-1955, 3.
Baron, Alain et al., "Novel Peptides Under Development . . . " current Drug Targets Immune Endocrine and Metabolic Disorders, vol. 2 No. 1 Apr. 2002.
Becker, K. L., et al "Procalcitonin and the Calcitonin Gene Family of Peptides in Inflammation . . . ", JCEM (2004) 1512-1525, 89 (4).
Campfield, L. Arthur, et al "Recombinant Mouse OB Protein:.Evidence for a Peripheral Signal Linking Adiposity and Central Neural Networks", Science (1995) 546-549, 269.
Cooper, G. J. S., et al "Amylin and the Amylin Gene: Structure, Function and Relationship to Islet Amyloid and to Diabetes Mellitus", Biochim Biophys Acta (1989) 247-258, 1014.
Cooper, G. J. S., et al "Purification and Characterization of a Peptide from Amyloid-Rich Pancreases of Type 2 Diabetic Patients", Proc. Natl. Acad. Sci. (1987) 8628-8632, 84.
Cox, James E., "Inhibitory Effects of Cholecystokinin Develop Through Interaction With Duodenal Signals", Behav Brain Res (1990) 35-44, 38.
Crawley, Jacqueline N., et al "Biological Actions of Cholecystokinin", Peptides (1994) 731-755, 15 (4 )WLEY, Jacqueline N., et al "Biological Actions of Cholecystokinin", Peptides (1994) 731-755, 15 (4).
Dasgupta, P., et al "Antiproliferative and Gh-Inhibitory Activity of Chimeric Peptides Consisting of GHRP-6 and Somatostatin", Biochem Biophys Res Commun (1999) 379-384, 259.
Dulawa, Stephanie C., et al "Cholecystokinin and Estradiol Synergistically Potentiate Satiety in Rats" Peptides (1994) 913-918, 15(5).
Eberlein, Gert A., et al "A New Molecular Form of PYY: Structural Characterization of Human PYY(3-36) and PYY (1-36)" Peptides (1989) 797-803, 10.
Eng et al., "Purification and Structure of Exendin-3, a New Pancreatic Secretagogue Isolated from Heloderma horrid urn Venom," J. Bioi. Chern., vol. 265 No. 33 20259-62 (1990).
Eng et al., "Isolation and Characterization of Exendin-4, an Exendin-3 Analogue, from *Heloderma suspectum* Venom," J. Bioi. Chern., vol. 267 No. 11 7402-05 (1992).
Farquhar, Michelle, et al "Novel Mastoparan Analogs Induce Differential Secretion from Mast Cells", Chern Bioi (2002) 63-70, 9.

(56) References Cited

OTHER PUBLICATIONS

Goke, R., et al "Glucagon-Like Peptide-1 (7-36) Amide is a New Incretin/Enterogastrone Candidate" J Biol Chem (1991) 135-144, 21.

Goke, R., et al "Exendin-4 is a High Potency Agonist and Truncated Exendin-(9-39)-amide an Antagonist . . . ", J Biol Chem (1993) 19650-19655, 268(26).

Grandt, D., et al "Two Molecular Forms of Peptide YY (PYY) are Abundant in Human Blood: Characterization . . . ", Regulatory Peptides (1994) 151-159, 51.

Halaas, Jeffrey L., et al "Weight-Reducing Effects of the Plasma Protein Encoded by the Obese Gene", Science (1995) 543-546, 269.

Hinson, Joy P., et al "Adrenomedullin, a Multifunctional Regulatory Peptide", Endocrine Reviews (2000) 138-167, 21 (2).

Hinton, Veronica, et al "Combined Injection Potentiates the Satiety Effects of Pancreatic Glucagon, Cholecystokinin, and Bombesin", Brain Res Bull (1986) 615-619, 17.

Hojo, Keiko, et al "Amino Acids and Peptides. Part 39: A Bivalent Poly(ethylene glycol) Hybrid Containing . . . " Bioorg Med Chem Lett (2001) 1429-1432, 11.

Howl, John, et al "Chimeric Hormones and Neuropeptides", Clin Sci (1997) 605-606, 93.

Howl, John, et al "Chimeric Strategies for the Rational Design of Bioactive Analogs of Small Peptide Hormones", FASEB J. (1997) 582-590, 11.

Keire, David A., et al "Solution Structure of Monomeric Peptide YY Supports the Functional Significance of the PP-Fold", Biochemistry (2000) 9935-9942, 39.

Kimmel, Joe R., et al "Isolation and Characterization of chicken Insulin" Endocrinology (1968) 1323-1330, 83.

Le Sauter, Joseph, et al "Pancreatic Glucagon and Cholecystokinin Synergistically Inhibit Sham Feeding in Rats" Am J Physiol (1987) R719-R725, 253.

Lieverse, R. J., et al "Role of Cholecystokinin in the Regulation of Satiation and Satiety in Humans", Ann N.Y. Acad Sci (1994) 268-272, 713.

Lutz, T. A., et al "Different Influence of CGRP (8-37), an Amylin and CGRP Antagonist, on the Anorectic Effects . . . " Peptides (1997) 643-649, 18(5).

Mohri, Hiroshi, et al "Effects of Hybrid Peptide Analogs to Receptor Recognition Domains on . . . " Thromb Haemost (1993) 490-495, 69.

Mojsov, Svetlana "Structural Requirements for Biological Activity of Glucagon-like Peptide-1" Int J Pept Protein Res (1992) 333-343, 40.

Montrose-Rafizadeh, C., et al "Structure-Function Analysis of Exendin-4 GLP-1 Analogs", Diabetes (1996) 152A, 45 (abstract 553).

Pelleymounter, Mary Ann, et al "Effects of the Obese Gene Product on Body Weight Regulation in Ob/Ob Mice", Science (1995) 540-543, 269.

Raufman, Jean-Pierre, et al "Exendin-3, a Novel Peptide from Heloderma Horridum Venom, Interacts with Vasoactive . . . ", J. Biol Chem (1991) 2897-2902, 266.

Roh, Jaesook, et al "Intermedin Is a Calcitonin/Calcitonin Gene-related Peptide Family Peptide Acting through the Calcitonin . . . ", J Biol Chem (2004) 7264-7274, 279.

Sexton, P.M., et al "Calcitonin", Current Medicinal Chemistry (1999) 1067-1093, 6.

Schepp, Wolfgang, et al "Exendin-4 and Exendin-(9-39) NH2: Agonist and Antagonist, Respectively . . . ", Eur J Pharmacal (1994) 183-191, 269.

Shin, Song Yub, et al "Cecropin A-Magainin 2 Hybrid Peptides Having Potent Antimicrobial Activity with Low Hemolytic Effect" Biochem Mol Biollnt (1998) 1119-1126, 44(6).

Smith, G. P., et al "Satiating Effect of Cholecystokinin" Ann N.Y. Acad Sci (1994) 236-241, 713.

Tatemoto, Kazuhiko "Isolation and Characterization of Peptide YY (PYY), a Candidate Gut Hormone that Inhibits Pancreatic . . . " Proc Natl Acad Sci (1982) 2514-2518, 79(8).

Tatemoto, Kazuhiko, et al "Neuropeptide Y—a Novel Brain Peptide with Structural Similarities to Peptide YY and Pancreatic Polypeptide", Nature (1982) 659-660, 29.

Teyssen, Stephan, et al "Inhibition of Canine Exocrine Pancreatic Secretion by Peptide YY is Mediated by PYY-Preferring Y2 Receptors", Pancreas (1996) 80-88, 13(1).

Udvardy, M., et al "Hybrid Peptide Containing RGDF (Arg-Giy-Asp-Phe) Coupled with the Carboxy Terminal . . . " Blood Coagul Fibrinolysis (1995) 11-16, 6.

Wade, D., et al "Antibacterial Peptides Designed as Analogs or Hybrids of Cecropins and Melittin" Int J Pept Protein Res ( 1992) 429-436, 40.

Walsh, John H. "Gastrointestinal Hormones", Johnson, L.R., New York: Raven Press (1994) 1-128, 3rd Edition.

Canadian Office Action issued in International Patent Application No. 2,617,649, dated Feb. 1, 2012, 3 pages.

Chinese Office Action issued in International Patent Application No. 200680037664.9, dated Nov. 22, 2012, 7 pages.

European Search Report issued in International Patent Application No. 10012633.3 - 2405, dated Nov. 13, 2012, 11 pages.

European Search Report issued in International Patent Application No. 10 012 633.3-1410, dated Jul. 24, 2013.

Daniel J. Drucker, U.S. Appl. No. 08/669,791, filed Jun. 28, 1996.

* cited by examiner

Figure 1: Effect in DIO Mouse of Exendin/PYY Hybrids
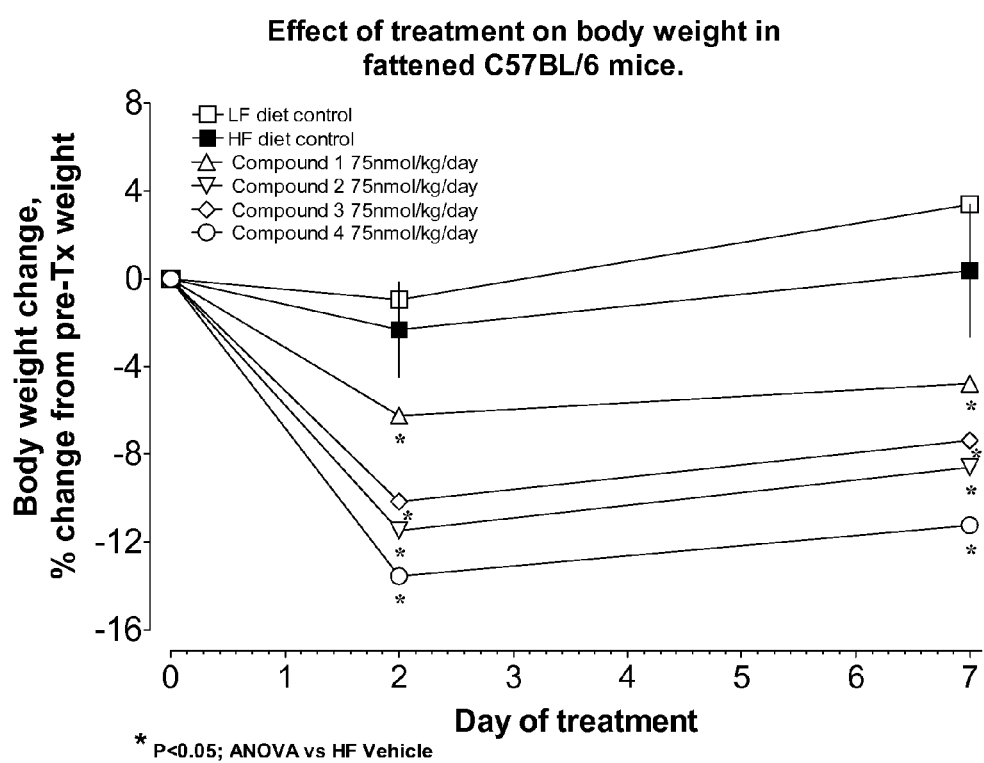

Figure 2: Effect in DIO Mouse of Exendin/Amylin Hybrids
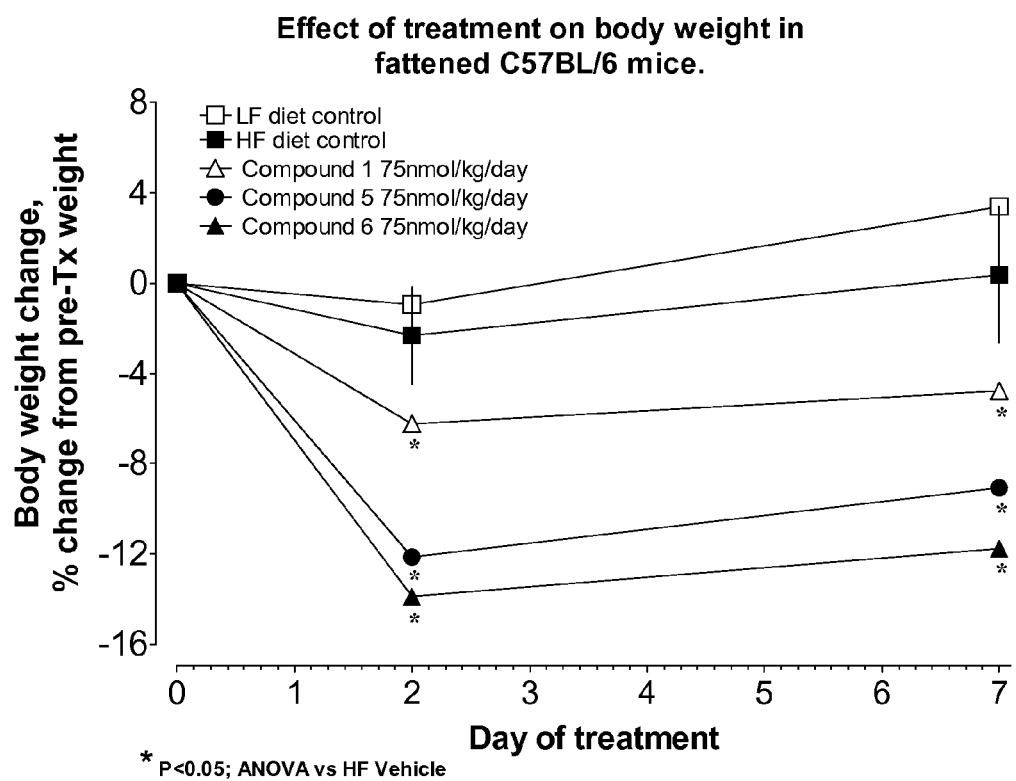

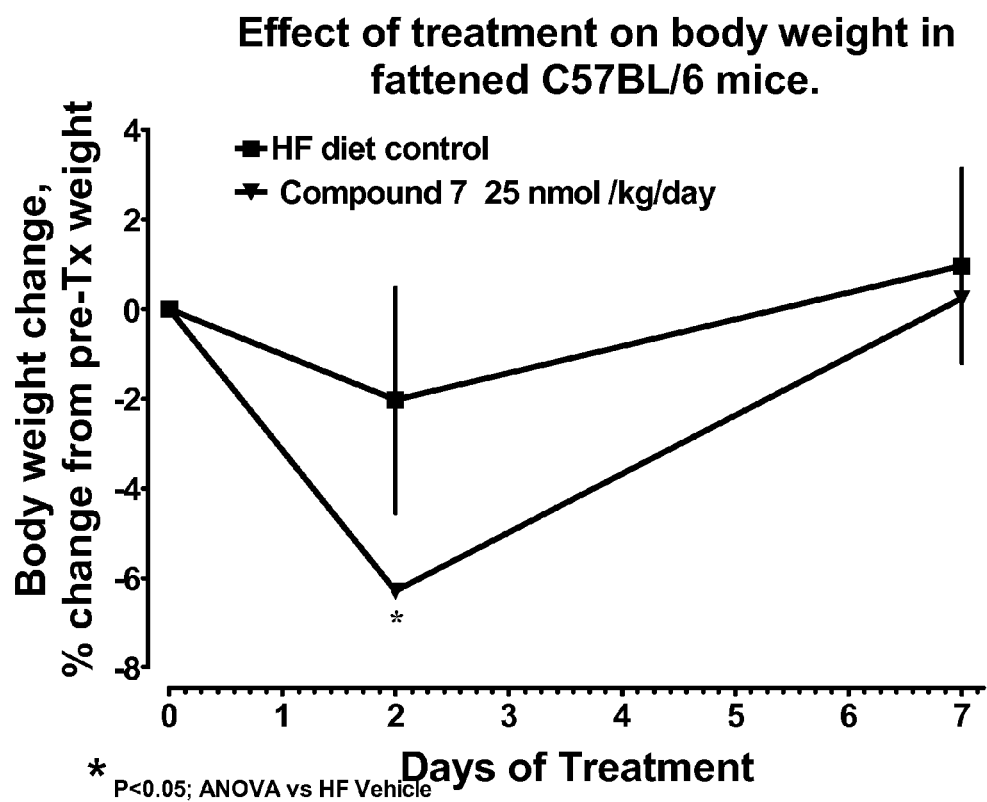
Figure 3A: Effect in DIO of Exendin/CCk-8 Hybrids

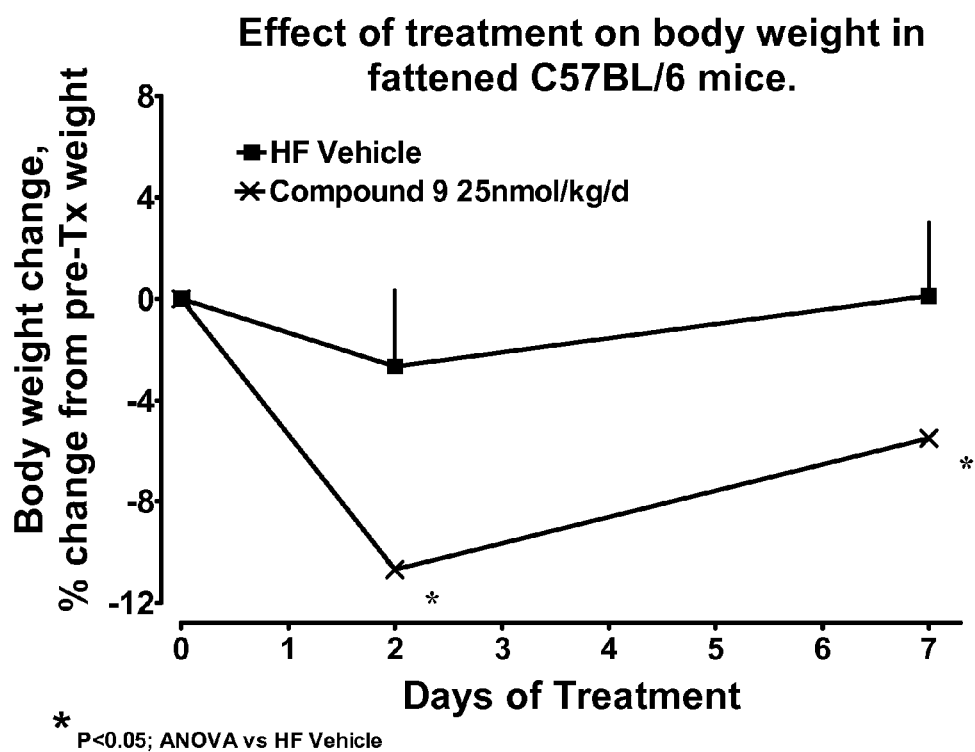
Figure 3B: Effect in DIO of Exendin/CCk-8 Hybrids

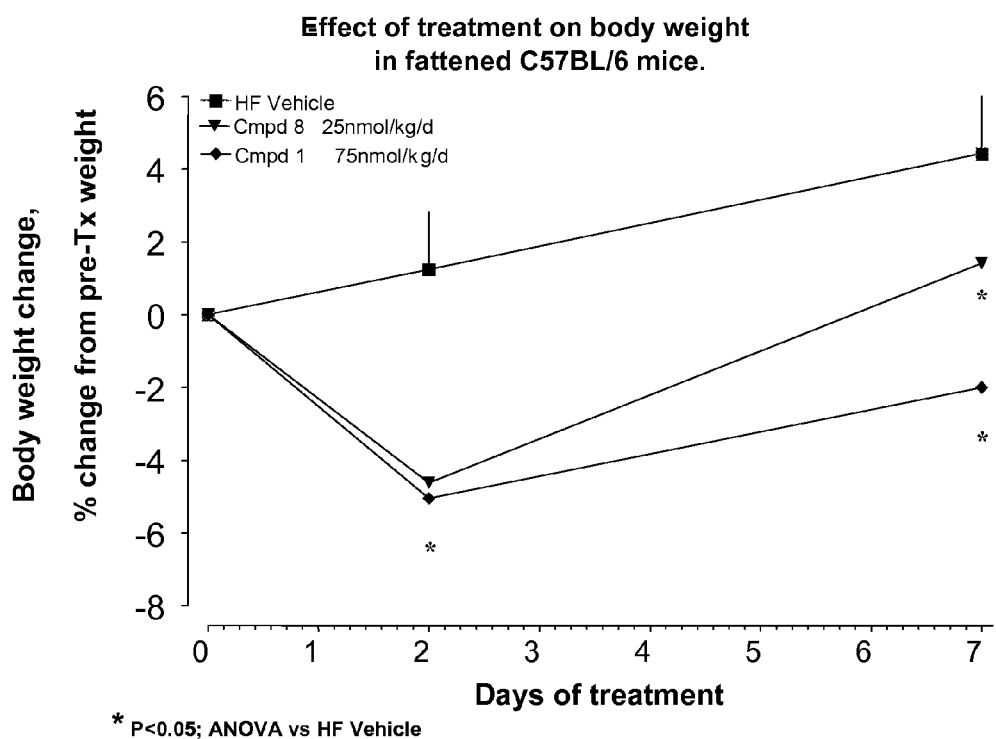
Figure 3C: Effect in DIO of Exendin/CCk-8 Hybrids

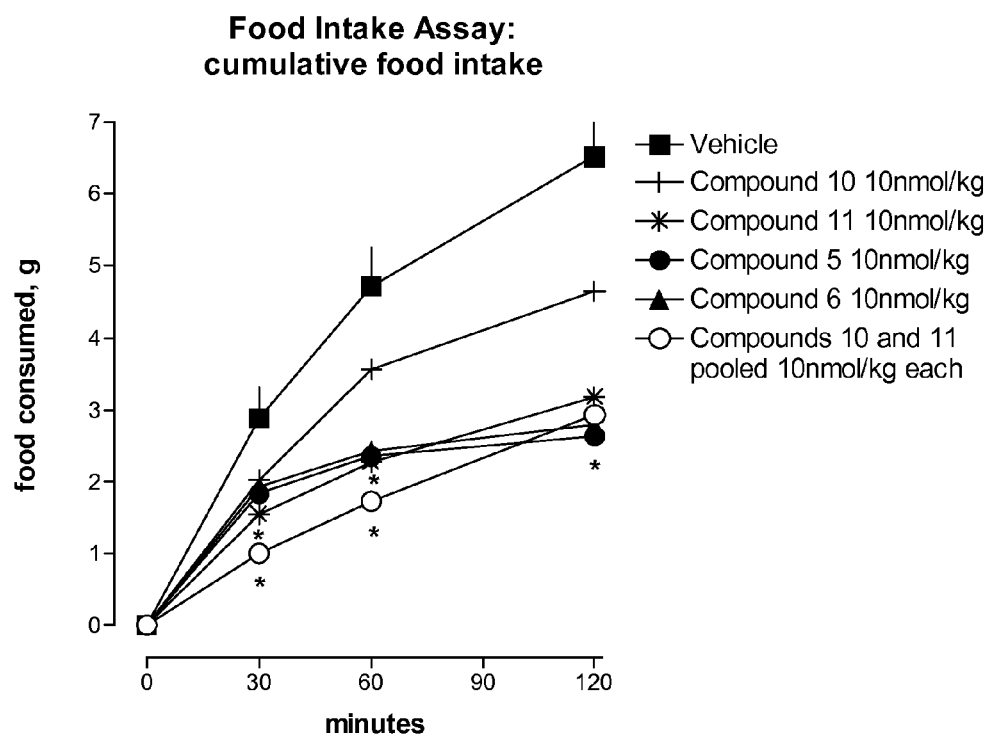
Figure 4A. Effect of Compounds of the Invention in Food Intake Assay (Compared to Parent Compounds)

Figure 4B. Effect of Compounds of the Invention in Food Intake Assay (Compared to Parent Compounds)
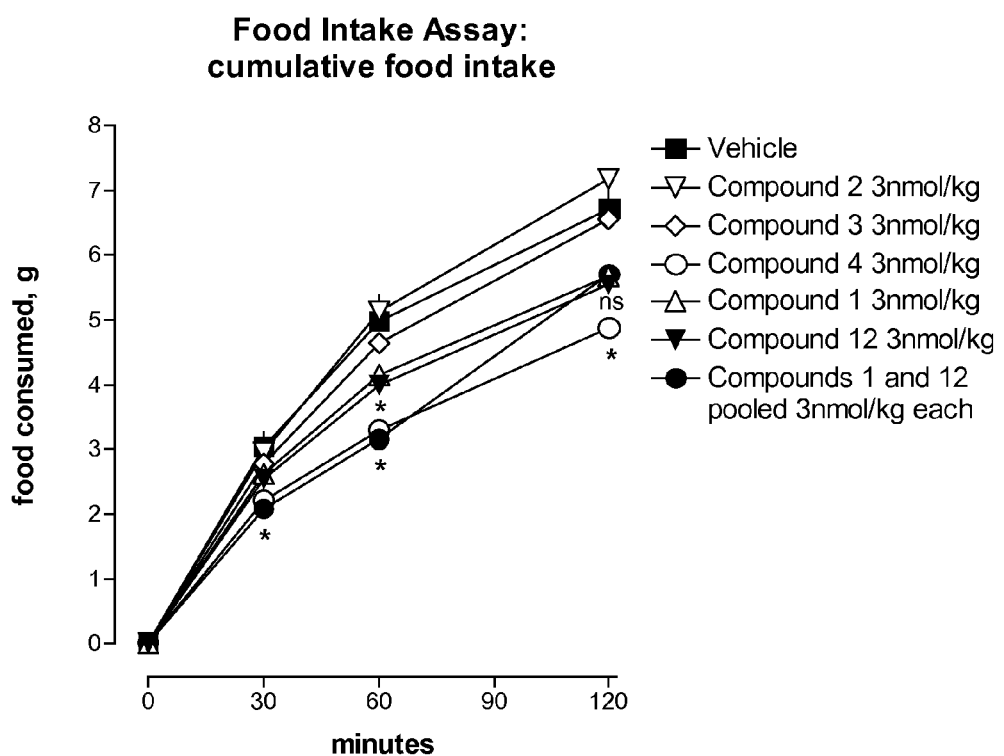

Figure 5A. Effect of Compounds of the Invention on Blood Glucose
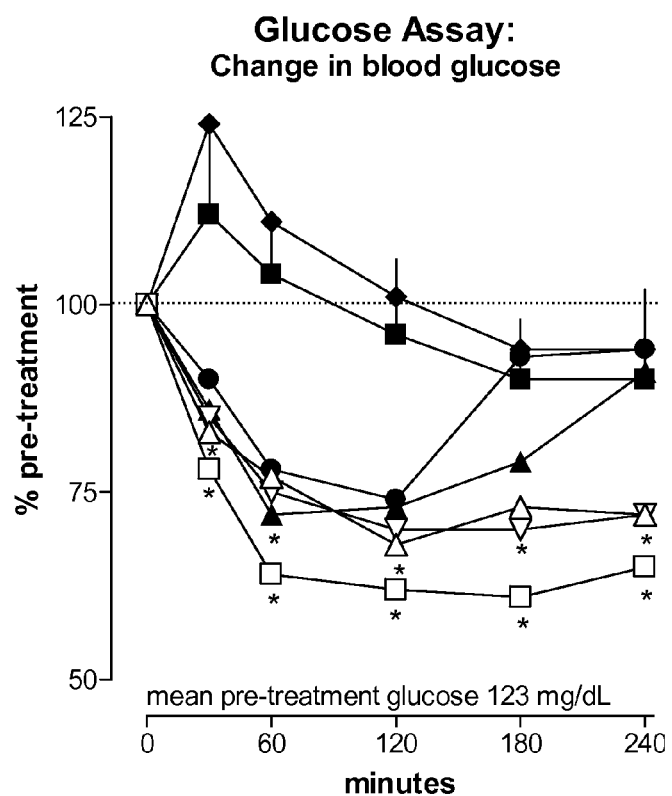
Glucose Assay Legend:
■ Vehicle
▲ Compound 11          16 nmol/kg
◆ Compound 10          16 nmol/kg
● Compound 10 with 11  16 nmol/kg each
▽ Compound 15          16 nmol/kg
☐ Compound 14          16 nmol/kg
△ Compound 5           16 nmol/kg Figure 5B. Effect of Compounds of the Invention in Food Intake Assay
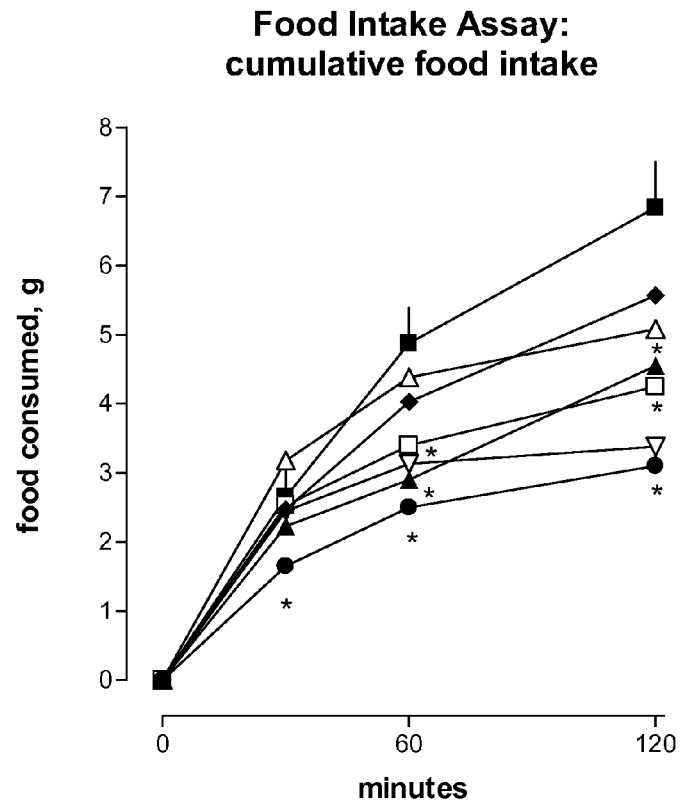
Food Intake Assay Legend:
■ Vehicle
▲ Compound 11        3nmol/kg
◆ Compound 10        3nmol/kg
● Compounds 10 with 11   3nmol/kg each
▽ Compound 15        3nmol/kg
□ Compound 14        3nmol/kg
△ Compound 5         3nmol/kg

SEQUENCE LISTING

```
<160> NUMBER OF SEQ ID NOS: 399

<210> SEQ ID NO 1
<211> LENGTH: 54
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<223> OTHER INFORMATION: C-term amidated

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Ala Ser Leu Arg His Tyr Leu Asn Leu
        35                  40                  45

Val Thr Arg Gln Arg Tyr
    50

<210> SEQ ID NO 2
<211> LENGTH: 51
```

```
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<223> OTHER INFORMATION: C-term amidated

<400> SEQUENCE: 2

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser Arg His Tyr Leu Asn Leu Val Thr Arg
         35                  40                  45

Gln Arg Tyr
         50

<210> SEQ ID NO 3
<211> LENGTH: 58
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<223> OTHER INFORMATION: C-term amidated

<400> SEQUENCE: 3

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser Asn Arg Tyr Tyr Ala Ser Leu Arg His
         35                  40                  45

Tyr Leu Asn Leu Val Thr Arg Gln Arg Tyr
         50                  55

<210> SEQ ID NO 4
<211> LENGTH: 56
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<221> NAME/KEY: MOD_RES
<222> LOCATION: (40)..(41)
<223> OTHER INFORMATION: Beta-alanine
<220> FEATURE:
<223> OTHER INFORMATION: C-term amidated

<400> SEQUENCE: 4

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser Xaa Xaa Ala Ser Leu Arg His Tyr Leu
         35                  40                  45

Asn Leu Val Thr Arg Gln Arg Tyr
         50                  55

<210> SEQ ID NO 5
<211> LENGTH: 53
<212> TYPE: PRT
```

<213> ORGANISM: Artificial Sequence
<220> FEATURE:
<223> OTHER INFORMATION: Description of Artificial Sequence: Chimeric
      lizard and human construct
<220> FEATURE:
<221> NAME/KEY: MOD_RES
<222> LOCATION: (40)..(41)
<223> OTHER INFORMATION: Beta-alanine
<220> FEATURE:
<223> OTHER INFORMATION: C-term amidated

<400> SEQUENCE: 5

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser Xaa Xaa Arg His Tyr Leu Asn Leu Val
        35                  40                  45

Thr Arg Gln Arg Tyr
        50

<210> SEQ ID NO 6
<211> LENGTH: 47
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<221> NAME/KEY: MOD_RES
<222> LOCATION: (40)..(41)
<223> OTHER INFORMATION: Beta-alanine
<220> FEATURE:
<223> OTHER INFORMATION: C-term amidated

<400> SEQUENCE: 6

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser Xaa Xaa Val Thr Arg Gln Arg Tyr
        35                  40                  45

<210> SEQ ID NO 7
<211> LENGTH: 43
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<223> OTHER INFORMATION: C-term amidated

<400> SEQUENCE: 7

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Ala Ser Leu Arg
            20                  25                  30

His Tyr Leu Asn Leu Val Thr Arg Gln Arg Tyr
        35                  40

<210> SEQ ID NO 8
<211> LENGTH: 40
<212> TYPE: PRT
<213> ORGANISM: Artificial Sequence
<220> FEATURE:
<223> OTHER INFORMATION: Description of Artificial Sequence: Chimeric lizard and human construct
<220> FEATURE:
<223> OTHER INFORMATION: C-term amidated

<400> SEQUENCE: 8

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Arg His Tyr Leu
            20                  25                  30

Asn Leu Val Thr Arg Gln Arg Tyr
        35                  40

<210> SEQ ID NO 9
<211> LENGTH: 47
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<223> OTHER INFORMATION: C-term amidated

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Asn Arg Tyr Tyr
            20                  25                  30

Ala Ser Leu Arg His Tyr Leu Asn Leu Val Thr Arg Gln Arg Tyr
        35                  40                  45

<210> SEQ ID NO 10
<211> LENGTH: 45
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<221> NAME/KEY: MOD_RES
<222> LOCATION: (29)..(30)
<223> OTHER INFORMATION: Beta-alanine
<220> FEATURE:
<223> OTHER INFORMATION: C-term amidated

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Xaa Ala Ser
            20                  25                  30

Leu Arg His Tyr Leu Asn Leu Val Thr Arg Gln Arg Tyr
        35                  40                  45

<210> SEQ ID NO 11
<211> LENGTH: 42
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<221> NAME/KEY: MOD_RES
<222> LOCATION: (29)..(30)
<223> OTHER INFORMATION: Beta-alanine
<220> FEATURE:
<223> OTHER INFORMATION: C-term amidated

<400> SEQUENCE: 11

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Xaa Arg His
            20                  25                  30

Tyr Leu Asn Leu Val Thr Arg Gln Arg Tyr
        35                  40

<210> SEQ ID NO 12
<211> LENGTH: 36
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<221> NAME/KEY: MOD_RES
<222> LOCATION: (29)..(30)
<223> OTHER INFORMATION: Beta-alanine
<220> FEATURE:
<223> OTHER INFORMATION: C-term amidated

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Xaa Val Thr
            20                  25                  30

Arg Gln Arg Tyr
        35

<210> SEQ ID NO 13
<211> LENGTH: 47
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<223> OTHER INFORMATION: C-term amidated

<400> SEQUENCE: 13

His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn Asn Arg Tyr Tyr
            20                  25                  30

Ala Ser Leu Arg His Tyr Leu Asn Leu Val Thr Arg Gln Arg Tyr
        35                  40                  45

<210> SEQ ID NO 14
<211> LENGTH: 43
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<223> OTHER INFORMATION: C-term amidated

<400> SEQUENCE: 14

His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn Ala Ser Leu Arg
            20                  25                  30

His Tyr Leu Asn Leu Val Thr Arg Gln Arg Tyr
        35                  40

```
<210> SEQ ID NO 15
<211> LENGTH: 40
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<223> OTHER INFORMATION: C-term amidated

<400> SEQUENCE: 15

His Gly Glu Gly Ala Phe Thr Ser Asp Leu Ser Lys Gln Leu Glu Glu
 1               5                  10                  15

Glu Ala Val Arg Leu Phe Ile Glu Phe Leu Lys Asn Arg His Tyr Leu
            20                  25                  30

Asn Leu Val Thr Arg Gln Arg Tyr
        35                  40

<210> SEQ ID NO 16
<211> LENGTH: 36
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<223> OTHER INFORMATION: C-term amidated

<400> SEQUENCE: 16

His Gly Glu Gly Ala Phe Thr Ser Asp Leu Ser Lys Gln Leu Glu Glu
 1               5                  10                  15

Glu Asn Arg Tyr Tyr Ala Ser Leu Arg His Tyr Leu Asn Leu Val Thr
            20                  25                  30

Arg Gln Arg Tyr
        35

<210> SEQ ID NO 17
<211> LENGTH: 45
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<221> NAME/KEY: MOD_RES
<222> LOCATION: (29)..(30)
<223> OTHER INFORMATION: Beta-alanine
<220> FEATURE:
<223> OTHER INFORMATION: C-term amidated

<400> SEQUENCE: 17

His Gly Glu Gly Ala Phe Thr Ser Asp Leu Ser Lys Gln Leu Glu Glu
 1               5                  10                  15

Glu Ala Val Arg Leu Phe Ile Glu Phe Leu Lys Asn Xaa Xaa Ala Ser
            20                  25                  30

Leu Arg His Tyr Leu Asn Leu Val Thr Arg Gln Arg Tyr
        35                  40                  45

<210> SEQ ID NO 18
<211> LENGTH: 42
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<221> NAME/KEY: MOD_RES
<222> LOCATION: (29)..(30)
```

```
<223> OTHER INFORMATION: Beta-alanine
<220> FEATURE:
<223> OTHER INFORMATION: C-term amidated

<400> SEQUENCE: 18

His Gly Glu Gly Ala Phe Thr Ser Asp Leu Ser Lys Gln Leu Glu Glu
 1               5                  10                  15

Glu Ala Val Arg Leu Phe Ile Glu Phe Leu Lys Asn Xaa Xaa Arg His
            20                  25                  30

Tyr Leu Asn Leu Val Thr Arg Gln Arg Tyr
        35                  40

<210> SEQ ID NO 19
<211> LENGTH: 36
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<221> NAME/KEY: MOD_RES
<222> LOCATION: (29)..(30)
<223> OTHER INFORMATION: Beta-alanine
<220> FEATURE:
<223> OTHER INFORMATION: C-term amidated

<400> SEQUENCE: 19

His Gly Glu Gly Ala Phe Thr Ser Asp Leu Ser Lys Gln Leu Glu Glu
 1               5                  10                  15

Glu Ala Val Arg Leu Phe Ile Glu Phe Leu Lys Asn Xaa Xaa Val Thr
            20                  25                  30

Arg Gln Arg Tyr
        35

<210> SEQ ID NO 20
<211> LENGTH: 47
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<221> NAME/KEY: MOD_RES
<222> LOCATION: (41)
<223> OTHER INFORMATION: Tyr(SO3)
<220> FEATURE:
<223> OTHER INFORMATION: C-term amidated

<400> SEQUENCE: 20

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser Asp Tyr Met Gly Trp Met Asp Phe
        35                  40                  45

<210> SEQ ID NO 21
<211> LENGTH: 36
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<221> NAME/KEY: MOD_RES
<222> LOCATION: (30)
<223> OTHER INFORMATION: Tyr(SO3)
<220> FEATURE:
```

-continued

<223> OTHER INFORMATION: C-term amidated

<400> SEQUENCE: 21

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Asp Tyr Met Gly
            20                  25                  30

Trp Met Asp Phe
        35

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<221> NAME/KEY: MOD_RES
<222> LOCATION: (30)
<223> OTHER INFORMATION: Phe(CH2SO3)
<220> FEATURE:
<223> OTHER INFORMATION: C-term amidated

<400> SEQUENCE: 22

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Asp Phe Met Gly
            20                  25                  30

Trp Met Asp Phe
        35

<210> SEQ ID NO 23
<211> LENGTH: 37
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<221> NAME/KEY: MOD_RES
<222> LOCATION: (29)
<223> OTHER INFORMATION: 8-amino-3,6-dioxactoanoyl
<220> FEATURE:
<221> NAME/KEY: MOD_RES
<222> LOCATION: (31)
<223> OTHER INFORMATION: Tyr(SO3)
<220> FEATURE:
<223> OTHER INFORMATION: C-term amidated

<400> SEQUENCE: 23

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Asp Tyr Met
            20                  25                  30

Gly Trp Met Asp Phe
            35

<210> SEQ ID NO 24
<211> LENGTH: 37
<212> TYPE: PRT
<213> ORGANISM: Artificial Sequence
<220> FEATURE:
<223> OTHER INFORMATION: Description of Artificial Sequence: Chimeric
      lizard and human construct
<220> FEATURE:
<221> NAME/KEY: MOD_RES
<222> LOCATION: (29)

```
<223> OTHER INFORMATION: 8-amino-3,6-dioxactoanoyl
<220> FEATURE:
<221> NAME/KEY: MOD_RES
<222> LOCATION: (31)
<223> OTHER INFORMATION: Phe(CH2SO3)
<220> FEATURE:
<223> OTHER INFORMATION: C-term amidated

<400> SEQUENCE: 24

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Asp Phe Met
            20                  25                  30

Gly Trp Met Asp Phe
        35

<210> SEQ ID NO 25
<211> LENGTH: 59
<212> TYPE: PRT
<213> ORGANISM: Artificial Sequence
<220> FEATURE:
<223> OTHER INFORMATION: Description of Artificial Sequence: Chimeric
      lizard, human and salmon construct
<220> FEATURE:
<223> OTHER INFORMATION: C-term amidated

<400> SEQUENCE: 25

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Lys Cys Asn Thr Ala
            20                  25                  30

Thr Cys Val Leu Gly Arg Leu Ser Gln Glu Leu His Arg Leu Gln Thr
        35                  40                  45

Tyr Pro Arg Thr Asn Thr Gly Ser Asn Thr Tyr
    50                  55

<210> SEQ ID NO 26
<211> LENGTH: 37
<212> TYPE: PRT
<213> ORGANISM: Artificial Sequence
<220> FEATURE:
<223> OTHER INFORMATION: Description of Artificial Sequence: Chimeric
      lizard, human and salmon construct
<220> FEATURE:
<223> OTHER INFORMATION: C-term amidated

<400> SEQUENCE: 26

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Lys Ala Asn Thr Ala
            20                  25                  30

Thr Ala Val Leu Gly
        35

<210> SEQ ID NO 27
<211> LENGTH: 61
<212> TYPE: PRT
<213> ORGANISM: Artificial Sequence
<220> FEATURE:
<223> OTHER INFORMATION: Description of Artificial Sequence: Chimeric
      lizard, human and salmon construct
<220> FEATURE:
<221> NAME/KEY: MOD_RES
<222> LOCATION: (29)
<223> OTHER INFORMATION: 12-Ado
<220> FEATURE:
<223> OTHER INFORMATION: C-term amidated
```

<400> SEQUENCE: 27

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Lys Cys Asn
             20                  25                  30

Thr Ala Thr Cys Val Leu Gly Arg Leu Ser Gln Glu Leu His Arg Leu
         35                  40                  45

Gln Thr Tyr Pro Arg Thr Asn Thr Gly Ser Asn Thr Tyr
     50                  55                  60

<210> SEQ ID NO 28
<211> LENGTH: 60
<212> TYPE: PRT
<213> ORGANISM: Artificial Sequence
<220> FEATURE:
<223> OTHER INFORMATION: Description of Artificial Sequence: Chimeric
      lizard, human and salmon construct
<220> FEATURE:
<221> NAME/KEY: MOD_RES
<222> LOCATION: (29)
<223> OTHER INFORMATION: 12-Ado
<220> FEATURE:
<223> OTHER INFORMATION: C-term amidated

<400> SEQUENCE: 28

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Cys Asn Thr
             20                  25                  30

Ala Thr Cys Val Leu Gly Arg Leu Ser Gln Glu Leu His Arg Leu Gln
         35                  40                  45

Thr Tyr Pro Arg Thr Asn Thr Gly Ser Asn Thr Tyr
     50                  55                  60

<210> SEQ ID NO 29
<211> LENGTH: 61
<212> TYPE: PRT
<213> ORGANISM: Artificial Sequence
<220> FEATURE:
<223> OTHER INFORMATION: Description of Artificial Sequence: Chimeric
      lizard, human and salmon construct
<220> FEATURE:
<221> NAME/KEY: MOD_RES
<222> LOCATION: (29)
<223> OTHER INFORMATION: 3,6-dioxactoanoyl
<220> FEATURE:
<223> OTHER INFORMATION: C-term amidated

<400> SEQUENCE: 29

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Lys Cys Asn
             20                  25                  30

Thr Ala Thr Cys Val Leu Gly Arg Leu Ser Gln Glu Leu His Arg Leu
         35                  40                  45

Gln Thr Tyr Pro Arg Thr Asn Thr Gly Ser Asn Thr Tyr
     50                  55                  60

<210> SEQ ID NO 30
<211> LENGTH: 60
<212> TYPE: PRT
<213> ORGANISM: Artificial Sequence
<220> FEATURE:
<223> OTHER INFORMATION: Description of Artificial Sequence: Chimeric lizard, human and salmon construct
<220> FEATURE:
<221> NAME/KEY: MOD_RES
<222> LOCATION: (29)
<223> OTHER INFORMATION: 3,6-dioxactoanoyl
<220> FEATURE:
<223> OTHER INFORMATION: C-term amidated

<400> SEQUENCE: 30

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Cys Asn Thr
            20                  25                  30

Ala Thr Cys Val Leu Gly Arg Leu Ser Gln Glu Leu His Arg Leu Gln
        35                  40                  45

Thr Tyr Pro Arg Thr Asn Thr Gly Ser Asn Thr Tyr
    50                  55                  60

<210> SEQ ID NO 31
<211> LENGTH: 61
<212> TYPE: PRT
<213> ORGANISM: Artificial Sequence
<220> FEATURE:
<223> OTHER INFORMATION: Description of Artificial Sequence: Chimeric
      lizard, human and salmon construct
<220> FEATURE:
<221> NAME/KEY: MOD_RES
<222> LOCATION: (29)
<223> OTHER INFORMATION: 5-Apa
<220> FEATURE:
<223> OTHER INFORMATION: C-term amidated

<400> SEQUENCE: 31

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Lys Cys Asn
            20                  25                  30

Thr Ala Thr Cys Val Leu Gly Arg Leu Ser Gln Glu Leu His Arg Leu
        35                  40                  45

Gln Thr Tyr Pro Arg Thr Asn Thr Gly Ser Asn Thr Tyr
    50                  55                  60

<210> SEQ ID NO 32
<211> LENGTH: 60
<212> TYPE: PRT
<213> ORGANISM: Artificial Sequence
<220> FEATURE:
<223> OTHER INFORMATION: Description of Artificial Sequence: Chimeric
      lizard, human and salmon construct
<220> FEATURE:
<221> NAME/KEY: MOD_RES
<222> LOCATION: (29)
<223> OTHER INFORMATION: 5-Apa
<220> FEATURE:
<223> OTHER INFORMATION: C-term amidated

<400> SEQUENCE: 32

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Cys Asn Thr
            20                  25                  30

Ala Thr Cys Val Leu Gly Arg Leu Ser Gln Glu Leu His Arg Leu Gln
        35                  40                  45

Thr Tyr Pro Arg Thr Asn Thr Gly Ser Asn Thr Tyr
    50                  55                  60

<210> SEQ ID NO 33
<211> LENGTH: 62
<212> TYPE: PRT
<213> ORGANISM: Artificial Sequence
<220> FEATURE:
<223> OTHER INFORMATION: Description of Artificial Sequence: Chimeric
      lizard, human and salmon construct
<220> FEATURE:
<221> NAME/KEY: MOD_RES
<222> LOCATION: (29)..(30)
<223> OTHER INFORMATION: Beta-alanine
<220> FEATURE:
<223> OTHER INFORMATION: C-term amidated

<400> SEQUENCE: 33

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Xaa Lys Cys
            20                  25                  30

Asn Thr Ala Thr Cys Val Leu Gly Arg Leu Ser Gln Glu Leu His Arg
        35                  40                  45

Leu Gln Thr Tyr Pro Arg Thr Asn Thr Gly Ser Asn Thr Tyr
    50                  55                  60

<210> SEQ ID NO 34
<211> LENGTH: 61
<212> TYPE: PRT
<213> ORGANISM: Artificial Sequence
<220> FEATURE:
<223> OTHER INFORMATION: Description of Artificial Sequence: Chimeric
      lizard, human and salmon construct
<220> FEATURE:
<221> NAME/KEY: MOD_RES
<222> LOCATION: (29)..(30)
<223> OTHER INFORMATION: Beta-alanine
<220> FEATURE:
<223> OTHER INFORMATION: C-term amidated

<400> SEQUENCE: 34

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Xaa Cys Asn
            20                  25                  30

Thr Ala Thr Cys Val Leu Gly Arg Leu Ser Gln Glu Leu His Arg Leu
        35                  40                  45

Gln Thr Tyr Pro Arg Thr Asn Thr Gly Ser Asn Thr Tyr
    50                  55                  60

<210> SEQ ID NO 35
<211> LENGTH: 61
<212> TYPE: PRT
<213> ORGANISM: Artificial Sequence
<220> FEATURE:
<223> OTHER INFORMATION: Description of Artificial Sequence: Chimeric
      lizard, human and salmon construct
<220> FEATURE:
<221> NAME/KEY: MOD_RES
<222> LOCATION: (29)
<223> OTHER INFORMATION: 4,7,10-trioxa-13-tridecanamine succinimidyl
<220> FEATURE:
<223> OTHER INFORMATION: C-term amidated

<400> SEQUENCE: 35

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Lys Cys Asn
            20                  25                  30

Thr Ala Thr Cys Val Leu Gly Arg Leu Ser Gln Glu Leu His Arg Leu
            35                  40                  45

Gln Thr Tyr Pro Arg Thr Asn Thr Gly Ser Asn Thr Tyr
        50                  55                  60

<210> SEQ ID NO 36
<211> LENGTH: 60
<212> TYPE: PRT
<213> ORGANISM: Artificial Sequence
<220> FEATURE:
<223> OTHER INFORMATION: Description of Artificial Sequence: Chimeric
      lizard, human and salmon construct
<220> FEATURE:
<221> NAME/KEY: MOD_RES
<222> LOCATION: (29)
<223> OTHER INFORMATION: 4,7,10-trioxa-13-tridecanamine succinimidyl
<220> FEATURE:
<223> OTHER INFORMATION: C-term amidated

<400> SEQUENCE: 36

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Cys Asn Thr
            20                  25                  30

Ala Thr Cys Val Leu Gly Arg Leu Ser Gln Glu Leu His Arg Leu Gln
        35                  40                  45

Thr Tyr Pro Arg Thr Asn Thr Gly Ser Asn Thr Tyr
    50                  55                  60

<210> SEQ ID NO 37
<211> LENGTH: 43
<212> TYPE: PRT
<213> ORGANISM: Artificial Sequence
<220> FEATURE:
<223> OTHER INFORMATION: Description of Artificial Sequence: Chimeric
      human and salmon construct
<220> FEATURE:
<221> NAME/KEY: MOD_RES
<222> LOCATION: (2)
<223> OTHER INFORMATION: Tyr(SO3)
<220> FEATURE:
<223> OTHER INFORMATION: C-term amidated

<400> SEQUENCE: 37

Asp Tyr Met Gly Trp Met Asp Phe Gly Lys Arg Lys Cys Asn Thr Ala
 1               5                  10                  15

Thr Cys Ala Thr Gln Arg Leu Ala Asn Glu Leu Val Arg Leu Gln Thr
            20                  25                  30

Tyr Pro Arg Thr Asn Val Gly Ser Asn Thr Tyr
        35                  40

<210> SEQ ID NO 38
<211> LENGTH: 36
<212> TYPE: PRT
<213> ORGANISM: Homo sapiens
<220> FEATURE:
<223> OTHER INFORMATION: C-term amidated

<400> SEQUENCE: 38

Lys Cys Asn Thr Ala Thr Cys Ala Thr Gln Arg Leu Ala Asn Phe Leu
 1               5                  10                  15

Val Arg Arg Tyr Tyr Ala Ser Leu Arg His Tyr Leu Asn Leu Val Thr
            20                  25                  30

Arg Gln Arg Tyr
        35

```
<210> SEQ ID NO 39
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)
<223> OTHER INFORMATION: Isocaproyl-Ser
<220> FEATURE:
<221> NAME/KEY: MOD_RES
<222> LOCATION: (6)
<223> OTHER INFORMATION: Aib
<220> FEATURE:
<221> NAME/KEY: MOD_RES
<222> LOCATION: (7)
<223> OTHER INFORMATION: Lys(formyl)
<220> FEATURE:
<221> NAME/KEY: MOD_RES
<222> LOCATION: (13)
<223> OTHER INFORMATION: Aib
<220> FEATURE:
<221> NAME/KEY: MOD_RES
<222> LOCATION: (14)
<223> OTHER INFORMATION: Lys(formyl)
<220> FEATURE:
<223> OTHER INFORMATION: C-term amidated

<400> SEQUENCE: 39

Ser Thr Ala Val Leu Xaa Lys Leu Ser Gln Glu Leu Xaa Lys Leu Gln
 1               5                  10                  15

Thr Asn Arg Tyr Tyr Ala Ser Leu Arg His Tyr Leu Asn Leu Val Thr
            20                  25                  30

Arg Gln Arg Tyr
        35

<210> SEQ ID NO 40
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)
<223> OTHER INFORMATION: Isocaproyl-Ser
<220> FEATURE:
<221> NAME/KEY: MOD_RES
<222> LOCATION: (6)
<223> OTHER INFORMATION: Aib
<220> FEATURE:
<221> NAME/KEY: MOD_RES
<222> LOCATION: (7)
<223> OTHER INFORMATION: Lys(formyl)
<220> FEATURE:
<221> NAME/KEY: MOD_RES
<222> LOCATION: (13)
<223> OTHER INFORMATION: Aib
<220> FEATURE:
<221> NAME/KEY: MOD_RES
<222> LOCATION: (14)
<223> OTHER INFORMATION: Lys(formyl)
<220> FEATURE:
<223> OTHER INFORMATION: C-term amidated

<400> SEQUENCE: 40

Ser Thr Ala Val Leu Xaa Lys Leu Ser Gln Glu Leu Xaa Lys Leu Glu
 1               5                  10                  15

Leu Asn Arg Tyr Tyr Ala Ser Leu Arg His Tyr Leu Asn Leu Val Thr
```

Arg Gln Arg Tyr
        35

<210> SEQ ID NO 41
<211> LENGTH: 43
<212> TYPE: PRT
<213> ORGANISM: Homo sapiens
<220> FEATURE:
<221> NAME/KEY: MOD_RES
<222> LOCATION: (1)
<223> OTHER INFORMATION: Amidated terminus
<220> FEATURE:
<221> NAME/KEY: MOD_RES
<222> LOCATION: (7)
<223> OTHER INFORMATION: Sulfonated Tyr
<220> FEATURE:
<221> NAME/KEY: MOD_RES
<222> LOCATION: (9)
<223> OTHER INFORMATION: Succinoyl-Cys

<400> SEQUENCE: 41

Phe Asp Met Trp Gly Met Tyr Asp Cys Ile Lys Pro Glu Ala Pro Gly
 1               5                  10                  15

Glu Asp Ala Ser Pro Glu Glu Leu Asn Arg Tyr Tyr Ala Ser Leu Arg
            20                  25                  30

His Tyr Leu Asn Leu Val Thr Arg Gln Arg Tyr
        35                  40

<210> SEQ ID NO 42
<211> LENGTH: 43
<212> TYPE: PRT
<213> ORGANISM: Homo sapiens
<220> FEATURE:
<221> NAME/KEY: MOD_RES
<222> LOCATION: (1)
<223> OTHER INFORMATION: Amidated terminus
<220> FEATURE:
<221> NAME/KEY: MOD_RES
<222> LOCATION: (7)
<223> OTHER INFORMATION: Sulfonated Tyr
<220> FEATURE:
<221> NAME/KEY: MOD_RES
<222> LOCATION: (9)
<223> OTHER INFORMATION: Bis-Cys(N-Acetyl)

<400> SEQUENCE: 42

Phe Asp Met Trp Gly Met Tyr Asp Cys Ile Lys Pro Glu Ala Pro Gly
 1               5                  10                  15

Glu Asp Ala Ser Pro Glu Glu Leu Asn Arg Tyr Tyr Ala Ser Leu Arg
            20                  25                  30

His Tyr Leu Asn Leu Val Thr Arg Gln Arg Tyr
        35                  40

<210> SEQ ID NO 43
<211> LENGTH: 43
<212> TYPE: PRT
<213> ORGANISM: Homo sapiens
<220> FEATURE:
<221> NAME/KEY: MOD_RES
<222> LOCATION: (1)
<223> OTHER INFORMATION: Amidated terminus
<220> FEATURE:
<221> NAME/KEY: MOD_RES
<222> LOCATION: (7)
<223> OTHER INFORMATION: Sulfonated Tyr
<220> FEATURE:
<221> NAME/KEY: MOD_RES
<222> LOCATION: (9)
<223> OTHER INFORMATION: Gly-Aminoxymethylcarbonyl

```
<220> FEATURE:
<223> OTHER INFORMATION: C-term amidated

<400> SEQUENCE: 43

Phe Asp Met Trp Gly Met Tyr Asp Gly Ile Lys Pro Glu Ala Pro Gly
 1               5                  10                  15

Glu Asp Ala Ser Pro Glu Glu Leu Asn Arg Tyr Tyr Ala Ser Leu Arg
                20                  25                  30

His Tyr Leu Asn Leu Val Thr Arg Gln Arg Tyr
            35                  40

<210> SEQ ID NO 44
<211> LENGTH: 37
<212> TYPE: PRT
<213> ORGANISM: Rattus sp.

<400> SEQUENCE: 44

Lys Cys Asn Thr Ala Thr Cys Ala Thr Gln Arg Leu Ala Asn Phe Leu
 1               5                  10                  15

Val Arg Ser Ser Asn Asn Leu Gly Pro Val Leu Pro Pro Thr Asn Val
                20                  25                  30

Gly Ser Asn Thr Tyr
            35

<210> SEQ ID NO 45
<211> LENGTH: 37
<212> TYPE: PRT
<213> ORGANISM: Homo sapiens

<400> SEQUENCE: 45

Lys Cys Asn Thr Ala Thr Cys Ala Thr Gln Arg Leu Ala Asn Phe Leu
 1               5                  10                  15

Val His Ser Ser Asn Asn Phe Gly Ala Ile Leu Ser Ser Thr Asn Val
                20                  25                  30

Gly Ser Asn Thr Tyr
            35

<210> SEQ ID NO 46
<211> LENGTH: 52
<212> TYPE: PRT
<213> ORGANISM: Homo sapiens

<400> SEQUENCE: 46

Tyr Arg Gln Ser Met Asn Asn Phe Gln Gly Leu Arg Ser Phe Gly Cys
 1               5                  10                  15

Arg Phe Gly Thr Cys Thr Val Gln Lys Leu Ala His Gln Ile Tyr Gln
                20                  25                  30

Phe Thr Asp Lys Asp Lys Asp Asn Val Ala Pro Arg Ser Lys Ile Ser
            35                  40                  45

Pro Gln Gly Tyr
        50

<210> SEQ ID NO 47
<211> LENGTH: 32
<212> TYPE: PRT
<213> ORGANISM: Oncorhynchus sp.

<400> SEQUENCE: 47

Cys Ser Asn Leu Ser Thr Cys Val Leu Gly Lys Leu Ser Gln Glu Leu
 1               5                  10                  15

His Lys Leu Gln Thr Tyr Pro Arg Thr Asn Thr Gly Ser Gly Thr Pro
```

```
                20                  25                  30
```

\<210\> SEQ ID NO 48
\<211\> LENGTH: 32
\<212\> TYPE: PRT
\<213\> ORGANISM: Homo sapiens

\<400\> SEQUENCE: 48

```
Cys Gly Asn Leu Ser Thr Cys Met Leu Gly Thr Tyr Thr Gln Asp Phe
 1               5                  10                  15

Asn Lys Phe His Thr Phe Pro Gln Thr Ala Ile Gly Val Gly Ala Pro
                20                  25                  30
```

\<210\> SEQ ID NO 49
\<211\> LENGTH: 37
\<212\> TYPE: PRT
\<213\> ORGANISM: Homo sapiens

\<400\> SEQUENCE: 49

```
Ala Cys Asp Thr Ala Thr Cys Val Thr His Arg Leu Ala Gly Leu Leu
 1               5                  10                  15

Ser Arg Ser Gly Gly Val Val Lys Asn Asn Phe Val Pro Thr Asn Val
                20                  25                  30

Gly Ser Lys Ala Phe
                35
```

\<210\> SEQ ID NO 50
\<211\> LENGTH: 37
\<212\> TYPE: PRT
\<213\> ORGANISM: Homo sapiens

\<400\> SEQUENCE: 50

```
Ala Cys Asn Thr Ala Thr Cys Val Thr His Arg Leu Ala Gly Leu Leu
 1               5                  10                  15

Ser Arg Ser Gly Gly Met Val Lys Ser Asn Phe Val Pro Thr Asn Val
                20                  25                  30

Gly Ser Lys Ala Phe
                35
```

\<210\> SEQ ID NO 51
\<211\> LENGTH: 47
\<212\> TYPE: PRT
\<213\> ORGANISM: Homo sapiens

\<400\> SEQUENCE: 51

```
Thr Gln Ala Gln Leu Leu Arg Val Gly Cys Val Leu Gly Thr Cys Gln
 1               5                  10                  15

Val Gln Asn Leu Ser His Arg Leu Trp Gln Leu Met Gly Pro Ala Gly
                20                  25                  30

Arg Gln Asp Ser Ala Pro Val Asp Pro Ser Ser Pro His Ser Tyr
                35                  40                  45
```

\<210\> SEQ ID NO 52
\<211\> LENGTH: 40
\<212\> TYPE: PRT
\<213\> ORGANISM: Homo sapiens

\<400\> SEQUENCE: 52

```
Val Gly Cys Val Leu Gly Thr Cys Gln Val Gln Asn Leu Ser His Arg
 1               5                  10                  15

Leu Trp Gln Leu Met Gly Pro Ala Gly Arg Gln Asp Ser Ala Pro Val
                20                  25                  30
```

-continued

```
Asp Pro Ser Ser Pro His Ser Tyr
        35                  40

<210> SEQ ID NO 53
<211> LENGTH: 47
<212> TYPE: PRT
<213> ORGANISM: Mus musculus

<400> SEQUENCE: 53

Pro His Ala Gln Leu Leu Arg Val Gly Cys Val Leu Gly Thr Cys Gln
1               5                   10                  15

Val Gln Asn Leu Ser His Arg Leu Trp Gln Leu Val Arg Pro Ala Gly
            20                  25                  30

Arg Arg Asp Ser Ala Pro Val Asp Pro Ser Ser Pro His Ser Tyr
        35                  40                  45

<210> SEQ ID NO 54
<211> LENGTH: 40
<212> TYPE: PRT
<213> ORGANISM: Mus musculus

<400> SEQUENCE: 54

Val Gly Cys Val Leu Gly Thr Cys Gln Val Gln Asn Leu Ser His Arg
1               5                   10                  15

Leu Trp Gln Leu Val Arg Pro Ala Gly Arg Arg Asp Ser Ala Pro Val
            20                  25                  30

Asp Pro Ser Ser Pro His Ser Tyr
        35                  40

<210> SEQ ID NO 55
<211> LENGTH: 8
<212> TYPE: PRT
<213> ORGANISM: Homo sapiens
<220> FEATURE:
<221> NAME/KEY: MOD_RES
<222> LOCATION: (2)
<223> OTHER INFORMATION: Tyr(SO3)

<400> SEQUENCE: 55

Asp Tyr Met Gly Trp Met Asp Phe
1               5

<210> SEQ ID NO 56
<211> LENGTH: 167
<212> TYPE: PRT
<213> ORGANISM: Homo sapiens

<400> SEQUENCE: 56

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
```

```
                      100                 105                 110
Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165
```

<210> SEQ ID NO 57
<211> LENGTH: 36
<212> TYPE: PRT
<213> ORGANISM: Homo sapiens

<400> SEQUENCE: 57

```
Tyr Pro Ile Lys Pro Glu Ala Pro Gly Glu Asp Ala Ser Pro Glu Glu
 1               5                  10                  15

Leu Asn Arg Tyr Tyr Ala Ser Leu Arg His Tyr Leu Asn Leu Val Thr
                20                  25                  30

Arg Gln Arg Tyr
        35
```

<210> SEQ ID NO 58
<211> LENGTH: 34
<212> TYPE: PRT
<213> ORGANISM: Homo sapiens

<400> SEQUENCE: 58

```
Ile Lys Pro Glu Ala Pro Gly Glu Asp Ala Ser Pro Glu Glu Leu Asn
 1               5                  10                  15

Arg Tyr Tyr Ala Ser Leu Arg His Tyr Leu Asn Leu Val Thr Arg Gln
                20                  25                  30

Arg Tyr
```

<210> SEQ ID NO 59
<211> LENGTH: 37
<212> TYPE: PRT
<213> ORGANISM: Homo sapiens

<400> SEQUENCE: 59

```
His Asp Glu Phe Glu Arg His Ala Glu Gly Thr Phe Thr Ser Asp Val
 1               5                  10                  15

Ser Ser Thr Leu Glu Gly Gln Ala Ala Leu Glu Phe Ile Ala Trp Leu
                20                  25                  30

Val Lys Gly Arg Gly
        35
```

<210> SEQ ID NO 60
<211> LENGTH: 37
<212> TYPE: PRT
<213> ORGANISM: Xenopus laevis
<220> FEATURE:
<221> NAME/KEY: MOD_RES
<222> LOCATION: (37)
<223> OTHER INFORMATION: Ser-OH

<400> SEQUENCE: 60

```
His Ala Glu Gly Thr Tyr Thr Asn Asp Val Thr Glu Tyr Leu Glu Glu
 1               5                  10                  15

Lys Ala Ala Lys Glu Phe Ile Glu Trp Leu Ile Lys Gly Lys Pro Lys
```

```
                    20                  25                  30

Lys Ile Arg Tyr Ser
            35

<210> SEQ ID NO 61
<211> LENGTH: 30
<212> TYPE: PRT
<213> ORGANISM: Homo sapiens

<400> SEQUENCE: 61

His Ala Glu Gly Thr Phe Thr Ser Asp Val Ser Ser Tyr Leu Glu Gly
  1               5                  10                  15

Gln Ala Ala Leu Glu Phe Ile Ala Trp Leu Val Lys Gly Arg
                20                  25                  30

<210> SEQ ID NO 62
<211> LENGTH: 33
<212> TYPE: PRT
<213> ORGANISM: Homo sapiens

<400> SEQUENCE: 62

His Ala Asp Gly Ser Phe Ser Asp Glu Met Asn Thr Ile Leu Asp Asn
  1               5                  10                  15

Leu Ala Ala Arg Asp Phe Ile Asn Trp Leu Ile Glu Thr Lys Ile Thr
                20                  25                  30

Asp

<210> SEQ ID NO 63
<211> LENGTH: 31
<212> TYPE: PRT
<213> ORGANISM: Xenopus sp.
<220> FEATURE:
<221> NAME/KEY: MOD_RES
<222> LOCATION: (31)
<223> OTHER INFORMATION: Pro-OH

<400> SEQUENCE: 63

His Ala Glu Gly Thr Phe Thr Asn Asp Met Thr Asn Tyr Leu Glu Glu
  1               5                  10                  15

Lys Ala Ala Lys Glu Phe Val Gly Trp Leu Ile Lys Gly Arg Pro
                20                  25                  30

<210> SEQ ID NO 64
<211> LENGTH: 37
<212> TYPE: PRT
<213> ORGANISM: Homo sapiens

<400> SEQUENCE: 64

His Ser Gln Gly Thr Phe Thr Ser Asp Tyr Ser Lys Tyr Leu Asp Ser
  1               5                  10                  15

Arg Arg Ala Gln Asp Phe Val Gln Trp Leu Met Asn Thr Lys Arg Asn
                20                  25                  30

Arg Asn Asn Ile Ala
            35

<210> SEQ ID NO 65
<211> LENGTH: 39
<212> TYPE: PRT
<213> ORGANISM: Heloderma suspectum

<400> SEQUENCE: 65

His Ser Asp Gly Thr Phe Thr Ser Asp Leu Ser Lys Gln Met Glu Glu
  1               5                  10                  15
```

Glu Ala Val Arg Leu Phe Ile Glu Trp Leu Lys Asn Gly Gly Pro Ser
            20                  25                  30

Ser Gly Ala Pro Pro Ser
            35

<210> SEQ ID NO 66
<211> LENGTH: 39
<212> TYPE: PRT
<213> ORGANISM: Heloderma suspectum

<400> SEQUENCE: 66

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 67
<211> LENGTH: 37
<212> TYPE: PRT
<213> ORGANISM: Homo sapiens

<400> SEQUENCE: 67

Lys Cys Asn Thr Ala Thr Cys Ala Thr Gln Arg Leu Ala Asn Phe Leu
 1               5                  10                  15

Val His Ser Ser Asn Asn Phe Gly Pro Ile Leu Pro Pro Thr Asn Val
            20                  25                  30

Gly Ser Asn Thr Tyr
            35

<210> SEQ ID NO 68
<211> LENGTH: 36
<212> TYPE: PRT
<213> ORGANISM: Homo sapiens

<400> SEQUENCE: 68

Cys Asn Thr Ala Thr Cys Ala Thr Gln Arg Leu Ala Asn Phe Leu Val
 1               5                  10                  15

His Ser Ser Asn Asn Phe Gly Ala Ile Leu Ser Ser Thr Asn Val Gly
            20                  25                  30

Ser Asn Thr Tyr
            35

<210> SEQ ID NO 69
<211> LENGTH: 37
<212> TYPE: PRT
<213> ORGANISM: Homo sapiens

<400> SEQUENCE: 69

Lys Cys Asn Thr Ala Thr Cys Ala Thr Gln Arg Leu Ala Asn Phe Leu
 1               5                  10                  15

Val His Ser Ser Asn Asn Phe Gly Pro Val Leu Pro Pro Thr Asn Val
            20                  25                  30

Gly Ser Asn Thr Tyr
            35

<210> SEQ ID NO 70
<211> LENGTH: 37
<212> TYPE: PRT
<213> ORGANISM: Homo sapiens

```
<400> SEQUENCE: 70

Lys Cys Asn Thr Ala Thr Cys Ala Thr Gln Arg Leu Ala Asn Phe Leu
  1               5                  10                  15

Val Arg Ser Ser Asn Asn Phe Gly Pro Ile Leu Pro Ser Thr Asn Val
             20                  25                  30

Gly Ser Asn Thr Tyr
         35

<210> SEQ ID NO 71
<211> LENGTH: 36
<212> TYPE: PRT
<213> ORGANISM: Homo sapiens

<400> SEQUENCE: 71

Cys Asn Thr Ala Thr Cys Ala Thr Gln Arg Leu Ala Asn Phe Leu Val
  1               5                  10                  15

Arg Ser Ser Asn Asn Phe Gly Pro Ile Leu Pro Ser Thr Asn Val Gly
             20                  25                  30

Ser Asn Thr Tyr
         35

<210> SEQ ID NO 72
<211> LENGTH: 37
<212> TYPE: PRT
<213> ORGANISM: Homo sapiens

<400> SEQUENCE: 72

Lys Cys Asn Thr Ala Thr Cys Ala Thr Gln Arg Leu Ala Asn Phe Leu
  1               5                  10                  15

Val Arg Ser Ser Asn Asn Phe Gly Pro Ile Leu Pro Pro Thr Asn Val
             20                  25                  30

Gly Ser Asn Thr Tyr
         35

<210> SEQ ID NO 73
<211> LENGTH: 36
<212> TYPE: PRT
<213> ORGANISM: Homo sapiens

<400> SEQUENCE: 73

Cys Asn Thr Ala Thr Cys Ala Thr Gln Arg Leu Ala Asn Phe Leu Val
  1               5                  10                  15

Arg Ser Ser Asn Asn Phe Gly Pro Ile Leu Pro Pro Thr Asn Val Gly
             20                  25                  30

Ser Asn Thr Tyr
         35

<210> SEQ ID NO 74
<211> LENGTH: 36
<212> TYPE: PRT
<213> ORGANISM: Homo sapiens

<400> SEQUENCE: 74

Cys Asn Thr Ala Thr Cys Ala Thr Gln Arg Leu Ala Asn Phe Leu Val
  1               5                  10                  15

His Ser Ser Asn Asn Phe Gly Pro Ile Leu Pro Pro Thr Asn Val Gly
             20                  25                  30

Ser Asn Thr Tyr
         35
```

-continued

<210> SEQ ID NO 75
<211> LENGTH: 37
<212> TYPE: PRT
<213> ORGANISM: Homo sapiens

<400> SEQUENCE: 75

Lys Cys Asn Thr Ala Thr Cys Ala Thr Gln Arg Leu Ala Asn Phe Leu
1               5                   10                  15

Val His Ser Ser Asn Asn Phe Gly Pro Val Leu Pro Pro Thr Asn Val
            20                  25                  30

Gly Ser Asn Thr Tyr
            35

<210> SEQ ID NO 76
<211> LENGTH: 37
<212> TYPE: PRT
<213> ORGANISM: Homo sapiens
<220> FEATURE:
<223> OTHER INFORMATION: 2,7-Cyclo bridge

<400> SEQUENCE: 76

Lys Asp Asn Thr Ala Thr Lys Ala Thr Gln Arg Leu Ala Asn Phe Leu
1               5                   10                  15

Val His Ser Ser Asn Asn Phe Gly Ala Ile Leu Pro Ser Thr Asn Val
            20                  25                  30

Gly Ser Asn Thr Tyr
            35

<210> SEQ ID NO 77
<211> LENGTH: 36
<212> TYPE: PRT
<213> ORGANISM: Homo sapiens

<400> SEQUENCE: 77

Cys Asn Thr Ala Thr Cys Ala Thr Gln Arg Leu Ala Asn Phe Leu Val
1               5                   10                  15

His Ser Ser Asn Asn Phe Gly Ala Ile Leu Ser Ser Thr Asn Val Gly
            20                  25                  30

Ser Asn Thr Tyr
            35

<210> SEQ ID NO 78
<211> LENGTH: 37
<212> TYPE: PRT
<213> ORGANISM: Homo sapiens

<400> SEQUENCE: 78

Ala Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
            35

<210> SEQ ID NO 79
<211> LENGTH: 37
<212> TYPE: PRT
<213> ORGANISM: Homo sapiens

<400> SEQUENCE: 79

Lys Ala Asn Thr Ala Thr Cys Ala Thr Gln Arg Leu Ala Asn Phe Leu
1               5                   10                  15

```
Val His Ser Ser Asn Asn Phe Gly Ala Ile Leu Ser Ser Thr Asn Val
            20                  25                  30

Gly Ser Asn Thr Tyr
        35

<210> SEQ ID NO 80
<211> LENGTH: 37
<212> TYPE: PRT
<213> ORGANISM: Homo sapiens

<400> SEQUENCE: 80

Lys Ala Asn Thr Ala Thr Ala Ala Thr Gln Arg Leu Ala Asn Phe Leu
  1               5                  10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 81
<211> LENGTH: 37
<212> TYPE: PRT
<213> ORGANISM: Homo sapiens

<400> SEQUENCE: 81

Ser Cys Asn Thr Ala Thr Cys Ala Thr Gln Arg Leu Ala Asn Phe Leu
  1               5                  10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 82
<211> LENGTH: 37
<212> TYPE: PRT
<213> ORGANISM: Homo sapiens

<400> SEQUENCE: 82

Lys Cys Asn Thr Ala Thr Cys Ala Thr Gln Arg Leu Ala Asn Phe Leu
  1               5                  10                  15

Val His Ser Ser Asn Asn Phe Gly Ala Ile Leu Ser Pro Thr Asn Val
            20                  25                  30

Gly Ser Asn Thr Tyr
        35

<210> SEQ ID NO 83
<211> LENGTH: 37
<212> TYPE: PRT
<213> ORGANISM: Homo sapiens

<400> SEQUENCE: 83

Lys Cys Asn Thr Ala Thr Cys Ala Thr Gln Arg Leu Ala Asn Phe Leu
  1               5                  10                  15

Val His Ser Ser Asn Asn Phe Gly Pro Ile Leu Pro Ser Thr Asn Val
            20                  25                  30

Gly Ser Asn Thr Tyr
        35

<210> SEQ ID NO 84
<211> LENGTH: 36
<212> TYPE: PRT
<213> ORGANISM: Homo sapiens
```

<400> SEQUENCE: 84

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Ser Thr Asn Val Gly
            20                  25                  30

Ser Asn Thr Tyr
        35

<210> SEQ ID NO 85
<211> LENGTH: 37
<212> TYPE: PRT
<213> ORGANISM: Homo sapiens

<400> SEQUENCE: 85

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Pro Thr Asn Val
            20                  25                  30

Gly Ser Asn Thr Tyr
        35

<210> SEQ ID NO 86
<211> LENGTH: 37
<212> TYPE: PRT
<213> ORGANISM: Homo sapiens

<400> SEQUENCE: 86

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Ser Thr Asn Val
            20                  25                  30

Gly Ser Asn Thr Tyr
        35

<210> SEQ ID NO 87
<211> LENGTH: 36
<212> TYPE: PRT
<213> ORGANISM: Homo sapiens

<400> SEQUENCE: 87

Cys Asn Thr Ala Thr Cys Ala Thr Gln Arg Leu Ala Asn Phe Leu Val
1               5                   10                  15

His Ser Ser Asn Asn Leu Gly Pro Val Leu Pro Ser Thr Asn Val Gly
            20                  25                  30

Ser Asn Thr Tyr
        35

<210> SEQ ID NO 88
<211> LENGTH: 37
<212> TYPE: PRT
<213> ORGANISM: Homo sapiens

<400> SEQUENCE: 88

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Ser Thr Asn Val
            20                  25                  30

Gly Ser Asn Thr Tyr
        35

<210> SEQ ID NO 89
<211> LENGTH: 37
<212> TYPE: PRT
<213> ORGANISM: Homo sapiens

<400> SEQUENCE: 89

Lys Cys Asn Thr Ala Thr Cys Ala Thr Gln Arg Leu Ala Asn Phe Leu
 1               5                  10                  15

Val Arg Ser Ser Asn Asn Leu Gly Pro Ile Leu Pro Pro Thr Asn Val
             20                  25                  30

Gly Ser Asn Thr Tyr
         35

<210> SEQ ID NO 90
<211> LENGTH: 37
<212> TYPE: PRT
<213> ORGANISM: Homo sapiens

<400> SEQUENCE: 90

Lys Cys Asn Thr Ala Thr Cys Ala Thr Gln Arg Leu Ala Asn Phe Leu
 1               5                  10                  15

Val Arg Ser Ser Asn Asn Leu Gly Pro Ile Leu Pro Ser Thr Asn Val
             20                  25                  30

Gly Ser Asn Thr Tyr
         35

<210> SEQ ID NO 91
<211> LENGTH: 37
<212> TYPE: PRT
<213> ORGANISM: Homo sapiens

<400> SEQUENCE: 91

Lys Cys Asn Thr Ala Thr Cys Ala Thr Gln Arg Leu Ala Asn Phe Leu
 1               5                  10                  15

Ile His Ser Ser Asn Asn Leu Gly Pro Ile Leu Pro Pro Thr Asn Val
             20                  25                  30

Gly Ser Asn Thr Tyr
         35

<210> SEQ ID NO 92
<211> LENGTH: 37
<212> TYPE: PRT
<213> ORGANISM: Homo sapiens

<400> SEQUENCE: 92

Lys Cys Asn Thr Ala Thr Cys Ala Thr Gln Arg Leu Ala Asn Phe Leu
 1               5                  10                  15

Ile His Ser Ser Asn Asn Phe Gly Pro Ile Leu Pro Pro Thr Asn Val
             20                  25                  30

Gly Ser Asn Thr Tyr
         35

<210> SEQ ID NO 93
<211> LENGTH: 36
<212> TYPE: PRT
<213> ORGANISM: Homo sapiens

<400> SEQUENCE: 93

Cys Asn Thr Ala Thr Cys Ala Thr Gln Arg Leu Ala Asn Phe Leu Ile
 1               5                  10                  15

His Ser Ser Asn Asn Leu Gly Pro Ile Leu Pro Pro Thr Asn Val Gly

```
                    20                  25                  30

Ser Asn Thr Tyr
        35

<210> SEQ ID NO 94
<211> LENGTH: 37
<212> TYPE: PRT
<213> ORGANISM: Homo sapiens

<400> SEQUENCE: 94

Lys Cys Asn Thr Ala Thr Cys Ala Thr Gln Arg Leu Ala Asn Phe Leu
 1               5                  10                  15

Ile Arg Ser Ser Asn Asn Leu Gly Ala Ile Leu Ser Ser Thr Asn Val
                20                  25                  30

Gly Ser Asn Thr Tyr
        35

<210> SEQ ID NO 95
<211> LENGTH: 37
<212> TYPE: PRT
<213> ORGANISM: Homo sapiens

<400> SEQUENCE: 95

Lys Cys Asn Thr Ala Thr Cys Ala Thr Gln Arg Leu Ala Asn Phe Leu
 1               5                  10                  15

Ile Arg Ser Ser Asn Asn Leu Gly Ala Val Leu Ser Pro Thr Asn Val
                20                  25                  30

Gly Ser Asn Thr Tyr
        35

<210> SEQ ID NO 96
<211> LENGTH: 37
<212> TYPE: PRT
<213> ORGANISM: Homo sapiens

<400> SEQUENCE: 96

Lys Cys Asn Thr Ala Thr Cys Ala Thr Gln Arg Leu Ala Asn Phe Leu
 1               5                  10                  15

Ile Arg Ser Ser Asn Asn Leu Gly Pro Val Leu Pro Pro Thr Asn Val
                20                  25                  30

Gly Ser Asn Thr Tyr
        35

<210> SEQ ID NO 97
<211> LENGTH: 37
<212> TYPE: PRT
<213> ORGANISM: Homo sapiens

<400> SEQUENCE: 97

Lys Cys Asn Thr Ala Thr Cys Ala Thr Gln Arg Leu Thr Asn Phe Leu
 1               5                  10                  15

Val His Ser Ser His Asn Leu Gly Ala Ala Leu Leu Pro Thr Asp Val
                20                  25                  30

Gly Ser Asn Thr Tyr
        35

<210> SEQ ID NO 98
<211> LENGTH: 37
<212> TYPE: PRT
<213> ORGANISM: Homo sapiens

<400> SEQUENCE: 98
```

-continued

Lys Cys Asn Thr Ala Thr Cys Ala Thr Gln Arg Leu Thr Asn Phe Leu
1               5                   10                  15

Val His Ser Ser His Asn Leu Gly Ala Ala Ser Leu Pro Thr Asp Val
            20                  25                  30

Gly Ser Asn Thr Tyr
            35

<210> SEQ ID NO 99
<211> LENGTH: 36
<212> TYPE: PRT
<213> ORGANISM: Homo sapiens

<400> SEQUENCE: 99

Cys Asn Thr Ala Thr Cys Ala Thr Gln Arg Leu Thr Asn Phe Leu Val
1               5                   10                  15

His Ser Ser His Asn Leu Gly Ala Ala Leu Pro Ser Thr Asp Val Gly
            20                  25                  30

Ser Asn Thr Tyr
            35

<210> SEQ ID NO 100
<211> LENGTH: 37
<212> TYPE: PRT
<213> ORGANISM: Homo sapiens

<400> SEQUENCE: 100

Lys Cys Asn Thr Ala Thr Cys Ala Thr Gln Arg Leu Thr Asn Phe Leu
1               5                   10                  15

Val Arg Ser Ser His Asn Leu Gly Ala Ala Leu Ser Pro Thr Asp Val
            20                  25                  30

Gly Ser Asn Thr Tyr
            35

<210> SEQ ID NO 101
<211> LENGTH: 37
<212> TYPE: PRT
<213> ORGANISM: Homo sapiens

<400> SEQUENCE: 101

Lys Cys Asn Thr Ala Thr Cys Ala Thr Gln Arg Leu Thr Asn Phe Leu
1               5                   10                  15

Val Arg Ser Ser His Asn Leu Gly Ala Ile Leu Pro Pro Thr Asp Val
            20                  25                  30

Gly Ser Asn Thr Tyr
            35

<210> SEQ ID NO 102
<211> LENGTH: 37
<212> TYPE: PRT
<213> ORGANISM: Homo sapiens

<400> SEQUENCE: 102

Lys Cys Asn Thr Ala Thr Cys Ala Thr Gln Arg Leu Thr Asn Phe Leu
1               5                   10                  15

Val Arg Ser Ser His Asn Leu Gly Pro Ala Leu Pro Pro Thr Asp Val
            20                  25                  30

Gly Ser Asn Thr Tyr
            35

<210> SEQ ID NO 103

```
<211> LENGTH: 32
<212> TYPE: PRT
<213> ORGANISM: Oncorhynchus sp.

<400> SEQUENCE: 103

Cys Ser Asn Leu Ser Thr Cys Gly Leu Gly Lys Leu Ser Glu Glu Leu
 1               5                  10                  15

His Lys Leu Gln Thr Tyr Pro Arg Thr Asn Thr Gly Ser Gly Thr Arg
            20                  25                  30

<210> SEQ ID NO 104
<211> LENGTH: 32
<212> TYPE: PRT
<213> ORGANISM: Oncorhynchus sp.

<400> SEQUENCE: 104

Cys Ser Asn Leu Ser Thr Cys Val Leu Gly Lys Leu Ser Glu Glu Leu
 1               5                  10                  15

His Lys Leu Gln Thr Leu Pro Arg Thr Asn Thr Gly Ser Gly Thr Arg
            20                  25                  30

<210> SEQ ID NO 105
<211> LENGTH: 31
<212> TYPE: PRT
<213> ORGANISM: Oncorhynchus sp.

<400> SEQUENCE: 105

Cys Gly Ser Leu Ser Thr Cys Gly Leu Gly Lys Leu Ser Glu Glu Leu
 1               5                  10                  15

His Lys Leu Gln Thr Pro Arg Thr Asn Thr Gly Ser Gly Thr Arg
            20                  25                  30

<210> SEQ ID NO 106
<211> LENGTH: 32
<212> TYPE: PRT
<213> ORGANISM: Oncorhynchus sp.

<400> SEQUENCE: 106

Cys Ser Asn Leu Ser Thr Cys Val Leu Gly Lys Leu Ser Glu Glu Leu
 1               5                  10                  15

His Lys Leu Gln Thr Tyr Pro Arg Thr Asn Thr Gly Ser Gly Thr Pro
            20                  25                  30

<210> SEQ ID NO 107
<211> LENGTH: 32
<212> TYPE: PRT
<213> ORGANISM: Oncorhynchus sp.

<400> SEQUENCE: 107

Cys Ser Asn Leu Ser Thr Cys Val Leu Gly Lys Leu Ser Gln Glu Leu
 1               5                  10                  15

His Arg Leu Gln Thr Tyr Pro Arg Thr Asn Thr Gly Ser Gly Thr Pro
            20                  25                  30

<210> SEQ ID NO 108
<211> LENGTH: 32
<212> TYPE: PRT
<213> ORGANISM: Oncorhynchus sp.

<400> SEQUENCE: 108

Cys Ser Asn Leu Ser Thr Cys Val Leu Gly Arg Leu Ser Gln Glu Leu
 1               5                  10                  15

His Arg Leu Gln Thr Tyr Pro Arg Thr Asn Thr Gly Ser Gly Thr Pro
```

```
                    20                  25                  30

<210> SEQ ID NO 109
<211> LENGTH: 32
<212> TYPE: PRT
<213> ORGANISM: Oncorhynchus sp.

<400> SEQUENCE: 109

Cys Ser Asn Leu Ser Thr Cys Val Leu Gly Lys Leu Ser Glu Glu Leu
 1               5                  10                  15

His Arg Leu Gln Thr Tyr Pro Arg Thr Asn Thr Gly Ser Gly Thr Pro
                20                  25                  30

<210> SEQ ID NO 110
<211> LENGTH: 32
<212> TYPE: PRT
<213> ORGANISM: Oncorhynchus sp.

<400> SEQUENCE: 110

Cys Ser Asn Leu Ser Thr Cys Val Leu Gly Arg Leu Ser Glu Glu Leu
 1               5                  10                  15

His Arg Leu Gln Thr Tyr Pro Arg Thr Asn Thr Gly Ser Gly Thr Pro
                20                  25                  30

<210> SEQ ID NO 111
<211> LENGTH: 37
<212> TYPE: PRT
<213> ORGANISM: Homo sapiens
<220> FEATURE:
<221> NAME/KEY: MOD_RES
<222> LOCATION: (36)
<223> OTHER INFORMATION: D-Ser

<400> SEQUENCE: 111

Ala Cys Asn Thr Ala Thr Cys Val Thr His Arg Leu Ala Gly Leu Leu
 1               5                  10                  15

Ser Arg Ser Gly Gly Met Val Lys Ser Asn Phe Val Pro Thr Asn Val
                20                  25                  30

Gly Ser Lys Ser Phe
                35

<210> SEQ ID NO 112
<211> LENGTH: 37
<212> TYPE: PRT
<213> ORGANISM: Homo sapiens
<220> FEATURE:
<221> NAME/KEY: MOD_RES
<222> LOCATION: (36)
<223> OTHER INFORMATION: D-Thr

<400> SEQUENCE: 112

Ala Cys Asn Thr Ala Thr Cys Val Thr His Arg Leu Ala Gly Leu Leu
 1               5                  10                  15

Ser Arg Ser Gly Gly Met Val Lys Ser Asn Phe Val Pro Thr Asn Val
                20                  25                  30

Gly Ser Lys Thr Phe
                35

<210> SEQ ID NO 113
<211> LENGTH: 37
<212> TYPE: PRT
<213> ORGANISM: Homo sapiens
<220> FEATURE:
<221> NAME/KEY: MOD_RES
<222> LOCATION: (36)
```

<223> OTHER INFORMATION: D-Asp

<400> SEQUENCE: 113

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Asp Phe
        35

<210> SEQ ID NO 114
<211> LENGTH: 37
<212> TYPE: PRT
<213> ORGANISM: Homo sapiens
<220> FEATURE:
<221> NAME/KEY: MOD_RES
<222> LOCATION: (36)
<223> OTHER INFORMATION: D-Asn

<400> SEQUENCE: 114

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Asn Phe
        35

<210> SEQ ID NO 115
<211> LENGTH: 37
<212> TYPE: PRT
<213> ORGANISM: Homo sapiens

<400> SEQUENCE: 115

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ser Phe
        35

<210> SEQ ID NO 116
<211> LENGTH: 37
<212> TYPE: PRT
<213> ORGANISM: Homo sapiens
<220> FEATURE:
<221> NAME/KEY: MOD_RES
<222> LOCATION: (36)
<223> OTHER INFORMATION: Hse

<400> SEQUENCE: 116

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Xaa Phe
        35

<210> SEQ ID NO 117
<211> LENGTH: 37
<212> TYPE: PRT
<213> ORGANISM: Homo sapiens

<400> SEQUENCE: 117

```
Ala Cys Asn Thr Ala Thr Cys Val Thr His Arg Leu Ala Gly Leu Leu
 1               5                  10                  15

Ser Arg Ser Gly Gly Met Val Lys Ser Asn Phe Val Pro Thr Asn Val
                20                  25                  30

Gly Ser Lys Asp Phe
        35
```

<210> SEQ ID NO 118
<211> LENGTH: 37
<212> TYPE: PRT
<213> ORGANISM: Homo sapiens

<400> SEQUENCE: 118

```
Ala Cys Asn Thr Ala Thr Cys Val Thr His Arg Leu Ala Gly Leu Leu
 1               5                  10                  15

Ser Arg Ser Gly Gly Met Val Lys Ser Asn Phe Val Pro Thr Asn Val
                20                  25                  30

Gly Ser Lys Thr Phe
        35
```

<210> SEQ ID NO 119
<211> LENGTH: 37
<212> TYPE: PRT
<213> ORGANISM: Homo sapiens

<400> SEQUENCE: 119

```
Ala Cys Asn Thr Ala Thr Cys Val Thr His Arg Leu Ala Gly Leu Leu
 1               5                  10                  15

Ser Arg Ser Gly Gly Met Val Lys Ser Asn Phe Val Pro Thr Asn Val
                20                  25                  30

Gly Ser Lys Asn Phe
        35
```

<210> SEQ ID NO 120
<211> LENGTH: 48
<212> TYPE: PRT
<213> ORGANISM: Mus musculus

<400> SEQUENCE: 120

```
Thr Gln Ala Gln Leu Leu Arg Val Gly Cys Gly Asn Leu Ser Thr Cys
 1               5                  10                  15

Gln Val Gln Asn Leu Ser His Arg Leu Trp Gln Leu Met Gly Pro Ala
                20                  25                  30

Gly Arg Gln Asp Ser Ala Pro Val Asp Pro Ser Ser Pro His Ser Tyr
                35                  40                  45
```

<210> SEQ ID NO 121
<211> LENGTH: 47
<212> TYPE: PRT
<213> ORGANISM: Mus musculus

<400> SEQUENCE: 121

```
Thr Gln Ala Gln Leu Leu Arg Val Gly Cys Asp Thr Ala Thr Cys Gln
 1               5                  10                  15

Val Gln Asn Leu Ser His Arg Leu Trp Gln Leu Met Gly Pro Ala Gly
                20                  25                  30

Arg Gln Asp Ser Ala Pro Val Asp Pro Ser Ser Pro His Ser Tyr
            35                  40                  45
```

<210> SEQ ID NO 122
<211> LENGTH: 47

```
<212> TYPE: PRT
<213> ORGANISM: Mus musculus

<400> SEQUENCE: 122

Thr Gln Ala Gln Leu Leu Arg Val Gly Met Val Leu Gly Thr Met Gln
 1               5                  10                  15

Val Gln Asn Leu Ser His Arg Leu Trp Gln Leu Met Gly Pro Ala Gly
                20                  25                  30

Arg Gln Asp Ser Ala Pro Val Asp Pro Ser Ser Pro His Ser Tyr
            35                  40                  45

<210> SEQ ID NO 123
<211> LENGTH: 47
<212> TYPE: PRT
<213> ORGANISM: Mus musculus

<400> SEQUENCE: 123

Thr Gln Ala Gln Leu Leu Arg Val Gly Cys Val Leu Gly Thr Cys Gln
 1               5                  10                  15

Val Gln Asn Leu Ser His Arg Leu Trp Gln Leu Met Gly Pro Ala Gly
                20                  25                  30

Arg Gln Asp Ser Ala Pro Val Glu Pro Ser Ser Pro His Ser Tyr
            35                  40                  45

<210> SEQ ID NO 124
<211> LENGTH: 47
<212> TYPE: PRT
<213> ORGANISM: Mus musculus

<400> SEQUENCE: 124

Thr Gln Ala Gln Leu Leu Arg Val Gly Cys Val Leu Gly Thr Cys Gln
 1               5                  10                  15

Val Gln Asn Leu Ser His Arg Leu Trp Gln Leu Met Gly Pro Ala Gly
                20                  25                  30

Arg Gln Glu Ser Ala Pro Val Glu Pro Ser Ser Pro His Ser Tyr
            35                  40                  45

<210> SEQ ID NO 125
<211> LENGTH: 42
<212> TYPE: PRT
<213> ORGANISM: Mus musculus

<400> SEQUENCE: 125

Thr Gln Ala Gln Leu Leu Arg Val Gly Cys Val Leu Gly Thr Cys Gln
 1               5                  10                  15

Val Gln Asn Leu Ser His Arg Leu Trp Gln Leu Arg Gln Asp Ser Ala
                20                  25                  30

Pro Val Asp Pro Ser Ser Pro His Ser Tyr
            35                  40

<210> SEQ ID NO 126
<211> LENGTH: 40
<212> TYPE: PRT
<213> ORGANISM: Mus musculus

<400> SEQUENCE: 126

Thr Gln Ala Gln Leu Leu Arg Val Gly Cys Val Leu Gly Thr Cys Gln
 1               5                  10                  15

Val Gln Asn Leu Ser His Arg Leu Trp Gln Leu Asp Ser Ala Pro Val
                20                  25                  30

Asp Pro Ser Ser Pro His Ser Tyr
```

35          40

<210> SEQ ID NO 127
<211> LENGTH: 41
<212> TYPE: PRT
<213> ORGANISM: Mus musculus

<400> SEQUENCE: 127

Arg Val Gly Cys Val Leu Gly Thr Cys Gln Val Gln Asn Leu Ser His
1               5                   10                  15

Arg Leu Trp Gln Leu Met Gly Pro Ala Gly Arg Gln Asp Ser Ala Pro
            20                  25                  30

Val Asp Pro Ser Ser Pro His Ser Tyr
        35                  40

<210> SEQ ID NO 128
<211> LENGTH: 40
<212> TYPE: PRT
<213> ORGANISM: Mus musculus

<400> SEQUENCE: 128

Val Gly Cys Val Leu Gly Thr Cys Gln Val Gln Asn Leu Ser His Arg
1               5                   10                  15

Leu Trp Gln Leu Met Gly Pro Ala Gly Arg Gln Asp Ser Ala Pro Val
            20                  25                  30

Glu Pro Ser Ser Pro His Ser Tyr
        35                  40

<210> SEQ ID NO 129
<211> LENGTH: 35
<212> TYPE: PRT
<213> ORGANISM: Mus musculus

<400> SEQUENCE: 129

Val Gly Cys Val Leu Gly Thr Cys Gln Val Gln Asn Leu Ser His Arg
1               5                   10                  15

Leu Trp Gln Leu Arg Gln Asp Ser Ala Pro Val Glu Pro Ser Ser Pro
            20                  25                  30

His Ser Tyr
        35

<210> SEQ ID NO 130
<211> LENGTH: 39
<212> TYPE: PRT
<213> ORGANISM: Mus musculus

<400> SEQUENCE: 130

Gly Cys Val Leu Gly Thr Cys Gln Val Gln Asn Leu Ser His Arg Leu
1               5                   10                  15

Trp Gln Leu Met Gly Pro Ala Gly Arg Gln Asp Ser Ala Pro Val Asp
            20                  25                  30

Pro Ser Ser Pro His Ser Tyr
        35

<210> SEQ ID NO 131
<211> LENGTH: 34
<212> TYPE: PRT
<213> ORGANISM: Mus musculus

<400> SEQUENCE: 131

Gly Cys Asn Thr Ala Thr Cys Gln Val Gln Asn Leu Ser His Arg Leu
1               5                   10                  15

Trp Gln Leu Arg Gln Asp Ser Ala Pro Val Asp Pro Ser Ser Pro His
            20                  25                  30

Ser Tyr

<210> SEQ ID NO 132
<211> LENGTH: 34
<212> TYPE: PRT
<213> ORGANISM: Mus musculus

<400> SEQUENCE: 132

Gly Cys Asn Thr Ala Thr Cys Gln Val Gln Asn Leu Ser His Arg Leu
 1               5                  10                  15

Trp Gln Leu Arg Gln Asp Ser Ala Pro Val Glu Pro Ser Ser Pro His
            20                  25                  30

Ser Tyr

<210> SEQ ID NO 133
<211> LENGTH: 35
<212> TYPE: PRT
<213> ORGANISM: Mus musculus

<400> SEQUENCE: 133

Gly Cys Ser Asn Leu Ser Thr Cys Gln Val Gln Asn Leu Ser His Arg
 1               5                  10                  15

Leu Trp Gln Leu Arg Gln Asp Ser Ala Pro Val Glu Pro Ser Ser Pro
            20                  25                  30

His Ser Tyr
        35

<210> SEQ ID NO 134
<211> LENGTH: 35
<212> TYPE: PRT
<213> ORGANISM: Mus musculus

<400> SEQUENCE: 134

Gly Cys Gly Asn Leu Ser Thr Cys Gln Val Gln Asn Leu Ser His Arg
 1               5                  10                  15

Leu Trp Gln Leu Arg Gln Asp Ser Ala Pro Val Glu Pro Ser Ser Pro
            20                  25                  30

His Ser Tyr
        35

<210> SEQ ID NO 135
<211> LENGTH: 34
<212> TYPE: PRT
<213> ORGANISM: Mus musculus

<400> SEQUENCE: 135

Gly Cys Val Leu Gly Thr Cys Gln Val Gln Asn Leu Ser His Arg Leu
 1               5                  10                  15

Trp Gln Leu Arg Gln Glu Ser Ala Pro Val Glu Pro Ser Ser Pro His
            20                  25                  30

Ser Tyr

<210> SEQ ID NO 136
<211> LENGTH: 38
<212> TYPE: PRT
<213> ORGANISM: Mus musculus

<400> SEQUENCE: 136

-continued

Cys Val Leu Gly Thr Cys Gln Val Gln Asn Leu Ser His Arg Leu Trp
1               5                   10                  15

Gln Leu Met Gly Pro Ala Gly Arg Gln Asp Ser Ala Pro Val Asp Pro
            20                  25                  30

Ser Ser Pro His Ser Tyr
        35

<210> SEQ ID NO 137
<211> LENGTH: 32
<212> TYPE: PRT
<213> ORGANISM: Mus musculus

<400> SEQUENCE: 137

Gln Val Gln Asn Leu Ser His Arg Leu Trp Gln Leu Met Gly Pro Ala
1               5                   10                  15

Gly Arg Gln Asp Ser Ala Pro Val Asp Pro Ser Ser Pro His Ser Tyr
            20                  25                  30

<210> SEQ ID NO 138
<211> LENGTH: 31
<212> TYPE: PRT
<213> ORGANISM: Mus musculus

<400> SEQUENCE: 138

Val Gln Asn Leu Ser His Arg Leu Trp Gln Leu Met Gly Pro Ala Gly
1               5                   10                  15

Arg Gln Asp Ser Ala Pro Val Asp Pro Ser Ser Pro His Ser Tyr
            20                  25                  30

<210> SEQ ID NO 139
<211> LENGTH: 30
<212> TYPE: PRT
<213> ORGANISM: Mus musculus

<400> SEQUENCE: 139

Val Gln Asn Leu Ser His Arg Leu Gln Leu Met Gly Pro Ala Gly Arg
1               5                   10                  15

Gln Asp Ser Ala Pro Val Asp Pro Ser Ser Pro His Ser Tyr
            20                  25                  30

<210> SEQ ID NO 140
<211> LENGTH: 30
<212> TYPE: PRT
<213> ORGANISM: Mus musculus

<400> SEQUENCE: 140

Gly Thr Met Gln Val Gln Asn Leu Ser His Arg Leu Trp Gln Leu Arg
1               5                   10                  15

Gln Asp Ser Ala Pro Val Glu Pro Ser Ser Pro His Ser Tyr
            20                  25                  30

<210> SEQ ID NO 141
<211> LENGTH: 8
<212> TYPE: PRT
<213> ORGANISM: Homo sapiens
<220> FEATURE:
<221> NAME/KEY: MOD_RES
<222> LOCATION: (2)
<223> OTHER INFORMATION: Tyr(SO3H)

<400> SEQUENCE: 141

Asp Tyr Met Gly Trp Met Asp Phe
1               5

<210> SEQ ID NO 142
<211> LENGTH: 8
<212> TYPE: PRT
<213> ORGANISM: Homo sapiens

<400> SEQUENCE: 142

Asp Tyr Met Gly Trp Met Asp Phe
 1               5

<210> SEQ ID NO 143
<211> LENGTH: 6
<212> TYPE: PRT
<213> ORGANISM: Homo sapiens

<400> SEQUENCE: 143

Met Gly Trp Met Asp Phe
 1               5

<210> SEQ ID NO 144
<211> LENGTH: 5
<212> TYPE: PRT
<213> ORGANISM: Homo sapiens

<400> SEQUENCE: 144

Gly Trp Met Asp Phe
 1               5

<210> SEQ ID NO 145
<211> LENGTH: 4
<212> TYPE: PRT
<213> ORGANISM: Homo sapiens

<400> SEQUENCE: 145

Trp Met Asp Phe
 1

<210> SEQ ID NO 146
<211> LENGTH: 9
<212> TYPE: PRT
<213> ORGANISM: Homo sapiens
<220> FEATURE:
<221> NAME/KEY: MOD_RES
<222> LOCATION: (3)
<223> OTHER INFORMATION: Tyr(SO3H)

<400> SEQUENCE: 146

Lys Asp Tyr Met Gly Trp Met Asp Phe
 1               5

<210> SEQ ID NO 147
<211> LENGTH: 9
<212> TYPE: PRT
<213> ORGANISM: Homo sapiens

<400> SEQUENCE: 147

Lys Asp Tyr Met Gly Trp Met Asp Phe
 1               5

<210> SEQ ID NO 148
<211> LENGTH: 7
<212> TYPE: PRT
<213> ORGANISM: Homo sapiens

<400> SEQUENCE: 148

Lys Met Gly Trp Met Asp Phe
 1               5

<210> SEQ ID NO 149
<211> LENGTH: 6
<212> TYPE: PRT
<213> ORGANISM: Homo sapiens

<400> SEQUENCE: 149

Lys Gly Trp Met Asp Phe
 1               5

<210> SEQ ID NO 150
<211> LENGTH: 5
<212> TYPE: PRT
<213> ORGANISM: Homo sapiens

<400> SEQUENCE: 150

Lys Trp Met Asp Phe
 1               5

<210> SEQ ID NO 151
<211> LENGTH: 167
<212> TYPE: PRT
<213> ORGANISM: Homo sapiens

<400> SEQUENCE: 151

Met His Trp Gly Thr Leu Cys Gly Phe Leu Trp Leu Trp Pro Tyr Leu
 1               5                  10                  15

Phe Tyr Val Gln Ala Val Pro Ile Gln Lys Val Gln Asp Asp Thr Lys
             20                  25                  30

Thr Leu Ile Lys Thr Ile Val Thr Arg Ile Asp Asp Ile Ser His Thr
         35                  40                  45

Gln Ser Val Ser Ser Lys Gln Lys Val Thr Gly Leu Asp Phe Ile Pro
     50                  55                  60

Gly Leu His Pro Ile Leu Thr Leu Ser Lys Met Asp Gln Thr Leu Ala
 65                  70                  75                  80

Val Tyr Gln Gln Ile Leu Thr Ser Met Pro Ser Arg Asn Val Ile Gln
                 85                  90                  95

Ile Ser Asn Asp Leu Glu Asn Leu Arg Asp Leu Leu His Val Leu Ala
                100                 105                 110

Phe Ser Lys Ser Cys His Leu Pro Trp Ala Ser Gly Leu Glu Thr Leu
            115                 120                 125

Asp Ser Leu Gly Gly Val Leu Glu Ala Ser Gly Tyr Ser Thr Glu Val
        130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 152
<211> LENGTH: 167
<212> TYPE: PRT
<213> ORGANISM: Homo sapiens

<400> SEQUENCE: 152

Met His Trp Gly Thr Leu Cys Gly Phe Leu Trp Leu Trp Pro Tyr Leu
 1               5                  10                  15

Phe Tyr Val Gln Ala Val Pro Ile Gln Lys Val Gln Asp Asp Thr Lys
             20                  25                  30

Thr Leu Ile Lys Thr Ile Val Thr Arg Ile Glu Asp Ile Ser His Thr
         35                  40                  45

```
Gln Ser Val Ser Ser Lys Gln Lys Val Thr Gly Leu Asp Phe Ile Pro
             50                  55                  60

Gly Leu His Pro Ile Leu Thr Leu Ser Lys Met Asp Gln Thr Leu Ala
 65                  70                  75                  80

Val Tyr Gln Gln Ile Leu Thr Ser Met Pro Ser Arg Asn Val Ile Gln
                 85                  90                  95

Ile Ser Asn Asp Leu Glu Asn Leu Arg Asp Leu Leu His Val Leu Ala
                100                 105                 110

Phe Ser Lys Ser Cys His Leu Pro Trp Ala Ser Gly Leu Glu Thr Leu
                115                 120                 125

Asp Ser Leu Gly Gly Val Leu Glu Ala Ser Gly Tyr Ser Thr Glu Val
                130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 153
<211> LENGTH: 167
<212> TYPE: PRT
<213> ORGANISM: Homo sapiens

<400> SEQUENCE: 153

Met His Trp Gly Thr Leu Cys Gly Phe Leu Trp Leu Trp Pro Tyr Leu
 1               5                  10                  15

Phe Tyr Val Gln Ala Val Pro Ile Gln Lys Val Gln Asp Asp Thr Lys
                 20                  25                  30

Thr Leu Ile Lys Thr Ile Val Thr Arg Ile Asn Asp Ile Ser His Ala
             35                  40                  45

Gln Ser Val Ser Ser Lys Gln Lys Val Thr Gly Leu Asp Phe Ile Pro
             50                  55                  60

Gly Leu His Pro Ile Leu Thr Leu Ser Lys Met Asp Gln Thr Leu Ala
 65                  70                  75                  80

Val Tyr Gln Gln Ile Leu Thr Ser Met Pro Ser Arg Asn Val Ile Gln
                 85                  90                  95

Ile Ser Asn Asp Leu Glu Asn Leu Arg Asp Leu Leu His Val Leu Ala
                100                 105                 110

Phe Ser Lys Ser Cys His Leu Pro Trp Ala Ser Gly Leu Glu Thr Leu
                115                 120                 125

Asp Ser Leu Gly Gly Val Leu Glu Ala Ser Gly Tyr Ser Thr Glu Val
                130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 154
<211> LENGTH: 167
<212> TYPE: PRT
<213> ORGANISM: Homo sapiens

<400> SEQUENCE: 154

Met His Trp Gly Thr Leu Cys Gly Phe Leu Trp Leu Trp Pro Tyr Leu
 1               5                  10                  15

Phe Tyr Val Gln Ala Val Pro Ile Gln Lys Val Gln Asp Asp Thr Lys
                 20                  25                  30
```

```
Thr Leu Ile Lys Thr Ile Val Thr Arg Ile Asn Asp Ile Ser His Thr
            35                  40                  45

Glu Ser Val Ser Ser Lys Gln Lys Val Thr Gly Leu Asp Phe Ile Pro
        50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 155
<211> LENGTH: 166
<212> TYPE: PRT
<213> ORGANISM: Homo sapiens

<400> SEQUENCE: 155

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Ser Val Ser Ser Lys Gln Lys Val Thr Gly Leu Asp Phe Ile Pro Gly
    50                  55                  60

Leu His Pro Ile Leu Thr Leu Ser Lys Met Asp Gln Thr Leu Ala Val
65                  70                  75                  80

Tyr Gln Gln Ile Leu Thr Ser Met Pro Ser Arg Asn Val Ile Gln Ile
                85                  90                  95

Ser Asn Asp Leu Glu Asn Leu Arg Asp Leu Leu His Val Leu Ala Phe
            100                 105                 110

Ser Lys Ser Cys His Leu Pro Trp Ala Ser Gly Leu Glu Thr Leu Asp
        115                 120                 125

Ser Leu Gly Gly Val Leu Glu Ala Ser Gly Tyr Ser Thr Glu Val Val
130                 135                 140

Ala Leu Ser Arg Leu Gln Gly Ser Leu Gln Asp Met Leu Trp Gln Leu
145                 150                 155                 160

Asp Leu Ser Pro Gly Cys
                165

<210> SEQ ID NO 156
<211> LENGTH: 167
<212> TYPE: PRT
<213> ORGANISM: Homo sapiens

<400> SEQUENCE: 156

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
```

```
                    20                  25                  30
Thr Leu Ile Lys Thr Ile Val Thr Arg Ile Asn Asp Ile Ser His Thr
            35                  40                  45

Gln Ser Val Ser Ser Lys Gln Lys Val Thr Gly Leu Asp Phe Ile Pro
        50                  55                  60

Gly Leu His Pro Ile Leu Thr Leu Ser Lys Ala Asp Gln Thr Leu Ala
 65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 157
<211> LENGTH: 167
<212> TYPE: PRT
<213> ORGANISM: Homo sapiens

<400> SEQUENCE: 157

Met His Trp Gly Thr Leu Cys Gly Phe Leu Trp Leu Trp Pro Tyr Leu
 1               5                  10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ser Lys Gln Lys Val Thr Gly Leu Asp Phe Ile Pro
        50                  55                  60

Gly Leu His Pro Ile Leu Thr Leu Ser Lys Met Asp Gln Thr Leu Ala
 65                  70                  75                  80

Val Tyr Gln Gln Ile Leu Thr Ser Leu Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 158
<211> LENGTH: 167
<212> TYPE: PRT
<213> ORGANISM: Homo sapiens

<400> SEQUENCE: 158

Met His Trp Gly Thr Leu Cys Gly Phe Leu Trp Leu Trp Pro Tyr Leu
 1               5                  10                  15
```

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asp Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 159
<211> LENGTH: 167
<212> TYPE: PRT
<213> ORGANISM: Homo sapiens

<400> SEQUENCE: 159

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Glu Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 160
<211> LENGTH: 167
<212> TYPE: PRT
<213> ORGANISM: Homo sapiens

<400> SEQUENCE: 160

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
            85                  90                  95

Ile Ala Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
            115                 120                 125

Asp Ser Leu Gly Gly Val Leu Glu Ala Ser Gly Tyr Ser Thr Glu Val
            130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 161
<211> LENGTH: 167
<212> TYPE: PRT
<213> ORGANISM: Homo sapiens

<400> SEQUENCE: 161

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
            85                  90                  95

Ile Ser Asn Asp Leu Glu Asn Leu Arg Asp Leu Leu His Val Leu Ala
            100                 105                 110

Phe Ser Lys Ser Ser His Leu Pro Trp Ala Ser Gly Leu Glu Thr Leu
            115                 120                 125

Asp Ser Leu Gly Gly Val Leu Glu Ala Ser Gly Tyr Ser Thr Glu Val
            130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 162
<211> LENGTH: 167
<212> TYPE: PRT
<213> ORGANISM: Homo sapiens

<400> SEQUENCE: 162

| Met | His | Trp | Gly | Thr | Leu | Cys | Gly | Phe | Leu | Trp | Leu | Trp | Pro | Tyr | Leu |
|---|---|---|---|---|---|---|---|---|---|---|---|---|---|---|---|
| 1 | | | | 5 | | | | | 10 | | | | | 15 | |

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ser Lys Gln Lys Val Thr Gly Leu Asp Phe Ile Pro
        50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Leu Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 163
<211> LENGTH: 167
<212> TYPE: PRT
<213> ORGANISM: Homo sapiens

<400> SEQUENCE: 163

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ser Lys Gln Lys Val Thr Gly Leu Asp Phe Ile Pro
        50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Ser
                165

<210> SEQ ID NO 164
<211> LENGTH: 167
<212> TYPE: PRT

<213> ORGANISM: Homo sapiens

<400> SEQUENCE: 164

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asp Asp Ile Ser His Thr
        35                  40                  45

Glu Ser Val Ser Ser Lys Gln Lys Val Thr Gly Leu Asp Phe Ile Pro
50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
            85                  90                  95

Ile Ser Asn Asp Leu Glu Asn Leu Arg Asp Leu Leu His Val Leu Ala
        100                 105                 110

Phe Ser Lys Ser Cys His Leu Pro Trp Ala Ser Gly Leu Glu Thr Leu
    115                 120                 125

Asp Ser Leu Gly Gly Val Leu Glu Ala Ser Gly Tyr Ser Thr Glu Val
130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 165
<211> LENGTH: 167
<212> TYPE: PRT
<213> ORGANISM: Homo sapiens

<400> SEQUENCE: 165

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asp Asp Ile Ser His Thr
        35                  40                  45

Gln Ser Val Ser Ser Lys Gln Lys Val Thr Gly Leu Asp Phe Ile Pro
50                  55                  60

Gly Leu His Pro Ile Leu Thr Leu Ser Lys Ala Asp Gln Thr Leu Ala
65                  70                  75                  80

Val Tyr Gln Gln Ile Leu Thr Ser Met Pro Ser Arg Asn Val Ile Gln
            85                  90                  95

Ile Ser Asn Asp Leu Glu Asn Leu Arg Asp Leu Leu His Val Leu Ala
        100                 105                 110

Phe Ser Lys Ser Cys His Leu Pro Trp Ala Ser Gly Leu Glu Thr Leu
    115                 120                 125

Asp Ser Leu Gly Gly Val Leu Glu Ala Ser Gly Tyr Ser Thr Glu Val
130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 166

```
<211> LENGTH: 167
<212> TYPE: PRT
<213> ORGANISM: Homo sapiens

<400> SEQUENCE: 166

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Leu Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Ser His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 167
<211> LENGTH: 167
<212> TYPE: PRT
<213> ORGANISM: Homo sapiens

<400> SEQUENCE: 167

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Glu Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Ser
                165
```

```
<210> SEQ ID NO 168
<211> LENGTH: 31
<212> TYPE: PRT
<213> ORGANISM: Homo sapiens

<400> SEQUENCE: 168

His Ala Gln Gly Thr Phe Thr Ser Asp Val Ser Ser Tyr Leu Glu Gly
 1               5                  10                  15

Gln Ala Ala Leu Glu Phe Ile Ala Trp Leu Val Lys Gly Arg Gly
            20                  25                  30

<210> SEQ ID NO 169
<211> LENGTH: 31
<212> TYPE: PRT
<213> ORGANISM: Homo sapiens
<220> FEATURE:
<221> NAME/KEY: MOD_RES
<222> LOCATION: (3)
<223> OTHER INFORMATION: D-Gln

<400> SEQUENCE: 169

His Ala Gln Gly Thr Phe Thr Ser Asp Val Ser Ser Tyr Leu Glu Gly
 1               5                  10                  15

Gln Ala Ala Leu Glu Phe Ile Ala Trp Leu Val Lys Gly Arg Gly
            20                  25                  30

<210> SEQ ID NO 170
<211> LENGTH: 31
<212> TYPE: PRT
<213> ORGANISM: Homo sapiens

<400> SEQUENCE: 170

His Ala Glu Gly Thr Phe Thr Ser Asp Thr Ser Lys Tyr Leu Glu Gly
 1               5                  10                  15

Gln Ala Ala Leu Glu Phe Ile Ala Trp Leu Val Lys Gly Arg Gly
            20                  25                  30

<210> SEQ ID NO 171
<211> LENGTH: 31
<212> TYPE: PRT
<213> ORGANISM: Homo sapiens

<400> SEQUENCE: 171

His Ala Glu Gly Thr Phe Thr Ser Asp Val Ser Lys Tyr Leu Glu Gly
 1               5                  10                  15

Gln Ala Ala Leu Glu Phe Ile Ala Trp Leu Val Lys Gly Arg Gly
            20                  25                  30

<210> SEQ ID NO 172
<211> LENGTH: 30
<212> TYPE: PRT
<213> ORGANISM: Homo sapiens

<400> SEQUENCE: 172

His Gly Glu Gly Thr Phe Thr Ser Asp Val Ser Ser Tyr Leu Glu Gly
 1               5                  10                  15

Gln Ala Ala Leu Glu Phe Ile Ala Trp Leu Val Lys Gly Arg
            20                  25                  30

<210> SEQ ID NO 173
<211> LENGTH: 31
<212> TYPE: PRT
<213> ORGANISM: Homo sapiens
```

```
<400> SEQUENCE: 173

His Ala Gln Gly Thr Phe Thr Ser Asp Val Ser Ser Tyr Leu Glu Gly
 1               5                  10                  15

Gln Ala Ala Leu Glu Phe Ile Ala Trp Leu Val Lys Gly Arg Gly
            20                  25                  30

<210> SEQ ID NO 174
<211> LENGTH: 31
<212> TYPE: PRT
<213> ORGANISM: Homo sapiens
<220> FEATURE:
<221> NAME/KEY: MOD_RES
<222> LOCATION: (3)
<223> OTHER INFORMATION: D-Gln

<400> SEQUENCE: 174

His Ala Gln Gly Thr Phe Thr Ser Asp Val Ser Ser Tyr Leu Glu Gly
 1               5                  10                  15

Gln Ala Ala Leu Glu Phe Ile Ala Trp Leu Val Lys Gly Arg Gly
            20                  25                  30

<210> SEQ ID NO 175
<211> LENGTH: 31
<212> TYPE: PRT
<213> ORGANISM: Homo sapiens
<220> FEATURE:
<221> NAME/KEY: MOD_RES
<222> LOCATION: (3)
<223> OTHER INFORMATION: acetyl-Lys

<400> SEQUENCE: 175

His Ala Lys Gly Thr Phe Thr Ser Asp Val Ser Ser Tyr Leu Glu Gly
 1               5                  10                  15

Gln Ala Ala Leu Glu Phe Ile Ala Trp Leu Val Lys Gly Arg Gly
            20                  25                  30

<210> SEQ ID NO 176
<211> LENGTH: 31
<212> TYPE: PRT
<213> ORGANISM: Homo sapiens

<400> SEQUENCE: 176

His Ala Thr Gly Thr Phe Thr Ser Asp Val Ser Ser Tyr Leu Glu Gly
 1               5                  10                  15

Gln Ala Ala Leu Glu Phe Ile Ala Trp Leu Val Lys Gly Arg Gly
            20                  25                  30

<210> SEQ ID NO 177
<211> LENGTH: 31
<212> TYPE: PRT
<213> ORGANISM: Homo sapiens
<220> FEATURE:
<221> NAME/KEY: MOD_RES
<222> LOCATION: (3)
<223> OTHER INFORMATION: D-Thr

<400> SEQUENCE: 177

His Ala Thr Gly Thr Phe Thr Ser Asp Val Ser Ser Tyr Leu Glu Gly
 1               5                  10                  15

Gln Ala Ala Leu Glu Phe Ile Ala Trp Leu Val Lys Gly Arg Gly
            20                  25                  30

<210> SEQ ID NO 178
<211> LENGTH: 31
<212> TYPE: PRT
```

<213> ORGANISM: Homo sapiens

<400> SEQUENCE: 178

His Ala Asn Gly Thr Phe Thr Ser Asp Val Ser Ser Tyr Leu Glu Gly
1               5                   10                  15

Gln Ala Ala Leu Glu Phe Ile Ala Trp Leu Val Lys Gly Arg Gly
            20                  25                  30

<210> SEQ ID NO 179
<211> LENGTH: 31
<212> TYPE: PRT
<213> ORGANISM: Homo sapiens
<220> FEATURE:
<221> NAME/KEY: MOD_RES
<222> LOCATION: (3)
<223> OTHER INFORMATION: D-Asn

<400> SEQUENCE: 179

His Ala Asn Gly Thr Phe Thr Ser Asp Val Ser Ser Tyr Leu Glu Gly
1               5                   10                  15

Gln Ala Ala Leu Glu Phe Ile Ala Trp Leu Val Lys Gly Arg Gly
            20                  25                  30

<210> SEQ ID NO 180
<211> LENGTH: 31
<212> TYPE: PRT
<213> ORGANISM: Homo sapiens

<400> SEQUENCE: 180

His Ala Glu Gly Thr Phe Thr Ser Asp Val Ser Ser Tyr Leu Glu Ser
1               5                   10                  15

Arg Arg Ala Gln Glu Phe Ile Ala Trp Leu Val Lys Gly Arg Gly
            20                  25                  30

<210> SEQ ID NO 181
<211> LENGTH: 31
<212> TYPE: PRT
<213> ORGANISM: Homo sapiens

<400> SEQUENCE: 181

His Ala Glu Gly Thr Phe Thr Ser Asp Thr Ser Lys Tyr Leu Glu Gly
1               5                   10                  15

Gln Ala Ala Leu Glu Phe Ile Ala Trp Leu Val Lys Gly Arg Gly
            20                  25                  30

<210> SEQ ID NO 182
<211> LENGTH: 31
<212> TYPE: PRT
<213> ORGANISM: Homo sapiens

<400> SEQUENCE: 182

His Ala Glu Gly Thr Phe Thr Ser Asp Val Ser Lys Tyr Leu Glu Gly
1               5                   10                  15

Gln Ala Ala Leu Glu Phe Ile Ala Trp Leu Val Lys Gly Arg Gly
            20                  25                  30

<210> SEQ ID NO 183
<211> LENGTH: 31
<212> TYPE: PRT
<213> ORGANISM: Homo sapiens

<400> SEQUENCE: 183

His Ala Glu Gly Thr Phe Thr Ser Asp Val Ser Ser Tyr Leu Glu Gly
1               5                   10                  15

```
Arg Ala Ala Leu Glu Phe Ile Ala Trp Leu Val Lys Gly Arg Gly
            20                  25                  30

<210> SEQ ID NO 184
<211> LENGTH: 31
<212> TYPE: PRT
<213> ORGANISM: Homo sapiens

<400> SEQUENCE: 184

His Ala Glu Gly Thr Phe Thr Ser Asp Val Ser Ser Tyr Leu Glu Gly
 1               5                  10                  15

Gln Arg Ala Leu Glu Phe Ile Ala Trp Leu Val Lys Gly Arg Gly
            20                  25                  30

<210> SEQ ID NO 185
<211> LENGTH: 39
<212> TYPE: PRT
<213> ORGANISM: Heloderma suspectum

<400> SEQUENCE: 185

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
            35

<210> SEQ ID NO 186
<211> LENGTH: 39
<212> TYPE: PRT
<213> ORGANISM: Heloderma suspectum

<400> SEQUENCE: 186

His Gly Glu Gly Ala Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
            35

<210> SEQ ID NO 187
<211> LENGTH: 39
<212> TYPE: PRT
<213> ORGANISM: Heloderma suspectum

<400> SEQUENCE: 187

His Gly Glu Gly Thr Phe Thr Ser Asp Leu Ser Lys Gln Leu Glu Glu
 1               5                  10                  15

Glu Ala Val Arg Leu Ala Ile Glu Phe Leu Lys Asn Gly Gly Pro Ser
            20                  25                  30

Ser Gly Ala Pro Pro Pro Ser
            35

<210> SEQ ID NO 188
<211> LENGTH: 37
<212> TYPE: PRT
<213> ORGANISM: Xenopus laevis
<220> FEATURE:
<221> NAME/KEY: MOD_RES
<222> LOCATION: (37)
<223> OTHER INFORMATION: Ser-OH

<400> SEQUENCE: 188
```

His Ala Glu Gly Thr Phe Thr Ser Asp Val Thr Gln Gln Leu Asp Glu
1               5                   10                  15

Lys Ala Ala Lys Glu Phe Ile Asp Trp Leu Ile Asn Gly Gly Pro Ser
            20                  25                  30

Lys Glu Ile Ile Ser
        35

<210> SEQ ID NO 189
<211> LENGTH: 37
<212> TYPE: PRT
<213> ORGANISM: Homo sapiens

<400> SEQUENCE: 189

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Pro Ser Thr Asn Val
            20                  25                  30

Gly Ser Asn Thr Tyr
        35

<210> SEQ ID NO 190
<211> LENGTH: 28
<212> TYPE: PRT
<213> ORGANISM: Heloderma suspectum

<400> SEQUENCE: 190

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn
            20                  25

<210> SEQ ID NO 191
<211> LENGTH: 36
<212> TYPE: PRT
<213> ORGANISM: Homo sapiens

<400> SEQUENCE: 191

Lys Cys Asn Thr Ala Thr Cys Ala Thr Gln Arg Leu Ala Asn Phe Leu
1               5                   10                  15

Val His Arg Tyr Tyr Ala Ser Leu Arg His Tyr Leu Asn Leu Val Thr
            20                  25                  30

Arg Gln Arg Tyr
        35

<210> SEQ ID NO 192
<211> LENGTH: 36
<212> TYPE: PRT
<213> ORGANISM: Homo sapiens

<400> SEQUENCE: 192

Tyr Pro Leu Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 193
<211> LENGTH: 36
<212> TYPE: PRT
<213> ORGANISM: Homo sapiens

<400> SEQUENCE: 193

Tyr Pro Val Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 194
<211> LENGTH: 36
<212> TYPE: PRT
<213> ORGANISM: Homo sapiens

<400> SEQUENCE: 194

Tyr Pro Ile Arg Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 195
<211> LENGTH: 36
<212> TYPE: PRT
<213> ORGANISM: Homo sapiens

<400> SEQUENCE: 195

Tyr Pro Ile Gln Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 196
<211> LENGTH: 36
<212> TYPE: PRT
<213> ORGANISM: Homo sapiens

<400> SEQUENCE: 196

Tyr Pro Ile Asn Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 197
<211> LENGTH: 36
<212> TYPE: PRT
<213> ORGANISM: Homo sapiens

<400> SEQUENCE: 197

Tyr Pro Ile Lys Pro Glu Ala Pro Gly Glu Asp Ala Ser Pro Glu Glu
1               5                   10                  15

Leu Asn Arg Tyr Tyr Ala Ser Leu Lys His Tyr Leu Asn Leu Val Thr
            20                  25                  30

Arg Gln Arg Tyr
        35

-continued

<210> SEQ ID NO 198
<211> LENGTH: 36
<212> TYPE: PRT
<213> ORGANISM: Homo sapiens

<400> SEQUENCE: 198

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Pro Arg Tyr
        35

<210> SEQ ID NO 199
<211> LENGTH: 36
<212> TYPE: PRT
<213> ORGANISM: Homo sapiens

<400> SEQUENCE: 199

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg His Arg Tyr
        35

<210> SEQ ID NO 200
<211> LENGTH: 36
<212> TYPE: PRT
<213> ORGANISM: Homo sapiens

<400> SEQUENCE: 200

Tyr Pro Ile Lys Pro Glu Ala Pro Gly Glu Asp Ala Pro Ala Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 201
<211> LENGTH: 36
<212> TYPE: PRT
<213> ORGANISM: Homo sapiens

<400> SEQUENCE: 201

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Leu Thr
            20                  25                  30

Arg Pro Arg Tyr
        35

<210> SEQ ID NO 202
<211> LENGTH: 35
<212> TYPE: PRT
<213> ORGANISM: Homo sapiens

<400> SEQUENCE: 202

Tyr Pro Ile Pro Glu Ala Pro Gly Glu Asp Ala Ser Pro Glu Glu Leu
1               5                   10                  15

Asn Arg Tyr Tyr Ala Ser Leu Arg His Tyr Leu Asn Leu Val Thr Arg

```
                    20                  25                  30

Gln Arg Tyr
        35

<210> SEQ ID NO 203
<211> LENGTH: 43
<212> TYPE: PRT
<213> ORGANISM: Artificial Sequence
<220> FEATURE:
<223> OTHER INFORMATION: Description of Artificial Sequence: Chimeric
      human and salmon construct
<220> FEATURE:
<221> NAME/KEY: MOD_RES
<222> LOCATION: (2)
<223> OTHER INFORMATION: Phe(CH2SO3)

<400> SEQUENCE: 203

Asp Phe Met Gly Trp Met Asp Phe Gly Lys Arg Lys Cys Asn Thr Ala
1               5                   10                  15

Thr Cys Ala Thr Gln Arg Leu Ala Asn Glu Leu Val Arg Leu Gln Thr
            20                  25                  30

Tyr Pro Arg Thr Asn Val Gly Ser Asn Thr Tyr
        35                  40

<210> SEQ ID NO 204
<211> LENGTH: 31
<212> TYPE: PRT
<213> ORGANISM: Homo sapiens

<400> SEQUENCE: 204

His Ala Glu Gly Thr Phe Thr Ser Asp Val Ser Ser Thr Leu Glu Gly
1               5                   10                  15

Gln Ala Ala Leu Glu Phe Ile Ala Trp Leu Val Lys Gly Arg Gly
            20                  25                  30

<210> SEQ ID NO 205
<211> LENGTH: 29
<212> TYPE: PRT
<213> ORGANISM: Homo sapiens

<400> SEQUENCE: 205

Glu Gly Thr Phe Thr Ser Asp Val Ser Ser Thr Leu Glu Gly Gln Ala
1               5                   10                  15

Ala Leu Glu Phe Ile Ala Trp Leu Val Lys Gly Arg Gly
            20                  25

<210> SEQ ID NO 206
<211> LENGTH: 28
<212> TYPE: PRT
<213> ORGANISM: Homo sapiens

<400> SEQUENCE: 206

Glu Gly Thr Phe Thr Ser Asp Val Ser Ser Thr Leu Glu Gly Gln Ala
1               5                   10                  15

Ala Leu Glu Phe Ile Ala Trp Leu Val Lys Gly Arg
            20                  25

<210> SEQ ID NO 207
<211> LENGTH: 31
<212> TYPE: PRT
<213> ORGANISM: Heloderma suspectum

<400> SEQUENCE: 207

Asp Leu Ser Lys Gln Met Glu Glu Glu Ala Val Arg Leu Phe Ile Glu
```

```
                1               5              10              15
Trp Leu Lys Asn Gly Gly Pro Ser Ser Gly Ala Pro Pro Pro Ser
                20                      25                      30
```

<210> SEQ ID NO 208
<211> LENGTH: 4
<212> TYPE: PRT
<213> ORGANISM: Homo sapiens

<400> SEQUENCE: 208

```
Trp Met Asp Phe
  1
```

<210> SEQ ID NO 209
<211> LENGTH: 5
<212> TYPE: PRT
<213> ORGANISM: Homo sapiens

<400> SEQUENCE: 209

```
Gly Trp Met Asp Phe
  1               5
```

<210> SEQ ID NO 210
<211> LENGTH: 36
<212> TYPE: PRT
<213> ORGANISM: Homo sapiens

<400> SEQUENCE: 210

```
Lys Cys Asn Thr Ala Thr Cys Ala Thr Gln Arg Leu Ala Asn Phe Leu
  1               5                  10                  15
Val His Ser Ser Asn Asn Phe Gly Ala Ile Leu Ser Ser Thr Asn Val
                20                  25                  30
Gly Ser Asn Thr
                35
```

<210> SEQ ID NO 211
<211> LENGTH: 35
<212> TYPE: PRT
<213> ORGANISM: Homo sapiens

<400> SEQUENCE: 211

```
Lys Cys Asn Thr Ala Thr Cys Ala Thr Gln Arg Leu Ala Asn Phe Leu
  1               5                  10                  15
Val His Ser Ser Asn Asn Phe Gly Ala Ile Leu Ser Ser Thr Asn Val
                20                  25                  30
Gly Ser Asn
                35
```

<210> SEQ ID NO 212
<211> LENGTH: 20
<212> TYPE: PRT
<213> ORGANISM: Homo sapiens

<400> SEQUENCE: 212

```
Lys Cys Asn Thr Ala Thr Cys Ala Thr Gln Arg Leu Ala Asn Phe Leu
  1               5                  10                  15
Val His Ser Ser
                20
```

<210> SEQ ID NO 213
<211> LENGTH: 18
<212> TYPE: PRT
<213> ORGANISM: Homo sapiens

<400> SEQUENCE: 213

Lys Cys Asn Thr Ala Thr Cys Ala Thr Gln Arg Leu Ala Asn Phe Leu
 1               5                  10                  15

Val His

<210> SEQ ID NO 214
<211> LENGTH: 17
<212> TYPE: PRT
<213> ORGANISM: Homo sapiens

<400> SEQUENCE: 214

Lys Cys Asn Thr Ala Thr Cys Ala Thr Gln Arg Leu Ala Asn Phe Leu
 1               5                  10                  15

Val

<210> SEQ ID NO 215
<211> LENGTH: 16
<212> TYPE: PRT
<213> ORGANISM: Homo sapiens

<400> SEQUENCE: 215

Lys Cys Asn Thr Ala Thr Cys Ala Thr Gln Arg Leu Ala Asn Phe Leu
 1               5                  10                  15

<210> SEQ ID NO 216
<211> LENGTH: 15
<212> TYPE: PRT
<213> ORGANISM: Homo sapiens

<400> SEQUENCE: 216

Lys Cys Asn Thr Ala Thr Cys Ala Thr Gln Arg Leu Ala Asn Phe
 1               5                  10                  15

<210> SEQ ID NO 217
<211> LENGTH: 7
<212> TYPE: PRT
<213> ORGANISM: Homo sapiens

<400> SEQUENCE: 217

Lys Cys Asn Thr Ala Thr Cys
 1               5

<210> SEQ ID NO 218
<211> LENGTH: 25
<212> TYPE: PRT
<213> ORGANISM: Homo sapiens

<400> SEQUENCE: 218

Met Leu Gly Thr Tyr Thr Gln Asp Phe Asn Lys Phe His Thr Phe Pro
 1               5                  10                  15

Gln Thr Ala Ile Gly Val Gly Ala Pro
             20                  25

<210> SEQ ID NO 219
<211> LENGTH: 20
<212> TYPE: PRT
<213> ORGANISM: Homo sapiens

<400> SEQUENCE: 219

Met Leu Gly Thr Tyr Thr Gln Asp Phe Asn Lys Phe His Thr Phe Pro
 1               5                  10                  15

Gln Thr Ala Ile

<210> SEQ ID NO 220
<211> LENGTH: 19
<212> TYPE: PRT
<213> ORGANISM: Homo sapiens

<400> SEQUENCE: 220

Met Leu Gly Thr Tyr Thr Gln Asp Phe Asn Lys Phe His Thr Phe Pro
1               5                   10                  15

Gln Thr Ala

<210> SEQ ID NO 221
<211> LENGTH: 3
<212> TYPE: PRT
<213> ORGANISM: Homo sapiens

<400> SEQUENCE: 221

Met Leu Gly
1

<210> SEQ ID NO 222
<211> LENGTH: 9
<212> TYPE: PRT
<213> ORGANISM: Homo sapiens

<400> SEQUENCE: 222

Lys Phe His Thr Phe Pro Gln Thr Ala
1               5

<210> SEQ ID NO 223
<211> LENGTH: 10
<212> TYPE: PRT
<213> ORGANISM: Homo sapiens

<400> SEQUENCE: 223

Lys Phe His Thr Phe Pro Gln Thr Ala Ile
1               5                   10

<210> SEQ ID NO 224
<211> LENGTH: 10
<212> TYPE: PRT
<213> ORGANISM: Homo sapiens

<400> SEQUENCE: 224

Gln Asn Leu Ser His Arg Leu Trp Gln Leu
1               5                   10

<210> SEQ ID NO 225
<211> LENGTH: 146
<212> TYPE: PRT
<213> ORGANISM: Homo sapiens

<400> SEQUENCE: 225

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
        50                  55                  60

Leu Thr Ser Met Pro Ser Arg Asn Val Ile Gln Ile Ser Asn Asp Leu

```
                65                  70                  75                  80
Glu Asn Leu Arg Asp Leu Leu His Val Leu Ala Phe Ser Lys Ser Cys
                    85                  90                  95
His Leu Pro Trp Ala Ser Gly Leu Glu Thr Leu Asp Ser Leu Gly Gly
                100                 105                 110
Val Leu Glu Ala Ser Gly Tyr Ser Thr Glu Val Val Ala Leu Ser Arg
            115                 120                 125
Leu Gln Gly Ser Leu Gln Asp Met Leu Trp Gln Leu Asp Leu Ser Pro
        130                 135                 140
Gly Cys
145

<210> SEQ ID NO 226
<211> LENGTH: 18
<212> TYPE: PRT
<213> ORGANISM: Homo sapiens

<400> SEQUENCE: 226

Lys Val Thr Gly Leu Asp Phe Ile Pro Gly Leu His Pro Ile Leu Thr
  1               5                  10                  15

Leu Ser

<210> SEQ ID NO 227
<211> LENGTH: 35
<212> TYPE: PRT
<213> ORGANISM: Homo sapiens

<400> SEQUENCE: 227

Tyr Pro Ile Lys Pro Glu Ala Pro Gly Glu Asp Ala Ser Pro Glu Glu
  1               5                  10                  15

Leu Asn Arg Tyr Tyr Ala Ser Leu Arg His Tyr Leu Asn Leu Val Thr
            20                  25                  30

Arg Gln Arg
        35

<210> SEQ ID NO 228
<211> LENGTH: 30
<212> TYPE: PRT
<213> ORGANISM: Homo sapiens

<400> SEQUENCE: 228

Tyr Pro Ile Lys Pro Glu Ala Pro Gly Glu Asp Ala Ser Pro Glu Glu
  1               5                  10                  15

Leu Asn Arg Tyr Tyr Ala Ser Leu Arg His Tyr Leu Asn Leu
            20                  25                  30

<210> SEQ ID NO 229
<211> LENGTH: 25
<212> TYPE: PRT
<213> ORGANISM: Homo sapiens

<400> SEQUENCE: 229

Tyr Pro Ile Lys Pro Glu Ala Pro Gly Glu Asp Ala Ser Pro Glu Glu
  1               5                  10                  15

Leu Asn Arg Tyr Tyr Ala Ser Leu Arg
            20                  25

<210> SEQ ID NO 230
<211> LENGTH: 15
<212> TYPE: PRT
<213> ORGANISM: Homo sapiens
```

<400> SEQUENCE: 230

Tyr Pro Ile Lys Pro Glu Ala Pro Gly Glu Asp Ala Ser Pro Glu
1               5                   10                  15

<210> SEQ ID NO 231
<211> LENGTH: 10
<212> TYPE: PRT
<213> ORGANISM: Homo sapiens

<400> SEQUENCE: 231

Tyr Pro Ile Lys Pro Glu Ala Pro Gly Glu
1               5                   10

<210> SEQ ID NO 232
<211> LENGTH: 35
<212> TYPE: PRT
<213> ORGANISM: Homo sapiens

<400> SEQUENCE: 232

Pro Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Leu Val Thr Arg
            20                  25                  30

Gln Arg Tyr
        35

<210> SEQ ID NO 233
<211> LENGTH: 33
<212> TYPE: PRT
<213> ORGANISM: Homo sapiens

<400> SEQUENCE: 233

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 234
<211> LENGTH: 32
<212> TYPE: PRT
<213> ORGANISM: Homo sapiens

<400> SEQUENCE: 234

Pro Glu Ala Pro Gly Glu Asp Ala Ser Pro Glu Glu Leu Asn Arg Tyr
1               5                   10                  15

Tyr Ala Ser Leu Arg His Tyr Leu Asn Leu Val Thr Arg Gln Arg Tyr
            20                  25                  30

<210> SEQ ID NO 235
<211> LENGTH: 29
<212> TYPE: PRT
<213> ORGANISM: Homo sapiens

<400> SEQUENCE: 235

His Ala Glu Gly Thr Phe Thr Ser Asp Val Ser Ser Thr Leu Glu Gly
1               5                   10                  15

Gln Ala Ala Leu Glu Phe Ile Ala Trp Leu Val Lys Gly
            20                  25

<210> SEQ ID NO 236

```
<211> LENGTH: 27
<212> TYPE: PRT
<213> ORGANISM: Heloderma suspectum

<400> SEQUENCE: 236

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys
            20                  25

<210> SEQ ID NO 237
<211> LENGTH: 28
<212> TYPE: PRT
<213> ORGANISM: Heloderma suspectum

<400> SEQUENCE: 237

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 238
<211> LENGTH: 29
<212> TYPE: PRT
<213> ORGANISM: Heloderma suspectum

<400> SEQUENCE: 238

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly
            20                  25

<210> SEQ ID NO 239
<211> LENGTH: 30
<212> TYPE: PRT
<213> ORGANISM: Heloderma suspectum

<400> SEQUENCE: 239

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 240
<211> LENGTH: 28
<212> TYPE: PRT
<213> ORGANISM: Heloderma suspectum

<400> SEQUENCE: 240

His Gly Glu Gly Ala Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 241
<211> LENGTH: 27
<212> TYPE: PRT
<213> ORGANISM: Heloderma suspectum

<400> SEQUENCE: 241

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys
            20                  25
```

<210> SEQ ID NO 242
<211> LENGTH: 6
<212> TYPE: PRT
<213> ORGANISM: Homo sapiens

<400> SEQUENCE: 242

Val Gly Ser Asn Thr Tyr
 1               5

<210> SEQ ID NO 243
<211> LENGTH: 5
<212> TYPE: PRT
<213> ORGANISM: Homo sapiens

<400> SEQUENCE: 243

Gly Ser Asn Thr Tyr
 1               5

<210> SEQ ID NO 244
<211> LENGTH: 4
<212> TYPE: PRT
<213> ORGANISM: Homo sapiens

<400> SEQUENCE: 244

Ser Asn Thr Tyr
 1

<210> SEQ ID NO 245
<211> LENGTH: 6
<212> TYPE: PRT
<213> ORGANISM: Homo sapiens

<400> SEQUENCE: 245

Ile Ser Pro Gln Gly Tyr
 1               5

<210> SEQ ID NO 246
<211> LENGTH: 5
<212> TYPE: PRT
<213> ORGANISM: Homo sapiens

<400> SEQUENCE: 246

Ser Pro Gln Gly Tyr
 1               5

<210> SEQ ID NO 247
<211> LENGTH: 4
<212> TYPE: PRT
<213> ORGANISM: Homo sapiens

<400> SEQUENCE: 247

Pro Gln Gly Tyr
 1

<210> SEQ ID NO 248
<211> LENGTH: 6
<212> TYPE: PRT
<213> ORGANISM: Homo sapiens

<400> SEQUENCE: 248

Ile Gly Val Gly Ala Pro
 1               5

```
<210> SEQ ID NO 249
<211> LENGTH: 5
<212> TYPE: PRT
<213> ORGANISM: Homo sapiens

<400> SEQUENCE: 249

Gly Val Gly Ala Pro
 1               5

<210> SEQ ID NO 250
<211> LENGTH: 4
<212> TYPE: PRT
<213> ORGANISM: Homo sapiens

<400> SEQUENCE: 250

Val Gly Ala Pro
 1

<210> SEQ ID NO 251
<211> LENGTH: 6
<212> TYPE: PRT
<213> ORGANISM: Homo sapiens

<400> SEQUENCE: 251

Val Gly Ser Lys Ala Phe
 1               5

<210> SEQ ID NO 252
<211> LENGTH: 5
<212> TYPE: PRT
<213> ORGANISM: Homo sapiens

<400> SEQUENCE: 252

Gly Ser Lys Ala Phe
 1               5

<210> SEQ ID NO 253
<211> LENGTH: 4
<212> TYPE: PRT
<213> ORGANISM: Homo sapiens

<400> SEQUENCE: 253

Ser Lys Ala Phe
 1

<210> SEQ ID NO 254
<211> LENGTH: 6
<212> TYPE: PRT
<213> ORGANISM: Homo sapiens

<400> SEQUENCE: 254

Ser Ser Pro His Ser Tyr
 1               5

<210> SEQ ID NO 255
<211> LENGTH: 5
<212> TYPE: PRT
<213> ORGANISM: Homo sapiens

<400> SEQUENCE: 255

Ser Pro His Ser Tyr
 1               5

<210> SEQ ID NO 256
<211> LENGTH: 4
<212> TYPE: PRT
```

<213> ORGANISM: Homo sapiens

<400> SEQUENCE: 256

Pro His Ser Tyr
 1

<210> SEQ ID NO 257
<211> LENGTH: 12
<212> TYPE: PRT
<213> ORGANISM: Homo sapiens

<400> SEQUENCE: 257

Arg His Tyr Leu Asn Leu Val Thr Arg Gln Arg Tyr
 1               5                  10

<210> SEQ ID NO 258
<211> LENGTH: 11
<212> TYPE: PRT
<213> ORGANISM: Homo sapiens

<400> SEQUENCE: 258

His Tyr Leu Asn Leu Val Thr Arg Gln Arg Tyr
 1               5                  10

<210> SEQ ID NO 259
<211> LENGTH: 10
<212> TYPE: PRT
<213> ORGANISM: Homo sapiens

<400> SEQUENCE: 259

Tyr Leu Asn Leu Val Thr Arg Gln Arg Tyr
 1               5                  10

<210> SEQ ID NO 260
<211> LENGTH: 9
<212> TYPE: PRT
<213> ORGANISM: Homo sapiens

<400> SEQUENCE: 260

Leu Asn Leu Val Thr Arg Gln Arg Tyr
 1               5

<210> SEQ ID NO 261
<211> LENGTH: 8
<212> TYPE: PRT
<213> ORGANISM: Homo sapiens

<400> SEQUENCE: 261

Asn Leu Val Thr Arg Gln Arg Tyr
 1               5

<210> SEQ ID NO 262
<211> LENGTH: 7
<212> TYPE: PRT
<213> ORGANISM: Homo sapiens

<400> SEQUENCE: 262

Leu Val Thr Arg Gln Arg Tyr
 1               5

<210> SEQ ID NO 263
<211> LENGTH: 6
<212> TYPE: PRT
<213> ORGANISM: Homo sapiens

<400> SEQUENCE: 263

Val Thr Arg Gln Arg Tyr
1               5

<210> SEQ ID NO 264
<211> LENGTH: 5
<212> TYPE: PRT
<213> ORGANISM: Homo sapiens

<400> SEQUENCE: 264

Thr Arg Gln Arg Tyr
1               5

<210> SEQ ID NO 265
<211> LENGTH: 11
<212> TYPE: PRT
<213> ORGANISM: Homo sapiens

<400> SEQUENCE: 265

Arg His Tyr Leu Asn Leu Val Thr Arg Gln Arg
1               5                   10

<210> SEQ ID NO 266
<211> LENGTH: 10
<212> TYPE: PRT
<213> ORGANISM: Homo sapiens

<400> SEQUENCE: 266

His Tyr Leu Asn Leu Val Thr Arg Gln Arg
1               5                   10

<210> SEQ ID NO 267
<211> LENGTH: 9
<212> TYPE: PRT
<213> ORGANISM: Homo sapiens

<400> SEQUENCE: 267

Tyr Leu Asn Leu Val Thr Arg Gln Arg
1               5

<210> SEQ ID NO 268
<211> LENGTH: 8
<212> TYPE: PRT
<213> ORGANISM: Homo sapiens

<400> SEQUENCE: 268

Leu Asn Leu Val Thr Arg Gln Arg
1               5

<210> SEQ ID NO 269
<211> LENGTH: 7
<212> TYPE: PRT
<213> ORGANISM: Homo sapiens

<400> SEQUENCE: 269

Asn Leu Val Thr Arg Gln Arg
1               5

<210> SEQ ID NO 270
<211> LENGTH: 6
<212> TYPE: PRT
<213> ORGANISM: Homo sapiens

<400> SEQUENCE: 270

Leu Val Thr Arg Gln Arg
1               5

<210> SEQ ID NO 271
<211> LENGTH: 5
<212> TYPE: PRT
<213> ORGANISM: Homo sapiens

<400> SEQUENCE: 271

Val Thr Arg Gln Arg
 1               5

<210> SEQ ID NO 272
<211> LENGTH: 4
<212> TYPE: PRT
<213> ORGANISM: Homo sapiens

<400> SEQUENCE: 272

Thr Arg Gln Arg
 1

<210> SEQ ID NO 273
<211> LENGTH: 9
<212> TYPE: PRT
<213> ORGANISM: Xenopus sp.

<400> SEQUENCE: 273

Gly Lys Pro Lys Lys Ile Arg Tyr Ser
 1               5

<210> SEQ ID NO 274
<211> LENGTH: 8
<212> TYPE: PRT
<213> ORGANISM: Xenopus sp.

<400> SEQUENCE: 274

Lys Pro Lys Lys Ile Arg Tyr Ser
 1               5

<210> SEQ ID NO 275
<211> LENGTH: 8
<212> TYPE: PRT
<213> ORGANISM: Xenopus sp.

<400> SEQUENCE: 275

Gly Trp Leu Ile Lys Gly Arg Pro
 1               5

<210> SEQ ID NO 276
<211> LENGTH: 7
<212> TYPE: PRT
<213> ORGANISM: Xenopus sp.

<400> SEQUENCE: 276

Trp Leu Ile Lys Gly Arg Pro
 1               5

<210> SEQ ID NO 277
<211> LENGTH: 9
<212> TYPE: PRT
<213> ORGANISM: Heloderma suspectum

<400> SEQUENCE: 277

Pro Ser Ser Gly Ala Pro Pro Ser
 1               5

<210> SEQ ID NO 278

```
<211> LENGTH: 8
<212> TYPE: PRT
<213> ORGANISM: Heloderma suspectum

<400> SEQUENCE: 278

Ser Ser Gly Ala Pro Pro Pro Ser
 1               5

<210> SEQ ID NO 279
<211> LENGTH: 7
<212> TYPE: PRT
<213> ORGANISM: Heloderma suspectum

<400> SEQUENCE: 279

Ser Gly Ala Pro Pro Pro Ser
 1               5

<210> SEQ ID NO 280
<211> LENGTH: 6
<212> TYPE: PRT
<213> ORGANISM: Heloderma suspectum

<400> SEQUENCE: 280

Gly Ala Pro Pro Pro Ser
 1               5

<210> SEQ ID NO 281
<211> LENGTH: 5
<212> TYPE: PRT
<213> ORGANISM: Heloderma suspectum

<400> SEQUENCE: 281

Ala Pro Pro Pro Ser
 1               5

<210> SEQ ID NO 282
<211> LENGTH: 4
<212> TYPE: PRT
<213> ORGANISM: Heloderma suspectum

<400> SEQUENCE: 282

Pro Pro Pro Ser
 1

<210> SEQ ID NO 283
<211> LENGTH: 30
<212> TYPE: PRT
<213> ORGANISM: Xenopus sp.

<400> SEQUENCE: 283

Thr Asn Asp Val Thr Glu Tyr Leu Glu Glu Lys Ala Ala Lys Glu Phe
 1               5                  10                  15

Ile Glu Trp Leu Ile Lys Gly Lys Pro Lys Lys Ile Arg Tyr
             20                  25                  30

<210> SEQ ID NO 284
<211> LENGTH: 28
<212> TYPE: PRT
<213> ORGANISM: Heloderma suspectum

<400> SEQUENCE: 284

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
             20                  25
```

```
<210> SEQ ID NO 285
<211> LENGTH: 7
<212> TYPE: PRT
<213> ORGANISM: Homo sapiens

<400> SEQUENCE: 285

Lys Ala Asn Thr Ala Thr Ala
 1               5

<210> SEQ ID NO 286
<211> LENGTH: 20
<212> TYPE: PRT
<213> ORGANISM: Oncorhynchus sp.

<400> SEQUENCE: 286

Val Leu Gly Arg Leu Ser Glu Glu Leu His Arg Leu Gln Thr Tyr Pro
 1               5                  10                  15

Arg Thr Asn Thr
            20

<210> SEQ ID NO 287
<211> LENGTH: 8
<212> TYPE: PRT
<213> ORGANISM: Homo sapiens

<400> SEQUENCE: 287

Asp Phe Met Gly Trp Met Asp Phe
 1               5

<210> SEQ ID NO 288
<211> LENGTH: 20
<212> TYPE: PRT
<213> ORGANISM: Oncorhynchus sp.

<400> SEQUENCE: 288

Val Leu Gly Lys Leu Ser Glu Glu Leu His Lys Leu Gln Thr Tyr Pro
 1               5                  10                  15

Arg Thr Asn Thr
            20

<210> SEQ ID NO 289
<211> LENGTH: 20
<212> TYPE: PRT
<213> ORGANISM: artificial
<220> FEATURE:
<223> OTHER INFORMATION: Chimeric human and salmon construct

<400> SEQUENCE: 289

Val Leu Gly Arg Leu Ser Gln Glu Leu His Arg Leu Gln Thr Tyr Pro
 1               5                  10                  15

Arg Thr Asn Thr
            20

<210> SEQ ID NO 290
<211> LENGTH: 36
<212> TYPE: PRT
<213> ORGANISM: homo sapiens

<400> SEQUENCE: 290

Ala Pro Leu Glu Pro Val Tyr Pro Gly Asp Asn Ala Thr Pro Glu Gln
 1               5                  10                  15

Met Ala Gln Tyr Ala Ala Asp Leu Arg Arg Tyr Ile Asn Met Leu Thr
            20                  25                  30
```

Arg Pro Arg Tyr
        35

<210> SEQ ID NO 291
<211> LENGTH: 38
<212> TYPE: PRT
<213> ORGANISM: mus musculus
<220> FEATURE:
<221> NAME/KEY: misc_feature
<223> OTHER INFORMATION: C-term amidated

<400> SEQUENCE: 291

Val Ile Leu Ser Leu Asp Val Pro Ile Gly Leu Leu Arg Ile Leu Leu
 1               5                  10                  15

Glu Gln Ala Arg Tyr Lys Ala Ala Arg Asn Gln Ala Ala Thr Asn Ala
            20                  25                  30

Gln Ile Leu Ala His Val
        35

<210> SEQ ID NO 292
<211> LENGTH: 24
<212> TYPE: PRT
<213> ORGANISM: Homo sapiens

<400> SEQUENCE: 292

Trp Ser Pro Gly Ala Arg Asn Gln Gly Gly Ala Arg Ala Leu Leu
 1               5                  10                  15

Leu Leu Leu Ala Glu Arg Phe Pro
            20

<210> SEQ ID NO 293
<211> LENGTH: 18
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 293

Thr Gln Ser Gln Arg Glu Arg Ala Glu Gln Asn Arg Ile Ile Phe Asp
 1               5                  10                  15

Ser Val

<210> SEQ ID NO 294
<211> LENGTH: 40
<212> TYPE: PRT
<213> ORGANISM: Homo sapiens
<220> FEATURE:
<221> NAME/KEY: misc_feature
<223> OTHER INFORMATION: C-term amidated

<400> SEQUENCE: 294

Asp Asn Pro Ser Leu Ser Ile Asp Leu Thr Phe His Leu Leu Arg Thr
 1               5                  10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 295
<211> LENGTH: 20
<212> TYPE: PRT
<213> ORGANISM: Homo sapiens

```
<400> SEQUENCE: 295

Ser Phe His Tyr Leu Arg Ser Arg Asp Ala Ser Ser Gly Glu Glu
 1               5                  10                  15

Glu Gly Lys Glu
            20

<210> SEQ ID NO 296
<211> LENGTH: 13
<212> TYPE: PRT
<213> ORGANISM: Homo sapiens

<400> SEQUENCE: 296

Ala Gln Ala Ala Ala Asn Ala His Leu Met Ala Gln Ile
 1               5                  10

<210> SEQ ID NO 297
<211> LENGTH: 21
<212> TYPE: PRT
<213> ORGANISM: Homo sapiens

<400> SEQUENCE: 297

Asp Asn Pro Ser Leu Ser Ile Asp Leu Thr Phe His Leu Leu Arg Thr
 1               5                  10                  15

Leu Leu Glu Leu Ala
            20

<210> SEQ ID NO 298
<211> LENGTH: 26
<212> TYPE: PRT
<213> ORGANISM: Homo sapiens

<400> SEQUENCE: 298

Thr Lys Phe Thr Leu Ser Leu Asp Val Pro Thr Asn Ile Met Asn Leu
 1               5                  10                  15

Leu Phe Asn Ile Ala Lys Ala Lys Asn Leu
            20                  25

<210> SEQ ID NO 299
<211> LENGTH: 38
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 299

Phe Thr Leu Ser Leu Asp Val Pro Thr Asn Ile Met Asn Leu Leu Phe
 1               5                  10                  15

Asn Ile Ala Lys Ala Lys Asn Leu Arg Ala Gln Ala Ala Ala Asn Ala
            20                  25                  30

His Leu Met Ala Gln Ile
        35

<210> SEQ ID NO 300
<211> LENGTH: 38
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 300

Phe Leu Phe His Tyr Ser Lys Thr Gln Lys Leu Gly Lys Ser Asn Val
 1               5                  10                  15
```

Val Glu Glu Leu Gln Ser Pro Phe Ala Ser Gln Ser Arg Gly Tyr Phe
            20                  25                  30

Leu Phe Arg Pro Arg Asn
            35

<210> SEQ ID NO 301
<211> LENGTH: 28
<212> TYPE: PRT
<213> ORGANISM: Homo sapiens

<400> SEQUENCE: 301

Ser Leu Arg Arg Ser Ser Cys Phe Gly Gly Arg Met Asp Arg Ile Gly
 1               5                  10                  15

Ala Gln Ser Gly Leu Gly Cys Asn Ser Phe Arg Tyr
            20                  25

<210> SEQ ID NO 302
<211> LENGTH: 32
<212> TYPE: PRT
<213> ORGANISM: rat

<400> SEQUENCE: 302

Asn Ser Lys Met Ala His Ser Ser Cys Phe Gly Gln Lys Ile Asp
 1               5                  10                  15

Arg Ile Gly Ala Val Ser Arg Leu Gly Cys Asp Gly Leu Arg Leu Phe
            20                  25                  30

<210> SEQ ID NO 303
<211> LENGTH: 32
<212> TYPE: PRT
<213> ORGANISM: Homo sapiens

<400> SEQUENCE: 303

Ser Pro Lys Met Val Gln Gly Ser Gly Cys Phe Gly Arg Lys Met Asp
 1               5                  10                  15

Arg Ile Ser Ser Ser Ser Gly Leu Gly Cys Lys Val Leu Arg Arg His
            20                  25                  30

<210> SEQ ID NO 304
<211> LENGTH: 22
<212> TYPE: PRT
<213> ORGANISM: porcine

<400> SEQUENCE: 304

Gly Leu Ser Lys Gly Cys Phe Gly Leu Lys Leu Asp Arg Ile Gly Ser
 1               5                  10                  15

Met Ser Gly Leu Gly Cys
            20

<210> SEQ ID NO 305
<211> LENGTH: 8
<212> TYPE: PRT
<213> ORGANISM: porcine
<220> FEATURE:
<221> NAME/KEY: MISC_FEATURE
<223> OTHER INFORMATION: C-term amidated

<400> SEQUENCE: 305

Tyr Phe Leu Phe Arg Pro Arg Asn
 1               5

<210> SEQ ID NO 306
<211> LENGTH: 23

```
<212> TYPE: PRT
<213> ORGANISM: rat
<220> FEATURE:
<221> NAME/KEY: MISC_FEATURE
<223> OTHER INFORMATION: C-term amidated

<400> SEQUENCE: 306

Tyr Lys Val Asn Glu Tyr Gln Gly Pro Val Ala Pro Ser Gly Gly Phe
 1               5                  10                  15

Phe Leu Phe Arg Pro Arg Asn
            20

<210> SEQ ID NO 307
<211> LENGTH: 9
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 307

Gly Tyr Phe Leu Phe Arg Pro Arg Asn
 1               5

<210> SEQ ID NO 308
<211> LENGTH: 25
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 308

Phe Arg Val Asp Glu Glu Phe Gln Ser Pro Phe Ala Ser Gln Ser Arg
 1               5                  10                  15

Gly Tyr Phe Leu Phe Arg Pro Arg Asn
            20                  25

<210> SEQ ID NO 309
<211> LENGTH: 36
<212> TYPE: PRT
<213> ORGANISM: Artificial
<220> FEATURE:
<223> OTHER INFORMATION: Hybrid of human CCK and human PYY
<220> FEATURE:
<221> NAME/KEY: MISC_FEATURE
<223> OTHER INFORMATION: C-term amidated
<220> FEATURE:
<221> NAME/KEY: MISC_FEATURE
<223> OTHER INFORMATION: N-terminal (head) to N-terminal (head) linked
<220> FEATURE:
<221> NAME/KEY: MOD_RES
<222> LOCATION: (1)..(1)
<223> OTHER INFORMATION: C-term amidated
<220> FEATURE:
<221> NAME/KEY: MOD_RES
<222> LOCATION: (7)..(7)
<223> OTHER INFORMATION: Sulfated Tyrosine
<220> FEATURE:
<221> NAME/KEY: MOD_RES
<222> LOCATION: (9)..(9)
<223> OTHER INFORMATION: Succinoyl-Cys

<400> SEQUENCE: 309

Phe Asp Met Trp Gly Met Tyr Asp Cys Glu Asp Ala Ser Pro Glu Glu
 1               5                  10                  15

Leu Asn Arg Tyr Tyr Ala Ser Leu Arg His Tyr Leu Asn Leu Val Thr
            20                  25                  30

Arg Gln Arg Tyr
```

-continued

```
<210> SEQ ID NO 310
<211> LENGTH: 36
<212> TYPE: PRT
<213> ORGANISM: Artificial
<220> FEATURE:
<223> OTHER INFORMATION: Hybrid of human CCK and human PYY
<220> FEATURE:
<221> NAME/KEY: MISC_FEATURE
<223> OTHER INFORMATION: C-term amidated
<220> FEATURE:
<221> NAME/KEY: MISC_FEATURE
<223> OTHER INFORMATION: N-terminal (head) to N-terminal (head) linked
<220> FEATURE:
<221> NAME/KEY: MOD_RES
<222> LOCATION: (1)..(1)
<223> OTHER INFORMATION: C-term amidated
<220> FEATURE:
<221> NAME/KEY: MOD_RES
<222> LOCATION: (7)..(7)
<223> OTHER INFORMATION: Sulfated Tyrosine
<220> FEATURE:
<221> NAME/KEY: MOD_RES
<222> LOCATION: (9)..(9)
<223> OTHER INFORMATION: Bis-Cys(N-Acetyl)

<400> SEQUENCE: 310

Phe Asp Met Trp Gly Met Tyr Asp Cys Glu Asp Ala Ser Pro Glu Glu
 1               5                  10                  15

Leu Asn Arg Tyr Tyr Ala Ser Leu Arg His Tyr Leu Asn Leu Val Thr
             20                  25                  30

Arg Gln Arg Tyr
         35

<210> SEQ ID NO 311
<211> LENGTH: 36
<212> TYPE: PRT
<213> ORGANISM: Artificial
<220> FEATURE:
<223> OTHER INFORMATION: Hybrid of human CCK and human PYY
<220> FEATURE:
<221> NAME/KEY: MISC_FEATURE
<223> OTHER INFORMATION: C-term amidated
<220> FEATURE:
<221> NAME/KEY: MISC_FEATURE
<223> OTHER INFORMATION: N-terminal (head) to N-terminal (head) linked
<220> FEATURE:
<221> NAME/KEY: MOD_RES
<222> LOCATION: (1)..(1)
<223> OTHER INFORMATION: C-term amidated
<220> FEATURE:
<221> NAME/KEY: MOD_RES
<222> LOCATION: (7)..(7)
<223> OTHER INFORMATION: para(CH2SO3)Phe
<220> FEATURE:
<221> NAME/KEY: MOD_RES
<222> LOCATION: (9)..(9)
<223> OTHER INFORMATION: Gly-Aminoxymethylcarbonyl

<400> SEQUENCE: 311

Phe Asp Met Trp Gly Met Phe Asp Gly Glu Asp Ala Ser Pro Glu Glu
 1               5                  10                  15

Leu Asn Arg Tyr Tyr Ala Ser Leu Arg His Tyr Leu Asn Leu Val Thr
             20                  25                  30

Arg Gln Arg Tyr
         35

<210> SEQ ID NO 312
<211> LENGTH: 63
<212> TYPE: PRT
```

```
<213> ORGANISM: Artificial
<220> FEATURE:
<223> OTHER INFORMATION: Hybrid lizard, human and salmon construct

<400> SEQUENCE: 312

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Gly Lys
            20                  25                  30

Cys Asn Thr Ala Thr Cys Val Leu Gly Arg Leu Ser Gln Glu Leu His
        35                  40                  45

Arg Leu Gln Thr Tyr Pro Arg Thr Asn Thr Gly Ser Asn Thr Tyr
    50                  55                  60

<210> SEQ ID NO 313
<211> LENGTH: 62
<212> TYPE: PRT
<213> ORGANISM: Artificial
<220> FEATURE:
<223> OTHER INFORMATION: Hybrid lizard, human and salmon construct

<400> SEQUENCE: 313

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Gly Cys
            20                  25                  30

Asn Thr Ala Thr Cys Val Leu Gly Arg Leu Ser Gln Glu Leu His Arg
        35                  40                  45

Leu Gln Thr Tyr Pro Arg Thr Asn Thr Gly Ser Asn Thr Tyr
    50                  55                  60

<210> SEQ ID NO 314
<211> LENGTH: 25
<212> TYPE: PRT
<213> ORGANISM: porcine

<400> SEQUENCE: 314

Phe Lys Val Asp Glu Glu Phe Gln Gly Pro Ile Val Ser Gln Asn Arg
 1               5                  10                  15

Arg Tyr Phe Leu Phe Arg Pro Arg Asn
            20                  25

<210> SEQ ID NO 315
<211> LENGTH: 33
<212> TYPE: PRT
<213> ORGANISM: Homo sapiens

<400> SEQUENCE: 315

Ile Leu Gln Arg Gly Ser Gly Thr Ala Ala Val Asp Phe Thr Lys Lys
 1               5                  10                  15

Asp His Thr Ala Thr Trp Gly Arg Pro Phe Phe Leu Phe Arg Pro Arg
            20                  25                  30

Asn

<210> SEQ ID NO 316
<211> LENGTH: 36
<212> TYPE: PRT
<213> ORGANISM: Homo sapiens

<400> SEQUENCE: 316

Leu Val Gln Pro Arg Gly Ser Arg Asn Gly Pro Gly Pro Trp Gln Gly
 1               5                  10                  15
```

Gly Arg Arg Lys Phe Arg Arg Gln Arg Pro Arg Leu Ser His Lys Gly
            20                  25                  30

Pro Met Pro Phe
        35

<210> SEQ ID NO 317
<211> LENGTH: 14
<212> TYPE: PRT
<213> ORGANISM: Homo sapiens

<400> SEQUENCE: 317

Pro Glu Arg Pro Arg Leu Ser His Lys Gly Pro Met Pro Phe
 1               5                  10

<210> SEQ ID NO 318
<211> LENGTH: 31
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 318

Ser Arg Thr His Arg His Ser Met Glu Ile Arg Thr Pro Asp Ile Asn
 1               5                  10                  15

Pro Ala Trp Tyr Ala Ser Arg Gly Ile Arg Pro Val Gly Arg Phe
            20                  25                  30

<210> SEQ ID NO 319
<211> LENGTH: 20
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 319

Thr Pro Asp Ile Asn Pro Ala Trp Tyr Ala Ser Arg Gly Ile Arg Pro
 1               5                  10                  15

Val Gly Arg Phe
            20

<210> SEQ ID NO 320
<211> LENGTH: 34
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 320

Gln Leu Gly Pro Gln Gly Pro Pro His Leu Val Ala Asp Pro Ser Lys
 1               5                  10                  15

Lys Gln Gly Pro Trp Leu Glu Glu Glu Glu Ala Tyr Gly Trp Met
            20                  25                  30

Asp Phe

<210> SEQ ID NO 321
<211> LENGTH: 18
<212> TYPE: PRT
<213> ORGANISM: Homo sapiens
<220> FEATURE:
<221> NAME/KEY: MISC_FEATURE
<223> OTHER INFORMATION: C-term amidated
<220> FEATURE:

```
<221> NAME/KEY: MOD_RES
<222> LOCATION: (1)..(1)
<223> OTHER INFORMATION: pyroGlutamine

<400> SEQUENCE: 321

Pro Glu Gly Pro Trp Leu Glu Glu Glu Glu Ala Tyr Gly Trp Met
 1               5                  10                  15

Asp Phe

<210> SEQ ID NO 322
<211> LENGTH: 5
<212> TYPE: PRT
<213> ORGANISM: Homo sapiens
<220> FEATURE:
<221> NAME/KEY: MISC_FEATURE
<223> OTHER INFORMATION: C-term amidated
<220> FEATURE:
<221> NAME/KEY: MOD_RES
<222> LOCATION: (1)..(1)
<223> OTHER INFORMATION: bAla

<400> SEQUENCE: 322

Ala Trp Met Asp Phe
 1               5

<210> SEQ ID NO 323
<211> LENGTH: 33
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 323

Lys Ala Pro Ser Gly Arg Met Ser Ile Val Lys Asn Leu Gln Asn Leu
 1               5                  10                  15

Asp Pro Ser His Arg Ile Ser Asp Arg Asp Tyr Met Gly Trp Met Asp
             20                  25                  30

Phe

<210> SEQ ID NO 324
<211> LENGTH: 29
<212> TYPE: PRT
<213> ORGANISM: Homo sapiens

<400> SEQUENCE: 324

Gln Glu Gly Ala Pro Pro Gln Gln Ser Ala Arg Arg Asp Arg Met Pro
 1               5                  10                  15

Cys Arg Asn Phe Phe Trp Lys Thr Phe Ser Ser Cys Lys
             20                  25

<210> SEQ ID NO 325
<211> LENGTH: 17
<212> TYPE: PRT
<213> ORGANISM: Homo sapiens

<400> SEQUENCE: 325

Asp Arg Met Pro Cys Arg Asn Phe Phe Trp Lys Thr Phe Ser Ser Cys
 1               5                  10                  15

Lys

<210> SEQ ID NO 326
<211> LENGTH: 28
<212> TYPE: PRT
<213> ORGANISM: Homo sapiens
```

<400> SEQUENCE: 326

Ser Ala Asn Ser Asn Pro Ala Met Ala Pro Arg Glu Arg Lys Ala Gly
1               5                   10                  15
Cys Lys Asn Phe Phe Trp Lys Thr Phe Thr Ser Cys
            20                  25

<210> SEQ ID NO 327
<211> LENGTH: 14
<212> TYPE: PRT
<213> ORGANISM: Homo sapiens

<400> SEQUENCE: 327

Ala Gly Cys Lys Asn Phe Phe Trp Lys Thr Phe Thr Ser Cys
1               5                   10

<210> SEQ ID NO 328
<211> LENGTH: 27
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 328

Val Pro Leu Pro Ala Gly Gly Gly Thr Val Leu Thr Lys Met Tyr Pro
1               5                   10                  15
Arg Gly Asn His Trp Ala Val Gly His Leu Met
            20                  25

<210> SEQ ID NO 329
<211> LENGTH: 10
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 329

Gly Asn His Trp Ala Val Gly His Leu Met
1               5                   10

<210> SEQ ID NO 330
<211> LENGTH: 30
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 330

Leu Ser Trp Asp Leu Pro Glu Pro Arg Ser Arg Ala Ser Lys Ile Arg
1               5                   10                  15
Val His Ser Arg Gly Asn Leu Trp Ala Thr Gly His Phe Met
            20                  25                  30

<210> SEQ ID NO 331
<211> LENGTH: 10
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 331

Gly Asn Leu Trp Ala Thr Gly His Phe Met

```
                1               5                   10
```

<210> SEQ ID NO 332
<211> LENGTH: 9
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 332

```
Pro Phe Phe Leu Phe Arg Pro Arg Asn
 1               5
```

<210> SEQ ID NO 333
<211> LENGTH: 21
<212> TYPE: PRT
<213> ORGANISM: Homo sapiens

<400> SEQUENCE: 333

```
Lys Ile Pro Tyr Ile Leu Lys Arg Gln Leu Tyr Glu Asn Lys Pro Arg
 1               5                   10                  15

Arg Pro Tyr Ile Leu
            20
```

<210> SEQ ID NO 334
<211> LENGTH: 13
<212> TYPE: PRT
<213> ORGANISM: Homo sapiens

<400> SEQUENCE: 334

```
Gln Leu Tyr Glu Asn Lys Pro Arg Arg Pro Tyr Ile Leu
 1               5                   10
```

<210> SEQ ID NO 335
<211> LENGTH: 54
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 335

```
Gly Thr Ser Leu Ser Pro Pro Glu Ser Ser Gly Ser Pro Gln Gln
 1               5                   10                  15

Pro Gly Leu Ser Ala Pro His Ser Arg Gln Ile Pro Ala Pro Gln Gly
                20                  25                  30

Ala Val Leu Val Gln Arg Glu Lys Asp Leu Pro Asn Tyr Asn Trp Asn
            35                  40                  45

Ser Phe Gly Leu Arg Phe
        50
```

<210> SEQ ID NO 336
<211> LENGTH: 16
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 336

```
Glu Lys Asp Leu Pro Asn Tyr Asn Trp Asn Ser Phe Gly Leu Arg Phe
 1               5                   10                  15
```

<210> SEQ ID NO 337

```
<211> LENGTH: 31
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 337

Ser Ala Gly Ala Thr Ala Asn Leu Pro Leu Arg Ser Gly Arg Asn Met
 1               5                  10                  15

Glu Val Ser Leu Val Arg Arg Val Pro Asn Leu Pro Gln Arg Phe
            20                  25                  30

<210> SEQ ID NO 338
<211> LENGTH: 8
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 338

Val Pro Asn Leu Pro Gln Arg Phe
 1               5

<210> SEQ ID NO 339
<211> LENGTH: 32
<212> TYPE: PRT
<213> ORGANISM: Homo sapiens

<400> SEQUENCE: 339

Tyr Gly Gly Phe Leu Arg Arg Ile Arg Pro Lys Leu Lys Trp Asp Asn
 1               5                  10                  15

Gln Lys Arg Tyr Gly Gly Phe Leu Arg Arg Gln Phe Lys Val Val Thr
            20                  25                  30

<210> SEQ ID NO 340
<211> LENGTH: 13
<212> TYPE: PRT
<213> ORGANISM: Homo sapiens

<400> SEQUENCE: 340

Tyr Gly Gly Phe Leu Arg Arg Gln Phe Lys Val Val Thr
 1               5                  10

<210> SEQ ID NO 341
<211> LENGTH: 14
<212> TYPE: PRT
<213> ORGANISM: Homo sapiens
<220> FEATURE:
<221> NAME/KEY: MISC_FEATURE
<223> OTHER INFORMATION: C-term amide

<400> SEQUENCE: 341

Ser Leu Arg His Tyr Leu Asn Leu Val Thr Arg Gln Arg Tyr
 1               5                  10

<210> SEQ ID NO 342
<211> LENGTH: 38
<212> TYPE: PRT
<213> ORGANISM: Homo sapiens

<400> SEQUENCE: 342

Cys Ser Cys Ser Ser Leu Met Asp Lys Glu Cys Val Tyr Phe Cys His
 1               5                  10                  15

Leu Asp Ile Ile Trp Val Asn Thr Pro Glu His Val Val Pro Tyr Gly
```

-continued

```
                20                  25                  30
Leu Gly Ser Pro Arg Ser
        35

<210> SEQ ID NO 343
<211> LENGTH: 21
<212> TYPE: PRT
<213> ORGANISM: Homo sapiens

<400> SEQUENCE: 343

Cys Ser Cys Ser Ser Leu Met Asp Lys Glu Cys Val Tyr Phe Cys His
 1               5                  10                  15

Leu Asp Ile Ile Trp
            20

<210> SEQ ID NO 344
<211> LENGTH: 37
<212> TYPE: PRT
<213> ORGANISM: Homo sapiens

<400> SEQUENCE: 344

Cys Ser Cys Ser Ser Trp Leu Asp Lys Glu Cys Val Tyr Phe Cys His
 1               5                  10                  15

Leu Asp Ile Ile Trp Val Asn Thr Pro Glu Gln Thr Ala Pro Tyr Gly
            20                  25                  30

Leu Gly Asn Pro Pro
        35

<210> SEQ ID NO 345
<211> LENGTH: 21
<212> TYPE: PRT
<213> ORGANISM: Homo sapiens

<400> SEQUENCE: 345

Cys Ser Cys Ser Ser Trp Leu Asp Lys Glu Cys Val Tyr Phe Cys His
 1               5                  10                  15

Leu Asp Ile Ile Trp
            20

<210> SEQ ID NO 346
<211> LENGTH: 41
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 346

Cys Thr Cys Phe Thr Tyr Lys Asp Lys Glu Cys Val Tyr Tyr Cys His
 1               5                  10                  15

Leu Asp Ile Ile Trp Ile Asn Thr Pro Glu Gln Thr Val Pro Tyr Gly
            20                  25                  30

Leu Ser Asn Tyr Arg Gly Ser Phe Arg
        35                  40

<210> SEQ ID NO 347
<211> LENGTH: 21
<212> TYPE: PRT
<213> ORGANISM: Homo sapiens

<400> SEQUENCE: 347

Cys Thr Cys Phe Thr Tyr Lys Asp Lys Glu Cys Val Tyr Tyr Cys His
 1               5                  10                  15
```

Leu Asp Ile Ile Trp
            20

<210> SEQ ID NO 348
<211> LENGTH: 27
<212> TYPE: PRT
<213> ORGANISM: Homo sapiens

<400> SEQUENCE: 348

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro
            20                  25

<210> SEQ ID NO 349
<211> LENGTH: 10
<212> TYPE: PRT
<213> ORGANISM: Homo sapiens

<400> SEQUENCE: 349

Gly Ser Ser Phe Leu Ser Pro Glu His Gln
1               5                   10

<210> SEQ ID NO 350
<211> LENGTH: 37
<212> TYPE: PRT
<213> ORGANISM: Homo sapiens

<400> SEQUENCE: 350

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 351
<211> LENGTH: 29
<212> TYPE: PRT
<213> ORGANISM: Homo sapiens

<400> SEQUENCE: 351

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 352
<211> LENGTH: 42
<212> TYPE: PRT
<213> ORGANISM: Homo sapiens

<400> SEQUENCE: 352

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 353
<211> LENGTH: 30

```
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 353

Tyr Ala Glu Gly Thr Phe Ile Ser Asp Tyr Ser Ile Ala Met Asp Lys
 1               5                  10                  15

Ile His Gln Gln Asp Phe Val Asn Trp Leu Leu Ala Gln Lys
            20                  25                  30

<210> SEQ ID NO 354
<211> LENGTH: 30
<212> TYPE: PRT
<213> ORGANISM: Homo sapiens

<400> SEQUENCE: 354

Trp Tyr Lys His Val Ala Ser Pro Arg Tyr His Thr Val Gly Arg Ala
 1               5                  10                  15

Ala Gly Leu Leu Met Gly Leu Arg Arg Ser Pro Tyr Leu Trp
            20                  25                  30

<210> SEQ ID NO 355
<211> LENGTH: 23
<212> TYPE: PRT
<213> ORGANISM: Homo sapiens

<400> SEQUENCE: 355

Trp Tyr Lys His Val Ala Ser Pro Arg Tyr His Thr Val Gly Arg Ala
 1               5                  10                  15

Ala Gly Leu Leu Met Gly Leu
            20

<210> SEQ ID NO 356
<211> LENGTH: 38
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 356

His Ser Asp Gly Ile Phe Thr Asp Ser Tyr Ser Arg Tyr Arg Lys Gln
 1               5                  10                  15

Met Ala Val Lys Lys Tyr Leu Ala Ala Val Leu Gly Arg Tyr Lys
            20                  25                  30

Gln Arg Val Lys Asn Lys
        35

<210> SEQ ID NO 357
<211> LENGTH: 27
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 357

His Ser Asp Gly Ile Phe Thr Asp Ser Tyr Ser Arg Tyr Arg Lys Gln
 1               5                  10                  15

Met Ala Val Lys Lys Tyr Leu Ala Ala Val Leu
            20                  25
```

<210> SEQ ID NO 358
<211> LENGTH: 42
<212> TYPE: PRT
<213> ORGANISM: Homo sapiens

<400> SEQUENCE: 358

His Ala Asp Gly Val Phe Thr Ser Asp Phe Ser Lys Leu Leu Gly Gln
1               5                   10                  15

Leu Ser Ala Lys Lys Tyr Leu Glu Ser Leu Met Gly Lys Arg Val Ser
            20                  25                  30

Ser Asn Ile Ser Glu Asp Pro Val Pro Val
        35                  40

<210> SEQ ID NO 359
<211> LENGTH: 27
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 359

His Ala Asp Gly Val Phe Thr Ser Asp Phe Ser Lys Leu Leu Gly Gln
1               5                   10                  15

Leu Ser Ala Lys Lys Tyr Leu Glu Ser Leu Met
            20                  25

<210> SEQ ID NO 360
<211> LENGTH: 44
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 360

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 361
<211> LENGTH: 28
<212> TYPE: PRT
<213> ORGANISM: Homo sapiens

<400> SEQUENCE: 361

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser
            20                  25

<210> SEQ ID NO 362
<211> LENGTH: 84
<212> TYPE: PRT
<213> ORGANISM: Homo sapiens

<400> SEQUENCE: 362

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
           35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 363
<211> LENGTH: 37
<212> TYPE: PRT
<213> ORGANISM: Homo sapiens

<400> SEQUENCE: 363

Ser Val Ser Glu Ile Gln Leu Met His Asn Leu Gly Lys His Leu Asn
1               5                  10                  15

Ser Met Glu Arg Val Glu Trp Leu Arg Lys Lys Leu Gln Asp Val His
            20                  25                  30

Asn Phe Val Ala Leu
        35

<210> SEQ ID NO 364
<211> LENGTH: 34
<212> TYPE: PRT
<213> ORGANISM: Homo sapiens

<400> SEQUENCE: 364

Ser Val Ser Glu Ile Gln Leu Met His Asn Leu Gly Lys His Leu Asn
1               5                  10                  15

Ser Met Glu Arg Val Glu Trp Leu Arg Lys Lys Leu Gln Asp Val His
            20                  25                  30

Asn Phe

<210> SEQ ID NO 365
<211> LENGTH: 93
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 365

Ala Val Ser Glu His Gln Leu Leu His Asp Lys Gly Lys Ser Ile Gln
1               5                  10                  15

Asp Leu Arg Arg Arg Phe Phe Leu His His Leu Ile Ala Glu Ile His
            20                  25                  30

Thr Ala Glu Ile Arg Ala Thr Ser Glu Val Ser Pro Asn Ser Lys Pro
        35                  40                  45

Ser Pro Asn Thr Lys Asn His Pro Val Arg Gly Ser Asp Asp Glu Gly
        50                  55                  60

Arg Tyr Leu Thr Gln Glu Thr Asn Lys Val Glu Thr Tyr Lys Glu Gln
65                  70                  75                  80

Pro Leu Lys Thr Pro Gly Lys Lys Lys Gly Lys Pro
            85                  90

<210> SEQ ID NO 366
<211> LENGTH: 36
<212> TYPE: PRT
<213> ORGANISM: Homo sapiens -continued

```
<400> SEQUENCE: 366

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
                20                  25                  30

Thr Ala Glu Ile
            35

<210> SEQ ID NO 367
<211> LENGTH: 26
<212> TYPE: PRT
<213> ORGANISM: Homo sapiens

<400> SEQUENCE: 367

Tyr Val Met Gly His Phe Arg Trp Asp Arg Phe Gly Arg Arg Asn Ser
 1               5                  10                  15

Ser Ser Ser Gly Ser Ser Gly Ala Gly Gln
                20                  25

<210> SEQ ID NO 368
<211> LENGTH: 11
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 368

Tyr Val Met Gly His Phe Arg Trp Asp Arg Phe
 1               5                  10

<210> SEQ ID NO 369
<211> LENGTH: 39
<212> TYPE: PRT
<213> ORGANISM: Homo sapiens

<400> SEQUENCE: 369

Ser Tyr Ser Met Glu His Phe Arg Trp Gly Lys Pro Val Gly Lys Lys
 1               5                  10                  15

Arg Arg Pro Val Lys Val Tyr Pro Asn Gly Ala Glu Asp Glu Ser Ala
                20                  25                  30

Glu Ala Phe Pro Leu Glu Phe
            35

<210> SEQ ID NO 370
<211> LENGTH: 13
<212> TYPE: PRT
<213> ORGANISM: Homo sapiens
<220> FEATURE:
<221> NAME/KEY: MISC_FEATURE
<223> OTHER INFORMATION: C-term amidated

<400> SEQUENCE: 370

Ser Tyr Ser Met Glu His Phe Arg Trp Gly Lys Pro Val
 1               5                  10

<210> SEQ ID NO 371
<211> LENGTH: 31
<212> TYPE: PRT
<213> ORGANISM: Homo sapiens

<400> SEQUENCE: 371

Tyr Gly Gly Phe Met Thr Ser Glu Lys Ser Gln Thr Pro Leu Val Thr
 1               5                  10                  15
```

```
Leu Phe Lys Asn Ala Ile Ile Lys Asn Ala Tyr Lys Lys Gly Glu
            20                  25                  30

<210> SEQ ID NO 372
<211> LENGTH: 27
<212> TYPE: PRT
<213> ORGANISM: Homo sapiens

<400> SEQUENCE: 372

Tyr Gly Gly Phe Met Thr Ser Glu Lys Ser Gln Thr Pro Leu Val Thr
 1               5                  10                  15

Leu Phe Lys Asn Ala Ile Ile Lys Asn Ala Tyr
            20                  25

<210> SEQ ID NO 373
<211> LENGTH: 17
<212> TYPE: PRT
<213> ORGANISM: Homo sapiens

<400> SEQUENCE: 373

Tyr Gly Gly Phe Met Thr Ser Glu Lys Ser Gln Thr Pro Leu Val Thr
 1               5                  10                  15

Leu

<210> SEQ ID NO 374
<211> LENGTH: 16
<212> TYPE: PRT
<213> ORGANISM: Homo sapiens

<400> SEQUENCE: 374

Tyr Gly Gly Phe Met Thr Ser Glu Lys Ser Gln Thr Pro Leu Val Thr
 1               5                  10                  15

<210> SEQ ID NO 375
<211> LENGTH: 151
<212> TYPE: PRT
<213> ORGANISM: Homo sapiens

<400> SEQUENCE: 375

Met Ser Ser Phe Ser Thr Thr Thr Val Ser Phe Leu Leu Leu Leu Ala
 1               5                  10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45

Glu Lys Met Pro Leu Glu Asp Glu Val Val Pro Pro Gln Val Leu Ser
    50                  55                  60

Asp Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
    130                 135                 140

Gly Cys Asn Ser Phe Arg Tyr
145                 150
```

<210> SEQ ID NO 376
<211> LENGTH: 134
<212> TYPE: PRT
<213> ORGANISM: Homo sapiens

<400> SEQUENCE: 376

Met Asp Pro Gln Thr Ala Pro Ser Arg Ala Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Gly Leu Gly Cys
        115                 120                 125

Lys Val Leu Arg Arg His
    130

<210> SEQ ID NO 377
<211> LENGTH: 126
<212> TYPE: PRT
<213> ORGANISM: Homo sapiens

<400> SEQUENCE: 377

Met His Leu Ser Gln Leu Leu Ala Cys Ala Leu Leu Thr Leu Leu
1               5                   10                  15

Ser Leu Arg Pro Ser Glu Ala Lys Pro Gly Ala Pro Pro Lys Val Pro
            20                  25                  30

Arg Thr Pro Pro Ala Glu Glu Leu Ala Glu Pro Gln Ala Ala Gly Gly
        35                  40                  45

Gly Gln Lys Lys Gly Asp Lys Ala Pro Gly Gly Gly Ala Asn Leu
    50                  55                  60

Lys Gly Asp Arg Ser Arg Leu Leu Arg Asp Leu Arg Val Asp Thr Lys
65                  70                  75                  80

Ser Arg Ala Ala Trp Ala Arg Leu Leu Gln Glu His Pro Asn Ala Arg
                85                  90                  95

Lys Tyr Lys Gly Ala Asn Lys Lys Gly Leu Ser Lys Gly Cys Phe Gly
            100                 105                 110

Leu Lys Leu Asp Arg Ile Gly Ser Met Ser Gly Leu Gly Cys
        115                 120                 125

<210> SEQ ID NO 378
<211> LENGTH: 9
<212> TYPE: PRT
<213> ORGANISM: Lizard

<400> SEQUENCE: 378

His Ser Glu Gly Thr Phe Thr Ser Asp
1               5

<210> SEQ ID NO 379

```
<211> LENGTH: 59
<212> TYPE: PRT
<213> ORGANISM: Artificial
<220> FEATURE:
<223> OTHER INFORMATION: Hybrid lizard, human and salmon construct

<400> SEQUENCE: 379

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Lys Cys Asn Thr Ala
                20                  25                  30

Thr Cys Val Leu Gly Arg Leu Ser Glu Glu Leu His Arg Leu Gln Thr
            35                  40                  45

Tyr Pro Arg Thr Asn Thr Gly Ser Asn Thr Tyr
        50                  55

<210> SEQ ID NO 380
<211> LENGTH: 61
<212> TYPE: PRT
<213> ORGANISM: Artificial
<220> FEATURE:
<223> OTHER INFORMATION: Hybrid lizard, human and salmon construct
<220> FEATURE:
<221> NAME/KEY: MOD_RES
<222> LOCATION: (29)..(29)
<223> OTHER INFORMATION: 12-Ado

<400> SEQUENCE: 380

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Lys Cys Asn
                20                  25                  30

Thr Ala Thr Cys Val Leu Gly Arg Leu Ser Glu Glu Leu His Arg Leu
            35                  40                  45

Gln Thr Tyr Pro Arg Thr Asn Thr Gly Ser Asn Thr Tyr
        50                  55                  60

<210> SEQ ID NO 381
<211> LENGTH: 60
<212> TYPE: PRT
<213> ORGANISM: Artificial
<220> FEATURE:
<223> OTHER INFORMATION: Hybrid lizard, human and salmon construct
<220> FEATURE:
<221> NAME/KEY: MOD_RES
<222> LOCATION: (29)..(29)
<223> OTHER INFORMATION: 12-Ado

<400> SEQUENCE: 381

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Cys Asn Thr
                20                  25                  30

Ala Thr Cys Val Leu Gly Arg Leu Ser Glu Glu Leu His Arg Leu Gln
            35                  40                  45

Thr Tyr Pro Arg Thr Asn Thr Gly Ser Asn Thr Tyr
        50                  55                  60

<210> SEQ ID NO 382
<211> LENGTH: 61
<212> TYPE: PRT
<213> ORGANISM: Artificial
<220> FEATURE:
<223> OTHER INFORMATION: Hybrid lizard, human and salmon construct
<220> FEATURE:
```

```
<221> NAME/KEY: MOD_RES
<222> LOCATION: (29)..(29)
<223> OTHER INFORMATION: 3,6-dioxactoanoyl

<400> SEQUENCE: 382
```

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Lys Cys Asn
            20                  25                  30

Thr Ala Thr Cys Val Leu Gly Arg Leu Ser Glu Glu Leu His Arg Leu
        35                  40                  45

Gln Thr Tyr Pro Arg Thr Asn Thr Gly Ser Asn Thr Tyr
    50                  55                  60

```
<210> SEQ ID NO 383
<211> LENGTH: 60
<212> TYPE: PRT
<213> ORGANISM: Artificial
<220> FEATURE:
<223> OTHER INFORMATION: Hybrid lizard, human and salmon construct
<220> FEATURE:
<221> NAME/KEY: MOD_RES
<222> LOCATION: (29)..(29)
<223> OTHER INFORMATION: 3,6-dioxactoanoyl

<400> SEQUENCE: 383
```

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Cys Asn Thr
            20                  25                  30

Ala Thr Cys Val Leu Gly Arg Leu Ser Glu Glu Leu His Arg Leu Gln
        35                  40                  45

Thr Tyr Pro Arg Thr Asn Thr Gly Ser Asn Thr Tyr
    50                  55                  60

```
<210> SEQ ID NO 384
<211> LENGTH: 61
<212> TYPE: PRT
<213> ORGANISM: Artificial
<220> FEATURE:
<223> OTHER INFORMATION: Hybrid lizard, human and salmon construct
<220> FEATURE:
<221> NAME/KEY: MOD_RES
<222> LOCATION: (29)..(29)
<223> OTHER INFORMATION: 5-Apa

<400> SEQUENCE: 384
```

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Lys Cys Asn
            20                  25                  30

Thr Ala Thr Cys Val Leu Gly Arg Leu Ser Glu Glu Leu His Arg Leu
        35                  40                  45

Gln Thr Tyr Pro Arg Thr Asn Thr Gly Ser Asn Thr Tyr
    50                  55                  60

```
<210> SEQ ID NO 385
<211> LENGTH: 60
<212> TYPE: PRT
<213> ORGANISM: Artificial
<220> FEATURE:
<223> OTHER INFORMATION: Hybrid lizard, human and salmon construct
<220> FEATURE:
<221> NAME/KEY: MOD_RES
<222> LOCATION: (29)..(29)
```

<223> OTHER INFORMATION: 5-Apa

<400> SEQUENCE: 385

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Cys Asn Thr
            20                  25                  30

Ala Thr Cys Val Leu Gly Arg Leu Ser Glu Glu Leu His Arg Leu Gln
        35                  40                  45

Thr Tyr Pro Arg Thr Asn Thr Gly Ser Asn Thr Tyr
    50                  55                  60

<210> SEQ ID NO 386
<211> LENGTH: 62
<212> TYPE: PRT
<213> ORGANISM: Artificial
<220> FEATURE:
<223> OTHER INFORMATION: Hybrid lizard, human and salmon construct
<220> FEATURE:
<221> NAME/KEY: MOD_RES
<222> LOCATION: (29)..(30)
<223> OTHER INFORMATION: bAla

<400> SEQUENCE: 386

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Xaa Lys Cys
            20                  25                  30

Asn Thr Ala Thr Cys Val Leu Gly Arg Leu Ser Glu Glu Leu His Arg
        35                  40                  45

Leu Gln Thr Tyr Pro Arg Thr Asn Thr Gly Ser Asn Thr Tyr
    50                  55                  60

<210> SEQ ID NO 387
<211> LENGTH: 61
<212> TYPE: PRT
<213> ORGANISM: Artificial
<220> FEATURE:
<223> OTHER INFORMATION: Hybrid lizard, human and salmon construct
<220> FEATURE:
<221> NAME/KEY: MOD_RES
<222> LOCATION: (29)..(30)
<223> OTHER INFORMATION: bAla

<400> SEQUENCE: 387

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Xaa Xaa Cys Asn
            20                  25                  30

Thr Ala Thr Cys Val Leu Gly Arg Leu Ser Glu Glu Leu His Arg Leu
        35                  40                  45

Gln Thr Tyr Pro Arg Thr Asn Thr Gly Ser Asn Thr Tyr
    50                  55                  60

<210> SEQ ID NO 388
<211> LENGTH: 61
<212> TYPE: PRT
<213> ORGANISM: Artificial
<220> FEATURE:
<223> OTHER INFORMATION: Hybrid lizard, human and salmon construct
<220> FEATURE:
<221> NAME/KEY: MOD_RES
<222> LOCATION: (29)..(29)
<223> OTHER INFORMATION: 4,7,10-trioxa-13-tridecanamine succinimidyl

<400> SEQUENCE: 388

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Lys Cys Asn
            20                  25                  30

Thr Ala Thr Cys Val Leu Gly Arg Leu Ser Glu Glu Leu His Arg Leu
        35                  40                  45

Gln Thr Tyr Pro Arg Thr Asn Thr Gly Ser Asn Thr Tyr
    50                  55                  60

<210> SEQ ID NO 389
<211> LENGTH: 60
<212> TYPE: PRT
<213> ORGANISM: Artificial
<220> FEATURE:
<223> OTHER INFORMATION: Hybrid lizard, human and salmon construct
<220> FEATURE:
<221> NAME/KEY: MOD_RES
<222> LOCATION: (29)..(29)
<223> OTHER INFORMATION: 4,7,10-trioxa-13-tridecanamine succinimidyl

<400> SEQUENCE: 389

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Cys Asn Thr
            20                  25                  30

Ala Thr Cys Val Leu Gly Arg Leu Ser Glu Glu Leu His Arg Leu Gln
        35                  40                  45

Thr Tyr Pro Arg Thr Asn Thr Gly Ser Asn Thr Tyr
    50                  55                  60

<210> SEQ ID NO 390
<211> LENGTH: 43
<212> TYPE: PRT
<213> ORGANISM: Artificial
<220> FEATURE:
<223> OTHER INFORMATION: Hybrid human and salmon construct
<220> FEATURE:
<221> NAME/KEY: MOD_RES
<222> LOCATION: (2)..(2)
<223> OTHER INFORMATION: Tyr(SO3)

<400> SEQUENCE: 390

Asp Tyr Met Gly Trp Met Asp Phe Gly Lys Arg Lys Cys Asn Thr Ala
1               5                   10                  15

Thr Cys Ala Thr Gln Arg Leu Ala Asn Glu Leu Val Arg Leu Gln Thr
            20                  25                  30

Tyr Pro Arg Thr Asn Val Gly Ser Asn Thr Tyr
        35                  40

<210> SEQ ID NO 391
<211> LENGTH: 68
<212> TYPE: PRT
<213> ORGANISM: Artificial
<220> FEATURE:
<223> OTHER INFORMATION: Hybird lizard human construct
<220> FEATURE:
<221> NAME/KEY: MISC_FEATURE
<223> OTHER INFORMATION: C-term amidated
<220> FEATURE:
<221> NAME/KEY: MOD_RES
<222> LOCATION: (29)..(30)
<223> OTHER INFORMATION: bAla

<400> SEQUENCE: 391

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Xaa Phe Leu
                20                  25                  30

Phe His Tyr Ser Lys Thr Gln Lys Leu Gly Lys Ser Asn Val Val Glu
            35                  40                  45

Glu Leu Gln Ser Pro Phe Ala Ser Gln Ser Arg Gly Tyr Phe Leu Phe
        50                  55                  60

Arg Pro Arg Asn
65

<210> SEQ ID NO 392
<211> LENGTH: 55
<212> TYPE: PRT
<213> ORGANISM: Artificial
<220> FEATURE:
<223> OTHER INFORMATION: Hybrid lizard and human construct
<220> FEATURE:
<221> NAME/KEY: MISC_FEATURE
<223> OTHER INFORMATION: C-term amidated
<220> FEATURE:
<221> NAME/KEY: MOD_RES
<222> LOCATION: (29)..(30)
<223> OTHER INFORMATION: bAla

<400> SEQUENCE: 392

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Xaa Phe Arg
                20                  25                  30

Val Asp Glu Glu Phe Gln Ser Pro Phe Ala Ser Gln Ser Arg Gly Tyr
            35                  40                  45

Phe Leu Phe Arg Pro Arg Asn
        50                  55

<210> SEQ ID NO 393
<211> LENGTH: 39
<212> TYPE: PRT
<213> ORGANISM: Artificial
<220> FEATURE:
<223> OTHER INFORMATION: Hybrid lizard and human construct
<220> FEATURE:
<221> NAME/KEY: MISC_FEATURE
<223> OTHER INFORMATION: C-term amidated
<220> FEATURE:
<221> NAME/KEY: MOD_RES
<222> LOCATION: (29)..(30)
<223> OTHER INFORMATION: bAla

<400> SEQUENCE: 393

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Xaa Gly Tyr
                20                  25                  30

Phe Leu Phe Arg Pro Arg Asn
            35

<210> SEQ ID NO 394
<211> LENGTH: 62
<212> TYPE: PRT
<213> ORGANISM: Artificial
<220> FEATURE:
<223> OTHER INFORMATION: Hybrid lizard and human construct
<220> FEATURE:
<221> NAME/KEY: MOD_RES
<222> LOCATION: (29)..(30)

<223> OTHER INFORMATION: bAla

<400> SEQUENCE: 394

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Xaa Ser Pro
            20                  25                  30

Lys Met Val Gln Gly Ser Gly Cys Phe Gly Arg Lys Met Asp Arg Ile
        35                  40                  45

Ser Ser Ser Ser Gly Leu Gly Cys Lys Val Leu Arg Arg His
    50                  55                  60

<210> SEQ ID NO 395
<211> LENGTH: 73
<212> TYPE: PRT
<213> ORGANISM: Artificial
<220> FEATURE:
<223> OTHER INFORMATION: Hybrid lizard and human construct
<220> FEATURE:
<221> NAME/KEY: MOD_RES
<222> LOCATION: (40)..(41)
<223> OTHER INFORMATION: bAla

<400> SEQUENCE: 395

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Xaa Xaa Ser Pro Lys Met Val Gln Gly
        35                  40                  45

Ser Gly Cys Phe Gly Arg Lys Met Asp Arg Ile Ser Ser Ser Ser Gly
    50                  55                  60

Leu Gly Cys Lys Val Leu Arg Arg His
65                  70

<210> SEQ ID NO 396
<211> LENGTH: 32
<212> TYPE: PRT
<213> ORGANISM: Artificial
<220> FEATURE:
<223> OTHER INFORMATION: Hybrid salmon and human construct
<220> FEATURE:
<221> NAME/KEY: MISC_FEATURE
<223> OTHER INFORMATION: C-term amidated

<400> SEQUENCE: 396

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 397
<211> LENGTH: 39
<212> TYPE: PRT
<213> ORGANISM: Artificial
<220> FEATURE:
<223> OTHER INFORMATION: Hybrid human and salmon construct
<220> FEATURE:
<221> NAME/KEY: MOD_RES
<222> LOCATION: (4)..(4)
<223> OTHER INFORMATION: d-Leucine

<400> SEQUENCE: 397

Ser Ser Ser Leu Pro Gln Thr Lys Cys Asn Thr Ala Thr Cys Val Leu
1               5                   10                  15

```
Gly Arg Leu Ser Gln Glu Leu His Arg Leu Gln Thr Tyr Pro Arg Thr
            20                  25                  30

Asn Thr Gly Ser Asn Thr Tyr
            35

<210> SEQ ID NO 398
<211> LENGTH: 43
<212> TYPE: PRT
<213> ORGANISM: Artificial
<220> FEATURE:
<223> OTHER INFORMATION: Hybrid human and salmon construct
<220> FEATURE:
<221> NAME/KEY: MOD_RES
<222> LOCATION: (2)..(2)
<223> OTHER INFORMATION: para(CH2SO3)Phe

<400> SEQUENCE: 398

Asp Phe Met Gly Trp Met Asp Phe Gly Lys Arg Lys Cys Asn Thr Ala
 1               5                  10                  15

Thr Cys Ala Thr Gln Arg Leu Ala Asn Glu Leu Val Arg Leu Gln Thr
            20                  25                  30

Tyr Pro Arg Thr Asn Val Gly Ser Asn Thr Tyr
            35                  40

<210> SEQ ID NO 399
<211> LENGTH: 41
<212> TYPE: PRT
<213> ORGANISM: Homo sapiens

<400> SEQUENCE: 399

Ile Val Leu Ser Leu Asp Val Pro Ile Gly Leu Leu Gln Ile Leu Leu
 1               5                  10                  15

Glu Gln Ala Arg Ala Arg Ala Ala Arg Glu Gln Ala Thr Thr Asn Ala
            20                  25                  30

Arg Ile Leu Ala Arg Val Gly His Cys
            35                  40
```

HYBRID POLYPEPTIDES WITH SELECTABLE PROPERTIES

RELATED APPLICATIONS

This application is a continuation of U.S. application Ser. No. 11/206,903 filed Aug. 17, 2005, now U.S. Pat. No. 8,076,288 entitled "Hybrid Polypeptides With Selectable Properties", which is a continuation-in-part of U.S. application Ser. No. 11/201,664 filed Aug. 11, 2005, now abandoned, which is a continuation-in-part of U.S. application Ser. No. 11/055,093, filed Feb. 11, 2005, now abandoned, which claims priority to commonly-owned U.S. Provisional Application No. 60/543,407, filed Feb. 11, 2004, the disclosures of which are hereby incorporated by reference in their entirety, and to each of which priority is claimed.

SEQUENCE LISTING

The instant application contains a Sequence Listing which has been submitted in ASCII format via EFS-Web and is hereby incorporated by reference in its entirety. The ASCII copy, created on Jun. 12, 2012, is named "0701US-CON2—Seq_lst_6-12-12.txt" and is 178 KB file in size.

FIELD OF THE INVENTION

The present invention relates to peptide chemistry, and more particularly to hybrid polypeptides with selectable properties.

BACKGROUND OF THE INVENTION

Central to many metabolic diseases and disorders is the regulation of insulin levels and blood glucose levels. Insulin secretion is modulated in part by secretagogue hormones, termed as incretins, which are produced by enteroendocrine cells. The incretin hormone, glucagon-like peptide-1 ("GLP-1") is a peptide hormone secreted by intestinal cells that has been shown in multiple studies to produce an enhancing effect on insulin secretion. GLP-1 is processed from proglucagon in the gut and enhances nutrient-induced insulin release (Krcymann B., et al., Lancet, 2:1300-1303 (1987)). Various truncated forms of GLP-1, are known to stimulate insulin secretion (insulinotropic action) and cAMP formation [see, e.g., Mojsov, S., Int. J. Pep. Pro. Res., 40:333-343 (1992)]. A relationship between various in vitro laboratory experiments and mammalian, especially human, insulinotropic responses to exogenous administration of GLP-1, GLP1 (7-36) amide (SEQ ID NO: 61), and GLP1(7-37) acid (SEQ ID NO: 204) has been established (see, e.g., Nauck, M. A., et al., Diabetologia, 36:741-744 (1993); Gutniak, M., et al., New Eng. J. of Med., 326(20):1316-1322 (1992); Nauck, M. A., et al., J. Clin. Invest., 91:301-307 (1993); and Thorens, B., et al., Diabetes, 42:1219-1225 (1993)).

GLP1(7-36) amide (SEQ ID NO: 61) exerts a pronounced antidiabetogenic effect in insulin-dependent diabetics by stimulating insulin sensitivity and by enhancing glucose-induced insulin release at physiological concentrations (Gutniak M., et al., New Eng. J. Med., 326:1316-1322 (1992)). When administered to non-insulin dependent diabetics, GLP1(7-36) amide (SEQ ID NO: 61) stimulates insulin release, lowers glucagon secretion, inhibits gastric emptying and enhances glucose utilization (Nauck, 1993; Gutniak, 1992; Nauck, 1993). However, the use of GLP-1 type molecules for prolonged therapy of diabetes has been complicated because the serum half-life of such peptides is quite short.

More particularly, GLP-1 is a 30-amino acid peptide derived from proglucagon, a 160-amino acid prohormone. Actions of different prohormone convertases in the pancreas and intestine result in the production of glucagon and other ill-defined peptides, whereas cleavage of proglucagon results in the production of GLP-1 and GLP-2 as well as two other peptides. The amino acid sequence of GLP-1 is 100% homologous in all mammals studied so far, implying a critical physiological role. GLP-1 (7-37) acid is C-terminally truncated and amidated to form GLP-1 (7-36) NH2 (SEQ ID NO: 61). The biological effects and metabolic turnover of the free acid GLP-1 (7-37) OH (SEQ ID NO: 204), and the amide, GLP-1 (7-36) NH2 (SEQ ID NO: 61), are indistinguishable. By convention, the numbering of the amino acids is based on the processed GLP-1 (1-37) OH (SEQ ID NO: 59) from proglucagon. The biologically active GLP-1 is the result of further processing: GLP-1 (7-36) NH2 (SEQ ID NO: 61). Thus the first amino acid of GLP-1 (7-37) OH (SEQ ID NO: 204) or GLP-1 (7-36)NH$_2$ (SEQ ID NO: 61) is $^7$His.

In the gastrointestinal tract, GLP-1 is produced by L-cells of intestinal, colonic and rectal mucosa, in response to stimulation by intraluminal glucose. The plasma half-life of active GLP-1 is <5 minutes, and its metabolic clearance rate is around 12-13 minutes (Holst, Gastroenterology 107(6):1848-55 (1994)). The major protease involved in the metabolism of GLP-1 is dipeptidyl peptidase (DPP) IV (CD26) which cleaves the N-terminal His-Ala dipeptide, thus producing metabolites, GLP-1 (9-37) OH (SEQ ID NO: 205) or GLP-1 (9-36) NH$_2$ (SEQ ID NO: 206) which are variously described as inactive, weak agonist or antagonists of GLP-1 receptor. The GLP-1 receptor (GLP-1R) is a G protein coupled receptor of 463 amino acid and is localized in pancreatic beta cells, in the lungs, and to a lesser extent in the brain, adipose tissue and kidneys. The stimulation of GLP-1R by GLP-1 (7-37) OH (SEQ ID NO: 204) or GLP-1 (7-36) NH$_2$ (SEQ ID NO: 61) results in adenylate cyclase activation, cAMP synthesis, membrane depolarization, rise in intracellular calcium and increase in glucose-induced insulin secretion (Holz et al., J. Biol. Chem. 270(30):17749-57 (1995)).

GLP-1 is a potent insulin secretagogue that is secreted from the intestinal mucosa in response to food intake. The profound incretin effect of GLP-1 is underscored by the fact that GLP-1R knockout mice are glucose-intolerant. The incretin response of i.v. infused GLP-1 is preserved in diabetic subjects, though the incretin response to oral glucose in these patients is compromised. GLP-1 administration by infusion or sc injections controls fasting glucose levels in diabetic patients, and maintains the glucose threshold for insulin secretion (Gutniak et al., N. Engl. J. Med. 326:1316-22 (1992); Nauck et al., Diabet. Med. 13:(9 Suppl 5):539-543 (1996); Nauck et al., J. Clin. Endocrinol. Metab. 76:912-917 (1993)). GLP-1 has shown tremendous potential as a therapeutic agent capable of augmenting insulin secretion in a physiological manner, while avoiding hypoglycemia associated with sulfonylurea drugs.

Other important effects of GLP-1 on glucose homeostasis are suppression of glucagon secretion and inhibition of gastric motility. GLP-1 inhibitory actions on pancreatic alpha cell secretion of glucagon leads to decreases in hepatic glucose production via reduction in gluconeogenesis and glycogenolysis. This antiglucagon effect of GLP-1 is preserved in diabetic patients.

The so-called ileal brake effect of GLP-1, in which gastric motility and gastric secretion are inhibited, is effected via vagal efferent receptors or by direct action on intestinal smooth muscle. Reduction of gastric acid secretion by GLP-1 contributes to a lag phase in nutrient availability, thus obviating the need for rapid insulin response. In summary, the gastrointestinal effects of GLP-1 contribute significantly to delayed glucose and fatty acid absorption and modulate insulin secretion and glucose homeostasis.

GLP-1 has also been shown to induce beta cell specific genes, such as GLUT-1 transporter, insulin (via the interaction of PDX-1 with insulin gene promoter), and hexokinase-1. Thus GLP-1 could potentially reverse glucose intolerance normally associated with aging, as demonstrated by rodent experiments. In addition, GLP-1 may contribute to beta cell neogenesis and increase beta cell mass, in addition to restoring beta cell function during states of beta cell insufficiency.

Central effects of GLP-1 include increases in satiety coupled with decreases in food intake, effected via the action of hypothalamic GLP-1R. A 48 hour continuous SC infusion of GLP-1 in type II diabetic subjects, decreased hunger and food intake and increased satiety. These anorectic effects were absent in GLP-1R knock out mice.

Exendins are another family of peptides implicated in insulin secretion. Exendins are found in the saliva of the Gila-monster, a lizard endogenous to Arizona, and the Mexican Beaded Lizard. Exendin-3 is present in the saliva of *Heloderma horridum*, and exendin-4 is present in the saliva of *Heloderma suspectum* (Eng, J., et al., *J. Biol. Chem.*, 265: 20259-62, 1990; Eng., J., et al., *J. Biol. Chem.*, 267:7402-05 (1992)). The exendins have some sequence similarity to several members of the glucagon-like peptide family, with the highest identity, 53%, being to GLP-1 (Goke, et al., *J. Biol. Chem.*, 268:19650-55 (1993)).

Exendin-4 binds the GLP-1 receptors on insulin-secreting TC1 cells, at dispersed acinar cells from guinea pig pancreas, and at parietal cells from stomach; the peptide also stimulates somatostatin release and inhibits gastrin release in isolated stomachs (Goke, et al., *J. Biol. Chem.*, 268:19650-55 (1993); Schepp, et al., *Eur. J. Pharmacol.*, 69:183-91 (1994); Eissele, et al., *Life Sci.*, 55:629-34 (1994)). Exendin-3 and exendin-4 were found to bind the GLP-1 receptors on, to stimulating cAMP production in, and amylase release from, pancreatic acinar cells (Malhotra, R., et al., *Relulatory Peptides*, 41:149-56 (1992); Raufman, et al., *J. Biol. Chem.*, 267:21432-37 (1992); Singh, et al., *Regul. Pept.*, 53:47-59 (1994)). The use of the insulinotropic activities of exendin-3 and exendin-4 for the treatment of diabetes mellitus and the prevention of hyperglycemia has been proposed (Eng, U.S. Pat. No. 5,424,286).

Truncated exendin peptides such as exendin[9-39], a carboxyamidated molecule, and fragments 3-39 through 9-39 have been reported to be potent and selective antagonists of GLP-1 (Goke, et al., *J. Biol. Chem.*, 268:19650-55 (1993); Raufman, J. P., et al., *J. Biol. Chem.*, 266:2897-902 (1991); Schepp, W., et al., *Eur. J. Pharm.*, 269:183-91 (1994); Montrose-Rafizadeh, et al., *Diabetes*, 45(Suppl. 2):152A (1996)). Exendin[9-39] (SEQ ID NO: 207) blocks endogenous GLP-1 in vivo, resulting in reduced insulin secretion (Wang, et al., *J. Clin. Invest.*, 95:417-21 (1995); D'Alessio, et al., *J. Clin. Invest.*, 97:133-38 (1996)). The receptor apparently responsible for the insulinotropic effect of GLP-1 has been cloned from rat pancreatic islet cells (Thorens, B., *Proc. Natl. Acad. Sci. USA* 89:8641-8645 (1992)). Exendins and exendin[9-39] bind to the cloned GLP-1 receptor (rat pancreatic-cell GLP-1 receptor: Fehmann H C, et al., *Peptides*, 15 (3): 453-6 (1994); human GLP-1 receptor: Thorens B, et al., *Diabetes*, 42 (11): 1678-82 (1993)). In cells transfected with the cloned GLP-1 receptor, exendin-4 is an agonist, i.e., it increases cAMP, while exendin[9-39] (SEQ ID NO: 207) is an antagonist, i.e., it blocks the stimulatory actions of exendin-4 and GLP-1. Id.

More particularly, exendin-4 is a 39 amino acid C-terminal amidated peptide found in the saliva of the Gila Monster (*Heloderma suspectum*), with a 53% amino acid sequence identity to the GLP-1 peptide sequence. See, e.g., Eng, J., et al. "Isolation and Characterization of Exendin-4, and Exendin-3 Analogue from Heloderma suspectum Venom," *J. Bio. Chem.*, 267:11, p. 7402-7405 (1992), Young, A. A., et al., "Glucose-Lowering and Insulin-Sensitizing Actions of Exendin-4," *Diabetes*, Vol. 48, p. 1026-1034, May, 1999. In terms of its activity, exendin-4 is a highly specific agonist for the GLP-1 receptor, and, like GLP-1, is able to stimulate insulin secretion. Therefore, like GLP-1, exendin-4 is regarded as an insulinotropic peptide.

However, unlike GLP-1, exendin-4 has a relatively long half-life in humans, because of its resistance to the dipeptidyl peptidase IV which rapidly degrades the GLP-1 sequence in vivo. Furthermore, it has been shown that, as compared to GLP-1, exendin-4 has a stronger capability to stimulate insulin secretion, and that a lower concentration of exendin-4 may be used to obtain such stimulating activity. See, e.g., U.S. Pat. No. 5,424,286, herein incorporated by reference. Therefore exendin-4 peptides or derivatives thereof (for examples of such derivatives, see, e.g., U.S. Pat. No. 6,528,486, herein incorporated by reference, and its corresponding international application WO 01/04156) have a greater potential utility for the treatment of conditions involving the dysregulation of insulin levels (e.g., conditions such as diabetes) than either insulin or GLP-1.

Another family of peptide hormones implicated in metabolic diseases and disorders is the amylin family of peptide hormones, including amylin, calcitonin, calcitonin gene related peptide, adrenomedullin, and intermedin (also known as "AFP-6"). Amylin is a 37-amino acid peptide hormone. It was isolated, purified and chemically characterized as the major component of amyloid deposits in the islets of pancreases of human Type 2 diabetics (Cooper et al., *Proc. Natl. Acad. Sci.*, USA, 84:8628-8632 (1987)). The amylin molecule has two post-translational modifications: the C-terminus is amidated, and the cysteines in positions 2 and 7 are cross-linked to form an N-terminal loop. The sequence of the open reading frame of the human amylin gene shows the presence of the Lys-Arg dibasic amino acid proteolytic cleavage signal, prior to the N-terminal codon for Lys, and the Gly prior to the Lys-Arg proteolytic signal at the CLAIMS-terminal position, a typical sequence for amidation by protein amidating enzyme, PAM (Cooper et al., *Biochem. Biophys. Acta*, 1014:247-258 (1989)).

Amylin is believed to regulate gastric emptying, and suppress glucagon secretion and food intake, thus regulating the rate of glucose appearance in the circulation. It appears to complement the actions of insulin, which regulates the rate of glucose disappearance from the circulation and its uptake by peripheral tissues. These actions are supported by experimental findings in rodents and humans, which indicate that amylin complements the effects of insulin in postprandial glucose control by at least three independent mechanisms, all of which affect the rate of glucose appearance. First, amylin suppresses postprandial glucagon secretion. Compared to healthy adults, patients with type 1 diabetes have no circulating amylin and patients with type 2 diabetes have diminished postprandial amylin concentrations. Furthermore, infusion of an amylin specific monoclonal antibody, which bound circulating amylin, again resulted in greatly elevated glucagon concentrations relative to controls. Both of these results point to a physiological role of endogenous amylin in the regulation of postprandial glucagon secretion. Second, amylin slows gastrointestinal motility and gastric emptying. Finally, intrahypothalamic injections of rat amylin were shown to reduce feeding in rats and alter neurotransmitter metabolism in the hypothalamus. In certain studies, food intake was significantly reduced for up to eight hours following the intrahypothalamic injection of rat amylin and rat CGRP. In human trials, an amylin analog, pramlintide, has been shown to reduce weight or weight gain. Amylin may be beneficial in treating metabolic conditions such as diabetes and obesity. Amylin may also be used to treat pain, bone disorders, gastritis, to modulate lipids, in particular triglycerides, or to affect body composition such as the preferential loss of fat and sparing of lean tissue.

The hormone calcitonin (CT) was named for its secretion in response to induced hypercalcemia and its rapid hypocalcemic effect. It is produced in and secreted from neuroendocrine cells in the thyroid that have since been termed C cells. The best-studied action of CT(1-32) (SEQ ID NO: 48) is its effect on the osteoclast. In vitro effects of CT include the rapid loss of ruffled borders and decreased release of lysosomal enzymes. Ultimately, the inhibition of osteoclast functions by CT results in a decrease in bone resorption. However, neither a chronic reduction of serum CT in the case of thyroidectomy nor the increased serum CT found in medullary thyroid cancer appears to be associated with changes in serum calcium or bone mass. It is thus most likely that a major function of CT(1-32) (SEQ ID NO: 48) is to combat acute hypercalcemia in emergency situations and/or protect the skeleton during periods of "calcium stress" such as growth, pregnancy, and lactation. (Reviewed in Becker, *JCEM*, 89(4): 1512-1525 (2004) and Sexton, *Current Medicinal Chemistry* 6: 1067-1093 (1999)). Consistent with this is recent data from the calcitonin gene knockout mouse, which removes both the calcitonin and the CGRP-I peptides, that revealed that the mouse had normal levels of basal calcium-related values, but an increased calcemic response (Kurihara H, et al., *Hypertens Res.* 2003 February; 26 Suppl:S105-8).

CT has an effect on plasma calcium levels and inhibits osteoclast function and is widely used for the treatment of osteoporosis. Therapeutically, salmon CT (sCT) appears to increase bone density and decrease fracture rates with minimal adverse effects. CT has also been successfully used over the past 25 years as a therapy for Paget's disease of bone, which is a chronic skeletal disorder that may result in enlarged or deformed bones in one or more regions of the skeleton. CT is also widely used for its analgesic effect on bone pain experienced during osteoporosis, although the mechanism for this effect is not clearly understood.

Calcitonin gene related peptide (CGRP) is a neuropeptide whose receptors are widely distributed in the body, including the nervous system and the cardiovascular system. This peptide seems to modulate sensory neurotransmission and is one of the most potent endogenous vasodilatory peptide discovered to date. Reported biological effects for CGRP include: modulation of substance P in inflammation, nicotinic receptor activity at the neuromuscular junction, stimulation of pancreatic enzyme secretion, a reduction of gastric acid secretion, peripheral vasodilation, cardiac acceleration, neuromodulation, regulation of calcium metabolism, osteogenic stimulation, insulin secretion, an increase in body temperature and a decrease in food intake. (Wimalawansa, Amylin, calcitonin gene-related peptide, calcitonin and ADM: a peptide superfamily. *Crit. Rev Neurobiol.* 1997; 11(2-3):167-239). An important role of CGRP is to control blood flow to various organs by its potent vasodilatory actions, as evidenced by a decrease of mean arterial pressure following intravenous administration of α-CGRP. The vasodilatory actions are also supported by recent analysis of homozygous knockout CGRP mice, which demonstrated elevated peripheral vascular resistance and high blood pressure caused by increased peripheral sympathetic activity (Kurihara H, et al., Targeted disruption of ADM and αCGRP genes reveals their distinct biological roles. *Hypertens Res.* 2003 February; 26 Suppl:S105-8). Thus, CGRP appears to elicit vasodilatory effects, hypotensive effects and an increase in heart rate among other actions.

Prolonged infusion of CGRP into patients with congestive cardiac failure has shown a sustained beneficial effect on hemodynamic functions without adverse effects, suggesting a use in heart failure. Other indications of CGRP use include renal failure, acute and chronic coronary artery ischemia, treatment of cardiac arrhythmia, other peripheral vascular disease such as Raynaud's phenomenon, subarachnoid hemorrhage, hypertension, and pulmonary hypertension. Preeclamptic toxemia of pregnancy and preterm labor are also potentially treatable. (Wimalawansa, 1997). Recent therapeutic uses include the use of CGRP antagonists for the treatment of migraine headaches.

Adrenomedullin (ADM) is almost ubiquitously expressed with many more tissues containing the peptide than not. A published review of ADM, (Hinson, J. P. et al., *Endocrine Reviews* (2000) 21(2): 138-167) details its effects on the cardiovascular system, cellular growth, the central nervous system and the endocrine system, with a range of biological actions including vasodilation, cell growth, regulation of hormone secretion, and natriuresis. Studies in rat, cat, sheep, and man confirm that intravenous infusion of ADM results in potent and sustained hypotension, and is comparable to that of CGRP. However, the hypotensive effect of ADM on mean arterial pressure in the anesthetized rat is not inhibited by the CGRP antagonist $CGRP_{8-37}$ suggesting that this effect is not mediated via CGRP receptors. Acute or chronic administration of human ADM in rats, anesthetized, conscious or hypertensive, results in a significant decrease in total peripheral resistance accompanied by a fall in blood pressure, with a concomitant rise in heart rate, cardiac output and stroke volume.

ADM has also been proposed as an important factor in embryogenesis and differentiation and as an apoptosis survival factor for rat endothelial cells. This is supported by recent mouse ADM knockout studies, in which mice homozygous for loss of the ADM gene demonstrated defective vascular formation during embryogenesis and thus died mid-gestation. It was reported that ADM+/−heterozygous mice had high blood pressure along with susceptibility to tissue injury (Kurihara H, et al., *Hypertens Res.* 2003 February; 26 Suppl:S105-8).

ADM affects such endocrine organs as the pituitary, the adrenal gland, reproductive organs and the pancreas. The peptide appears to have a role in inhibiting ACTH release from the pituitary. In the adrenal gland, it appears to affect the secretory activity of the adrenal cortex in both rat and human and it increases adrenal blood flow, acting as a vasodilator in the adrenal vascular bed in intact rats. ADM has been shown to be present throughout the female reproductive tract and plasma levels are elevated in normal pregnancy. Studies in a rat model of preeclampsia show that ADM can reverse hypertension and decrease pup mortality when given to rats during late gestation. Because it did not have a similar effect in animals in early gestation or non-pregnant rats in the preeclampsia model, this suggests that ADM may play an important regulatory role in the utero-placental cardiovascular system. In the pancreas, ADM most likely plays an inhibitory role since it attenuated and delayed insulin response to an oral glucose challenge, resulting in initial elevated glucose levels. ADM can also affect renal function. A bolus administered peripherally can significantly lower mean arterial pressure and raise renal blood flow, glomerular filtration rate and urine flow. In some cases, there is also an increase in Na+ excretion.

ADM also has other peripheral effects on bone and on the lung. For bone, studies have supported a role beyond the cardiovascular system and fluid homeostasis and have demonstrated that ADM acts on fetal and adult rodent osteoblasts to increase cell growth comparable to those of known osteoblast growth factors such as transforming growth factor-P. This is important clinically as one of the major challenges in osteoporosis research is to develop a therapy that increases bone mass via osteoblastic stimulation. In the lung, ADM not only causes pulmonary vasodilation, but also inhibits bronchoconstriction induced by histamine or acetylcholine. Recent studies using aerosolized ADM to treat pulmonary hypertension in a rat model indicate that inhalation treatment of this condition is effective, as evidenced by the fact that mean pulmonary arterial pressure and total pulmonary resistance were markedly lower in rats treated with ADM than in those given saline. This result was achieved without an alteration in systemic arterial pressure or heart rate (Nagaya N et al., *Am J Physiol Heart Circ Physiol.* 2003; 285:H2125-31).

In healthy volunteers, i.v. infusion of ADM has been shown to reduce arterial pressure and to stimulate heart rate, cardiac output, plasma levels of cAMP, prolactin, norepinephrine and rennin. In these patients, there was little or no increase in urine volume or sodium excretion observed. In patients with heart failure or chronic renal failure, i.v. ADM had similar effects to those seen in normal subjects, and also induced diuresis and natriuresis, depending on the dose administered (Nicholls, M G et al. *Peptides.* 2001; 22:1745-1752) Experimental ADM treatment has also been shown to be beneficial in arterial and pulmonary hypertension, septic shock and ischemia/reperfusion injury (Beltowski J., *Pol J. Pharmacol.* 2004; 56:5-27). Other indications for ADM treatment include: peripheral vascular disease, subarachnoid hemorrhage, hypertension, preeclamptic toxemia of pregnancy and preterm labor, and osteoporosis.

Expression of AFP-6 (i.e., intermedin) is primarily in the pituitary and gastrointestinal tract. A specific receptor for AFP-6 has not been reported; however, binding studies indicate that AFP-6 binds to all the known receptors of the Amylin Family. AFP-6 has been shown to increase cAMP production in SK-N-MC and L6 cells expressing endogenous CGRP receptors and competes with labeled CGRP for binding to its receptors in these cells. In published in vivo studies, AFP-6 administration led to blood pressure reduction in both normal and spontaneously hypertensive rats, most likely via interactions with the CRLR/RAMP receptors. In vivo administration in mice led to a suppression of gastric emptying and food intake. (Roh et al. *J Biol. Chem.* 2004 Feb. 20; 279(8):7264-74.)

It has been reported that the biological actions of amylin family peptide hormones are generally mediated via binding to two closely related type II G protein-coupled receptors (GPCRs), the calcitonin receptor (CTR) and the calcitonin receptor like receptor (CRLR). Cloning and functional studies have shown that CGRP, ADM, and amylin interact with different combinations of CTR or the CRLR and the receptor activity modifying protein (RAMP). Many cells express multiple RAMPs. It is believed that co-expression of RAMPs and either the CTR or CRLR is required to generate functional receptors for calcitonin, CGRP, ADM, and amylin. The RAMP family comprises three members (RAMP1, -2, and -3), which share less then 30% sequence identity, but have a common topological organization. Co-expression of CRLR and RAMP1 leads to the formation of a receptor for CGRP. Co-expression of CRLR and RAMP2 leads to the formation of a receptor for ADM. Co-expression of CRLR and RAMP3 leads to the formation of a receptor for ADM and CGRP. Co-expression of hCTR2 and RAMP1 leads to the formation of a receptor for amylin and CGRP. Co-expression of hCTR2 and RAMP3 leads to the formation of a receptor for amylin.

Yet another peptide hormone family implicated in metabolic diseases and disorders is the leptin family. The mature form of circulating leptin is a 146-amino acid protein that is normally excluded from the CNS by the blood-brain barrier (BBB) and the blood-CSF barrier. See, e.g., Weigle et al., 1995. *J Clin Invest* 96: 2065-2070. Leptin is the afferent signal in a negative feedback loop regulating food intake and body weight. The leptin receptor is a member of the cytokine receptor family. Leptin's anorexigenic effect is dependent on binding to homodimer of the Ob-Rb isoform of this receptor which encodes a long intra-cytoplasmic domain that includes several motifs for protein-protein interaction. Ob-Rb is highly expressed in the hypothalamus suggesting that this brain region is an important site of leptin action. Mutation of the mouse ob gene has been demonstrated to result in a syndrome that exhibits-pathophysiology that includes: obesity, increased body fat deposition, hyperglycemia, hyperinsulinemia, hypothermia, and impaired thyroid and reproductive functions in both male and female homozygous ob/ob obese mice (see e.g., Ingalis, et al., 1950. *J Hered* 41: 317-318. Therapeutic uses for leptin or leptin receptor include (i) diabetes (see, e.g., PCT Patent Applications WO 98/55139, WO 98/12224, and WO 97/02004); (ii) hematopoiesis (see, e.g., PCT Patent Applications WO 97/27286 and WO 98/18486); (iii) infertility (see, e.g., PCT Patent Applications WO 97/15322 and WO 98/36763); and (iv) tumor suppression (see, e.g., PCT Patent Applications WO 98/48831), each of which are incorporated herein by reference in their entirety.

The leptin receptor (OB-R) gene has been cloned (GenBank Accession No. AF098792) and mapped to the db locus (see, e.g., Tartaglia, et al., 1995. Cell 83: 1263-1271). Several transcripts of the OB-R, resulting from alternative splicing, have also been identified. Defects in OB-R produce a syndrome in the mutant diabetic ob/ob mouse that is phenotypically identical to the ob/ob mouse (see, e.g., Ghilardi, et al., 1996. *Proc. Natl. Acad. Sci. USA* 93: 6231-6235). In contrast to ob/ob mice, however, administration of recombinant leptin to C57BLKS/J-m ob/ob mice does not result in reduced food intake and body weight (see, e.g., Roberts and Greengerg, 1996. *Nutrition Rev.* 54: 41-49).

Most leptin-related studies able to report weight loss activity from administration of recombinant leptin, leptin fragments and/or leptin receptor variants have administered said constructs directly into the ventricles of the brain. See e.g., Weigle, et al., 1995. *J Clin Invest* 96: 2065-2070; Barash, et al., 1996. *Endocrinology* 137: 3144-3147.

Other studies have shown significant weight loss activity due to administration of leptin peptides through intraperitoneally (i.p.) administration to test subjects. See, Grasso et al., 1997. *Endocrinology* 138: 1413-1418. Further, leptin fragments, and most particularly an 18 amino acid fragment comprising residues taken from full length human leptin, have been reported to function in weight loss, but only upon direct administration through an implanted cannula to the lateral brain ventricle of rats. See, e.g., PCT Patent Applications WO 97/46585, which is incorporated herein by reference in its entirety.

Another peptide hormone implicated in metabolic diseases and disorders is cholecystokinin (CCK). CCK was reportedly identified in 1928 from preparations of intestinal extracts by its ability to stimulate gallbladder contraction. Other biological actions of CCK have since been reported, including stimulation of pancreatic secretion, delayed gastric emptying, stimulation of intestinal motility and stimulation of insulin secretion. See Lieverse et al., *Ann. N.Y. Acad. Sci.* 713: 268-272 (1994). The actions of CCK, also reportedly include effects on cardiovascular function, respiratory function, neurotoxicity and seizures, cancer cell proliferation, analgesia, sleep, sexual and reproductive behaviors, memory, anxiety and dopamine-mediated behaviors. Crawley and Corwin, *Peptides* 15: 731-755 (1994). Other reported effects of CCK include stimulation of pancreatic growth, stimulation of gallbladder contraction, inhibition of gastric acid secretion, pancreatic polypeptide release and a contractile component of peristalsis. Additional reported effects of CCK include vasodilation. Walsh, "Gastrointestinal Hormones," In Physiology of the Gastrointestinal Tract (3d ed. 1994; Raven Press, New York).

It has been reported that injections of combinations of glucagon, CCK and bombesin potentiated the inhibition of intake of condensed milk test meals in nondeprived rats over the inhibitions observed with individual compounds. Hinton et al., *Brain Res. Bull.* 17:615-619 (1986). It has also been reported that glucagon and CCK synergistically inhibit sham feeding in rats. LeSauter and Geary, *Am. J. Physiol.* 253: R217-225 (1987); Smith and Gibbs, *Annals N.Y. Acad. Sci.* 713:236-241 (1994). It has also been suggested that estradiol and CCK can have a synergistic effect on satiety. Dulawa et al., *Peptides* 15:913-918 (1994); Smith and Gibbs, supra. It has also been proposed that signals arising from the small intestine in response to nutrients therein may interact synergistically with CCK to reduce food intake. Cox, *Behav. Brain Res.* 38:35-44 (1990). Additionally, it has been reported that CCK induces satiety in several species. For example, it has been reported that feeding depression was caused by CCK injected intraperitoneally in rats, intraarterially in pigs, intravenously in cats and pigs, into the cerebral ventricles in monkeys, rats, dogs and sheep, and intravenously in obese and non-obese humans. See Lieverse et al., supra. Studies from several laboratories have reportedly confirmed the behavioral specificity of low doses of CCK on inhibition in feeding, by comparing responding for food to responding for nonfood reinforcers in both monkeys and rats and by showing that CCK elicits the sequence of behaviors normally observed after meal ingestion (i.e., the postprandial satiety sequence). Additionally, comparison of behavior after CCK to behavior after food ingestion, alone or in combination with CCK has reportedly revealed behavioral similarities between CCK and food ingestion. Crawley and Corwin, supra. It has also been reported that CCK in physiological plasma concentrations inhibits food intake and increases satiety in both lean and obese humans. See Lieverse et al., supra.

CCK was characterized in 1966 as a 33-amino acid peptide. Crawley and Corwin, supra. Species-specific molecular variants of the amino acid sequence of CCK have been identified. The 33-amino acid sequence and a truncated peptide, its 8-amino acid C-terminal sequence (CCK-8) have been reportedly identified in pig, rat, chicken, chinchilla, dog and humans. A 39-amino acid sequence was reportedly found in pig, dog and guinea pig. A 58-amino acid sequence was reported to have been found in cat, dog and humans. Frog and turtle reportedly show 47-amino acid sequences homologous to both CCK and gastrin. Very fresh human intestine has been reported to contain small amounts of an even larger molecule, termed CCK-83. In the rat, a principal intermediate form has been reportedly identified, and is termed CCK-22. Walsh, "Gastrointestinal Hormones," In Physiology of the Gastrointestinal Tract (3d ed. 1994; Raven Press, New York). A non-sulfated CCK-8 and a tetrapeptide (termed CCK-4 (CCK (30-33); SEQ ID NO: 208) have been reported in rat brain. The C-terminal pentapeptide (termed CCK-4 (CCK(29-33); SEQ ID NO: 209) conserves the structural homology of CCK, and also homology with the neuropeptide, gastrin. The C-terminal sulfated octapeptide sequence, CCK-8, is reportedly relatively conserved across species. Cloning and sequence analysis of a cDNA encoding preprocholecystokinin from rat thyroid carcinoma, porcine brain, and porcine intestine reportedly revealed 345 nucleotides coding for a precursor to CCK, which is 115 amino acids and contains all of the CCK sequences previously reported to have been isolated. Crawley and Corwin, supra.

CCK is said to be distributed throughout the central nervous system and in endocrine cells and enteric nerves of the upper small intestine. CCK agonists include CCK itself (also referred to as CCK-33), CCK-8 (CCK(26-33); SEQ ID NO: 55), non-sulfated CCK-8, pentagastrin (CCK-5 or CCK(29-33); SEQ ID NO: 209), and the tetrapeptide, CCK-4 (CCK (30-33); SEQ ID NO: 208). At the pancreatic CCK receptor, CCK-8 reportedly displaced binding with a 1000-5000 greater potency than unsulfated CCK-8 or CCK-4, and CCK-8 has been reported to be approximately 1000-fold more potent than unsulfated CCK-8 or CCK-4 in stimulating pancreatic amylase secretion. Crawley and Corwin, supra. In homogenates from the cerebral cortex, CCK receptor binding was said to be displaced by unsulfated CCK-8 and by CCK-4 at concentrations that were equimolar, 10-fold or 100-fold greater than sulfated CCK-8. Id.

Receptors for CCK have been reportedly identified in a variety of tissues, and two primary subtypes have been described: type A receptors and type B receptors. Type A receptors have been reported in peripheral tissues including pancreas, gallbladder, pyloric sphincter and afferent vagal fibers, and in discrete areas of the brain. The type A receptor subtype ($CCK_A$) has been reported to be selective for the sulfated octapeptide. The Type B receptor subtype ($CCK_B$) has been identified throughout the brain and in the stomach, and reportedly does not require sulfation or all eight amino acids. See Reidelberger, *J. Nutr.* 124 (8 Suppl.) 1327S-1333S (1994); Crawley and Corwin, supra.

Yet another family of peptide hormones implicated in metabolic diseases and disorders is the pancreatic polypeptide family ("PPF"). Pancreatic polypeptide ("PP") was discovered as a contaminant of insulin extracts and was named by its organ of origin rather than functional importance (Kimmel et al., *Endocrinology* 83: 1323-30 (1968)). PP is a 36-amino acid peptide containing distinctive structural motifs. A related peptide was subsequently discovered in extracts of intestine and named Peptide YY ("PYY") because of the N- and C-terminal tyrosines (Tatemoto, *Proc. Natl. Acad. Sci. USA* 79: 2514-8 (1982)). A third related peptide was later found in extracts of brain and named Neuropeptide Y ("NPY") (Tatemoto, *Proc. Natl. Acad. Sci. USA* 79: 5485-9 (1982); Tatemoto et al., *Nature* 296: 659-60 (1982)).

These three related peptides have been reported to exert various biological effects. Effects of PP include inhibition of pancreatic secretion and relaxation of the gallbladder. Centrally administered PP produces modest increases in feeding that may be mediated by receptors localized to the hypothalamus and brainstem (reviewed in Gehlert, *Proc. Soc. Exp. Biol. Med.* 218: 7-22 (1998)).

Release of PYY occurs following a meal. An alternate molecular form of PYY is PYY(3-36) (SEQ ID NO: 58) (Eberlein et al., *Peptides* 10: 797-803 (1989); Grandt et al., *Regul. Pept.* 51: 151-9 (1994)). This fragment constitutes approximately 40% of total PYY-like immunoreactivity in human and canine intestinal extracts and about 36% of total plasma PYY immunoreactivity in a fasting state to slightly over 50% following a meal. It is apparently a dipeptidyl peptidase-IV (DPP4) cleavage product of PYY. PYY(3-36) (SEQ ID NO: 58) is reportedly a selective ligand at the Y2 and Y5 receptors, which appear pharmacologically unique in preferring N-terminally truncated (i.e., C-terminal fragments of) NPY analogs. Peripheral administration of PYY reportedly reduces gastric acid secretion, gastric motility, exocrine pancreatic secretion (Yoshinaga et al., *Am. J. Physiol.* 263: G695-701 (1992); Guan et al., *Endocrinology* 128: 911-6 (1991); Pappas et al., *Gastroenterology* 91: 1386-9 (1986)), gallbladder contraction and intestinal motility (Savage et al., *Gut* 28: 166-70 (1987)). The effects of central injection of PYY on gastric emptying, gastric motility and gastric acid secretion, as seen after direct injection in or around the hindbrain/brainstem (Chen and Rogers, *Am. J. Physiol.* 269: R787-92 (1995); Chen et al., *Regul. Pept.* 61: 95-98 (1996); Yang and Tache, Am. J. Physiol. 268: G943-8 (1995); Chen et al., *Neurogastroenterol. Motil.* 9: 109-16 (1997)), may differ from those effects observed after peripheral injection. For example, centrally administered PYY had some effects opposite to those described herein for peripherally injected PYY(3-36) (SEQ ID NO: 58) in that gastric acid secretion was stimulated, not inhibited. Gastric motility was suppressed only in conjunction with TRH stimulation, but not when administered alone, and was indeed stimulatory at higher doses through presumed interaction with PP receptors. PYY has been shown to stimulate food and water intake after central administration (Morley et al., *Brain Res.* 341: 200-3 (1985); Corp et al., *Am. J. Physiol.* 259: R317-23 (1990)).

Metabolic diseases and disorders take on many forms, including obesity, diabetes, dyslipidemia, insulin resistance, cellular apoptosis, etc. Obesity and its associated disorders are common and very serious public health problems in the United States and throughout the world. Upper body obesity is the strongest risk factor known for type 2 diabetes mellitus, and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia (see, e.g., Kopelman, *Nature* 404: 635-43 (2000)). It reduces life-span and carries a serious risk of co-morbidities above, as well disorders such as infections, varicose veins, acanthosis nigricans, eczema, exercise intolerance, insulin resistance, hypertension hypercholesterolemia, cholelithiasis, orthopedic injury, and thromboembolic disease (Rissanen et al., *Br. Med. J.* 301: 835-7 (1990)). Obesity is also a risk factor for the group of conditions called insulin resistance syndrome, or "Syndrome X." Recent estimate for the medical cost of obesity and associated disorders is $150 billion worldwide. The pathogenesis of obesity is believed to be multifactorial but the basic problem is that in obese subjects nutrient availability and energy expenditure do not come into balance until there is excess adipose tissue. Obesity is currently a poorly treatable, chronic, essentially intractable metabolic disorder. A therapeutic drug useful in weight reduction of obese persons could have a profound beneficial effect on their health.

Diabetes is a disorder of carbohydrate metabolism characterized by hyperglycemia and glucosuria resulting from insufficient production or utilization of insulin. Diabetes severely affects the quality of life of large parts of the populations in developed countries. Insufficient production of insulin is characterized as type 1 diabetes and insufficient utilization of insulin is type 2 diabetes. However, it is now widely recognized that there are many distinct diabetes related diseases which have their onset long before patients are diagnosed as having overt diabetes. Also, the effects from the suboptimal control of glucose metabolism in diabetes gives rise to a wide spectrum of related lipid and cardiovascular disorders.

Dyslipidemia, or abnormal levels of lipoproteins in blood plasma, is a frequent occurrence among diabetics. Dyslipidemia is typically characterized by elevated plasma triglycerides, low HDL (High Density Lipoprotein) cholesterol, normal to elevated levels of LDL (Low Density Lipoprotein) cholesterol and increased levels of small dense, LDL (Low Density Lipoprotein) particles in the blood. Dyslipidemia is one of the main contributors to the increased incidence of coronary events and deaths among diabetic subjects. Epidemiological studies have confirmed this by showing a several-fold increase in coronary deaths among diabetic subjects when compared with non-diabetic subjects. Several lipoprotein abnormalities have been described among diabetic subjects.

Insulin resistance is the diminished ability of insulin to exert its biologically action across a broad range of concentrations. In insulin resistance, the body secretes abnormally high amounts of insulin to compensate for this defect and a state of impaired glucose tolerance develops. Failing to compensate for the defective insulin action, the plasma glucose concentration inevitable rises, resulting in the clinical state of diabetes. It is being recognized that insulin resistance and relative hyperinsulinemia have a contributory role in obesity, hypertension, atherosclerosis and type 2 diabetes. The association of insulin resistance with obesity, hypertension and angina has been described as a syndrome, Syndrome X, having insulin resistance as the common pathogenic link.

Apoptosis is an active process of cellular self-destruction that is regulated by extrinsic and intrinsic signals occurring during normal development. It is well documented that apoptosis plays a key role in regulation of pancreatic endocrine beta cells. There is increasing evidence that in adult mammals the beta-cell mass is subject to dynamic changes to adapt insulin production for maintaining euglycemia in particular conditions, such as pregnancy and obesity. The control of beta cell mass depends on a subtle balance between cell proliferation, growth and programmed cell death (apoptosis). A disturbance of this balance may lead to impairment of glucose homeostasis. For example, it is noteworthy that glucose intolerance develops with aging when beta cell replication rates are reduced and human autopsy studies repeatedly showed a 40-60% reduction of beta cell mass in patients with non-insulin-dependent-diabetes mellitus compared with nondiabetic subjects. It is generally agreed that insulin resistance is an invariable accompaniment of obesity but that normoglycemia is maintained by compensatory hyperinsulinemia until the beta cells become unable to meet the increased demand for insulin, at which point type 2 diabetes begins.

Attempts to treat the multiple abnormalities associated with diabetes have prompted for the administration of several anti-diabetic medicaments in order to address these abnormalities in the different patients. Examples of anti-diabetic medicaments are proteins such as insulin and insulin analogues, and small molecules such as insulin sensitizers, insulin secretagogues and appetite regulating compounds.

There remains a need to develop polypeptides useful in the above described metabolic diseases, conditions, and disorders. Accordingly, it is an object of the present invention to provide hybrid polypeptides and methods for producing and using them. The compounds of the invention find use in the metabolic diseases, conditions, and disorders described above and herein.

All documents referred to herein are incorporated by reference into the present application as though fully set forth herein.

SUMMARY OF THE INVENTION

The present invention relates generally to novel, selectable hybrid polypeptides useful as agents for the treatment and prevention of metabolic diseases and disorders which can be alleviated by control of plasma glucose levels, insulin levels, and/or insulin secretion, such as diabetes and diabetes-related conditions. Such conditions and disorders include, but are not limited to, hypertension, dyslipidemia, cardiovascular disease, eating disorders, insulin-resistance, obesity, and diabetes mellitus of any kind, including type 1, type 2, and gestational diabetes.

In one aspect of the invention, hybrid polypeptides exhibiting at least one hormonal activity are provided. The hybrid polypeptides of the invention comprise at least two bio-active peptide hormone modules covalently linked together, wherein at least one of the bio-active peptide hormone modules exhibits at least one hormonal activity of a component peptide hormone. The bio-active peptide hormone modules are independently selected from: component peptide hormones, fragments of component peptide hormones that exhibit at least one hormonal activity of the component peptide hormones, analogs and derivatives of component peptide hormones that exhibit at least one hormonal activity of the component peptide hormones, fragments of analogs and derivatives of component peptide hormones that exhibit at least one hormonal activity of the component peptide hormones, and peptidic enhancers.

In one embodiment a hybrid polypeptide is exhibiting at least one hormonal activity, the hybrid polypeptide containing at least a first bio-active peptide hormone module covalently linked to at least one additional bio-active peptide hormone module; wherein the bio-active peptide hormone modules are independently selected from the group consisting of: component peptide hormones; fragments of component peptide hormones that exhibit at least one hormonal activity of the component peptide hormones; analogs and derivatives of component peptide hormones that exhibit at least one hormonal activity of the component peptide hormones; fragments of analogs and derivatives of component peptide hormones that exhibit at least one hormonal activity of the component peptide hormones; and peptidic enhancers. The component peptide hormones are typically independently selected from at least two of the group consisting of amylin, adrenomedullin (ADM), calcitonin (CT), calcitonin gene related peptide (CGRP), intermedin, cholecystokinin ("CCK"), leptin, peptide YY (PYY), glucagon-like peptide-1 (GLP-1), glucagon-like peptide 2 (GLP-2), oxyntomodulin (OXM), a natriuretic peptide, and exendin-4. Typically peptidic enhancers are independently selected from the group consisting of structural motifs of component peptide hormones that impart a desired chemical stability, conformational stability, metabolic stability, bioavailability, organ/tissue targeting, receptor interaction, protease inhibition, plasma protein binding, or other pharmacokinetic characteristic to the hybrid polypeptide, and structural motifs of analogs or derivatives of component peptide hormones that impart a desired chemical stability, conformational stability, metabolic stability, bioavailability, organ/tissue targeting, receptor interaction, protease inhibition, plasma protein binding, or other pharmacokinetic characteristic to the hybrid polypeptide. In yet a further embodiment at least one of the bio-active peptide hormone modules exhibits at least one hormonal activity of a component peptide hormone. In yet further alternative embodiments when the at least one bio-active peptide hormone module that exhibits at least one hormonal activity of a component peptide hormone is amylin, a fragment of amylin that exhibits at least one hormonal activity, an analog or derivative of amylin that exhibits at least one hormonal activity, or a fragment of an analog or derivative of amylin that exhibits at least one hormonal activity, and the at least one other bio-active peptide hormone module is CCK, a fragment of CCK that exhibits at least one hormonal activity, an analog or derivative of CCK that exhibits at least one hormonal activity, a fragment of an analog or derivative of CCK that exhibits at least one hormonal activity, CT, a fragment of CT that exhibits at least one hormonal activity, an analog or derivative of CT that exhibits at least one hormonal activity, or a fragment of an analog or derivative of CT that exhibits at least one hormonal activity, then the hybrid polypeptide can further contain at least three bio-active peptide hormone modules selected from at least three different component peptide hormones. In yet a further alternative embodiment, when the at least one bio-active peptide hormone module that exhibits at least one hormonal activity of a component peptide hormone is GLP-1, a fragment of GLP-1 that exhibits at least one hormonal activity, an analog or derivative of GLP-1 that exhibits at least one hormonal activity, or a fragment of an analog or derivative of GLP-1 that exhibits at least one hormonal activity, and the at least one other bio-active peptide hormone module is a peptidic enhancer comprising an exendin fragment, then the hybrid polypeptide can further contain at least three bio-active peptide hormone modules.

Component peptide hormones of the invention include: amylin, adrenomedullin (ADM), calcitonin (CT), calcitonin gene related peptide (CGRP), intermedin, cholecystokinin ("CCK"), leptin, peptide YY (PYY), glucagon-like peptide-1 (GLP-1), glucagon-like peptide 2 (GLP-2), oxyntomodulin (OXM), natriuretic peptides, and exendin-4;

Peptidic enhancers of the invention include: structural motifs of component peptide hormones that impart a desired chemical stability, conformational stability, metabolic stability, bioavailability, organ/tissue targeting, receptor interaction, protease inhibition, plasma protein binding, or other pharmacokinetic characteristic to the hybrid polypeptide, and structural motifs of analogs or derivatives of component peptide hormones that impart a desired chemical stability, conformational stability, metabolic stability, bioavailability, organ/tissue targeting, receptor interaction, protease inhibition, plama protein binding, or other pharmacokinetic characteristic to the hybrid polypeptide.

In another aspect of the invention, methods for treating or preventing obesity are provided, wherein the method comprises administering a therapeutically or prophylactically effective amount of a hybrid polypeptide of the invention to a subject in need thereof. In a preferred embodiment, the subject is an obese or overweight subject. While "obesity" is generally defined as a body mass index over 30, for purposes of this disclosure, any subject, including those with a body mass index of less than 30, who needs or wishes to reduce body weight is included in the scope of "obese." Subjects who are insulin resistant, glucose intolerant, or have any form of diabetes mellitus (e.g., type 1, 2 or gestational diabetes) can benefit from this method.

In yet another aspect of the invention, methods of reducing food intake, reducing nutrient availability, causing weight loss, treating diabetes mellitus or diabetes-associated conditions, and improving lipid profile (including reducing LDL cholesterol and triglyceride levels and/or changing HDL cholesterol levels) are provided, wherein the methods comprise administering to a subject an effective amount of a hybrid polypeptide of the invention. In a preferred embodiment, the methods of the invention are used to treat or prevent conditions or disorders which can be alleviated by reducing nutrient availability in a subject in need thereof, comprising administering to said subject a therapeutically or prophylactically effective amount of a hybrid polypeptide of the invention. In another embodiment, the methods of the invention are used to treat or prevent conditions or disorders which can be alleviated by control plasma glucose levels, insulin levels, and/or insulin secretion. In yet another embodiment, the methods of the invention are used to treat diabetes and/or diabetes-related conditions. Such conditions and disorders include, but are not limited to, hypertension, dyslipidemia, cardiovascular disease, eating disorders, insulin-resistance, obesity, and diabetes mellitus of any kind, including Type I, Type II, and gestational diabetes, diabetes complications (neuropathy (based on, e.g., neurotrophic actions of exendin-4), neuropathic pain (based on, e.g., amylin action), retinopathy, nephropathy, conditions of insufficient pancreatic beta cell mass (based on, e.g., islet neogenesis actions of exendin-4 and GLP-1).

The present invention also relates to pharmaceutical compositions comprising a therapeutically or prophylactically effective amount of at least one hybrid polypeptide of the invention, or a pharmaceutically acceptable salt thereof, together with pharmaceutically acceptable diluents, preservatives, solubilizers, emulsifiers, adjuvants and/or carriers useful in the delivery of the hybrid polypeptides.

These and other aspects of the invention will be more clearly understood with reference to the following preferred embodiments and detailed description.

BRIEF DESCRIPTION OF THE DRAWINGS

FIG. 1 demonstrates the effect of exemplary compounds of the invention in DIO mouse assay.

FIG. 2 demonstrates the effect of exemplary compounds of the invention in DIO mouse assay.

FIGS. 3A-3C demonstrate the effect of exemplary compounds of the invention in DIO mouse assay.

FIGS. 4A-4B demonstrate the effects of exemplary compounds of the invention in food intake assay, compared to parent peptide compounds.

FIGS. 5A-5B demonstrate the effects of exemplary compounds of the invention in blood glucose lowering assay and food intake assay, respectively.

DETAILED DESCRIPTION OF THE INVENTION

The present invention relates generally to novel, selectable hybrid polypeptides useful as agents for the treatment and prevention of metabolic diseases and disorders which can be alleviated by control of plasma glucose levels, insulin levels, and/or insulin secretion, such as diabetes and diabetes-related conditions. Such conditions and disorders include, but are not limited to, hypertension, dyslipidemia, cardiovascular disease, eating disorders, insulin-resistance, obesity, and diabetes mellitus of any kind, including type 1, type 2, and gestational diabetes.

In one aspect, the invention involves the modular assembly of physiologically, metabolically, and/or pharmacokinetically active peptidic modules that may be selectable based on "bio-activities", e.g., therapeutic efficacy, scope of function, duration of action, physicochemical properties, and/or other pharmacokinetic properties.

Without intending to be limited by theory, the present invention relates at least in part to a "toolbox" approach, wherein bio-active peptide hormone modules are linked in binary, tertiary or higher order combinations to create novel, efficacious therapeutic agents with selectable properties. The "bio-active peptide hormone modules" may be peptide hormones, peptide fragments with hormonal activity, or structural motifs of peptide hormones that impart chemical, metabolic, and/or other pharmacokinetic stability. The peptide hormones can include native peptide hormones, as well as peptide hormone analogs and derivatives, as known in the art and described herein.

In one aspect of the invention, it has been found that the combination of certain physicochemical characteristics of two or more peptide hormones into a single modality can facilitate intervention at several points in a dysfunctional metabolic circuit. As such, in one aspect of the invention, rationally-designed hybrid polypeptides are provided that integrate selectable bio-activities into a single polypeptide agent. In one embodiment, the selectable hybrid polypeptides of the invention may involve the use of chemically stable linkers to covalently attach the bio-active modules. In another embodiment, the selectable hybrid polypeptides of the invention may involve the use of cleavable linkers, which themselves may be or form part of a bio-active module.

Again, without intending to be limited by theory, design of the hybrid polypeptides of the present invention may generally involve: (1) the identification, selection and pairing of bio-active peptide hormone modules for desired efficacy and therapeutic use, and (2) the covalent linking of the bio-active modules (e.g. native peptide hormones, peptide hormone analogs or derivatives with hormonal activity, peptide hormone fragments with hormonal activity, stabilizing motifs, etc.) either directly or via a linker without loss of bio-activity of the component modules. In certain embodiments, module selection criteria may include, but not be limited to: (a) desired in vivo efficacy for desired therapeutic or prophylactic indication, such as an additive or a synergistic effect; (b) optional synergism or dual action of the linked modules for multiple therapeutic or prophylactic indications; and/or (c) a desired chemical stability, conformational stability, metabolic stability, bioavailability, organ/tissue targeting, receptor interaction, protease inhibition, plasma protein binding, and/or other pharmacokinetic characteristic.

The section headings are used herein for organizational purposes only, and are not to be construed as in any way limiting the subject matter described.

Hybrid Polypeptides of the Invention

As mentioned above, the present invention relates in part to hybrid polypeptides comprising at least two bio-active peptide hormone modules selectable from component peptide hormones described herein. The hybrid polypeptides of the present invention will generally be useful in the treatment and prevention of metabolic conditions and disorders. The hybrid polypeptides of the invention will exhibit at least one hormonal activity of a component peptide hormone, and may preferably include at least one additional bio-activity of a second component peptide hormone.

In one embodiment, the hybrid polypeptides of the invention may comprise at least two bio-active peptide hormone modules, wherein each of said at least two bio-active peptide hormone modules exhibits at least one hormonal activity of a component peptide hormone. In another embodiment, the hybrid polypeptides of the invention may comprise at least two bio-active peptide hormone modules, wherein at least one of said bio-active peptide hormone modules exhibits at least one hormonal activity of a component peptide hormone and at least one of said bio-active peptide hormone modules imparts a desired chemical stability, conformational stability, metabolic stability, bioavailability, organ/tissue targeting, receptor interaction, protease inhibition, plasma protein binding, and/or other pharmacokinetic characteristic to the hybrid polypeptide.

In a preferred embodiment, the hybrid polypeptides of the invention may have comparable or higher potency in the treatment and/or prevention of metabolic conditions and disorders, as compared to the component peptide hormones. In another embodiment, the hybrid polypeptides of the invention may have comparable or higher potency in the treatment and/or prevention of diabetes and/or diabetes-related disorders, as compared to the component peptide hormones. Alternatively, preferred hybrid polypeptides of the invention may exhibit improved ease of manufacture, stability, and/or ease of formulation, as compared to the component peptide hormones.

More particularly, the hybrid polypeptides of the present invention will generally comprise a first bio-active peptide hormone module covalently linked to at least one additional bio-active peptide hormone module. The bio-active peptide hormone modules may be covalently linked together in any manner known in the art, including but not limited to direct amide bonds or chemical linker groups, as described in further detail herein. In one embodiment, chemical linker groups may include peptide mimetics which induce or stabilize polypeptide conformation.

The first bio-active peptide hormone module may be selected from a first component peptide hormone, and may be a peptide hormone (including native peptide hormones as well as analogs and derivatives thereof), a peptide fragment with hormonal activity (including fragments of native peptides hormones as well as analogs and derivatives thereof), or a structural motif of a peptide hormone (including native peptide hormones as well as analogs and derivatives thereof) that imparts a desired chemical stability, conformational stability, metabolic stability, bioavailability, organ/tissue targeting, receptor interaction, protease inhibition, plasma protein binding, and/or other pharmacokinetic characteristic to the hybrid polypeptide. Likewise, the additional bio-active peptide module(s) may be selected from component peptide hormones, and may be a peptide hormone (including native peptide hormones as well as analogs and derivatives thereof), a peptide fragment with hormonal activity (including fragments of native peptides hormones as well as analogs and derivatives thereof), or a structural motif of a hormone peptide (including native peptide hormones as well as analogs and derivatives thereof) that imparts a desired chemical stability, conformational stability, metabolic stability, bioavailability, organ/tissue targeting, receptor interaction, protease inhibition, plasma protein binding, and/or other pharmacokinetic characteristic to the hybrid polypeptide. The first peptide hormone and the additional peptide hormone may be the same peptide hormone, may be from the same family of peptide hormones, or may be different peptide hormones, depending on the desired characteristics of the bio-active peptide hormone modules.

As used herein, the term "bio-active" refers to (1) biological activity in at least one in vivo hormonal pathway, or (2) modulation of the therapeutic efficacy, scope of function, duration of action, physicochemical properties, and/or other pharmacokinetic properties of such biological activity. Biological activity may be evaluated through target hormone receptor binding assays, or through metabolic studies that monitor a physiological indication, as known in the art and described herein. Modulation of the therapeutic efficacy, scope of function, duration of action, physicochemical properties, and/or other pharmacokinetic properties of such biological activity may be modified through changed in, e.g., chemical stability, conformational stability, metabolic stability, bioavailability, organ/tissue targeting, receptor interaction, protease inhibition, plasma protein binding, and/or other pharmacokinetic characteristics.

In one embodiment, the hybrid polypeptides of the invention retain at least about 25%, preferably about 30%, 40%, 50%, 60%, 70%, 80%, 90%, 95%, 98%, or 99% percent of the biological activity of a component peptide hormone. Preferred hybrid polypeptides are those having a potency in one of the metabolic-related assays known in the art or described herein (e.g., receptor binding, food intake, gastric emptying, pancreatic secretion, insulin secretion, blood glucose lowering, weight reduction, etc.) which is equal to or greater than the potency of component peptide hormone in that same assay. Alternatively, preferred hybrid polypeptides of the invention may exhibit improved ease of manufacture, stability, and/or ease of formulation, as compared to component peptide hormones.

In another embodiment, the hybrid polypeptides of the invention retain at least about 25%, preferably about 30%, 40%, 50%, 60%, 70%, 80%, 90%, 95%, 98%, or 99% percent of the biological activity of a native component peptide hormone with regard to the reduction of nutrient availability, the reduction of food intake, the effect of body weight gain, and/or the treatment and prevention of metabolic conditions and disorders. In yet another embodiment, the hybrid polypeptides of the invention exhibit at least about 110%, 125%, 130%, 140%, 150%, 200%, or more of the biological activity of a native peptide hormone with regard to the reduction of nutrient availability the reduction of food intake, the effect of body weight gain, and/or the treatment and prevention of metabolic conditions and disorders. In another embodiment, the hybrid polypeptides of the invention exhibit improved component peptide hormone receptor agonist activity.

1. Component Peptides Hormones, Analogs and Derivatives

Component peptide hormones generally include peptide hormones useful in the treatment or prevention of metabolic diseases and disorders including: (a) the amylin family, including amylin, adrenomedullin ("ADM"), calcitonin ("CT"), calcitonin gene related peptide ("CGRP"), intermedin (also known as "AFP-6") and related peptides; (b) cholecystokinin ("CCK"); (c) the leptin family, including leptin and leptin-like peptides; (d) the pancreatic polypeptide family, including pancreatic polypeptide ("PP") and peptide YY ("PYY"); (e) incretins and incretin mimetics, including: peptide hormones derived from the proglucagon gene such as: glucagon, glucagon-like peptide-1 ("GLP-1"), glucagon-like peptide 2 ("GLP-2"), and oxyntomodulin ("OXM"); and exendins such as: exendin-3, and exendin-4; and (f) natriuretic peptides including ANP, BNP, CNP, and urodilatin, their precursor forms and peptides derived therefrom (g) urocortin family and the (h) neuromedin family, and analogs, derivatives and fragments thereof. As discussed herein component peptide hormones of the invention also include analogs and derivatives that retain hormonal activity of these native peptide hormones. In one embodiment, such analogs and derivatives are agonists of the target hormone receptor.

By "amylin" is meant the human peptide hormone referred to as amylin and secreted from the beta cells of the pancreas, and species variations thereof, as described in U.S. Pat. No. 5,234,906, issued Aug. 10, 1993, for "Hyperglycemic Compositions," the contents of which are hereby incorporated by reference. More particularly, amylin is a 37-amino acid polypeptide hormone normally co-secreted with insulin by pancreatic beta cells in response to nutrient intake (see, e.g., Koda et al., Lancet 339:1179-1180, 1992). In this sense, "amylin," "wild-type amylin," and "native amylin," i.e., unmodified amylin, are used interchangeably.

By "adrenomedullin" or "ADM" is meant the human peptide hormone and species variants thereof. More particularly, ADM is generated from a 185 amino acid preprohormone through consecutive enzymatic cleavage and amidation. This process culminates in the liberation of a 52 amino acid bioactive peptide.

By "calcitonin" or "CT" is meant the human peptide hormone and species variants thereof, including salmon calcitonin ("sCT"). More particularly, CT is a 32 amino acid peptide cleaved from a larger prohormone. It contains a single disulfide bond, which causes the amino terminus to assume the shape of a ring. Alternative splicing of the calcitonin premRNA can yield a mRNA encoding calcitonin gene-related peptide; that peptide appears to function in the nervous and vascular systems. The calcitonin receptor has been cloned and shown to be a member of the seven-transmembrane, G protein-coupled receptor family.

By "calcitonin gene related peptide" or "CGRP" is meant the human peptide hormone and species variants thereof, in any physiological form.

By "intermedin" or "AFP-6" is meant the human peptide hormone and species variants thereof, in any physiological form.

By "cholecystokinin" or "CCK" is meant the human peptide hormone and species variants thereof. More particularly, CCK is a 33-amino acid sequence first identified in humans, and includes a 8-amino acid in vivo C-terminal fragment ("CCK-8") that has been reportedly demonstrated in pig, rat, chicken, chinchilla, dog and humans. Thus, the term CCK-33 will generally refer to human CCK(1-33), while CCK-8 (CCK(26-33); SEQ ID NO: 55) will refer to the C-terminal octapeptide generically in both the sulfated and unsulfated unless otherwise specified. Further, pentagastrin or CCK-5 will refer to the C-terminal peptide CCK(29-33) (SEQ ID NO: 209), and the CCK-4 will refer to the C-terminal tetrapeptide CCK(30-33) (SEQ ID NO: 208). However, as used herein, CCK will generally refer to all naturally occurring variations of the hormone, including CCK-33, CCK-8, CCK-5, and CCK-4, in the sulfated and unsulfated form unless otherwise specified.

By "leptin" is meant the naturally occurring leptin from any species, as well as biologically active D-isoforms, or fragments of naturally occurring leptin and variants thereof, and combinations of the preceding. Leptin is the polypeptide product of the ob gene as described in the International Patent Publication No. WO 96/05309, which is incorporated herein by reference in its entirety. Putative analogs and fragments of leptin are reported in U.S. Pat. No. 5,521,283, U.S. Pat. No. 5,532,336, PCT/US96/22308 and PCT/US96/01471, each of which is incorporated herein by reference in its entirety.

By "PP" is meant human pancreatic peptide polypeptide or species variants thereof, in any physiological form. Thus, the term "PP" includes both the human full length, 36 amino acid peptide as set forth in (SEQ ID NO: 290), and species variations of PP, including, e.g., murine, hamster, chicken, bovine, rat, and dog PP. In this sense, "PP," "wild-type PP," and "native PP," i.e., unmodified PP, are used interchangeably.

By "PYY" is meant human peptide YY polypeptide or species variants thereof, in any physiological form. Thus, the term "PYY" includes both the human full length, 36 amino acid peptide, and species variations of PYY, including e.g., murine, hamster, chicken, bovine, rat, and dog PYY. In this sense, "PYY" and "wild-type PYY" and "native PYY," i.e., unmodified PYY, are used interchangeably. In the context of the present invention, all modifications discussed with reference to the PYY analog polypeptides of the present invention are based on the 36 amino acid sequence of native human PYY.

By "GLP-1" is meant human glucagon like peptide-1 or species variants thereof, in any physiological form. The term "GLP-1" includes human GLP1(1-37) (SEQ ID NO: 59), GLP-1(7-37) (SEQ ID NO: 204), and GLP1(7-36)amide (SEQ ID NO: 61), with reference to the full length human GLP1(1-37) (SEQ ID NO: 59), and species variations of GLP-1, including, e.g., murine, hamster, chicken, bovine, rat, and dog PP. In this sense, "GLP-1," "wild-type GLP-1," and "native GLP-1," i.e., unmodified GLP-1, are used interchangeably.

By "GLP-2" is meant human glucagon like peptide-2 or species variants thereof, in any physiological form. More particularly, GLP-2 is a 33 amino acid peptide, co-secreted along with GLP-1 from intestinal endocrine cells in the small and large intestine.

By "OXM" is meant human oxyntomodulin or species variants thereof in any physiological form. More particularly, OXM is a 37 amino acid peptide that contains the 29 amino acid sequence of glucagon followed by an 8 amino acid carboxyterminal extension.

By "exendin" is meant a peptide hormone found in the saliva of the Gila-monster, a lizard endogenous to Arizona, and the Mexican Beaded Lizard, as well as species variants thereof. More particularly, Exendin-3 is present in the saliva of Heloderma horridum, and exendin-4 is present in the saliva of Heloderma suspectum (Eng, J., et al., J. Biol. Chem., 265: 20259-62, 1990; Eng., J., et al., J. Biol. Chem., 267:7402-05 (1992)). The exendins have some sequence similarity to several members of the glucagon-like peptide family, with the highest identity, 53%, being to GLP-1 (Goke, et al., J. Biol. Chem., 268:19650-55 (1993)). In this sense, "exendin," "wild-type exendin," and "native exendin," i.e., unmodified exendin, are used interchangeably.

By "urocortin" is meant a human urocortin peptide hormone or species variants thereof in any physiological form. More particularly, there are three human urocortins: Ucn-1, Ucn-2 and Ucn-3. For example, human urocortin 1 has the formula: Asp-Asn-Pro-Ser-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH2 (SEQ ID NO: 294). Rat-derived urocortin is identical but for 2 substitutions: Asp2 for Asn2 and Pro4 for Ser4. Human Ucn-2 has the sequence Ile Val Leu Ser Leu Asp Val Pro Ile Gly Leu Leu Gln Ile Leu Leu Glu Gln Ala Arg Ala Arg Ala Ala Arg Glu Gln Ala Thr Thr Asn Ala Arg Ile Leu Ala Arg Val Gly His Cys (SEQ ID NO: 399). Human Ucn-3 has the sequence Phe Thr Leu Ser Leu Asp Val Pro Thr Asn Ile Met Asn Leu Leu Phe Asn Ile Ala Lys Ala Lys Asn Leu Arg Ala Gln Ala Ala Ala Asn Ala His Leu Met Ala Gln Ile (SEQ ID NO: 299). Ucn-3 is preferably in amide form. Further urocortins and analogs are described in the literature, for example in U.S. Pat. No. 6,214,797. Urocortins Ucn-2 and Ucn-3, which retain the food-intake suppression and antihypertensive/cardioprotective/inotropic properties, find particular use in the hybrids of the invention. Stresscopin (Ucn-3) and Stresscopin-related peptide (Ucn 2), named for their ability to suppress the chronic HPA activation following a stressful stimulus such as dieting/fasting, are specific for the CRF type 2 receptor and do not activate CRF-R1 which mediates ACTH release. Hybrids comprising a urocortin, e.g., Ucn-2 or Ucn-3, are particularly useful for vasodilation and thus for cardiovascular uses as described herein, e.g. CHF. Urocortin containing hybrids of the invention find particular use in treating or preventing conditions associated with stimulating ACTH release, hypertension due to vasodilatory effects, inflammation mediated via other than ACTH elevation, hyperthermia, appetite disorder, congestive heart failure, stress, anxiety, and psoriasis. Such compounds are also useful for an antiproliferative effect, such as for treating or preventing cancers or tumor growth. Of particular interest are urocortin peptide hormone module combined with a natriuretic peptide module, amylin family, an exendin family, or a GLP1 family module to provide an enhanced cardiovascular benefit, e.g. treating CHF, as by providing a beneficial vasodilation effect.

By "neuromedin" is meant the neuromedin family of peptides including neuromedin U and S peptides, more particularly their active hormone sequences. For example, the native active human neuromedin U peptide hormone is neuromedin-U25: Phe Arg Val Asp Glu Glu Phe Gln Ser Pro Phe Ala Ser Gln Ser Arg Gly Tyr Phe Leu Phe Arg Pro Arg Asn (SEQ ID NO: 308), particularly in the amide form. Pig U25 has the sequence: FKVDEEFQGPIVSQNRRYFLFRPRN (SEQ ID NO: 314), particularly its amide form. Other neuromedin U family members include the following listed as their SWISS-PROT designations and entry numbers: NEUU_CANFA (P34962), NEUU_CAVPO (P34966), NEUU_CHICK (P34963), NEUU_HUMAN (P48645), NEUU_LITCE (P81872), NEUU_MOUSE (Q9QXK8), NEUU_PIG (P34964), NEUU_RABIT (P34965), NEUU_RANTE (P20056), and NEUU_RAT (P12760). Of particular interest are their processed active peptide hormones and analogs, derivatives and fragments thereof. Included in the neuromedin U family are various truncated or splice variants, e.g., FLFHYSKTQKLGKSNVVEELQSPFASQS-RGYFLFRPRN (SEQ ID NO: 300). Exemplary of the neuromedin S family is human neuromedin S with the sequence ILQRGSGTAAVDFTKKDHTATWGRPFFLFRPRN (SEQ ID NO: 315), particularly its amide form. Hybrids of the invention having neuromedin module will an anorexigenic effect, and thus have beneficial value in treating obesity, diabetes, reducing food intake, and other related conditions and disorders as described herein. Of particular interest are neuromedin modules combined with an amylin family peptide, an exendin peptide family or a GLP1 peptide family module.

As used herein, an "analog" refers to a peptide whose sequence was derived from that of a base reference peptide (e.g., PP, PYY, amylin, GLP-1, exendin, etc.), including insertions, substitutions, extensions, and/or deletions of the reference amino acid sequence, preferably having at least 50 or 55% amino acid sequence identity with the base peptide, more preferably having at least 70%, 80%, 90%, or 95% amino acid sequence identity with the base peptide. In one embodiment, such analogs may comprise conservative or non-conservative amino acid substitutions (including non-natural amino acids and L and D forms).

A "derivative" is defined as a molecule having the amino acid sequence of a native reference peptide or analog, but additionally having chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, constrained alkyls (e.g. branched, cyclic, fused, adamantyl) and N-acyl modifications. Modifications of the terminal carboxy group include, without limitation, the amide, lower alkyl amide, constrained alkyls (e.g. branched, cyclic, fused, adamantyl) alkyl, dialkyl amide, and lower alkyl ester modifications. Lower alkyl is C1-C4 alkyl. Furthermore, one or more side groups, or terminal groups, may be protected by protective groups known to the ordinarily-skilled peptide chemist. The α-carbon of an amino acid may be mono- or dimethylated.

By "agonist" is meant a compound which elicits a biological activity of native human reference peptide, preferably having a potency better than the reference peptide, or within five orders of magnitude (plus or minus) of potency compared to the reference peptide, more preferably 4, 3, 2, or 1 order of magnitude, when evaluated by art-known measures such as receptor binding/competition studies. In one embodiment, the terms refer to a compound which elicits a biological effect similar to that of native human reference peptide, for example a compound (1) having activity in the food intake, gastric emptying, pancreatic secretion, or weight loss assays similar to native human reference peptide, or (2) which binds specifically in a reference receptor assay or in a competitive binding assay with labeled reference peptide. Preferably, the agonists will bind in such assays with an affinity of greater than 1 μM, and more preferably with an affinity of greater than 1-5 nM. In another embodiment, the terms refer to a compound which elicits a biological effect in the treatment of diabetes or a diabetes related condition or disorder. Such agonists may comprise a polypeptide comprising an active fragment of a reference peptide or a small chemical molecule.

By "amino acid" and "amino acid residue" is meant natural amino acids, unnatural amino acids, and modified amino acid. Unless stated to the contrary, any reference to an amino acid, generally or specifically by name, includes reference to both the D and the L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to homo-lysine, homo-arginine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. Additional unnatural amino acids include modified amino acid residues which are chemically blocked, reversibly or irreversibly, or chemically modified on their N-terminal amino group or their side chain groups, as for example, N-methylated D and L amino acids or residues wherein the side chain functional groups are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide, a modified amino acid of alanine. Additional residues that can be incorporated are described in Sandberg et al., *J. Med. Chem.* 41: 2481-91, 1998.

As used herein: "5 Apa" means 5 amino-pentanoyl, "12 Ado" means 12-amino dodecanoyl, "PEG(8)" mean 3,6-dioxyoctanoyl, and "PEG(13)" means 1-amino-4,7,10-trioxa-13-tridecanamine succinimoyl.

As discussed herein native component peptide hormones are known in the art, as are their analogs and derivatives. For reference, the sequences of several native component peptide hormones are provided in Table 1.

TABLE 1

Exemplary Component Peptide Hormones

| Seq ID | Description | Sequence |
|---|---|---|
| 44 | Rat Amylin | KCNTATCATQRLANFLVRSSNNLGPVLPPTNVGSNTY |
| 45 | h-Amylin | KCNTATCATQRLANFLVHSSNNFGAILSSTNVGSNTY |
| 46 | h-ADM | YRQSMNNFQGLRSFGCRFGTCTVQKLAHQIYQFTDKDKDNVAPRSKISPQGY |
| 47 | s-CT | CSNLSTCVLGKLSQELHKLQTYPRTNTGSGTP |
| 48 | h-CT | CGNLSTCMLGTYTQDFNKFHTFPQTAIGVGAP |
| 49 | h-CGRP α | ACDTATCVTHRLAGLLSRSGGVVKNNFVPTNVGSKAF |
| 50 | h-CGRP β | ACNTATCVTHRLAGLLSRSGGMVKSNFVPTNVGSKAF |
| 51 | h-AFP-6 (1-47) | TQAQLLRVGCVLGTCQVQNLSHRLWQLMGPAGRQDSAPVDPSSPHSY |
| 52 | h-AFP-6 (8-47) | VGCVLGTCQVQNLSHRLWQLMGPAGRQDSAPVDPSSPHSY |
| 53 | Mouse AFP-6 (1-47) | PHAQLLRVGCVLGTCQVQNLSHRLWQLVRPAGRRDSAPVDPSSPHSY |
| 54 | Mouse AFP-6 (8-47) | VGCVLGTCQVQNLSHRLWQLVRPAGRRDSAPVDPSSPHSY |
| 55 | CCK-8-sulfated | DY(SO$_3$)MGWMDF |
| 56 | h-Leptin | MHWGTLCGFLWLWPYLFYVQAVPIQKVQDDTKTLIKTIVTRINDISHTQSVSSKQKVTGLDFIPGLHPILTLSKMDQTLAVYQQILTSMPSRNVIQISNDLENLRDLLHVLAFSKSCHLPWASGLETLDSLGGVLEASGYSTEVVALSRLQGSLQDMLWQLDLSPGC |
| 57 | h-PYY | YPIKPEAPGEDASPEELNRYYASLRHYLNLVTRQRY |
| 58 | h-PYY (3-36) | IKPEAPGEDASPEELNRYYASLRHYLNLVTRQRY |
| 59 | hGLP-1 (1-37) | HDEFERHAEGTFTSDVSSTLEGQAALEFIAWLVKGRG |
| 60 | Frog GLP-1 | HAEGTYTNDVTEYLEEKAAKEFIEWLIKGKPKKIRYS-OH; |
| 188 | Frog GLP-1 | HAEGTFTSDVTQQLDEKAAKEFIDWLINGGPSKEIIS-OH |
| 61 | h-GLP-1 (7-36) | HAEGTFTSDVSSYLEGQAALEFIAWLVKGR |
| 62 | h-GLP-2 | HADGSFSDEMNTILDNLAARDFINWLIETKITD |
| 63 | Frog GLP-2 | HAEGTFTNDMTNYLEEKAAKEFVGWLIKGRP-OH |
| 64 | OXM | HSQGTFTSDYSKYLDSRRAQDFVQWLMNTKRNRNNIA |
| 65 | Exendin-3 | HSDGTFTSDLSKQMEEEAVRLFIEWLKNGGPSSGAPPPS |
| 66 | Exendin-4 | HGEGTFTSDLSKQMEEEAVRLFIEWLKNGGPSSGAPPPS |
| 291 | Urocortin II (Mouse) | VILSLDVPIGLLRILLEQARYKAARNQAATNAQILAHV-NH2 |

TABLE 1-continued

Exemplary Component Peptide Hormones

| Seq ID | Description | Sequence |
|---|---|---|
| 292 | WP-24 (Urocortin) | WSPGARNQGGGARALLLLLAERFP-OH |
| 293 | TV-18 (Urocortin) | TQSQRERAEQNRIIFDSV-NH2 |
| 294 | Human Urocortin | DNPSLSIDLTFHLLRTLLELARTQSQRERAEQNRIIFDSV-NH2 |
| 295 | SE-20 (Urocortin-111/ Stresscopin) | SFHYLRSRDASSGEEEEGKE-OH |
| 296 | AI-13 (Urocortin-III/ Stresscopin) | AQAAANAHLMAQI-OH |
| 297 | DA-21 (Urocortin) | DNPSLSIDLTFHLLRTLLELA-OH |
| 298 | TL-26 (Urocortin-III/ Stresscopin) | TKFTLSLDVPTNIMNLLFNIAKAKNL-OH |
| 299 | Human Urocortin III | FTLSLDVPTNIMNLLFNIAKAKNLRAQAAANAHLMAQI-NH2 |
| 300 | FN-38 (SLM14) | FLFHYSKTQKLGKSNVVEELQSPFASQSRGYFLFRPRN-NH2 |
| 301 | alpha-Atrial Natriuretic Polypeptide (1-28) human, porcine, bovive | SLRRSSCFGGRMDRIGAQSGLGCNSFRY-OH |
| 302 | Brain natriuretic peptide, Rat; BNP, Rat | c(NSKMAHSSSCFGQKIDRIGAVSRLGCDGLRLF)-OH |
| 303 | Brain Natriuretic Peptide (BNP) (human) | SPKMVQGSGCFGRKMDRISSSSGLGCKVLRRH-OH |
| 304 | C-TYPE Natriuretic peptide, Porcine; Cnp, Porcine | GLSKGCFGLKLDRIGSMSGLGC-OH |
| 305 | Neuromedin U-8 (porcine) | YFLFRPRN-NH2 |
| 306 | Neuromedin U (rat) | YKVNEYQGPVAPSGGFFLFRPRN-NH2 |
| 307 | Neuromedin U-9 | GYFLFRPRN-NH2 |
| 308 | Neuromedin (U25), human | FRVDEEFQSPFASQSRGYFLFRPRN-NH2 |

These peptides are generally C-terminally amidated when expressed physiologically, but need not be for the purposes of the instant invention. In other words, the C-terminus of these peptides, as well as the hybrid polypeptides of the present invention, may have a free —OH or —NH₂ group. These peptides may also have other post-translational modifications. One skilled in the art will appreciate that the hybrid polypeptides of the present invention may also be constructed with an N-terminal methionine residue.

Exemplary peptide modules for use in the invention further include, N-terminally extendable peptide modules (and their analogs and fragments) including Apelin, which exists in forms, Apelin 36 and 13, both active at the AJP receptor (LVQPRGSRNGPGPWQGGRRKFRRQR-PRLSHKGPMPF—OH (SEQ ID NO: 316) and pERPRLSH-KGPMPF—OH (SEQ ID NO: 317)); Prolactin Releasing peptide, which exists in 2 forms, PRP31 and PRP20, equally active at GPR10 (SRTHRHSMEIRTPDINPAWYASRGIR-PVGRF—NH2 (SEQ ID NO: 318) and TPDINPAWYASR-GIRPVGRF—NH2 (SEQ ID NO: 319)); Gastrin, which exists as big gastrin and mini-gastrin, the bulk of activity however residing in resides in pentagastrin (QLGPQGPPHL-VADPSKKQGPWLEEEEEAYGWMDF-NH2 (SEQ ID NO: 320); pEGPWLEEEEEAYGWMDF-NH2 (SEQ ID NO: 321); beta-AWMDF-NH2 (SEQ ID NO: 322)); CCK, which exists as CCK33 or CCK8 (central vs. peripheral; KAPSGRMSIVKNLQNLDPSHRISDRDYMGWMDF-NH2 (SEQ ID NO: 323); DYMGWMDF-NH$_2$) (SEQ ID NO: 55); Cortistatin, which exists as cortistatin 17 or 29 (QEGAP-PQQSARRDRMPCRNFFWKTFSSCK-OH (SEQ ID NO: 324) and DRMPCRNFFWKTFSSCK-OH (SEQ ID NO: 325)); somatostatin, which exists as somatostatin 14 or 28 (SANSNPAMAPRERKAGCKNFFWKTFTSC—OH (SEQ ID NO: 326); AGCKNFFWKTFTSC—OH (SEQ ID NO: 327)); GRP for which a C-terminal 10 amino acid sequence possesses most of the activity (VPLPAGGGTVLTK-MYPRGNHWAVGHLM-NH$_2$ (SEQ ID NO: 328); GNH-WAVGHLM-NH$_2$ (SEQ ID NO: 329)); Neuromedin B for which a C-terminal 10 amino acid region possesses most of the activity (LSWDLPEPRSRASKIRVHSRGNLWAT-GHFM-NH2 (SEQ ID NO: 330); GNLWATGHFM-NH2 (SEQ ID NO: 331)); Neuromedin S for which a C-terminal 9 amino acid region possesses most of the activity (ILQRGS-GTAAVDFTKKDHTATWGRPFFLFRPRN—NH2 (SEQ ID NO: 315); PFFLFRPRN—NH2 (SEQ ID NO: 332)); Neuromedin U for which a C-terminal 9 amino acid region possesses most of the activity (FRVDEEFQSPFASQSRGY-FLFRPRN—NH2 (SEQ ID NO: 308); GYFLFRPRN—NH2 (SEQ ID NO: 307)); Neurotensin, which exists as long and short forms (KIPYILKRQLYENKPRRPYIL-OH (SEQ ID NO: 333); QLYENKPRRPYIL-OH) (SEQ ID NO: 334); Kiss-1 whose activity lies mainly in its C-terminus (GTSL-SPPPESSGSPQQPGLSAPHSRQIPAPQ-GAVLVQREKDLPNYNWNSFGLRF—NH$_2$ (SEQ ID NO: 335); EKDLPNYNWNSFGLRF—NH2 (SEQ ID NO: 336)); RF-amide-3, whose C-terminal fragments possess activity (SAGATANLPLRSGRNMEVSLVRRVPNLPQRF—NH$_2$ (SEQ ID NO: 337); VPNLPQRF—NH2 (SEQ ID NO: 338)); Dynorphin, which exists as big dynorphin (A) of dynorphin B (rimorphin) (YGGFLRRIRPKLKWDNQKRYGGFLR-RQFKVVT-OH (SEQ ID NO: 339); YGGFLRRQFKVVT-OH (SEQ ID NO: 340));

PYY whose C-terminal fragments are active at Y2 receptor (YPIKPEAPGEDASPEELNRYYASL-RHYLNLVTRQRY—NH2 (SEQ ID NO: 57); SLRHYLN-LVTRQRY—NH2 (SEQ ID NO: 341)); AFP-6 whose 7-47 region retains activity (TQAQLLRVGCVLGTC-QVQNLSHRLWQLMGPAGRQDSAPVDPSSPHSY—NH2 (SEQ ID NO: 51); VGCVLGTCQVQNLSHRL-WQLMGPAGRQDSAPVDPSSPHSY—NH2 (SEQ ID NO: 52)); the amylin family including adrenomdullin, calcitonin and CGRP; Oxytocin whose C-terminal amide is generally needed for activity and can tolerate N-terminal extensions.

Exemplary peptide modules for use in the invention further include, C-Terminally extendable peptide modules including, Endothelin I, II and III: ETI (CSCSSLMDKECVYFCHL-DIIWVNTPEHVVPYGLGSPRS—OH (SEQ ID NO: 342); CSCSSLMDKECVYFCHLDIIW-OH (SEQ ID NO: 343)), ETII (CSCSSWLDKECVYFCHLDIIWVNT-PEQTAPYGLGNPP—OH (SEQ ID NO: 344); CSCSS-WLDKECVYFCHLDIIW-OH (SEQ ID NO: 345)) and ETIII (CTCFTYKDKECVYYCHLDIIWIN-TPEQTVPYGLSNYRGSFR—NH2 (SEQ ID NO: 346); CTCFTYKDKECVYYCHLDIIW-OH (SEQ ID NO: 347)); ghrelin whose activity lies mainly in its first 10 residues (GSSFLSPEHQRVQQRKESKKPPAKLQP-OH (SEQ ID NO: 348); GSSFLSPEHQ-OH (SEQ ID NO: 349)); glucagons, including oxyntomodulin which is a C-terminally extended glucagon with glucagons-like activity (HSQGT-FTSDYSKYLDSRRAQDFVQWLMNTKRNRNNIA-OH (SEQ ID NO: 350); HSQGTFTSDYSKYLDSRRAQD-FVQWLMNT-OH (SEQ ID NO: 351)); GLP-1/GLP-2 whose activities are retained with or without a C-terminal amide; GIP, which circulates in 2 forms, GIP1-42 and GIP1-30, both fully active at GIP Receptor (YAEGTFISDYSIAM-DKIHQQDFVNWLLAQKGKKNDWKHNITQ-OH (SEQ ID NO: 352); YAEGTFISDYSIAMDKIHQQDFVNWL-LAQK-NH2 (SEQ ID NO: 353)); neuropeptide W, which exists as NPW23 and NPW30, equally active at GPR7 and 8 (WYKHVASPRYHTVGRAAGLLMGLRRSPYLW-OH (SEQ ID NO: 354); WYKHVASPRYHTVGRAAGLLMGL-OH (SEQ ID NO: 355)); PACAP which exists in 2 forms, PACAP27 and 38 (HSDGIFTDSYSRYRKQMAVKKY-LAAVLGKRYKQRVKNK-NH2 (SEQ ID NO: 356); HSDGIFTDSYSRYRKQMAVKKYLAAVL-NH2 (SEQ ID NO: 357)); PHI and PHV (HADGVFTSDFSKLLGQL-SAKKYLESLMGKRVSSNISEDPVPV-OH (SEQ ID NO: 358); HADGVFTSDFSKLLGQLSAKKYLESLM-NH2 (SEQ ID NO: 359)); GRF, which exists in 2 forms GRF29 and GRF40 (YADAIFTNSYRKVLGQLSARKLLQDIM-SRQQGESNQERGARARL-NH2 (SEQ ID NO: 360); YADAIFTNSYRKVLGQLSARKLLQDIMS-OH (SEQ ID NO: 361)); PTH 1-34 and 1-forms which possess activity of full length PTH 1-84 (SVSEIQLMHNLGKHLNS-MERVEWLRKKLQDVHNFVALGAPLAPRDAGSQRP-RKKED NVLVESHEKSLGEADKADVNVLTKAKSQ (SEQ ID NO: 362); SVSEIQLMHNLGKHLNS-MERVEWLRKKLQDVHNFVAL-OH (SEQ ID NO: 363); SVSEIQLMHNLGKHLNSMERVEWLRKKLQDVHNF—OH (SEQ ID NO: 364)) PTH-RP for which 1-36 possesses activity of full length 1-86 (AVSEHQLLHDKGKS-IQDLRRRFFLHHLIAEIHTAEIRATSEVSPNSKPSPN-TKNHPVRFG SDDEGRYLTQETNKVETYKEQPLKT-PGKKKKGKP-NH2 (SEQ ID NO: 365); AVSEHQLLHD-KGKSIQDLRRRFFLHHLIAEIHTAEI-OH (SEQ ID NO: 366)) gamma-MSH for which the shorter gamma-MSH1 and the longer gamma-MSH3 have similar activities (YVMGH-FRWDRFGRRNSSSSGSSGAGQ-OH (SEQ ID NO: 367); YVMGHFRWDRF—NH2 (SEQ ID NO: 368)); MSH for which alpha-MSH is an active portion of ACTH (SYSMEHFRWGKPVGKKRRPVKVYPN-GAEDESAEAFPLEF-OH (SEQ ID NO: 369); SYSMEH-FRWGKPV-NH2 (SEQ ID NO: 370)); and endorphins for which the A, delta, and γ endorphin are active subpeptides of the larger β endorphin (YGGFMTSEKSQTPLVTLFKNAI-IKNAYKKGE-OH (SEQ ID NO: 371); YGGFMTSEKSQT-PLVTLFKNAIIKNAY-OH (SEQ ID NO: 372); YGGFMTSEKSQTPLVTL-OH (SEQ ID NO: 373); YGG-FMTSEKSQTPLVT-OH (SEQ ID NO: 374)).

The analogs of the above component peptide hormones are known in the art, but generally include modifications such as substitutions, deletions, and insertions to the amino acid sequence of such component peptide hormones, and any combination thereof. The substitutions, insertions and deletions may be at the N-terminal or C-terminal end, or may be at internal portions of the component peptide hormone. In a preferred aspect, analogs of the component peptide hormones of the invention include one or more modifications of a "non-essential" amino acid residue. In the context of the invention, a "non-essential" amino acid residue is a residue that can be altered, i.e., deleted or substituted, in the native human amino acid sequence of the fragment, e.g., the component peptide hormone fragment, without abolishing or substantially reducing the component peptide hormone receptor agonist activity of the resulting analog.

Preferred substitutions include conserved amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine).

The present invention also relates to derivatives of the component peptide hormones. Such derivatives include component peptide hormones and analogs thereof conjugated to one or more water soluble polymer molecules, such as polyethylene glycol ("PEG") or fatty acid chains of various lengths (e.g., stearyl, palmitoyl, octanoyl, etc.), or by the addition of polyamino acids, such as poly-his, poly-arg, poly-lys, and poly-ala. Modifications to the component peptide hormones or analogs thereof can also include small molecule substituents, such as short alkyls and constrained alkyls (e.g., branched, cyclic, fused, adamantyl), and aromatic groups. The water soluble polymer molecules will preferably have a molecular weight ranging from about 500 to about 20,000 Daltons.

Such polymer-conjugations and small molecule substituent modifications may occur singularly at the N- or C-terminus or at the side chains of amino acid residues within the sequence of the hybrid polypeptides. Alternatively, there may be multiple sites of derivatization along the hybrid polypeptide. Substitution of one or more amino acids with lysine, aspartic acid, glutamic acid, or cysteine may provide additional sites for derivatization. See, e.g., U.S. Pat. Nos. 5,824,784 and 5,824,778. Preferably, the hybrid polypeptides may be conjugated to one, two, or three polymer molecules.

The water soluble polymer molecules are preferably lined to an amino, carboxyl, or thiol group, and may be linked by N or C terminus, or at the side chains of lysine, aspartic acid, glutamic acid, or cysteine. Alternatively, the water soluble polymer molecules may be linked with diamine and dicarboxylic groups. In a preferred embodiment, the hybrid polypeptides of the invention are conjugated to one, two, or three PEG molecules through an epsilon amino group on a lysine amino acid.

Derivatives of the invention also include component peptide hormones or analogs with chemical alterations to one or more amino acid residues. Such chemical alterations include amidation, glycosylation, acylation, sulfation, phosphorylation, acetylation, and cyclization. The chemical alterations may occur singularly at the N- or C-terminus or at the side chains of amino acid residues within the sequence of the PPF hybrid polypeptides. In one embodiment, the C-terminus of these peptides may have a free —OH or —NH$_2$ group. In another embodiment, the N-terminal end may be capped with an isobutyloxycarbonyl group, an isopropyloxycarbonyl group, an n-butyloxycarbonyl group, an ethoxycarbonyl group, an isocaproyl group (isocap), an octanyl group, an octyl glycine group (G(Oct)), or an 8-aminooctanic acid group. In a preferred embodiment, cyclization can be through the formation of disulfide bridges. Alternatively, there may be multiple sites of chemical alteration along the hybrid polypeptide.

2. The Amylin Family

As discussed herein component peptide hormones useful in the present invention include amylin family peptide hormones including amylin, adrenomedullin ("ADM"), calcitonin ("CT"), calcitonin gene related peptide ("CGRP"), intermedin (also known as "AFP-6") and related peptides. Native amylin family peptide hormones are known in art, as are functional peptide analogs and derivatives. Certain preferred native peptides, peptide analogs and derivatives are described herein, however it should be recognized that any known amylin family peptides that exhibit hormonal activity known in the art may be used in conjunction with the present invention.

Any amylin analog or derivative known in the art may be used in conjunction with the present invention. In one embodiment, the amylin analogs and derivatives have at least one hormonal activity of native amylin. In certain embodiments, the amylin analogs are agonists of a receptor which native amylin is capable of specifically binding. Preferred amylin analogs and derivatives include those described in US 2003/0026812 A1, which is hereby incorporated by reference.

Exemplary amylin analogs include:

| SEQ ID: | |
|---|---|
| 67 | $^{25,28,29}$Pro-h-amylin (pramlintide) |
| 68 | des-$^1$Lys-h-amylin |
| 69 | $^{25}$Pro,$^{26}$Val,$^{28,29}$Pro-h-amylin |
| 70 | $^{18}$Arg,$^{25,28}$Pro-h-amylin |
| 71 | des-$^1$Lys,$^{18}$Arg,$^{25,28}$Pro-h-amylin |
| 72 | $^{18}$Arg,$^{25,28,29}$Pro-h-amylin |
| 73 | des-$^1$Lys,$^{18}$Arg,$^{25,28,29}$Pro-h-amylin |
| 74 | des-$^1$,Lys$^{25,28,29}$Pro-h-amylin |
| 75 | $^{25}$Pro,$^{26}$Val,$^{28,29}$Pro-h-amylin |
| 76 | $^{28}$Pro-h-amylin, 2,7-Cyclo-[$^2$Asp,$^7$Lys]-h-amylin |
| 77 | $^{2-37}$h-amylin |
| 78 | $^1$Ala-h-amylin |
| 79 | $^2$Ala-h-amylin |
| 80 | $^{2,7}$Ala-h-amylin |
| 81 | $^1$Ser-h-amylin |
| 82 | $^{29}$Pro-h-amylin |
| 83 | $^{25,28}$Pro-h-amylin |
| 84 | des-$^1$Lys,$^{25,28}$Pro-h-amylin |
| 85 | $^{23}$Leu,$^{25}$Pro,$^{26}$Val,$^{28,29}$Pro-h-amylin |
| 86 | $^{23}$Leu$^{25}$Pro$^{26}$Val$^{28}$Pro-h-amylin |
| 87 | des-$^1$Lys,$^{23}$Leu,$^{25}$Pro,$^{26}$Val,$^{28}$Pro-h-amylin |
| 88 | $^{18}$Arg,$^{23}$Leu,$^{25}$Pro,$^{26}$Val,$^{28}$Pro-h-amylin |
| 89 | $^{18}$Arg,$^{23}$Leu,$^{25,28,29}$Pro-h-amylin |
| 90 | $^{18}$Arg$^{23}$Leu,$^{25,28}$Pro-h-amylin |
| 91 | $^{17}$Ile,$^{23}$Leu,$^{25,28,29}$Pro-h-amylin |
| 92 | $^{17}$Ile,$^{25,28,29}$Pro-h-amylin |
| 93 | des-$^1$Lys,$^{17}$Ile,$^{23}$Leu,$^{25,28,29}$Pro-h-amylin |
| 94 | $^{17}$Ile,$^{18}$Arg,$^{23}$Leu-h-amylin |
| 95 | $^{17}$Ile,$^{18}$Arg,$^{23}$Leu,$^{26}$Val,$^{29}$Pro-h-amylin |
| 96 | $^{17}$Ile,$^{18}$Arg,$^{23}$Leu,$^{25}$Pro,$^{26}$Val,$^{28,29}$Pro-h-amylin, |
| 97 | $^{13}$Thr,$^{21}$His,$^{23}$Leu,$^{26}$Ala,$^{28}$Leu,$^{29}$Pro,$^{31}$Asp-h-amylin |
| 98 | $^{13}$Thr,$^{21}$His,$^{23}$Leu,$^{26}$Ala,$^{29}$Pro,$^{31}$Asp-h-amylin |
| 99 | des-$^1$Lys,$^{13}$Thr,$^{21}$His,$^{23}$Leu,$^{26}$Ala,$^{28}$Pro,$^{31}$Asp-h-amylin |
| 100 | $^{13}$Thr,$^{18}$Arg,$^{21}$His,$^{23}$Leu,$^{26}$Ala,$^{29}$Pro,$^{31}$Asp-h-amylin |
| 101 | $^{13}$Thr,$^{18}$Arg,$^{21}$His,$^{23}$Leu,$^{28,29}$Pro,$^{31}$Asp-h-amylin |
| 102 | $^{13}$Thr,$^{18}$Arg,$^{21}$His,$^{23}$Leu,$^{25}$Pro,$^{26}$Ala,$^{28,29}$Pro,$^{31}$Asp-h-amylin |

As known in the art, such amylin analogs are preferably amidated, but within the context of the present invention, may optionally be in the acid form unless otherwise specified.

Any ADM analog or derivative known in the art may be used in conjunction with the present invention. In one embodiment, the ADM analogs and derivatives have at least one hormonal activity of native ADM. In certain embodiments, the ADM analogs are agonists of a receptor which native ADM is capable of specifically binding.

Any CT analog or derivative known in the art may be used in conjunction with the present invention. In one embodiment, the CT analogs and derivatives have at least one hormonal activity of native CT. In certain embodiments, the CT analogs are agonists of a receptor which native CT is capable of specifically binding. Preferred CT analogs and derivatives include those described in U.S. Pat. Nos. 4,652,627; 4,606,856; 4,604,238; 4,597,900; 4,537,716; 4,497,731; 4,495,097; 4,444,981; 4,414,149; 4,401,593; and 4,397,780, which are hereby incorporated by reference.

Exemplary CT analogs include:

| SEQ ID: | |
|---|---|
| 103 | $^8$Gly-CT |
| 104 | $^{22}$Leu-CT |
| 105 | $^2$Gly,$^3$Ser,$^8$Gly,$^{22}$des-Tyr-CT |
| 106 | $^{14}$Glu-sCT, |
| 107 | $^{18}$Arg-sCT, |
| 108 | $^{11,18}$Arg-sCT, |
| 109 | $^{14}$Glu,$^{18}$Arg-sCT, |
| 110 | $^{14}$Glu,$^{11,18}$Arg-sCT |

As known in the art, such CT analogs are preferably amidated, but within the context of the present invention, may optionally be in the acid form unless otherwise specified.

Any CGRP analog or derivative known in the art may be used in conjunction with the present invention. In one embodiment, the CGRP analogs and derivatives have at least one hormonal activity of native CGRP. In certain embodiments, the CGRP analogs are agonists of a receptor which native CGRP is capable of specifically binding. Preferred CGRP analogs and derivatives include those described in U.S. Pat. Nos. 4,697,002; and 4,687,839, which are hereby incorporated by reference.

Exemplary CGRP analogs include:

| SEQ ID: | |
|---|---|
| 111 | $^{36}$D-Ser-CGRP |
| 112 | $^{36}$D-Thr-CGRP |
| 113 | $^{36}$D-Asp-CGRP |
| 114 | $^{36}$D-Asn-CGRP |
| 115 | $^{36}$Ser-CGRP |
| 116 | $^{36}$Hse-CGRP |
| 117 | $^{36}$Asp-CGRP |
| 118 | $^{36}$Thr-CGRP |
| 119 | $^{36}$Asn-CGRP |

Any AFP-6 analog or derivative known in the art may be used in conjunction with the present invention. In one embodiment, the AFP-6 analogs and derivatives have at least one hormonal activity of native AFP-6. In certain embodiments, the AFP-6 analogs are agonists of a receptor which native AFP-6 is capable of specifically binding. Preferred AFP-6 analogs and derivatives include those described in WO 2003/022304, which is hereby incorporated by reference.

Exemplary AFP-6 analogs include:

| SEQ ID: | |
|---|---|
| 120 | TQAQLLRVGCGNLSTCQVQNLSHRLWQLMGPAGRQDSAPVDPSSPHSY |
| 121 | TQAQLLRVGCDTATCQVQNLSHRLWQLMGPAGRQDSAPVDPSSPHSY |
| 122 | TQAQLLRVGMVLGTMQVQNLSHRLWQLMGPAGRQDSAPVDPSSPHSY |
| 123 | TQAQLLRVGCVLGTCQVQNLSHRLWQLMGPAGRQDSAPVEPSSPHSY |
| 124 | TQAQLLRVGCVLGTCQVQNLSHRLWQLMGPAGRQESAPVEPSSPHSY |
| 125 | TQAQLLRVGCVLGTCQVQNLSHRLWQL----RQDSAPVDPSSPHSY |
| 126 | TQAQLLRVGCVLGTCQVQNLSHRLWQL----DSAPVDPSSPHSY |
| 127 | RVGCVLGTCQVQNLSHRLWQLMGPAGRQDSAPVDPSSPHSY |
| 128 | VGCVLGTCQVQNLSHRLWQLMGPAGRQDSAPVEPSSPHSY |
| 129 | VGCVLGTCQVQNLSHRLWQL----RQDSAPVEPSSPHSY |
| 130 | GCVLGTCQVQNLSHRLWQLMGPAGRQDSAPVDPSSPHSY |
| 131 | GCNTATCQVQNLSHRLWQL----RQDSAPVDPSSPHSY |
| 132 | GCNTATCQVQNLSHRLWQL----RQDSAPVEPSSPHSY |
| 133 | GCSNLSTCQVQNLSHRLWQL----RQDSAPVEPSSPHSY |
| 134 | GCGNLSTCQVQNLSHRLWQL----RQDSAPVEPSSPHSY |
| 135 | GCVLGTCQVQNLSHRLWQL----RQESAPVEPSSPHSY |
| 136 | CVLGTCQVQNLSHRLWQLMGPAGRQDSAPVDPSSPHSY |
| 137 | QVQNLSHRLWQLMGPAGRQDSAPVDPSSPHSY |
| 138 | VQNLSHRLWQLMGPAGRQDSAPVDPSSPHSY |
| 139 | VQNLSHRL----QLMGPAGRQDSAPVDPSSPHSY |
| 140 | GTMQVQNLSHRLWQL----RQDSAPVEPSSPHSY |

As known in the art, such AFP-6 analogs are preferably amidated, but within the context of the present invention, may optionally be in the acid form unless otherwise specified.

3. The CCK Family

CCKs, including hCCK and species variants, and various analogs thereof are known in the art. Generally, CCK has a 33-amino acid sequence first identified in humans, and includes a 8-amino acid in vivo C-terminal fragment ("CCK-8") that has been reportedly demonstrated in pig, rat, chicken, chinchilla, dog and humans. Other species variants include a 39-amino acid sequence found in pig, dog and guinea pig, and a 58-amino acid found in cat, dog and humans, and a 47-amino acid sequences homologous to both CCK and gastrin. The C-terminal tyrosine-sulfated octapeptide sequence (CCK-8) is relatively conserved across species, and may be the minimum sequence for biological activity in the periphery of rodents. Thus, the term CCK-33 will generally refer to human CCK(1-33), while CCK-8 (CCK(26-33); SEQ ID NO: 55) will refer to the C-terminal octapeptide generically in both the sulfated and unsulfated unless otherwise specified. Further, pentagastrin or CCK-5 will refer to the C-terminal peptide CCK(29-33) (SEQ ID NO: 209), and the CCK-4 will refer to the C-terminal tetrapeptide CCK(30-33) (SEQ ID NO: 208).

The type A receptor subtype ($CCK_A$) has been reported to be selective for the sulfated octapeptide. The Type B receptor subtype ($CCK_B$) has been identified throughout the brain and in the stomach, and reportedly does not require sulfation or all eight amino acids.

Various in vivo and in vitro screening methods for CCK analogs are known in the art. Examples include in vivo assays involving the contraction of the dog or guinea pig gallbladder after rapid intravenous injection of the compound to be tested for CCK-like activity, and in vitro assays using strips of rabbit gallbladder. See Walsh, "Gastrointestinal Hormones", In Physiology of the Gastrointestinal Tract (3d ed. 1994; Raven Press, New York).

Certain exemplary CCKs and CCK analogs with CCK activity include:

| SEQ ID: | |
|---|---|
| 141 | $DY(SO_3H)MGWMDF$ |
| 142 | DYMGWMDF |
| 143 | MGWMDF |
| 144 | GWMDF |
| 145 | WMDF |
| 146 | $KDY(SO_3H)MGWMDF$ |
| 147 | KDYMGWMDF |
| 148 | KMGWMDF |
| 149 | KGWMDF |
| 150 | KWMDF |

As known in the art, such CCK peptides are preferably amidated, but within the context of the present invention, may optionally be in the acid form unless otherwise specified.

4. The Leptin Family

Component peptide hormones useful in the present invention also include leptin family peptide hormones. Native leptin family peptide hormones are known in art, as are functional peptide analogs and derivatives. Certain preferred native peptides, peptide analogs and derivatives are described herein, however it should be recognized that any known amylin family peptides that exhibit hormonal activity known in the art may be used in conjunction with the present invention.

Any leptin analog or derivative known in the art may be used in conjunction with the present invention. In one embodiment, the leptin analogs and derivatives have at least one hormonal activity of native leptin. In certain embodiments, the leptin analogs are agonists of a receptor which native leptin is capable of specifically binding. Preferred leptin analogs and derivatives include those described in, e.g., WO 2004/039832, WO 98/55139, WO 98/12224, and WO 97/02004, all of which are hereby incorporated by reference.

Exemplary leptin analogs include those where the amino acid at position 43 is substituted with Asp or Glu; position 48 is substituted Ala; position 49 is substituted with Glu, or absent; position 75 is substituted with Ala; position 89 is substituted with Leu; position 93 is substituted with Asp or Glu; position 98 is substituted with Ala; position 117 is substituted with Ser, position 139 is substituted with Leu, position 167 is substituted with Ser, and any combination thereof.

Certain exemplary leptin and leptin analogs with leptin activity include:

| SEQ ID: | |
|---|---|
| 151 | $^{43}$Asp-leptin |
| 152 | $^{43}$Glu-leptin |
| 153 | $^{48}$Ala-leptin |
| 154 | $^{49}$Glu-leptin |
| 155 | $^{49}$Des-AA-leptin |
| 156 | $^{75}$Ala-leptin |
| 157 | $^{89}$Leu-leptin |
| 158 | $^{93}$Asp-leptin |
| 159 | $^{93}$Glu-leptin |
| 160 | $^{98}$Ala-leptin |
| 161 | $^{117}$Ser-leptin |
| 162 | $^{139}$Leu-leptin |
| 163 | $^{167}$Ser-leptin |
| 164 | $^{43}$Asp, $^{49}$Glu-leptin |
| 165 | $^{43}$Asp, $^{75}$Ala-leptin |
| 166 | $^{89}$Leu, $^{117}$Ser-leptin |
| 167 | $^{93}$Glu, $^{167}$Ser-leptin |

5. The PPF Family

Component peptide hormones useful in the present invention also include PPF peptide hormones, including PP and PYY. Native PPF peptide hormones are known in art, as are functional peptide analogs and derivatives. Certain preferred native peptides, peptide analogs and derivatives are described herein, however it should be recognized that any known amylin family peptides that exhibit hormonal activity known in the art may be used in conjunction with the present invention.

Any PPF analog or derivative known in the art may be used in conjunction with the present invention. In one embodiment, the PPF analogs and derivatives have at least one hormonal activity of a native PPF polypeptide. In certain embodiments, the PPF analogs are agonists of a receptor which native PPF polypeptide is capable of specifically binding. Preferred PPF analogs and derivatives include those described in WO 03/026591 and WO 03/057235, which are herein incorporated by reference in their entirety.

In one embodiment, preferred PPF analogs and derivatives that exhibit at least one PPF hormonal activity generally comprise at least two PYY motifs including a polyproline motif and C-terminal tail motif. Such analogs are generally described in U.S. Provisional Application No. 60/543,406 filed Feb. 11, 2004, which is herein incorporated by reference. Other preferred PPF analogs are disclosed in PCT/US2005/004351, entitled "Pancreatic Polypeptide Family Motifs and Polypeptides Comprising the Same", the contents of which is hereby incorporated by reference. By way of background, research has suggested that the differences in Y receptor binding affinities are correlated with secondary and tertiary structural differences. See, e.g., Keire et al., *Biochemistry* 2000, 39, 9935-9942. Native porcine PYY has been characterized as including two C-terminal helical segments from residues 17 to 22 and 25 to 33 separated by a kink at residues 23, 24, and 25, a turn centered around residues 12-14, and the N-terminus folded near residues 30 and 31. Further, full-length porcine PYY has been characterized as including the PP fold, stabilized by hydrophobic interactions among residues in the N- and C-termini. See id.

A "PYY motif" is generally a structural component, primary, secondary, or tertiary, of a native PP family polypeptide that is critical to biological activity, i.e., biological activity is substantially decreased in the absence or disturbance of the motif Preferred PYY motifs include the N-terminal polyproline type II motif of a native PP family polypeptide, the type II β-turn motif of native PP family polypeptide, the α-helical motif at the C-terminal end of native PP family polypeptide, and the C-terminal tail motif of native PP family polypeptide.

More particularly, in the N-terminal polyproline region, amino acids corresponding to residues 5 and 8 of a native PP family polypeptide are generally conserved as a proline. The type II β-turn motif will generally include amino acids corresponding to residues 12-14 of a native PP family polypeptide. The α-helical motif can generally extend from amino acids corresponding to approximately residue 14 of a native PP family polypeptide to any point up to and including the C-terminal end, so long as the α-helical motif includes a sufficient number of amino acid residues such that an α-helical turn is formed in solution. The α-helical motif can also include amino acid substitutions, insertions and deletions to the native PP family sequence, so long as the α-helical turn is still formed in solution. The C-terminal tail motif generally includes amino acids corresponding to approximately the last 10 residues of a native PP family polypeptide, more preferably the last 7, 6, or 5 residues of a native PP family polypeptide, and more preferably amino acid residues 32-35.

Preferred PYY analogs include those with internal deletions, insertions, and substitutions in areas of the PYY molecule not corresponding to the polyproline motif and/or the C-terminal tail motif. For instance, internal deletions at positions 4, 6, 7, 9, or 10 are envisioned.

6. Incretins and Incretin Mimetics

Component peptide hormones useful in the present invention also include GLP-1 peptide hormones. Native GLP-1 peptide hormones, including GLP1(1-37) (SEQ ID NO: 59), GLP1(7-37) (SEQ ID NO: 204), and GLP1(7-36)amide (SEQ ID NO: 61), are known in art, as are functional peptide analogs and derivatives. As used herein, GLP-1 refers to all native forms of GLP-1 peptide hormones. Certain preferred native peptides, peptide analogs and derivatives are described herein, however it should be recognized that any known GLP-1 peptides that exhibit hormonal activity known in the art may be used in conjunction with the present invention.

Any GLP-1 peptide analog or derivative known in the art may be used in conjunction with the present invention. In one embodiment, the GLP-1 peptide analogs and derivatives have at least one hormonal activity of a native GLP-1 peptide. In certain embodiments, the GLP-1 peptide analogs are agonists of a receptor which a native GLP-1 peptide is capable of specifically binding. Preferred GLP-1 peptide analogs and derivatives include those described in, e.g., WO 91/11457, which is hereby incorporated by reference.

GLP-1 analogs known in the art include:

| SEQ ID: | |
|---|---|
| 168 | $^9$Gln-GLP-1(7-37) |
| 169 | D-$^9$Gln-GLP-1(7-37) |
| 170 | $^{16}$Thr-$^{18}$Lys-GLP-1(7-37) |
| 171 | $^{18}$Lys-GLP-1(7-37) |
| 172 | $^8$Gly-GLP-1 (7-36) |
| 173 | $^9$Gln-GLP-1 (7-37) |
| 174 | D-$^9$Gln-GLP-1 (7-37) |
| 175 | acetyl-$^9$Lys-GLP-1(7-37) |
| 176 | $^9$Thr-GLP-1(7-37) |
| 177 | D-$^9$Thr-GLP-1 (7-37) |
| 178 | $^9$Asn-GLP-1 (7-37) |
| 179 | D-$^9$Asn-GLP-1 (7-37) |
| 180 | $^{22}$Ser$^{23}$Arg$^{24}$Arg$^{26}$Gln-GLP-1(7-37) |
| 181 | $^{16}$Thr$^{18}$Lys-GLP-1(7-37) |
| 182 | $^{18}$Lys-GLP-1(7-37) |
| 183 | $^{23}$Arg-GLP-1(7-37) |
| 184 | $^{24}$Arg-GLP-1(7-37) |

As known in the art, such GLP-1 analogs may preferably be amidated, but within the context of the present invention, may optionally be in the acid form unless otherwise specified.

Other GLP-1 analogs and derivatives are disclosed in U.S. Pat. No. 5,545,618 which is incorporated herein by reference. A preferred group of GLP-1 analogs and derivatives include those disclosed in U.S. Pat. No. 6,747,006, which is herein incorporated by reference in its entirety. The use in the present invention of a molecule described in U.S. Pat. No. 5,188,666, which is expressly incorporated by reference, is also contemplated. Another group of molecules for use in the present invention includes compounds described in U.S. Pat. No. 5,512,549, which is expressly incorporated herein by reference. Another preferred group of GLP-1 compounds for use in the present invention is disclosed in WO 91/11457, which is herein incorporated by reference.

Component peptide hormones useful in the present invention also include GLP-2 peptide hormones. Native GLP-2 peptide hormones, e.g., rat GLP-2 and its homologous including ox GLP-2, porcine GLP-2, degu GLP-2, bovine GLP-2, guinea pig GLP-2, hamster GLP-2, human GLP-2, rainbow trout GLP-2, and chicken GLP-2, are known in art, as are functional peptide analogs and derivatives. Certain preferred native peptides, peptide analogs and derivatives are described herein, however it should be recognized that any known GLP-2 peptides that exhibit hormonal activity known in the art may be used in conjunction with the present invention.

Any GLP-2 peptide analog or derivative known in the art may be used in conjunction with the present invention. In one embodiment, the GLP-2 peptide analogs and derivatives have at least one hormonal activity of a native GLP-2 peptide. In certain embodiments, the GLP-2 peptide analogs are agonists of a receptor which a native GLP-2 peptide is capable of specifically binding. Preferred GLP-2 peptide analogs and derivatives include those described in, e.g., U.S. Ser. No. 08/669,791 and PCT Application PCT/CA97/00252, both of which are hereby incorporated by reference. Specific GLP-2 analogs known in the art include: rat or human GLP-2 altered at position 2 to confer DPP-IV resistance by substituting a Gly for an Ala.

Component peptide hormones useful in the present invention also include oxyntomodulin (OXM) peptide hormones. Native OXM peptide hormones are known in art, as are functional peptide analogs and derivatives. Certain preferred native peptides, peptide analogs and derivatives are described herein, however it should be recognized that any known OXM peptides that exhibit hormonal activity known in the art may be used in conjunction with the present invention.

Any OXM peptide analog or derivative known in the art may be used in conjunction with the present invention. In one embodiment, the OXM peptide analogs and derivatives have at least one hormonal activity of a native OXM peptide. In certain embodiments, the OXM peptide analogs are agonists of a receptor which a native OXM peptide is capable of specifically binding.

Component peptide hormones useful in the present invention also include exendin peptide hormones. Native exendin peptide hormones are known in art, as are functional peptide analogs and derivatives. Certain preferred native peptides, peptide analogs and derivatives are described herein, however it should be recognized that any known exendin peptides that exhibit hormonal activity known in the art may be used in conjunction with the present invention.

Any exendin peptide analog or derivative known in the art may be used in conjunction with the present invention. In one embodiment, the exendin peptide analogs and derivatives have at least one hormonal activity of a native exendin peptide. In certain embodiments, the exendin peptide analogs are agonists of a receptor which a native exendin peptide is capable of specifically binding.

Exemplary exendin analogs include:

| SEQ ID: | |
|---|---|
| 185 | $^{14}$Leu,$^{25}$Phe-exendin-4 |
| 186 | $^{5}$Ala,$^{14}$Leu,$^{25}$Phe-exendin-4 |
| 187 | $^{14}$Leu,$^{22}$Ala,$^{25}$Phe-exendin-4 |

As known in the art, such exendin analogs are preferably amidated, but within the context of the present invention, may optionally be in the acid form unless otherwise specified.

Additional exemplary exendin analogs and derivatives are described in PCT Application Serial No. PCT/US98/16387 filed Aug. 6, 1998, entitled "Novel Exendin Agonist Compounds," which claims the benefit of U.S. patent application Ser. No. 60/055,404, filed Aug. 8, 1997, both of which are herein incorporated by reference. Other exendin analogs and derivatives are described in PCT Application Serial No. PCT/US98/24210, filed Nov. 13, 1998, entitled "Novel Exendin Agonist Compounds," which claims the benefit of U.S. Provisional Application No. 60/065,442 filed Nov. 14, 1997, both of which are herein incorporated by reference. Still other exendin analogs and derivatives are described in PCT Application Serial No. PCT/US98/24273, filed Nov. 13, 1998, entitled "Novel Exendin Agonist Compounds," which claims the benefit of U.S. Provisional Application No. 60/066,029 filed Nov. 14, 1997, both of which are herein incorporated by reference. Still other exendin analogs and derivatives are described in PCT Application Serial No. PCT/US97/14199, filed Aug. 8, 1997, entitled "Methods for Regulating Gastrointestinal Activity," which is a continuation-in-part of U.S. patent application Ser. No. 08/694,954 filed Aug. 8, 1996, both of which are hereby incorporated by reference. Still other exendin analogs and derivatives are described in PCT Application Serial No. PCT/US98/00449, filed Jan. 7, 1998, entitled "Use of Exendins and Agonists Thereof for the Reduction of Food Intake," which claims priority to U.S. Provisional Application No. 60/034,905 filed Jan. 7, 1997, both of which are hereby incorporated by reference. Yet other exendin analogs and derivatives are described in US 2004/0209803 A1, filed Dec. 19, 2003, entitled "Compositions for the Treatment and Prevention of Neuropathy," which is hereby incorporated by reference.

vii. Natriuretic Peptides.

Natriuretic peptides are a family of hormones that consist of atrial natriuretic peptide (ANP), brain natriuretic peptide (BNP), and C-type natriuretic peptide (CNP). They are synthesized and stored as 3 distinct precursor prohormones, which are the 126 amino acid ANP, 108 amino acid BNP, and 104 amino acid CNP. They are each encoded by separate genes and have distinct sites of synthesis and mechanisms of regulation. Parental natriuretic peptide sequences include:

| SEQ ID NO: 375 | 151 amino acid human ANP preprohormone | MSSFSTTTVSFLLLLAFQLLGQTRANPM YNAVSNADLMDFKNLLDHLEEKMPLEDE VVPPQVLSDPNEEAGAALSPLPEVPPWT GEVSPAQRDGGALGRGPWDSSDRSALLK SKLRALLTAPRSLRRSSCFGGRMDRIGA QSGLGCNSFRY |
|---|---|---|
| SEQ ID NO: 376 | 134 amino acid human BNP preprohormone | MDPQTAPSRALLLLLFLHLAFLGGRSHP LGSPGSASDLETSGLQEQRNHLQGKLSE LQVEQTSLEPLQESPRPTGVWKSREVAT EGIRGHRKMVLYTLRAPRSPKMVQGSGC FGRKMDRISSSSGLGCKVLRRH |
| SEQ ID NO: 377 | 126 amino acid human CNP preproCNP | MHLSQLLACALLLTLLSLRPSEAKPGAP PKVPRTPPAEELAEPQAAGGGQKKGDKA PGGGGANLKGDRSRLLRDLRVDTKSRAA WARLLQEHPNARKYKGANKKGLSKGCFG LKLDRIGSMSGLGC |

The main site of synthesis of the ANP prohormone is the atrial myocyte where it is synthesized as a 151-amino acid preprohormone. Removal of a 25-amino acid signal peptide from its N terminal end occurs in the endoplasmic reticulum, leaving a 126-amino acid ANP prohormone (ProANP), the main storage form of ANP within the heart. The prohormone consists of 4 biologically active peptide segments: amino acids 1-30 (ProANF 1-30, also known as long acting Na stimulator), 31-67 (ProANF 31-67, also known as vessel dilator), 79-98 (ProANF 79-98, also known as potassium excreter), and 99-126 (ANF, also known as atrial natriuretic factor).

BNP was originally isolated from porcine brain but in humans it is synthesized and secreted from the left ventricle. Sequence analysis reveals that preproBNP consists of 134 residues and is cleaved to a 108-amino acid ProBNP. Cleavage of a 32-amino acid sequence from the C-terminal end of ProBNP results in human BNP (77-108), which is the physiologically active form in plasma.

CNP is the third member of the natriuretic peptide system and is primarily found in human vascular endothelial cells, kidney, and porcine brain. High concentrations of CNP are also found in human hypothalamus and midbrain. In humans, preproCNP is a 126-amino acid precursor processed into proCNP by cleavage of 23 residues from its N-terminal end. This 23-amino acid sequence serves as a signal peptide. The terminal 22 (105-126) amino acids are cleaved from proCNP to yield a biologically active form of CNP.

Urodilatin is a kidney-derived member of the natriuretic peptide family and is formed from the same ANP prohormone and consists of amino acids 95-126. Except for the 4 amino acid N terminal extension, it is identical to ANF (99-126). Urodilatin appears to be an important regulator of sodium and water handling in the kidney, as well as a mediator of sodium excretion in patients with congestive heart failure (CHF).

Natriuretic peptides exert their biologic effects by binding to high-affinity receptors on the surface of target cells. Three subtypes of NPRs—NPR-A, NPR-B, and NPRC—have been isolated. Consequently, in one embodiment is provided a method to screen hybrids for natriuretic receptor binding and/or activation. Natriuretic peptides including prohormone variants can impart numerous natriuretic peptide hormone activities to hybrids of the invention. In other embodiments of interest are natriuretic antagonist hybrids. Natriuresis is the excretion of an excessively large amount of sodium into the urine. Natriuresis is similar to diuresis (the excretion of an unusually large quantity of urine), except that in natriuresis the urine is exceptionally salty. Natriuresis occurs with some diuretics and diseases (as of the adrenal) and can lead to the salt-losing syndrome characterized by dehydration, vomiting, low blood pressure, and the risk of sudden death. Exogenous administration of the 4 independent circulating peptides of the ANP prohormone (1-30, 31-67, 79-98, and 99-126) produce in vivo vasodilation, diuresis, suppression of the renin-angiotensin-aldosterone system and enhanced natriuresis and/or kaliuresis. ProANF 1-30, ProANF 31-67 and ANF 99-126 each have natriuretic, blood pressure lowering and diuretic properties with ProANF 31-67 and ANF 99-126 having the greatest impact on blood pressure. There are varying effects of the ANP peptides on potassium homeostasis: ProANF 79-98 stimulates potassium excretion, whereas ProANF 31-67 spares potassium loss by inhibiting Na/K ATPase in the medullary collecting duct cells. Specific to ANF 99-126 is a dose-dependent inhibition of angiotensin II-mediated aldosterone secretion, whereas proANF 31-67 has the property of inducing natriuresis through generation of prostaglandin.

BNP produces similar biologic effects as ANF in normal humans. Infusions of BNP in normal men produced a 2-fold increase in sodium excretion, 50% reduction in plasma renin, angiotensin II and aldosterone secretion as well as a reduction in plasma volume.

CNP induces cardiovascular effects similar to the other natriuretic peptides but does not appear to mediate any renal effects. When CNP is infused in anesthetized dogs at equivalent doses of ANF, plasma cGMP rose with a concomitant reduction in mean arterial pressure, right atrial pressure and cardiac output, but glomerular filtration rate, renal blood flow and sodium excretion decreased.

Natriuretic peptides can provide therapeutic benefit in heart failure. Congestive heart failure (CHF) is associated with increases in vasopressin, endothelin, and with activation of the renin-angiotensin-aldosterone system, and sympathetic nervous systems, mediating vasoconstriction, sodium and water retention, and negative vascular and cardiac remodeling. These effects occur despite the elevated levels of the natriuretic peptides in patients with heart failure. In one embodiment of the invention are hybrids that provide increased or therapeutic serum levels of natriuretic peptide activity for treatment or prevention of cardiac related diseases and conditions, including CHF. Although ANF infusion in normal individuals can result in a sustained increase in sodium excretion and urine flow rates, in the heart failure patient a marked beneficial reduction in renal response can be obtained. BNP infusion markedly increases sodium excretion in patients with heart failure and exerts significant beneficial hemodynamic effects. As compared with ANP, the diuretic and natriuretic effects of BNP are significantly greater. BNP is cleared more slowly than ANP and exerts other effects including suppressing aldosterone secretion and increasing serum levels of ANP. BNP peptides can also provide a beneficial decrease in pulmonary capillary wedge pressure, systemic vascular resistance, right atrial pressure and systolic blood pressure, with an increase in cardiac index in patients hospitalized for symptomatic CHF. In patients with decompensated heart failure, natriuretic peptide hybrids can provide a beneficial decrease in pulmonary capillary wedge pressure and an improved dyspnea score. (Dyspnea is an unpleasant sensation of difficulty in breathing, typically associated with early stages of cardiac heart failure.) The hybrids containing one, two or three natriuretic hormone functions provide methods of administration of pharmaceutically active compositions that are useful for both the prophylactic and therapeutic treatment of CHF patients, preferably CHF patients that are decompensated, patients with chronic CHF, and patients with hypertension. The natriuretic portion(s) of a hybrid is sufficient to provide a therapeutically effective amount of a natriuertic peptide to such patient when administered in a therapeutically effective dose over a therapeutically effective period.

As discussed herein any of the family of therapeutically effective natriuretic peptides or their analogs can be used. Useful natriuretic peptides include, for example, atrial natriuretic peptide (ANP), brain natriuretic peptide (BNP or B-type natriuretic peptide) and C-type natriuretic peptide (CNP). Sequences of useful forms of natriuretic peptides are disclosed in U.S. Patent Publication 20010027181, which is incorporated herein by reference. Examples of ANPs include human ANP (Kangawa et al., BBRC 118:131 (1984)) or that from various species, including pig and rat ANP (Kangawa et al., BBRC 121:585 (1984)). Such ANPs comprise 28 amino acids. Such ANPs may be administered as a peptide having a ring structure of ANP (formation of a disulfide bond based on Cys), and a C-terminal portion succeeding the ring structure. An example of such a peptide is a peptide having amino acid residues at the 7-position to the 28-position of ANP is provided in U.S. Patent Application Publication No. 20010027181. Another example is frog ANP. Specific examples of BNPs that can be used in the methods of the invention include human BNP (hBNP). Human BNP comprises 32 amino acids and involves the formation of a disulfide bond (Sudoh et al., *BBRC* 159:1420 (1989)) and U.S. Pat. Nos. 5,114,923, 5,674,710, 5,674,710, and 5,948,761, each of which is incorporated by reference. Various BNP's of origin other than human, including as pig BNP and rat BNP, are also known, and can be used. A further example is chicken BNP. Examples of CNPs that can be used in the methods of the invention include pig CNP. Pig CNP comprises 22 amino acids and involves the formation of a disulfide bond, like the above-described ANP and BNP (Sudoh et al., BBRC 168:863 (1990)) (human and rat have the same amino acid sequence), chicken CNP (Arimura et al., BBRC 174:142 (1991)). Frog CNP (Yoshihara et al., *BBRC* 173:591 (1990) can also be used. As discussed herein, one skilled in the art can apply modifications, such as a deletion, substitution, addition or insertion, and/or chemical modification to amino acid residues in the amino acid sequence of a known natriuretic peptide as desired, by known methods. The resulting compound is a compound which has the activity of acting on a receptor of the starting ANP, BNP or CNP. Analogs having this activity, therefore, are included in the hybrids for use in accordance with the methods of the present invention.

In another embodiment, the hybrids containing one or more natriuretic functions can be used in treating hypertension. In one embodiment a natriuretic hybrid will have no deleterious effect on heart rate and is not associated with arrhythmias. In one embodiment the hybrid will comprise at least one, two or three natriuretic peptide functions, for example, both ANP and BNP activity. One or more natriuretic hormone functions can be combined with any other hormone function or peptidic enhancer, as described herein. In another embodiment the natriuretic portion(s) is a more stable analog having an extended in vivo half-life when compared with that of a native natriuretic peptide. Analogs that prevent undesirable cleavage by endogenous enzymes such as NEP are also envisioned. The natriuretic containing hybrids are also further directed to hypertension reduction, diuresis inducement, natriuresis inducement, vascular conduct dilatation or relaxation, natriuretic peptide receptors (such as NPR-A) binding, renin secretion suppression from the kidney, aldostrerone secretion suppression from the adrenal gland, treatment of cardiovascular diseases and disorders, reducing, stopping or reversing cardiac remodeling in congestive heart failure, treatment of renal diseases and disorders; treatment or prevention of ischemic stroke, and treatment of asthma. Hybrids can be administered to patients that would benefit from inducing natriuresis, diuresis and vasodilatation. Hybrids can be administered alone or in combination with one or more of the following types of compounds: ACE inhibitors, beta-blockers, diuretics, spironolactone, digoxin, anticoagulation and antiplatelet agents, and angiotensin receptor blockers. Additional diseases or conditions include renal disorders and diseases, asthma, hypertension and pulmonary hypertension. Hybrids are also useful to treat inflammatory-related diseases, erectile dysfunction and hypercholesterolemia.

Bio-Active Peptide Hormone Modules

As discussed herein the hybrid polypeptides of the present invention generally comprise at least two bio-active peptide hormone modules covalently linked together. The bio-active peptide hormone modules may be: (a) native component peptide hormones, (b) analogs or derivatives of native component peptide hormones that retain hormonal activity, (c) fragments of native component peptide hormones that retain hormonal activity, (d) fragments of analogs or derivatives of native component peptide hormones that retain hormonal activity, (e) structural motifs of native component peptide hormones that impart a desired chemical stability, conformational stability, metabolic stability, bioavailability, organ/tissue targeting, receptor interaction, protease inhibition, plasma protein binding, and/or other pharmacokinetic characteristic to the hybrid polypeptide; or (f) structural motifs of analogs or derivatives of native component peptide hormones that impart a desired chemical stability, conformational stability, metabolic stability, bioavailability, organ/tissue targeting, receptor interaction, protease inhibition, plasma protein binding, and/or other pharmacokinetic characteristic to the hybrid polypeptide. The structural motifs of (e) and (f) will collectively be referred to herein as "peptidic enhancers".

Preferred bio-active peptide hormone modules include native peptide hormones selected from: amylin, ADM, CT, CGRP, intermedin, CCK(1-33), CCK-8, leptin, PYY(1-36) (SEQ ID NO: 57), PYY(3-36) (SEQ ID NO: 58), GLP1(1-37) (SEQ ID NO: 59), GLP1(7-37) (SEQ ID NO: 204), GLP1(7-36) (SEQ ID NO: 61), GLP-2, OXM, exendin-3, exendin-4, natriuretic peptide hormones, urocortin family peptides, e.g., Ucn-2 and Ucn-3, neuromedin family peptides, e.g. neuromedin U25 or splice variants, and ANP, BNP, CNP or urodilatin.

Other preferred bio-active peptide hormone modules include analogs and derivatives of a component peptide hormone selected from: amylin, ADM, CT, CGRP, intermedin, CCK, leptin, PYY(1-36) (SEQ ID NO: 57), PYY(3-36) (SEQ ID NO: 58), GLP-1(1-37) (SEQ ID NO: 59), GLP1(7-37) (SEQ ID NO: 204), GLP1(7-36) (SEQ ID NO: 61), GLP-2, OXM, exendin-3, and exendin-4, natriuretic peptide hormones, urocortin family peptides, e.g., Ucn-2 and Ucn-3, neuromedin family peptides, e.g. neuromedin U25 or splice variants, and ANP, BNP, CNP or urodilatin, wherein the analog or derivative exhibits at least one hormonal activity of the component peptide hormone. The analog may comprise one or more insertions, deletions, or substitutions of the amino acid sequence of the component peptide hormone, and the derivative may comprise one or more chemical modifications of an amino acid residue of an analog or component peptide hormone, as described more fully herein and known in the art.

More specifically, analogs and derivatives may be selected from any described above and/or known in the art. Particularly preferred analogs and derivatives that exhibit at least one hormonal activity useful as bio-active peptide hormone modules of the invention include the following:

Amylin: $^{2}$Ala-h-amylin, (SEQ ID NO: 79)

$^{2,7}$Ala-h-amylin, (SEQ ID NO: 80)

$^{28}$Pro-h-amylin, (SEQ ID NO: 189)

-continued
$^{25,28}$Pro-h-amylin, (SEQ ID NO: 83)

$^{25,28,29}$Pro-h-amylin, (SEQ ID NO: 67)

$^{25}$Pro,$^{26}$Val,$^{28,29}$Pro-h-amylin, (SEQ ID NO: 69)

$^{18}$Arg,$^{25,28}$Pro-h-amylin, (SEQ ID NO: 70)

$^{18}$Arg,$^{25,28,29}$Pro-h-amylin, (SEQ ID NO: 72)

$^{25}$Pro,$^{26}$Val,$^{28,29}$Pro-h-amylin, (SEQ ID NO: 75)

$^{18}$Arg,$^{23}$Leu,$^{25,28,29}$Pro-h-amylin, (SEQ ID NO: 89)

$^{18}$Arg$^{23}$Leu,$^{25,28}$Pro-h-amylin, (SEQ ID NO: 90) and $^{2,7}$-Cyclo-[$^{2}$Asp,$^{7}$Lys]-h-amylin (SEQ ID NO: 76)

CT: $^{14}$Glu-sCT, (SEQ ID NO: 106)

$^{18}$Arg-sCT, (SEQ ID NO: 107)

$^{11,18}$Arg-sCT, (SEQ ID NO: 108)

$^{14}$Glu,$^{18}$Arg-sCT, (SEQ ID NO: 109)

$^{14}$Glu,$^{11,18}$Arg-sCT (SEQ ID NO: 110)

CGRP: $^{36}$D-Ser-CGRP, (SEQ ID NO: 111)

$^{36}$D-Thr-CGRP, (SEQ ID NO: 112)

$^{36}$D-Asp-CGRP, (SEQ ID NO: 113)

$^{36}$D-Asn-CGRP, (SEQ ID NO: 114)

$^{36}$Ser-CGRP, (SEQ ID NO: 115)

$^{36}$Hse-CGRP, (SEQ ID NO: 116)

$^{36}$Asp-CGRP, (SEQ ID NO: 117)

$^{36}$Thr-CGRP, (SEQ ID NO: 118)

$^{36}$Asn-CGRP (SEQ ID NO: 119)

AFP-6: TQAQLLRVGCGNLSTCQVQNLSHRLWQLMGPAGRQDSAPVDPS SPHSY, (SEQ ID NO: 120)

TQAQLLRVGCDTATCQVQNLSHRLWQLMGPAGRQDSAPVDPSS PHSY, (SEQ ID NO: 121)

TQAQLLRVGMVLGTMQVQNLSHRLWQLMGPAGRQDSAPVDPSS PHSY, (SEQ ID NO: 122)

TQAQLLRVGCVLGTCQVQNLSHRLWQLMGPAGRQDSAPVEPSS PHSY, (SEQ ID NO: 123)

TQAQLLRVGCVLGTCQVQNLSHRLWQLMGPAGRQESAPVEPSS PHSY, (SEQ ID NO: 124)

CCK: DY(OSO$_3$H)MGWMDF, (SEQ ID NO: 141)

DYMGWMDF, (SEQ ID NO: 142)

MGWMDF, (SEQ ID NO: 143)

GWMDF, (SEQ ID NO: 144)

WMDF, (SEQ ID NO: 145)

KDY(OSO$_3$H)MGWMDF, (SEQ ID NO: 146)

-continued

KDYMGWMDF, (SEQ ID NO: 147)

KMGWMDF, (SEQ ID NO: 148)

KGWMDF, (SEQ ID NO: 149)

KWMDF (SEQ ID NO: 150)

Leptin: $^{43}$Asp-leptin, (SEQ ID NO: 151)

$^{43}$Glu-leptin, (SEQ ID NO: 152)

$^{48}$Ala-leptin, (SEQ ID NO: 153)

$^{49}$Glu-leptin, (SEQ ID NO: 154)

$^{49}$Des-AA-leptin, (SEQ ID NO: 155)

$^{75}$Ala-leptin, (SEQ ID NO: 156)

$^{89}$Leu-leptin, (SEQ ID NO: 157)

$^{93}$Asp-leptin, (SEQ ID NO: 158)

$^{93}$Glu-leptin, (SEQ ID NO: 159)

$^{98}$Ala-leptin, (SEQ ID NO: 160)

$^{139}$Leu-leptin, (SEQ ID NO: 162)

PYY: $^{3}$Leu-PYY, (SEQ ID NO: 192)

$^{3}$Val-PYY, (SEQ ID NO: 193)

$^{4}$Arg-PYY, (SEQ ID NO: 194)

$^{4}$Gln-PYY, (SEQ ID NO: 195)

$^{4}$Asn-PYY, (SEQ ID NO: 196)

$^{25}$Lys-PYY, (SEQ ID NO: 197)

$^{34}$Pro-PYY, (SEQ ID NO: 198)

$^{34}$His-PYY, (SEQ ID NO: 199)

$^{1,36}$Tyr-PYY, (SEQ ID NO: 57)

$^{13}$Pro$^{14}$Ala-PYY, (SEQ ID NO: 200)

$^{31}$Leu$^{34}$Pro-PYY, (SEQ ID NO: 201)

des-AA-4-PYY (SEQ ID NO: 202)

GLP-1 $^{9}$Gln-GLP-1(7-37), (SEQ ID NO: 168)

D-$^{9}$Gln-GLP-1(7-37), (SEQ ID NO: 169)

$^{16}$Thr-$^{18}$Lys-GLP-1(7-37), (SEQ ID NO: 170)

$^{18}$Lys-GLP-1(7-37), (SEQ ID NO: 171)

$^{8}$Gly-GLP-1 (7-36), (SEQ ID NO: 172)

$^{9}$Gln-GLP-1 (7-37), (SEQ ID NO: 173)

D-$^{9}$Gln-GLP-1 (7-37), (SEQ ID NO: 174)

acetyl-$^{9}$Lys-GLP-1(7-37), (SEQ ID NO: 175)

$^{9}$Thr-GLP-1(7-37), (SEQ ID NO: 176)

D-$^{9}$Thr-GLP-1 (7-37), (SEQ ID NO: 177)

$^{9}$Asn-GLP-1 (7-37), (SEQ ID NO: 178)

D-$^{9}$Asn-GLP-1 (7-37), (SEQ ID NO: 179)

$^{22}$Ser$^{23}$Arg$^{24}$Arg$^{26}$Gln-GLP-1(7-37), (SEQ ID NO: 180)

-continued $^{16}$Thr$^{18}$Lys-GLP-1(7-37), (SEQ ID NO: 181)

$^{18}$Lys-GLP-1(7-37), (SEQ ID NO: 182)

$^{23}$Arg-GLP-1(7-37), (SEQ ID NO: 183)

$^{24}$Arg-GLP-1(7-37) (SEQ ID NO: 184)

Exendin $^{14}$Leu,$^{25}$Phe-exendin-4, (SEQ ID NO: 185)

$^{14}$Leu,$^{25}$Phe-exendin-4, (SEQ ID NO: 185)

$^{5}$Ala,$^{14}$Leu,$^{25}$Phe-exendin-4, (SEQ ID NO: 186) and $^{14}$Leu,$^{22}$Ala,$^{25}$Phe-exendin-4. (SEQ ID NO: 187)

As known in the art, such peptide compounds may preferably be amidated, but within the context of the present invention, may optionally be in the acid form unless otherwise specified.

Still other preferred bioactive peptide hormone modules include fragments of a component peptide hormone selected from: amylin, ADM, CT, CGRP, intermedin, CCK, leptin, PYY(1-36) (SEQ ID NO: 57), PYY(3-36) (SEQ ID NO: 58), GLP1(1-37) (SEQ ID NO: 59), GLP1(7-37) (SEQ ID NO: 204), GLP1(7-36) (SEQ ID NO: 61), GLP-2, OXM, a natriuretic peptide, exendin-3, and exendin-4, urocortin family peptides, e.g., Ucn-2 and Ucn-3, neuromedin family peptides, e.g. neuromedin U25 or splice variants, and ANP, BNP, CNP or urodilatin, wherein the fragment exhibits at least one hormonal activity of the component peptide hormone.

Yet other preferred bioactive peptide hormone modules include fragments of analogs or derivatives of a component peptide hormone selected from: amylin, ADM, CT, CGRP, intermedin, CCK, leptin, PYY(1-36) (SEQ ID NO: 57), PYY (3-36) (SEQ ID NO: 58), GLP1(1-37) (SEQ ID NO: 59), GLP1(7-37) (SEQ ID NO: 204), GLP1(7-36) (SEQ ID NO: 61), GLP-2, OXM, ANP, BNP, CNP, urodilatin, exendin-3, exendin-4, a natriuretic peptide hormones, urocortin family peptides, e.g., Ucn-2 and Ucn-3, neuromedin family peptides, e.g. neuromedin U25 or splice variants, and ANP, BNP, CNP or urodilatin, wherein the fragment exhibits at least one hormonal activity of the component peptide hormone. Again, the analog may comprise one or more insertions, deletions, or substitutions of the amino acid sequence of the component peptide hormone, and the derivative may comprise one or more chemical modifications of an amino acid residue of an analog or component peptide hormone, as described more fully herein and known in the art.

Certain preferred fragments that exhibit at least one hormonal activity include the following. However, it should be understood that combinations of the above-described analogs and derivatives taken with fragments known in the art, including the preferred fragments described below, are contemplated.

| | |
|---|---|
| Amylin: | amylin(1-36) (SEQ ID NO: 210), amylin(1-35) (SEQ ID NO: 211), amylin(1-20) (SEQ ID NO: 212), amylin(1-18) (SEQ ID NO: 213), amylin(1-17) (SEQ ID NO: 214), amylin (1-16) (SEQ ID NO: 215), amylin(1-15) (SEQ ID NO: 216), amylin(1-7) (SEQ ID NO: 217) |
| CT: | CT(8-32) (SEQ ID NO: 218), CT(8-27) (SEQ ID NO: 219), CT(8-26) (SEQ ID NO: 220), CT(8-10) (SEQ ID NO: 221), CT(18-26) (SEQ ID NO: 222), CT(18-27) (SEQ ID NO: 223) |
| AFP-6: | AFP-6(18-27) (SEQ ID NO: 224) |
| CCK: | CCK-8, CCK-5, CCK-4 |

| | |
|---|---|
| Leptin: | leptin (22-167) (SEQ ID NO: 225),<br>leptin(56-73) (SEQ ID NO: 226) |
| PYY: | PYY(1-35) (SEQ ID NO: 227), PYY(1-30)<br>(SEQ ID NO: 228), PYY(1-25) (SEQ ID NO: 229),<br>PYY(1-15) (SEQ ID NO: 230), PYY(1-10)<br>(SEQ ID NO: 231), PYY(2-36) (SEQ ID NO: 232),<br>PYY(3-36) (SEQ ID NO: 58), PYY(4-36)<br>(SEQ ID NO: 233), PYY(5-36) (SEQ ID NO: 234) |
| GLP-1 | GLP-1(7-37) (SEQ ID NO: 204), GLP-1(7-36)<br>(SEQ ID NO: 61), GLP-1(7-35) (SEQ ID NO: 235) |
| Exendin | exendin-4(1-27) (SEQ ID NO: 236), exendin-4(1-28)<br>(SEQ ID NO: 237), exendin-4(1-29) (SEQ ID NO: 238),<br>exendin-4(1-30) (SEQ ID NO: 239) or longer |

Again, as known in the art, such peptide compounds may preferably be amidated, but within the context of the present invention, may optionally be in the acid form unless otherwise specified. Further, the above preferred fragments may be combined with any of the analogs or derivatives discussed herein or known in the art. For example, preferred analog fragments may include $^{5}$Ala,$^{14}$Leu,$^{25}$Phe-exendin-4(1-28) (SEQ ID NO: 240), $^{14}$Leu$^{25}$Phe-exendin-4(1-27) (SEQ ID NO: 241), $^{5}$Ala,$^{14}$Leu,$^{25}$Phe-exendin-4(1-28) (SEQ ID NO: 240), $^{14}$Leu,$^{25}$Phe-exendin-4(1-27) (SEQ ID NO: 241), or any other combinations of the disclosed fragments, analogs, and derivatives.

Yet other preferred bio-active peptide modules include "peptidic enhancer", i.e., structural motifs of component peptide hormones (including analogs and derivatives thereof) that impart a desired chemical stability, conformational stability, metabolic stability bioavailability, organ/tissue targeting, receptor interaction, protease inhibition, plasma protein binding, and/or other pharmacokinetic characteristic to the hybrid polypeptide. Exemplary peptidic enhancers include the following. Again, it should be understood that combinations of the above-described analogs and derivatives taken together with the following bio-active peptide modules are contemplated. For example, the last six amino acid residues of amylin family peptide hormone analogs and derivatives known in the art and/or described above are also contemplated as preferred bio-active peptide modules.

| | |
|---|---|
| Amylin Family | amylin(32-37) (SEQ ID NO: 242),<br>amylin(33-37) (SEQ ID NO: 243),<br>amylin(34-37) (SEQ ID NO: 244),<br>amylin(35-37), amylin(36-37), amylin(37),<br>ADM(47-52) (SEQ ID NO: 245),<br>ADM(48-52) (SEQ ID NO: 246),<br>ADM(49-52) (SEQ ID NO: 247),<br>ADM(50-52), ADM(51-52), ADM(52),<br>CT(27-32) (SEQ ID NO: 248),<br>CT(27-32) (SEQ ID NO: 249),<br>CT(28-32) (SEQ ID NO: 250),<br>CT(29-32), CT(30-32), CT(31-32), CT(32),<br>CGRP(32-37) (SEQ ID NO: 251),<br>CGRP(33-37) (SEQ ID NO: 252),<br>CGRP(34-37) (SEQ ID NO: 253),<br>CGRP(35-37), CGRP(36-37), CGRP(37),<br>intermedin (42-47) (SEQ ID NO: 254),<br>intermedin (43-47) (SEQ ID NO: 255),<br>intermedin (44-47) (SEQ ID NO: 256),<br>intermedin (45-47), intermedin (46-47),<br>intermedin (47) |
| PYY | PYY(25-36) (SEQ ID NO: 257),<br>PYY(26-36) (SEQ ID NO: 258),<br>PYY(27-36) (SEQ ID NO: 259),<br>PYY(28-36) (SEQ ID NO: 260),<br>PYY(29-36) (SEQ ID NO: 261),<br>PYY(30-36) (SEQ ID NO: 262),<br>PYY(31-36) (SEQ ID NO: 263),<br>PYY(32-36) (SEQ ID NO: 264),<br>PYY(25-35) (SEQ ID NO: 265),<br>PYY(26-35) (SEQ ID NO: 266),<br>PYY(27-35) (SEQ ID NO: 267),<br>PYY(28-35) (SEQ ID NO: 268),<br>PYY(29-35) (SEQ ID NO: 269),<br>PYY(30-35) (SEQ ID NO: 270),<br>PYY(31-35) (SEQ ID NO: 271),<br>PYY(32-35) (SEQ ID NO: 272) |
| GLP-1 and 2 | frog GLP-1(29-37) (SEQ ID NO: 273);<br>frog GLP-1(30-37) (SEQ ID NO: 274);<br>frog GLP-2(24-31) (SEQ ID NO: 275),<br>frog GLP-2(25-31) (SEQ ID NO: 276) |
| Exendin-4 | exendin-4(31-39) (SEQ ID NO: 277),<br>exendin-4(32-39) (SEQ ID NO: 278),<br>exendin-4(33-39) (SEQ ID NO: 279),<br>exendin-4(34-39) (SEQ ID NO: 280),<br>exendin-4(35-39) (SEQ ID NO: 281),<br>exendin-4(36-39) (SEQ ID NO: 282),<br>exendin-4(37-39), exendin-4(38-39), exendin-4(39) |

7. Peptide Module Selection Considerations, Spacers, and Linking Groups

The hybrid polypeptides of the present invention generally comprise at least two bio-active peptide hormone modules of the invention, wherein at least one of the bio-active peptide hormone modules exhibits at least one hormonal activity. The bio-active peptide hormone module that exhibits the at least one hormonal activity may be located at the N-terminal end of the hybrid polypeptide, the C-terminal end of the hybrid polypeptide, or in the event that the hybrid polypeptide comprises more than two bio-active peptide hormone modules, may be located in the internal portion of the hybrid polypeptide.

In certain embodiments, it may be preferable to locate the bio-active peptide hormone module exhibiting the at least one hormonal activity such that the C-terminal end of the bio-active peptide hormone module is amidated. Amidation of the C-terminal end of the bio-active peptide hormone module may be accomplished by locating the module at the C-terminal end of the hybrid peptide, or by configuring the module in the C-terminal-to-N-terminal direction at the N-terminal end of the hybrid polypeptide. In both configurations, the C-terminal end of the bio-active peptide hormone module is available for amidation. Specific component peptide hormones where C-terminal amidation may be preferable include amylin family peptide hormones, CCK, PYY, hGLP1(7-36) (SEQ ID NO: 61), and hGLP-2. Specific component peptide hormones where C-terminal amidation is not necessarily preferred (stated otherwise, where elongation at the C-terminal end of the module is easily tolerated) include exendin-4, exendin-4(1-28) (SEQ ID NO: 237), GLP1(7-37) (SEQ ID NO: 204), frog GLP1(7-36) (SEQ ID NO: 283), and frog GLP-2. However, if these component peptide hormones are located at the C-terminal end of the hybrid polypeptide, they may still be optionally amidated, and in fact may preferably be optionally amidated.

The bio-active peptide hormone modules may be covalently linked in any manner known in the art. Stable linkages may be used, or cleavable linkage may be used. In one embodiment, the carboxy of a first module may be directly linked to the amino of a second module. In another embodiment, linking groups may be used to attached modules. Further, if desired, spacers or turn inducers known in the art may be employed to stabilize the linkage. By way of example, where amidation of the C-terminal end of the N-terminally located bio-active peptide hormone module is not desired, the module may be attached to a second module directly, or using any appropriate linking group known in the art, such as, an alkyl; PEG; amino acid, e.g., Lys, Glu, β-Ala; polyaminoacids, e.g., poly-his, poly-arg, poly-lys, poly-ala, Gly-Lys-Arg (GKR) etc.; bifunctional linker (see, e.g., Pierce catalog, Rockford, Ill.); aminocaproyl ("Aca"), β-alanyl, 8-amino-3,6-dioxaoctanoyl, or other cleavable and non-cleavable linker known in the art. Specifically described herein, as if each were explicitly drawn, are embodiments of specific hybrids in which the linker in each exemplified linker-containing hybrid is replaced by a Gly linker, particularly embodiments where the Gly linker is Gly-Gly-Gly. As an example, for exemplified species $^{29}$5 Apa-Exendin(1-28)-$^{1}$des-Lys-hAmylin(1-7)-$^{11,18}$Arg-sCt(8-27)-hAmylin(33-37) (SEQ ID NO: 32) (see tables herein) its Gly linker species analog is also specifically intended and disclosed. This species is $^{29}$GlyGlyGly-Exendin(1-28)-$^{1}$des-Lys-hAmylin(1-7)-$^{11,18}$Arg-sCt(8-27)-hAmylin(33-37) (SEQ ID NO: 313), where the three glycines are located after the exendin (1-28) sequence. In one embodiment a linker or spacer is 1 to 30 residues long, in another embodiment 2 to 30 residues, and in yet another 3-30 residues long, and any integer length from 2 to 30 inclusive; each integer unit is contemplated, e.g. 2, 3, 4, 5, 6, 7, etc. In one embodiment a Gly linker is used, and in a particular embodiment a three residue linker Gly-Gly-Gly.

Where amidation of the C-terminal end of N-terminally located bio-active peptide hormone module is desired, the module may again be attached to a second module using any appropriate linking group known in the art. More specifically, in the event that a bio-active peptide hormone module exhibiting at least one hormonal activity has been configured in the C-terminal-to-N-terminal orientation, resulting in an amino to amino linkage, preferred linking groups include dicarboxylic acids, alkyls, PEGs, and amino acids such as Lys, Cys, and Glu.

As mentioned above, the hybrid polypeptides may also preferably include spacer to further stabilize the linkage of the bio-active peptide hormone modules. Any spacer or turn inducer known in the art may be used. By way of example, referred β-turn mimetics include mimic A and mimic B illustrated below, also Ala-Aib and Ala-Pro dipeptides. Their IUPAC names are Mimic A: N-(3S,6S,9S)-2-oxo-3-amino-1-azabicyclo[4.3.0]-nonane-9-carboxylic acid. Mimic B: N-(3S,6S,9R)-2-oxo-3-amino-7-thia-1-azabicyclo[4.3.0]-nonane-9-carboxylic acid.

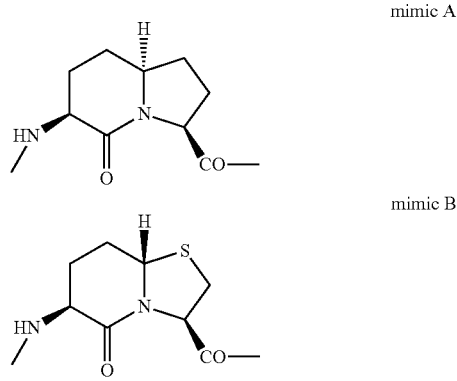

mimic A mimic B

8. Exemplary Combinations and Specific Embodiments

Exemplary combinations of bio-active peptide hormone modules to form the hybrid polypeptides of the invention include combinations of two or more bio-active peptide hormone modules selected from: native peptide hormones, analogs and derivatives of peptide hormones that exhibit at least one hormonal activity, fragments of native peptide hormones that exhibit at least one hormonal activity, fragments of analogs and derivatives of peptides hormones that exhibit at least one hormonal activity, and peptidic enhancers, with the proviso that at least one module exhibit at least one hormonal activity.

The hybrid polypeptides of the invention will include at least two bio-active peptide hormone modules, wherein each module is comprised from component peptide hormones. In the context of the present invention, the component peptide hormones of the hybrid polypeptide may be the same or different, with the proviso that at least two of the component peptide hormones are different. In a preferred embodiment, at least two of the component peptide hormones are from different peptide hormone families, e.g., the amylin family, CCK, the leptin family, PPF, the proglucagon family, the natriuretic peptide family, urocortin family peptides, e.g., Ucn-2 and Ucn-3, neuromedin family peptides, e.g. neuromedin U25 or splice variants, and ANP, BNP, CNP or urodilatin and the GLP-1 and exendin family.

In certain embodiments, the hybrid polypeptides of the invention may comprise two or more modules that exhibit at least one hormonal activity. For instance, the hybrid polypeptide may comprise a fragment of a first peptide hormone or analog that exhibits at least one hormonal activity covalently linked to a fragment of at least one additional peptide hormone analog. The additional fragment(s) may optionally exhibit at least one hormonal activity. The first peptide hormone may be the same or different from the additional peptide hormone(s), with the proviso that at least one of the additional peptide hormones are different from the first peptide hormone, and the first hormonal activity may be the same or different from the optional additional hormonal activity.

In other embodiments, the hybrid polypeptides of the invention may comprise one or more modules that exhibit at least one hormonal activity in combination with one or more peptidic enhancer modules. For instance, a fragment of a first peptide hormone that exhibits a at least one hormonal activity may be covalently linked to a peptidic enhancer, or a fragment of a first peptide hormone that exhibits at least one hormonal activity may be covalently linked to a second peptide hormone that exhibits at least one hormonal activity, which is in turn linked to a peptidic enhancer. Alternatively, a peptidic enhancer may be located between two peptide hormone modules as a stabilizing spacer. Again, the first peptide hormone may be the same or different from the second peptide hormone, and the first hormonal activity may be the same or different from the second hormonal activity.

In another embodiment, the hybrid polypeptides of the invention may comprise two, three, four, or more bio-active peptide hormone modules. Exemplary combinations include a module with a hormonal activity in combination with one, two, or three peptidic enhancers; two modules with a hormonal activity in combination with one or two peptidic enhancers; three modules with a hormonal activity in combination with one peptidic enhancer, etc.

The component peptide hormones are preferably selected from amylin, adrenomedullin, calcitonin, calcitonin gene related peptide, intermedin, cholecystokinin, leptin peptide YY, glucagon-like peptide-1, glucagon-like peptide 2, oxyntomodulin, ANP, BNP, CNP, urodilatin, natriuretic peptide hormones, urocortin family peptides, e.g., Ucn-2 and Ucn-3, neuromedin family peptides, e.g. neuromedin U25 or splice variants, and ANP, BNP, CNP or urodilatin or exendin-4.

More particularly, preferred module combinations include those involving combinations of exendin, amylin (and/or sCT), BNP, and PYY as the component peptide hormones. Particular combinations include exendin-4/PYY and PYY/exendin-4 combinations, with and without spacers or linking groups. Other combinations include exendin/amylin and amylin/exendin combinations, with and without spacers or linking groups. Yet other combinations include amylin/PYY and PYY/amylin combinations, with and without spacers or linking groups.

In one aspect, preferred module combinations include those involving a first module comprising exendin-4, a fragment of exendin-4 that exhibits at least one hormonal activity, an exendin-4 analog or derivative that exhibits at least one hormonal activity, or a fragment of an exendin-4 analog that exhibits at least one hormonal activity in combination with at least one additional bio-active peptide hormone module. In one embodiment, the first module is linked to one, two, or three additional bio-active peptide hormone modules.

In preferred embodiments, a first module comprising an exendin-4 peptide is linked to a second bio-active peptide hormone module comprising an amylin (and/or sCT) peptide that exhibits at least one hormonal activity. In another embodiment, the second module is further linked to a third bio-active peptide hormone module comprising a calcitonin peptide that exhibits at least one hormonal activity. In yet another embodiment, the third module may be further linked to a fourth bio-active peptide hormone module comprising a peptidic enhancer selected from amylin peptides. In one embodiment, the first module may be located at the C-terminal end of the hybrid polypeptide. Alternatively, the first module may be located at the N-terminal end of the hybrid polypeptide. In certain embodiments, spacers or linkers such as βAla may be inserted if desired to link the modules.

Preferred exendin-4 peptides include: exendin-4, exendin-4(1-27), exendin-4(1-28), $^{14}$Leu,$^{25}$Phe-exendin-4(1-28), and $^{5}$Ala,$^{14}$Leu,$^{25}$Phe-exendin-4(1-28). Also useful are exendin (7-15) and its Ser2 analog, HSEGTFTSD (SEQ ID NO. 378). Preferred amylin peptides that exhibit at least one hormonal activity include amylin, amylin fragments such as amylin(1-17), amylin (1-16), amylin(1-15), and amylin(1-7), and amylin analogs such as pramlintide, $^{2}$Ala-h-amylin, $^{2,7}$Ala-h-amylin, and fragments thereof. Preferred calcitonin peptides that exhibit at least one hormonal activity sCT, sCT fragments such as sCT(8-10), sCT(8-27), and, and calcitonin analogs such as $^{11,18}$Arg-sCT, $^{18}$Arg-sCT, $^{14}$Glu,$^{18}$Arg-sCT, $^{14}$Glu,$^{11,18}$Arg-sCT, and fragments thereof. Preferred amylin peptidic enhancers include amylin(32-37), amylin(33-37), and amylin(34-37), and analogs thereof. Amylin/sCT combinations useful in connection with the present invention include those disclosed in PCT/US2005/004631 Amylin Family Agonist, which is herein incorporated by reference. An amylin/sCT chimera particularly useful for creating hybrids of the invention is Compound 10 (described herein and in PCT/US2005/004631) and analogs and derivatives thereof.

Preferred exendin-4 peptides include: exendin-4, exendin-4(1-27) (SEQ ID NO: 236), exendin-4(1-28) (SEQ ID NO: 237), $^{14}$Leu,$^{25}$Phe-exendin-4(1-28) (SEQ ID NO: 284), and $^{5}$Ala,$^{14}$Leu,$^{25}$Phe-exendin-4(1-28) (SEQ ID NO: 240). Also useful are exendin(7-15) and its Ser2 analog, HSEGTFTSD (SEQ ID NO. 378). Preferred amylin peptides that exhibit at least one hormonal activity include amylin, amylin fragments such as amylin(1-17) (SEQ ID NO: 214), amylin (1-16) (SEQ ID NO: 215), amylin(1-15) (SEQ ID NO: 216), and amylin (1-7) (SEQ ID NO: 217), and amylin analogs such as pramlintide, $^{2}$Ala-h-amylin (SEQ ID NO: 79), $^{2,7}$Ala-h-amylin (SEQ ID NO: 80), and fragments thereof. Preferred calcitonin peptides that exhibit at least one hormonal activity sCT, sCT fragments such as sCT(8-10), sCT(8-27) (SEQ ID NO: 288), and, and calcitonin analogs such as $^{11,18}$Arg-sCT (SEQ ID NO: 108), $^{18}$Arg-sCT (SEQ ID NO: 107), $^{14}$Glu,$^{18}$Arg-sCT (SEQ ID NO: 109), $^{14}$Glu,$^{11,18}$Arg-sCT (SEQ ID NO: 110), and fragments thereof. Preferred amylin peptidic enhancers include amylin(32-37) (SEQ ID NO: 242), amylin(33-37) (SEQ ID NO: 243), and amylin(34-37) (SEQ ID NO: 244), and analogs thereof. Amylin/sCT combinations useful in connection with the present invention include those disclosed in PCT/US2005/004631, Amylin Family Agonist, which is herein incorporated by reference. An amylin/sCT chimera particularly useful for creating hybrids of the invention is Compound 10 (described herein and in PCT/US2005/004631) and analogs and derivatives thereof.

In one aspect, preferred module combinations include those involving a first module comprising exendin-4, a fragment of exendin-4 that exhibits at least one hormonal activity, an exendin-4 analog or derivative that exhibits at least one hormonal activity, or a fragment of an exendin-4 analog that exhibits at least one hormonal activity in combination with a peptidic enhancer. Preferred exendin-4 compounds include: exendin-4, exendin-4(1-27) (SEQ ID NO: 236), exendin-4(1-28) (SEQ ID NO: 237), $^{14}$Leu,$^{25}$Phe-exendin-4(1-28) (SEQ ID NO: 284), and $^{5}$Ala,$^{14}$Leu,$^{25}$Phe-exendin-4(1-28) (SEQ ID NO: 240). Preferred peptidic enhancers include: PYY(25-36) (SEQ ID NO: 257), PYY(30-36) (SEQ ID NO: 262) and PYY(31-36) (SEQ ID NO: 263). In one embodiment, the first module is located at the C-terminal end of the hybrid polypeptide and the peptidic enhancer is located at the N-terminal end of the hybrid polypeptide. Alternatively, the first module may be located at the N-terminal end of the hybrid polypeptide and the peptidic enhance may be located at the C-terminal end of the hybrid polypeptide. In certain embodiments, spacers or linkers such as βAla may be inserted if desired to attach the modules.

In another aspect, preferred module combinations include those involving a first module comprising exendin-4, a fragment of exendin-4 that exhibits at least one hormonal activity, an exendin-4 analog or derivative that exhibits at least one hormonal activity, or a fragment of an exendin-4 analog that exhibits at least one hormonal activity in combination with a second module comprising CCK, a fragment of CCK that exhibits at least one hormonal activity, a CCK analog or derivative that exhibits at least one hormonal activity, or a fragment of a CCK analog that exhibits at least one hormonal activity. Again, preferred exendin-4 compounds include: exendin-4, exendin-4(1-27) (SEQ ID NO: 236), exendin-4(1-28) (SEQ ID NO: 237), $^{14}$Leu,$^{25}$Phe-exendin-4(1-28) (SEQ ID NO: 284), $^{5}$Ala,$^{14}$Leu,$^{25}$Phe-exendin-4(1-28) (SEQ ID NO: 240), and $^{14}$Leu-exendin-4(1-28) (SEQ ID NO: 190). Preferred CCK compounds include: CCK-8, and CCK-8(Phe (CH$_2$SO$_3$)). In one embodiment, the first module is located at the C-terminal end of the hybrid polypeptide and the second module is located at the N-terminal end of the hybrid polypeptide. Alternatively, the first module may be located at the N-terminal end of the hybrid polypeptide and the peptidic enhance may be located at the C-terminal end of the hybrid polypeptide. In certain embodiments, spacers or linkers such as βAla may be inserted if desired to attach the modules.

In another aspect, preferred module combinations include those involving a first module comprising amylin, a fragment of amylin that exhibits at least one hormonal activity, an amylin analog or derivative that exhibits at least one hormonal activity, or a fragment of an amylin analog that exhibits at least one hormonal activity in combination with a second module comprising with a peptidic enhancer, such as PYY (25-36) (SEQ ID NO: 257) or PYY(30-36) (SEQ ID NO: 262). In one embodiment, the first module is located at the C-terminal end of the hybrid polypeptide and the peptidic enhancer is located at the N-terminal end of the hybrid polypeptide. Alternatively, the first module may be located at the N-terminal end of the hybrid polypeptide and the peptidic enhance may be located at the C-terminal end of the hybrid polypeptide. In certain embodiments, spacers or linkers such as βAla may be inserted if desired to attach the modules.

Other preferred module combinations include those involving combinations of exendin and CCK or amylin, calcitonin, and CCK as a tertiary combination. Particular combinations include exendin/CCK and CCK/exendin, with and without spacers or linkers and linking groups. Other combinations include CCK/amylin/calcitonin and CCK/amylin/calcitonin/amylin, with and without spacers or linking groups. Each module may independently be a peptidic enhancer or may exhibit a hormonal activity, depending on the desired properties of the hybrid polypeptide.

Yet other preferred module combinations include those involving combinations of exendin, amylin and calcitonin as tertiary and tetra-hybrid molecules. Exemplary combinations include exendin/amylin/calcitonin; exendin/amylin/calcitonin/amylin; amylin/calcitonin/exendin; and amylin/calcitonin/amylin/exendin combinations, with and without spacers or linking groups. Each module may independently be a peptidic enhancer or may exhibit a hormonal activity, depending on the desired properties of the hybrid polypeptide.

In one embodiment, when one of the bio-active peptide hormone module(s) that exhibits at least one hormonal activity is amylin or an analog or fragment thereof, and a second bio-active peptide hormone module comprises CCK, then the hybrid polypeptide should preferably comprise a third bio-active peptide hormone module selected from a different component peptide hormone. Exemplary third bio-active peptide hormone modules include calcitonins, more preferably salmon calcitonin, analogs or fragments thereof.

In another embodiment, when one of the bio-active peptide hormone module(s) that exhibits at least one hormonal activity is amylin or an analog or fragment thereof, and a second bio-active peptide hormone module comprises CT, then the hybrid polypeptide should preferably comprise a third bio-active peptide hormone module selected from a different component peptide hormone. Exemplary third bio-active peptide hormone modules include exendin-4, analogs or fragments thereof.

In yet another embodiment, when one of the bio-active peptide hormone module(s) that exhibits at least one hormonal activity is GLP-1 or an analog or fragment thereof, and a second bio-active peptide hormone module is a peptidic enhancer comprising an exendin fragment, then the hybrid polypeptide should preferably comprise a third bio-active peptide hormone module. Exemplary third bio-active peptide hormone modules include PYY (including analogs, derivatives and fragments thereof) and CCK (including analogs, derivatives and fragments thereof).

Within each of the combinations described herein, it is understood that reference to a component peptide hormone includes reference to analogs, derivatives, fragments, as well as peptidic enhancers related thereto.

In a preferred aspect, the hybrid polypeptides include:

| SEQ ID NO: | |
|---|---|
| 1 | Exendin-4-PYY(22-36) |
| 2 | Exendin-4-PYY(25-36) |
| 3 | Exendin-4-PYY(18-36) |
| 4 | Exendin-4-βAla-βAla-PYY(22-36) |
| 5 | Exendin-4-βAla-βAla-PYY(25-36) |
| 6 | Exendin-4-βAla-βAla-PYY(31-36) |
| 7 | Exendin-4(1-28)-PYY(22-36) |
| 8 | Exendin-4(1-28)-PYY(25-36) |
| 9 | Exendin-4(1-28)-PYY(18-36) |
| 10 | Exendin-4(1-28)-βAla-βAla-PYY(22-36) |
| 11 | Exendin-4(1-28)-βAla-βAla-PYY(25-36) |
| 12 | Exendin-4(1-28)-βAla-βAla-PYY(31-36) |
| 13 | $^5$Ala,$^{14}$Leu,$^{25}$Phe-Exendin-4(1-28)-PYY(18-36) |
| 14 | $^5$Ala,$^{14}$Leu,$^{25}$Phe-Exendin-4(1-28)-PYY(22-36) |
| 15 | $^5$Ala,$^{14}$Leu,$^{25}$Phe-Exendin-4(1-28)-PYY(25-36) |
| 16 | $^5$Ala,$^{14}$Leu,$^{25}$Phe-Exendin-4(1-17)-PYY(18-36) |
| 17 | $^5$Ala,$^{14}$Leu,$^{25}$Phe-Exendin-4(1-28)-βAla-βAla-PYY(22-36) |
| 18 | $^5$Ala,$^{14}$Leu,$^{25}$Phe-Exendin-4(1-28)-βAla-βAla-PYY(25-36) |
| 19 | $^5$Ala,$^{14}$Leu,$^{25}$Phe-Exendin-4(1-28)-βAla-βAla-PYY(31-36) |
| 20 | Exendin-4-CCK-8 |
| 21 | Exendin-4(1-28)-CCK-8 |
| 22 | Exendin-4(1-28)-CCK-8(Phe(CH$_2$SO$_3$)) |
| 23 | Exendin-4(1-28)-(8-amino-3,6-dioxactoanoyl)-CCK-8 |
| 24 | Exendin-4(1-28)-(8-amino-3,6-dioxactoanoyl)-CCK-8(Phe(CH$_2$SO$_3$)) |
| 25 | Exendin-4(1-27)-hAmylin(1-7)-$^{11,18}$Arg-sCT(8-27)-Amylin(33-37) |
| 26 | Exendin-4(1-27)-$^{2,7}$Ala-hAmylin(1-7)-sCT(8-10) |
| 27 | $^{29}$12 Ado-Exendin(1-28)-hAmylin(1-7)-$^{11,18}$Arg-sCt(8-27)-hAmylin(33-37) |
| 28 | $^{29}$12 Ado-Exendin(1-28)-$^1$des-Lys-hAmylin(1-7)-$^{11,18}$Arg-sCt(8-27)-hAmylin(33-37) |
| 29 | $^{29}$3,6-dioxaoctanoyl-Exendin(1-28)-hAmylin(1-7)-$^{11,18}$Arg-sCt(8-27)-hAmylin(33-37) |
| 30 | $^{29}$3,6-dioxaoctanoyl-Exendin(1-28)-$^1$des-Lys-hAmylin(1-7),$^{11,18}$Arg-sCt(8-27)-hAmylin(33-37) |
| 31 | $^{29}$5 Apa -Exendin(1-28)-hAmylin(1-7)-$^{11,18}$Arg-sCt(8-27)-hAmylin(33-37) |
| 32 | $^{29}$5 Apa -Exendin(1-28) -$^1$des-Lys-hAmylin(1-7)-$^{11,18}$Arg-sCt(8-27)-hAmylin(33-37) |
| 33 | $^{29}$βAla-βAla-Exendin(1-28),hAmylin(1-7)-$^{11,18}$Arg-sCt(8-27)-hAmylin(33-37) |
| 34 | $^{29}$βAla-βAla- Exendin(1-28)-$^1$des-Lys-hAmylin(1-7)-$^{11,18}$Arg-sCt(8-27)-hAmylin(33-37) |
| 35 | $^{29}$4,7,10-trioxa-13-tridecanamine succinimidyl-Exendin(1-28)-hAmylin(1-7)$^{11,18}$Arg-sCt(8-27)-hAmylin(33-37) |
| 36 | $^{29}$4,7,10-trioxa-13-tridecanamine succinimidyl-Exendin(1-28)-$^1$des-Lys-hAmylin(1-7)-$^{11,18}$Arg-sCt(8-27)-hAmylin(33-37) |
| 37 | CCK-8-GKR-$^{15}$G1u-hAmylin(1-17)-$^{18}$Arg-sCT(18-26)-Amylin(32-37) |
| 38 | Amylin(1-18)-PYY(19-36) |
| 39 | isocaproyl-STAVL-(Aib)-K(formyl)-LSQEL-(Aib)-K(formyl)-LQT-PYY(18-36) |
| 40 | isocaproyl-STAVL-(Aib)-K(formyl)-LSQEL-(Aib)-K(formyl)-L-PYY(16-36) |
| 41 | CCK-8-[Succinoyl-Cys]-PYY(3-36) |
| 42 | CCK-8-[Bis-Cys(N-Acetyl)]-PYY(3-36) |
| 43 | CCK-8-[Gly-Aminoxymethylcarbonyl]-PYY(3-36) |
| 379 | Exendin-4(1-27)-hAmylin(1-7)-$^{14}$Glu,$^{11,18}$Arg-sCT(8-27)-Amylin(33-37) |
| 380 | $^{29}$12 Ado-Exendin(1-28)-hAmylin(1-7)- $^{14}$Glu,$^{11,18}$Arg-sCt(8-27)-hAmylin(33-37) |
| 381 | $^{29}$12 Ado-Exendin(1-28)-$^1$des-Lys-hAmylin(1-7)-$^{14}$Glu,$^{11,18}$Arg-sCt(8-27)-hAmylin(33-37) |
| 382 | $^{29}$3,6-dioxaoctanoyl-Exendin(1-28)-hAmylin(1-7)-$^{14}$Glu,$^{11,18}$Arg-sCt(8-27)-hAmylin(33-37) |
| 383 | $^{29}$3,6-dioxaoctanoyl-Exendin(1-28)-$^1$des-Lys-hAmylin(1-7), $^{14}$Glu,$^{11,18}$Arg-sCt(8-27)-hAmylin(33-37) |
| 384 | $^{29}$5 Apa -Exendin(1-28)-hAmylin(1-7)- $^{14}$Glu,$^{11,18}$Arg-sCt(8-27)-hAmylin(33-37) |
| 385 | $^{29}$5 Apa-Exendin(1-28) -$^1$des-Lys-hAmylin(1-7)-$^{14}$Glu,$^{11,18}$Arg-sCt(8-27)-hAmylin(33-37) |
| 386 | $^{29}$βAla-βAla-Exendin(1-28),hAmylin(1-7)- $^{14}$Glu,$^{11,18}$Arg-sCt(8-27)-hAmylin(33-37) |

-continued

| SEQ ID NO: | |
|---|---|
| 387 | $^{29}$βAla-βAla-Exendin(1-28)-$^1$des-Lys-hAmylin(1-7)-$^{14}$Glu,$^{11,18}$Arg-sCt(8-27)-hAmylin(33-37) |
| 388 | $^{29}$4,7,10-trioxa-13-tridecanamine succinimidyl-Exendin(1-28)-hAmylin(1-7)-$^{14}$Glu,$^{11,18}$Arg-sCt(8-27)-hAmylin(33-37) |
| 389 | $^{29}$4,7,10-trioxa-13-tridecanamine succinimidyl-Exendin(1-28)-$^1$des-Lys-hAmylin(1-7)- $^{14}$Glu,$^{11,18}$Arg-sCt(8-27)-hAmylin(33-37) |
| 390 | CCK-8-GKR-$^{15}$Glu-hAmylin(1-17)-$^{18}$Arg-sCT(18-26)-Amylin(32-37) |

Exemplary exendin and neuromedin hybrids include

```
Exendin-(1-28)-beta-Ala-beta-Ala-FN-38:
                                    (SEQ ID NO: 391)
HGEGTFTSDLSKQMEEEAVRLFIEWLKN-beta-Ala-beta-Ala-

FLFHYSKTQKLGKSNVVEELQSPFASQSRGYFLFRPRN-NH2;

Exendin-(1-28)-beta-Ala-beta-Ala-Neuromedin(U25:)
                                    (SEQ ID NO: 392)
HGEGTFTSDLSKQMEEEAVRLFIEWLKN-beta-Ala-beta-Ala- FRVDEEFQSPFASQSRGYFLFRPRN-NH2;
and Exendin-(1-28)-beta-Ala-beta-Ala-Neuromedin(U-9):
                                    (SEQ ID NO: 393)
HGEGTFTSDLSKQMEEEAVRLFIEWLKN-beta-Ala-beta-Ala-

GYFLFRPRN-NH2.
```

The beta-Ala-beta-Ala spacer is optional, and can be replaced with Gly-Gly-Gly, a mini-PEG group, or other linker known in the art, particularly those described herein.

Exemplary exendin and natriuretic peptide hybrids include exendin-hBNP peptide hybrids, including

```
Exendin-(1-28)-beta-Ala-beta-Ala-hBNP:
                                    (SEQ ID NO: 394)
HGEGTFTSDLSKQMEEEAVRLFIEWLKN-beta-Ala-beta-Ala- SPKMVQGSGCFGRKMDRISSSSGLGCKVLRRH;
and Exendin-beta-Ala-beta-Ala-hBNP:
                                    (SEQ ID NO: 395)
HGEGTFTSDLSKQMEEEAVRLFIEWLKNGGPSSGAPPPS-beta-Alabeta-Ala-SPKMVQGSGCFGRKMDRISSSSGLGCKVLRRH.
```

As in all of the hybrids of the invention, a beta-Ala-beta-Ala spacer is optional, and can be replaced with Gly-Gly-Gly, a mini-PEG group, or other linker known in the art, particularly those described herein.

The hybrid polypeptides of the present invention may also comprise further modifications including, but are not limited to, substitution, deletion, and insertion to the amino acid sequence of such hybrid polypeptides and any combination thereof. In a preferred aspect, the hybrid polypeptides of the invention include one or more modifications of a "non-essential" amino acid residue. In the context of the invention, a "non-essential" amino acid residue is a residue that can be altered, i.e., deleted or substituted, in the native human amino acid sequence of the fragment, e.g., the component peptide hormone fragment, without abolishing or substantially reducing the component peptide hormone receptor agonist activity of the hybrid polypeptide.

Preferred substitutions include conserved amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine).

The present invention also relates to derivatives of the hybrid polypeptides. Such derivatives include hybrid polypeptides conjugated to one or more water soluble polymer molecules, such as polyethylene glycol ("PEG") or fatty acid chains of various lengths (e.g., stearyl, palmitoyl, octanoyl, etc.), or by the addition of polyamino acids, such as poly-his, poly-arg, poly-lys, and poly-ala. Modifications to the hybrid polypeptides can also include small molecule substituents, such as short alkyls and constrained alkyls (e.g., branched, cyclic, fused, adamantyl), and aromatic groups. The water soluble polymer molecules will preferably have a molecular weight ranging from about 500 to about 20,000 Daltons.

Such polymer-conjugations and small molecule substituent modifications may occur singularly at the N- or C-terminus or at the side chains of amino acid residues within the sequence of the hybrid polypeptides. Alternatively, there may be multiple sites of derivatization along the hybrid polypeptide. Substitution of one or more amino acids with lysine, aspartic acid, glutamic acid, or cysteine may provide additional sites for derivatization. See, e.g., U.S. Pat. Nos. 5,824,784 and 5,824,778. Preferably, the hybrid polypeptides may be conjugated to one, two, or three polymer molecules.

The water soluble polymer molecules are preferably linked to an amino, carboxyl, or thiol group, and may be linked by N or C terminus, or at the side chains of lysine, aspartic acid, glutamic acid, or cysteine. Alternatively, the water soluble polymer molecules may be linked with diamine and dicarboxylic groups. In a preferred embodiment, the hybrid polypeptides of the invention are conjugated to one, two, or three PEG molecules through an epsilon amino group on a lysine amino acid.

Hybrid polypeptide derivatives of the invention also include hybrid polypeptides with chemical alterations to one or more amino acid residues. Such chemical alterations include amidation, glycosylation, acylation, sulfation, phosphorylation, acetylation, and cyclization. The chemical alterations may occur singularly at the N- or C-terminus or at the side chains of amino acid residues within the sequence of the PPF hybrid polypeptides. In one embodiment, the C-terminus of these peptides may have a free —OH or —NH$_2$ group. In another embodiment, the N-terminal end may be capped with an isobutyloxycarbonyl group, an isopropyloxycarbonyl group, an n-butyloxycarbonyl group, an ethoxycarbonyl group, an isocaproyl group (isocap), an octanyl group, an octyl glycine group (G(Oct)), or an 8-aminooctanic acid group. In a preferred embodiment, cyclization can be through the formation of disulfide bridges. Alternatively, there may be multiple sites of chemical alteration along the hybrid polypeptide.

Examples of the hybrid polypeptides of the present invention are provided in the Sequence Listing and further discussed in the Examples section herein.

Use of Hybrid Polypeptides in the Treatment or Prevention of Metabolic Conditions or Disorders Hybrids of the invention can be useful for reducing food intake, reducing appetite, reducing caloric intake, inducing satiety, reducing nutrient availability, causing weight loss, affecting body composition, altering body energy content or energy expenditure, improving lipid profile (including reducing LDL cholesterol and triglyceride levels and/or changing HDL cholesterol levels), slowing gastrointestinal motility, delay gastric emptying, moderating the postprandial blood glucose excursions, preventing or inhibiting glucagon secretion, and decreasing blood pressure. In one embodiment such hybrids contain an exendin, GLP1, amylin and/or sCT portion.

Thus, in certain embodiments, the hybrids of the invention are useful for treating or preventing conditions or disorders which can be alleviated by reducing nutrient availability comprising administering to said subject a therapeutically or prophylactically effective amount of a compound of the invention. Such conditions and disorders include, but are not limited to, eating disorders, insulin-resistance, obesity, abnormal postprandial hyperglycemia, diabetes of any kind, including Type I, Type II, and gestational diabetes, Metabolic Syndrome, Dumping Syndrome, hypertension, dyslipidemia, cardiovascular disease, hyperlipidemia, sleep apnea, cancer, pulmonary hypertension, cholecystitis, and osteoarthritis. In one embodiment such hybrids contain an exendin, GLP1, amylin and/or sCT portion.

Exemplary peptide module pairings include cardioactive/protective peptides, for example a urocortin with a GLP-1 or exendin, an ANP, BNP or CNP with a GLP-1 or exendin, and a urocortin with an ANP, BNP or CNP Such hybrids will be cardioprotective and particularly useful for the related diseases and conditions described herein, including acute or chronic CHF, ischemia reperfusion, myocardial infarction, and for vasodilator actions useful to treat or prevent antihypertensive indications and angina. Ucn 2 and 3 are particularly useful in hybrids of the invention.

Non-limiting examples of a cardiovascular condition or disease are hypertension, myocardial ischemia, and myocardial reperfusion. Compounds of the invention may also be useful in treating or preventing other conditions associated with obesity including stroke, cancer (e.g., endometrial, breast, prostate, and colon cancer), gallbladder disease, sleep apnea, reduced fertility, and osteoarthritis, (see Lyznicki et al, *Am. Fam. Phys.* 63:2185, 2001). In other embodiments, compounds of the invention may be used to alter body composition for aesthetic reasons, to enhance one's physical capabilities, or to produce a leaner meat source. Hybrids are useful to change body composition by decreasing fat without significant decrease in muscle mass, thus producing a desirable loss of body fat while preserving lean body mass. In one embodiment such hybrids contain an exendin, GLP1, amylin and/or sCT portion.

In another general aspect, hybrids of the invention may be used to inhibit the secretion of ghrelin. Accordingly, compounds of the invention may be utilize this mechanism to treat or prevent ghrelin related disorders such as Prader-Willi syndrome, diabetes of all types and its complications, obesity, hyperphagia, hyperlipidemia, or other disorders associated with hypernutrition. In one embodiment such hybrids contain an exendin, GLP1, amylin and/or sCT portion.

In another general aspect, it is now recognized that hybrids containing amylin and/or sCT portions can be useful for treating or preventing Barrett's esophagus, Gastroesophageal Reflux Disease (GERD) and conditions associated therewith. Such conditions can include, but are not limited to, heartburn, heartburn accompanied by regurgitation of gastric/intestinal contents into the mouth or the lungs, difficulty in swallowing, coughing, intermittent wheezing and vocal cord inflammation (conditions associated with GERD), esophageal erosion, esophageal ulcer, esophageal stricture, Barrett's metaplasia (replacement of normal esophageal epithelium with abnormal epithelium), Barrett's adenocarcinoma, and pulmonary aspiration. Such hybrids have anti-secretory properties, such as inhibition of gastric acids, inhibition of bile acids, and inhibition of pancreatic enzymes. Moreover, such hybrids can have a gastroprotective effect, which renders them particularly useful in the treatment or prevention of Barrett's esophagus, and/or GERD and related or associated conditions as described herein.

In another general aspect, hybrids can be further be useful for treating or preventing pancreatitis, pancreatic carcinoma, and gastritis, particularly in the treatment and prevention of pancreatitis in patients who have undergone endoscopic retrograde cholangiopancreatography (ERCP). Amylin and/or sCT containing hybrid agonists can have a suprisingly superior therapeutic effect when combined with somatostatin. Accordingly, in certain embodiments, methods for treating or preventing pancreatitis comprise administering such hybrids and administering somatostatin and somatostatin agonists to a subject.

In another general aspect, hybrids are useful for decreasing bone resorption, decreasing plasma calcium, and inducing an analgesic effect, particularly to treat bone disorders such as osteopenia and osteoporosis. In yet other embodiments, hybrids are useful to treat pain and painful neuropathy. In one embodiment such hybrids contain an exendin, GLP1, amylin and/or sCT portion.

In another aspect of the invention, methods for treating or preventing obesity are provided, wherein the method comprises administering a therapeutically or prophylactically effective amount of a hybrid polypeptide to a subject in need thereof. In a preferred embodiment, the subject is an obese or overweight subject. While "obesity" is generally defined as a body mass index over 30, for purposes of this disclosure, any subject, including those with a body mass index of less than 30, who needs or wishes to reduce body weight is included in the scope of "obese." Subjects who are insulin resistant, glucose intolerant, or have any form of diabetes mellitus (e.g., type 1, 2 or gestational diabetes) can benefit from these hybrids. In one embodiment such hybrids contain an exendin, PYY, GLP1, amylin and/or sCT portion.

In other aspects of the invention, methods of reducing food intake, reducing nutrient availability, causing weight loss, affecting body composition, and altering body energy content or increasing energy expenditure, treating diabetes mellitus, and improving lipid profile (including reducing LDL cholesterol and triglyceride levels and/or changing HDL cholesterol levels) are provided, wherein the methods comprise administering to a subject an effective amount of a hybrid polypeptide of the invention. In a preferred embodiment, the methods of the invention are used to treat or prevent conditions or disorders which can be alleviated by reducing nutrient availability in a subject in need thereof, comprising administering to said subject a therapeutically or prophylactically effective amount of a hybrid polypeptide of the invention. Such conditions and disorders include, but are not limited to, hypertension, dyslipidemia, cardiovascular disease, eating disorders, insulin-resistance, obesity, and diabetes mellitus of any kind. In one embodiment such hybrids contain an exendin, PYY, GLP1, amylin and/or sCT portion.

Without intending to be limited by theory, it is believed that the effects of peripherally-administered hybrid polypeptides of the present invention in the reduction of food intake, in the delay of gastric emptying, in the reduction of nutrient availability, and in the causation of weight loss are determined by interactions with one or more unique receptor classes in, or similar to, those in the PP family. More particularly, it appears that a receptor or receptors similar to the PYY-preferring (or Y7) receptors are involved.

Additional assays useful to the invention include those that can determine the effect of PPF compounds on body composition. An exemplary assay can be one that involves utilization of a diet-induced obese (DIO) mouse model for metabolic disease. Prior to the treatment period, male C57BL/6J mice can be fed a high-fat diet (#D12331, 58% of calories from fat; Research Diets, Inc.) for 6 weeks beginning at 4 weeks of age. During the study, the mice can continue to eat their high-fat diet. Water can be provided ad libitum throughout the study. One group of similarly-aged non-obese mice can be fed a low-fat diet (#D12329, 11% of calories from fat) for purposes of comparing metabolic parameters to DIO groups.

DIO mice can be implanted with subcutaneous (SC) intrascapular osmotic pumps to deliver either vehicle (50% dimethylsulfoxide (DMSO) in water) or a compound of the invention. The pumps of the latter group can be set to deliver any amount, e.g., 1000 µg/kg/d of a compound of the invention for 7-28 days.

Body weights and food intake can be measured over regular intervals throughout the study periods. Respiratory quotient (RQ, defined as $CO_2$ production$\div O_2$ consumption) and metabolic rate can be determined using whole-animal indirect calorimetry (Oxymax, Columbus Instruments, Columbus, Ohio). The mice can be euthanized by isoflurane overdose, and an index of adiposity (bilateral epididymal fat pad weight) measured. Moreover, prior to determination of epididymal weight, body composition (lean mass, fat mass) for each mouse can be analyzed using a Dual Energy X-ray Absorptiometry (DEXA) instrument per manufacturer's instructions (Lunar Piximus, GE Imaging System). In the methods of the invention, preferred PPF polypeptide of the invention are those having a potency in one of the assays described herein (preferably food intake, gastric emptying, pancreatic secretion, weight reduction or body composition assays) which is greater than the potency of a component peptide hormone in that same assay.

In addition to the amelioration of hypertension in subjects in need thereof as a result of reduced food intake, weight loss, or treating obesity, compounds of the invention may be used to treat hypotension.

Compounds of the invention may also be useful for potentiating, inducing, enhancing or restoring glucose responsivity in pancreatic islets or cells. These actions may be useful for treating or preventing conditions associated with metabolic disorders such as those described above and in U.S. patent application no. US20040228846. Assays for determining such activity are known in the art. For example, in published U.S. patent application no. US20040228846 (incorporated by reference in its entirety), assays are described for islet isolation and culture as well as determining fetal islet maturation. In the examples of patent application US20040228846, intestine-derived hormone peptides including pancreatic polypeptide (PP), neuropeptide Y (NPY), neuropeptide K (NPK), PYY, secretin, glucagon-like peptide-1 (GLP-1) and bombesin were purchased from Sigma. Collagenase type XI was obtained from Sigma. RPMI 1640 culture medium and fetal bovine serum were obtained from Gibco. A radioimmunoassay kit containing anti-insulin antibody ($[^{125}I]$-RIA kit) was purchased from Linco, St Louis.

Post-partem rat islets were obtained from P-02 year old rats. Adult rat islets were obtained from 6-8 week old rats. Fetal rat islets were obtained as follows. Pregnant female rats were sacrificed on pregnancy day E21. Fetuses were removed from the uterus. 10-14 pancreata were dissected from each litter and washed twice in Hanks buffer. The pancreata were pooled, suspended in 6 ml 1 mg/ml collagenase (Type XI, Sigma) and incubated at 37° C. for 8-10 minutes with constant shaking. The digestion was stopped by adding 10 volumes of ice-cold Hanks buffer followed by three washes with Hanks buffer. The islets were then purified by Ficoll gradient and cultured in 10% fetal bovine serum (FBS)/RPMI medium with or without addition of 1 µM IBMX. At the end of five days, 20 islets were hand picked into each tube and assayed for static insulin release. Generally, islets were first washed with KRP buffer and then incubated with 1 ml of KRP buffer containing 3 mM (low) glucose for 30 minutes at 37° C. with constant shaking. After collecting the supernatant, the islets were then incubated with 17 mM (high) glucose for one hour at 37° C. The insulin released from low or high glucose stimulation were assayed by radioimmunoassay (RIA) using the $[^{125}I]$-RIA kit. E21 fetal islets were cultured for 5 days in the presence of 200 ng/ml PYY, PP, CCK, NPK, NPY, Secretin, GLP-1 or Bombesin.

An exemplary in vivo assay is also provided using the Zucker Diabetic Fatty (ZDF) male rat, an inbred (>F30 Generations) rat model that spontaneously expresses diabetes in all fa/fa males fed a standard rodent diet Purina 5008. In ZDF fa-fa males, hyperglycemia begins to develop at about seven weeks of age and glucose levels (fed) typically reach 500 mg/DL by 10 to 11 weeks of age. Insulin levels (fed) are high during the development of diabetes. However, by 19 weeks of age insulin drops to about the level of lean control litter mates. Triglyceride and cholesterol levels of obese rats are normally higher than those of leans. In the assay, three groups of 7-week old ZDF rats, with 6 rats per group, received the infusion treatment by ALZA pump for 14 days: 1) vehicle control, 2) and 3), PYY with two different doses, 100 pmol/kg/hr and 500 pmol/kg/hr respectively. Four measurements were taken before the infusion and after the infusion at day 7 and day 14: 1) plasma glucose level, 2) plasma insulin level, and 3) plasma triglycerides (TG) level, as well as oral glucose tolerance (OGTT) test. Accordingly, these assays can be used with compounds of the invention to test for desired activity.

Other uses contemplated for the hybrid polypeptides include methods for reducing aluminum (Al) concentrations in the central nervous system (see U.S. Pat. No. 6,734,166, incorporated by reference in its entirety) for treating, preventing, or delay the onset of Alzheimer's disease. Assays for determining effects on Al are known in the art and can be found in U.S. Pat. 6,734,166 using diploid and Ts mice. These mice were individually housed in Nalgene® brand metabolism or polypropylene cages and given three days to adjust to the cages before experimentation. Mice had free access to food (LabDiet® NIH Rat and Moust/Auto 6F5K52, St. Louis, Mo.) and water during the experiment except for the 16 hours prior to euthanasia when no food was provided. Mice were given daily subcutaneous injections of either active compound or saline. Mice were sacrificed at the end of day 13 for one experiment and day 3 for another, and samples were collected. Mice brain samples were weighted in clean teflon liners and prepared for analysis by microwave digestion in low trace element grade nitric acid. Samples were then analyzed for Al content using Inductively Coupled Plasma Mass Spectrometry (Nuttall et al., *Annals of Clinical and Laboratory Science* 25, 3, 264-271 (1995)). All tissue handling during analysis took place in a clean room environment utilizing HEPA air filtration systems to minimize background contamination. Hybrids of the invention are useful for prevention and treatment of nephropathy, including hypertensive and diabetic nephropathy, and nephropathy associated with insulin resistance and metabolic syndrome. Hybrids achieve these ends by, among other things, improving or preventing worsening of hypertension, endothelial function, renal function, and glomerulosclerosis. In one embodiment, the invention provides a method for preventing or treating nephropathy, including hypertensive and diabetic nephropathy, or that related to insulin resistance, comprising administering a compound of the invention. Hybrids find further use for improving endothelial function in a patient having reduced vasodilatory capacity, or having glomerulosclerosis or any other reduction in glomerular flow. Such improvement in endothelial function serves both to reduce hypertension and to improve the function of the capillaries of the glomeruli. In additional embodiments, the molecules of the invention are useful to prevent progression of nephropathy to ESRD, to prevent, slow the progression of, treat or ameliorate proteinuria and/or glomerulosclerosis. Hybrids are useful for reducing the risk of suffering from, preventing, or treating cardiac arrhythmias. Hybrids can provide anti-arrhythmic effects in patients with cardiac ischemia, cardiac ischemia-reperfusion, and congestive heart failure. For example, GLP-1 has been found to reduce cardiac injury and enhance recovery in patients with these disorders. Incretins, including GLP-1, are glucose-dependent insulinotropic hormones. GLP-1 and exendin effectively enhance peripheral glucose uptake without inducing dangerous hypoglycemia. They also strongly suppress glucagon secretion, independent of its insulinotropic action, and thereby powerfully reduce plasma free fatty acid (FFA) levels substantially more than can be accomplished with insulin. High FFA levels have been implicated as a major toxic mechanism during myocardial ischemia. In another embodiment hybrids are useful for preventing and treating cardiac arrhythmias that reliably reduce injury associated with reperfusion and ischemia, and enhance patient recovery. In yet a further embodiment hybrid treatment after acute stroke or hemorrhage, preferably intravenous administration, provides a means for optimizing insulin secretion, increasing brain anabolism, enhancing insulin effectiveness by suppressing glucagon, and maintaining euglycemia or mild hypoglycemia with no risk of severe hypoglycemia or other adverse side effects. In one embodiment such hybrids contain a GLP1 or exendin portion. In a further embodiment a GLP1 or exendin family module is combined with a natriuretic family peptide, an amylin family peptide, a urocortin family peptide module to obtain enhanced treatment or prevention of cardiovascular conditions or diseases, including CHF, as described herein.

In yet a further embodiment hybrids that are capable of lowering insulin resistance or increasing insulin sensitivity are useful to treat polycystic ovary syndrome (PCOS). Administering hybrids of the invention can reduce or prevent insulin resistance in a subject suffering from PCOS. In yet another embodiment hybrids prevent the onset of type-2 diabetes in a subject suffering from PCOS. Further hybrids can restore regular menses, ovulation, or fertility in a subject suffering from PCOS. In one embodiment such hybrids contain a GLP1 or an exendin portion for binding and activating a GLP1 receptor.

The compounds of the invention exhibit a broad range of biological activities, some related to their antisecretory and antimotility properties. The compounds may suppress gastrointestinal secretions by direct interaction with epithelial cells or, perhaps, by inhibiting secretion of hormones or neurotransmitters which stimulate intestinal secretion. Antisecretory properties include inhibition of gastric and/or pancreatic secretions and can be useful in the treatment or prevention of diseases and disorders including gastritis, pancreatitis, Barrett's esophagus, and Gastroesophageal Reflux Disease.

Compounds of the invention are useful in the treatment of any number of gastrointestinal disorders (see e.g., Harrison's Principles of Internal Medicine, McGraw-Hill Inco, N.Y., 12th Ed.) that are associated with excess intestinal electrolyte and water secretion as well as decreased absorption, e.g., infectious diarrhea, inflammatory diarrhea, short bowel syndrome, or the diarrhea which typically occurs following surgical procedures, e.g., ileostomy. Examples of infectious diarrhea include, without limitation, acute viral diarrhea, acute bacterial diarrhea (e.g., *salmonella, campylobacter*, and *clostridium* or due to protozoal infections), or traveller's diarrhea (e.g., Norwalk virus or rotavirus). Examples of inflammatory diarrhea include, without limitation, malabsorption syndrome, tropical sprue, chronic pancreatitis, Crohn's disease, diarrhea, and irritable bowel syndrome. It has also been discovered that the peptides of the invention can be used to treat an emergency or life-threatening situation involving a gastrointestinal disorder, e.g., after surgery or due to cholera.

Compounds of the invention may also be useful for treating or preventing intestinal damage as opposed to merely treating the symptoms associated with the intestinal damage (for example, diarrhea). Such damage to the intestine may be, or a result of, ulcerative colitis, inflammatory bowel disease, bowel atrophy, loss bowel mucosa, and/or loss of bowel mucosal function (see WO 03/105763, incorporated herein by reference in its entirety). Assays for such activity, as described in WO 03/105763, include 11 week old male HSD rats, ranging 250-300 grams housed in a 12:12 light:dark cycle, and allowed ad libitum access to a standard rodent diet (Teklad LM 485, Madison, Wis.) and water. The animals were fasted for 24 hours before the experiment. A simple and reproducible rat model of chronic colonic inflammation has been previously described by Morris G P, et al., "Hapten-induced model of chronic inflammation and ulceration in the rat colon." Gastroenterology. 1989; 96:795-803. It exhibits a relatively long duration of inflammation and ulceration, affording an opportunity to study the pathophysiology of colonic inflammatory disease in a specifically controlled fashion, and to evaluate new treatments potentially applicable to inflammatory bowel disease in humans.

Rats were anesthetized with 3% isofluorane and placed on a regulated heating pad set at 37° C. A gavage needle was inserted rectally into the colon 7 cm. The hapten trinitrobenzenesulfonic acid (TNBS) dissolved in 50% ethanol (v/v) was delivered into the lumen of the colon through the gavage needle at a dose of 30 mg/kg, in a total volume of 0 0.4-0.6 mL, as described in Mazelin, et al., *Juton Nery Syst*. 1998; 73:38 45. Control groups received saline solution (NaCl 0.9%) intracolonically.

Four days after induction of colitis, the colon was resected from anesthetized rats, which were then euthanized by decapitation. Weights of excised colon and spleen were measured, and the colons photographed for scoring of gross morphologic damage. Inflammation was defined as regions of hyperemia and bowel wall thickening.

Hybrid polypeptides of the invention may also be used to treat or prevent pancreatic tumors (e.g., inhibit the proliferation of pancreatic tumors). Methods of the invention include reducing the proliferation of tumor cells. The types of benign pancreatic tumor cells which may be treated in accordance with the present invention include serous cyst adenomas, microcystic tumors, and solid-cystic tumors. The method is also effective in reducing the proliferation of malignant pancreatic tumor cells such as carcinomas arising from the ducts, acini, or islets of the pancreas. U.S. Pat. No. 5,574,010 (incorporated by reference in its entirety) provides exemplary assays for testing anti-proliferative properties. For example, the '010 patent provides that PANC-1 and MiaPaCa-2 are two human pancreatic adenocarcinoma cancer cell lines which are available commercially from suppliers such as American Type Culture Collection, ATCC (Rockville, Md.). The two tumor cells were grown in RPMI-1640 culture media supplemented with 10% fetal bovine serum, 29.2 mg/L of glutamine, 25 µg gentamicin, 5 ml penicillin, streptomycin, and fungizone solution (JRH Biosciences, Lenexa, Kans.) at 37 degrees Celcius in a NAPCO water jacketed 5% $CO_2$ incubator. All cell lines were detached with 0.25% trypsin (Clonetics, San Diego, Calif.) once to twice a week when a confluent monolayer of tumor cells was achieved. Cells were pelleted for 7 minutes at 500 g in a refrigerated centrifuge at 4 degrees Celcius, and resuspended in trypsin free fortified RPMI 1640 culture media. Viable cells were counted on a hemocytometer slide with trypan blue.

Ten thousand, 20,000, 40,000 and 80,000 cells of each type were added to 96 well microculture plates (Costar, Cambridge, Mass.) in a total volume of 200 ul of culture media per well. Cells were allowed to adhere for 24 hours prior to addition of the PYY or test peptide. Fresh culture media was exchanged prior to addition of peptides. In vitro incubation of pancreatic tumor cells with either PYY or test compound was continued for 6 hours and 36 hours in length. PYY was added to cells at doses of 250 pmol, 25 pmol, and 2.5 pmol per well (N=14). Test compound was added to cells cultures at doses of 400 pmol, 40 pmol, and 4 pmol per well. Control wells received 2 ul of 0.9% saline to mimic the volume and physical disturbance upon adhered tumor cells. Each 96 well plate contained 18 control wells to allow for comparison within each plate during experimentation. Ninety-six (96) well plates were repeated 6 times with varying concentrations of PYY and test compound in both the PANC-1 and MiaPaCa-2 cells.

At the end of the incubation period, 3-(4,5-dimethylthiazolyl-2-yl)-2,5-diphenyltetrazolium bromide, MTr tetrazolium bromide (Sigma, St. Louis, Mo.) was added to fresh culture media at 0.5 mg/ml. Culture media was exchanged and tumor cells were incubated for 4 hours with MTT tetrazolium bromide at 37° C. At the end of incubation, culture media was aspirated. Formazon crystal precipitates were dissolved in 200 µl of dimethyl sulfoxide (Sigma, St. Louis, Mo.). Quantitation of solubilized formazon was performed by obtaining absorption readings at 500 nm wavelength on an ELISA reader (Molecular Devices, Menlo Park, Calif.). The MTT assay measures mitochondrial NADH dependent dehydrogenase activity, and it has been among the most sensitive and reliable method to quantitative in vitro chemotherapy responses of tumor cells. (Alley, M. C., et al., *Cancer Res.*, 48:589-601, 1988; Carmichael, J., et al., *Cancer Res.*, 47:936-942, 1987; McHale, A. P., et al., *Cancer Lett.*, 41:315-321, 1988; and Saxton, R. E., et al., *J. Clin. Laser Med. and Surg.*, 10(5):331-336, 1992.) Analysis of absorption readings at 550 nm were analyzed by grouping wells of the same test conditions and verifying differences occurring between control and the various peptide concentration treatments by one-way ANOVA.

An exemplary in vivo assay is also provided. The human pancreatic ductal adenocarcinoma Mia Paca-2 was examined for in vivo growth inhibition by peptide YY and test compound. Seventy thousand to 100,000 human Mia PaCa-2 cells were orthotopically transplanted into 48 male athymic mice. After one week, the animals were treated with either PYY or test compound at 200 pmol/kg/hr via mini-osmotic pumps for four weeks. The paired cultures received saline. At sacrifice, both tumor size and mass were measured. Control mice had significant human cancer growth within the pancreas as evidenced by histologic sections. At 9 weeks, ninety percent (90%) of control mice had substantial metastatic disease. Tumor mass was decreased by 60.5% in test treated mice and 27% in PYY treated mice.

Hybrids are also useful for the therapeutic and prophylactic treatment of neurological and nervous system disorders associated with neuronal loss or dysfunction, including, but not limited to, Parkinson's Disease, Alzheimer's Disease, Huntington's Disease, ALS, stroke, ADD, and neuropsychiatric syndromes, and to enhance or facilitate learning, memory and cognition in mammals. Particularly useful in this regard are hybrids containing an exendin or GLP1 active portion, more specifically comprising at least the N-terminal 7-15 amino acids or analog thereof, for example HSEGTFTSD (SEQ ID NO: 378).

For all indications, in preferred embodiments, the hybrid polypeptide of the invention is administered peripherally at a dose of about 0.5 ng to about 5 mg per day in single or divided doses or controlled continual release, or at about 0.01 ng/kg to about 500 ng/kg per dose, more preferably about 0.05 ng/kg to about 250 ng/kg, most preferably below about 50 ng/kg. Dosages in these ranges will vary with the potency of each analog or derivative, of course, and may be determined by one of skill in the art.

In the methods of the present invention, hybrid polypeptides of the invention may be administered separately or together with one or more other compounds and compositions that exhibit a long term or short-term action to reduce nutrient availability, including, but not limited to other compounds and compositions that comprise an amylin or amylin analog agonist, salmon calcitonin, a cholecystokinin (CCK) or CCK agonist, a leptin (OB protein) or leptin agonist, an exendin or exendin analog agonist, or a GLP-1 or GLP-1 analog agonist. Suitable amylin agonists include, for example, [$^{25,28,29}$Pro-] human amylin (SEQ ID NO: 67) (also known as "pramlintide," and described in U.S. Pat. Nos. 5,686,511 and 5,998,367). The CCK used is preferably CCK octapeptide (CCK-8), more preferably its sulfated form. Leptin is discussed in, for example, (Pelleymounter et al., Science 269: 540-3 (1995); Halaas et al., Science 269: 543-6 (1995); Campfield et al., Science 269: 546-9 (1995)). Suitable exendins include exendin-3 and exendin-4, and exendin agonist compounds include, for example, those described in PCT Publications WO 99/07404, WO 99/25727, and WO 99/25728.

Polypeptide Production and Purification

The hybrid polypeptides described herein may be prepared using standard recombinant techniques or chemical peptide synthesis techniques known in the art, e.g., using an automated or semi-automated peptide synthesizer, or both.

The hybrid polypeptides of the invention can be synthesized in solution or on a solid support in accordance with conventional techniques. Various automatic synthesizers are commercially available and can be used in accordance with known protocols. See, e.g., Stewart and Young, *Solid Phase Peptide Synthesis*, 2d. ed., Pierce Chemical Co. (1984); Tam et al., *J. Am. Chem. Soc.* 105: 6442 (1983); Merrifield, *Sci-* ence 232: 341-7 (1986); and Barany and Merrifield, *The Peptides*, Gross and Meienhofer, eds., Academic Press, New York, 1-284 (1979). Solid phase peptide synthesis may be carried out with an automatic peptide synthesizer (e.g., Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Peptides may also be assembled using an Advanced Chem Tech Synthesizer (Model MPS 350, Louisville, Ky.). Peptides may be purified by RP-HPLC (preparative and analytical) using, e.g., a Waters Delta Prep 3000 system and a C4, C8, or C18 preparative column (10µ, 2.2×25 cm; Vydac, Hesperia, Calif.). The active peptide can be readily synthesized and then screened in screening assays designed to identify reactive peptides.

The hybrid polypeptides of the present invention may alternatively be produced by recombinant techniques well known in the art. See, e.g., Sambrook et al., *Molecular Cloning: A Laboratory Manual*, 2d ed., Cold Spring Harbor (1989). These hybrid polypeptides produced by recombinant technologies may be expressed from a polynucleotide. One skilled in the art will appreciate that the polynucleotides, including DNA and RNA, that encode such the various fragments of the hybrid polypeptides may be obtained from the wild-type cDNA, taking into consideration the degeneracy of codon usage, or may be engineered as desired. These polynucleotide sequences may incorporate codons facilitating transcription and translation of mRNA in microbial hosts. Such manufacturing sequences may readily be constructed according to the methods well known in the art. See, e.g., WO 83/04053. The polynucleotides above may also optionally encode an N-terminal methionyl residue. Non-peptide compounds useful in the present invention may be prepared by art-known methods. For example, phosphate-containing amino acids and peptides containing such amino acids may be prepared using methods known in the art. See, e.g., Bartlett and Landen, *Bioorg. Chem.* 14: 356-77 (1986).

A variety of expression vector/host systems may be utilized to contain and express a hybrid polypeptide coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), WI 38, BHK, HepG2, 3T3, RIN, MDCK, A549, PC12, K562 and 293 cells. Exemplary protocols for the recombinant expression of the protein are described herein.

As such, polynucleotide sequences provided by the invention are useful in generating new and useful viral and plasmid DNA vectors, new and useful transformed and transfected procaryotic and eucaryotic host cells (including bacterial, yeast, and mammalian cells grown in culture), and new and useful methods for cultured growth of such host cells capable of expression of the present hybrid polypeptides. The polynucleotide sequences encoding hybrid polypeptides herein may be useful for gene therapy in instances where underproduction of the component peptide hormone(s) of the chimera would be alleviated, or the need for increased levels of such would be met.

The present invention also provides for processes for recombinant DNA production of the present hybrid polypeptides. Provided is a process for producing the hybrid polypeptides from a host cell containing nucleic acids encoding such hybrid polypeptides comprising: (a) culturing said host cell containing polynucleotides encoding such hybrid polypeptides under conditions facilitating the expression of such DNA molecule; and (b) obtaining such hybrid polypeptides.

Host cells may be prokaryotic or eukaryotic and include bacteria, mammalian cells (such as Chinese Hamster Ovary (CHO) cells, monkey cells, baby hamster kidney cells, cancer cells or other cells), yeast cells, and insect cells.

Mammalian host systems for the expression of the recombinant protein also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing, which cleaves a "prepro" form of the protein, may also be important for correct insertion, folding and/or function. Different host cells, such as CHO, HeLa, MDCK, 293, WI38, and the like, have specific cellular machinery and characteristic mechanisms for such post-translational activities, and may be chosen to ensure the correct modification and processing of the introduced foreign protein.

Alternatively, a yeast system may be employed to generate the hybrid polypeptides of the present invention. The coding region of the hybrid polypeptide cDNA is amplified by PCR. A DNA encoding the yeast pre-pro-alpha leader sequence is amplified from yeast genomic DNA in a PCR reaction using one primer containing nucleotides 1-20 of the alpha mating factor gene and another primer complementary to nucleotides 255-235 of this gene (Kurjan and Herskowitz, *Cell*, 30: 933-43 (1982)). The pre-pro-alpha leader coding sequence and hybrid polypeptide coding sequence fragments are ligated into a plasmid containing the yeast alcohol dehydrogenase (ADH2) promoter, such that the promoter directs expression of a fusion protein consisting of the pre-pro-alpha factor fused to the mature hybrid polypeptide. As taught by Rose and Broach, *Meth. Enz.* 185: 234-79, Goeddel ed., Academic Press, Inc., San Diego, Calif. (1990), the vector further includes an ADH2 transcription terminator downstream of the cloning site, the yeast "2-micron" replication origin, the yeast leu-2d gene, the yeast REP1 and REP2 genes, the *E. coli* β-lactamase gene, and an *E. coli* origin of replication. The β-lactamase and leu-2d genes provide for selection in bacteria and yeast, respectively. The leu-2d gene also facilitates increased copy number of the plasmid in yeast to induce higher levels of expression. The REP1 and REP2 genes encode proteins involved in regulation of the plasmid copy number.

The DNA construct described in the preceding paragraph is transformed into yeast cells using a known method, e.g., lithium acetate treatment (Steams et al., *Meth. Enz.* 185: 280-97 (1990)). The ADH2 promoter is induced upon exhaustion of glucose in the growth media (Price et al., *Gene* 55: 287 (1987)). The pre-pro-alpha sequence effects secretion of the fusion protein from the cells. Concomitantly, the yeast KEX2 protein cleaves the pre-pro sequence from the mature PYY analog polypeptides (Bitter et al., *Proc. Natl. Acad. Sci. USA* 81: 5330-4 (1984)).

Hybrid polypeptides of the invention may also be recombinantly expressed in yeast using a commercially available expression system, e.g., the *Pichia* Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol. The secreted hybrid polypeptide is purified from the yeast growth medium by, e.g., the methods used to purify hybrid polypeptide from bacterial and mammalian cell supernatants.

Alternatively, the cDNA encoding hybrid polypeptides may be cloned into the baculovirus expression vector pVL1393 (PharMingen, San Diego, Calif.). This hybrid polypeptide-containing vector is then used according to the manufacturer's directions (PharMingen) to infect *Spodoptera frugiperda* cells in sF9 protein-free media and to produce recombinant protein. The protein is purified and concentrated from the media using a heparin-Sepharose column (Pharmacia, Piscataway, N.J.) and sequential molecular sizing columns (Amicon, Beverly, Mass.), and resuspended in PBS. SDS-PAGE analysis shows a single band and confirms the size of the protein, and Edman sequencing on a Proton 2090 Peptide Sequencer confirms its N-terminal sequence.

For example, the DNA sequence encoding the hybrid polypeptide may be cloned into a plasmid containing a desired promoter and, optionally, a leader sequence (see, e.g., Better et al., Science 240: 1041-3 (1988)). The sequence of this construct may be confirmed by automated sequencing. The plasmid is then transformed into *E. coli*, strain MC1061, using standard procedures employing $CaCl_2$ incubation and heat shock treatment of the bacteria (Sambrook et al., supra). The transformed bacteria are grown in LB medium supplemented with carbenicillin, and production of the expressed protein is induced by growth in a suitable medium. If present, the leader sequence will affect secretion of the hybrid polypeptide and be cleaved during secretion. The secreted recombinant protein is purified from the bacterial culture media by the method described herein.

Alternatively, the hybrid polypeptides of the invention may be expressed in an insect system. Insect systems for protein expression are well known to those of skill in the art. In one such system, *Autographa californica* nuclear polyhedrosis virus (AcNPV) is used as a vector to express foreign genes in *Spodoptera frugiperda* cells or in *Trichoplusia larvae*. The hybrid polypeptide coding sequence is cloned into a nonessential region of the virus, such as the polyhedrin gene, and placed under control of the polyhedrin promoter. Successful insertion of hybrid polypeptide will render the polyhedrin gene inactive and produce recombinant virus lacking coat protein coat. The recombinant viruses are then used to infect *S. frugiperda* cells or *Trichoplusia larvae* in which hybrid polypeptide is expressed (Smith et al., *J. Virol.* 46: 584 (1983); Engelhard et al., *Proc. Natl. Acad. Sci. USA* 91: 3224-7 (1994)).

In another example, the DNA sequence encoding the hybrid polypeptide may be amplified by PCR and cloned into an appropriate vector, for example, pGEX-3X (Pharmacia, Piscataway, N.J.). The pGEX vector is designed to produce a fusion protein comprising glutathione-S-transferase (GST), encoded by the vector, and a protein encoded by a DNA fragment inserted into the vector's cloning site. The primers for the PCR may be generated to include, for example, an appropriate cleavage site. The recombinant fusion protein may then be cleaved from the GST portion of the fusion protein. The pGEX-3X/PYY analog polypeptide construct is transformed into *E. coli* XL-1 Blue cells (Stratagene, La Jolla, Calif.), and individual transformants are isolated and grown at 37° C. in LB medium (supplemented with carbenicillin) to an optical density at wavelength 600 nm of 0.4, followed by further incubation for 4 hours in the presence of 0.5 mM Isopropyl β-D-Thiogalactopyranoside (Sigma Chemical Co., St. Louis, Mo.). Plasmid DNA from individual transformants is purified and partially sequenced using an automated sequencer to confirm the presence of the desired PPF hybrid polypeptide-encoding gene insert in the proper orientation.

The fusion protein, expected to be produced as an insoluble inclusion body in the bacteria, may be purified as follows. Cells are harvested by centrifugation; washed in 0.15 M NaCl, 10 mM Tris, pH 8, 1 mM EDTA; and treated with 0.1 mg/mL lysozyme (Sigma Chemical Co.) for 15 min. at room temperature. The lysate is cleared by sonication, and cell debris is pelleted by centrifugation for 10 min. at 12,000×g. The fusion protein-containing pellet is resuspended in 50 mM Tris, pH 8, and 10 mM EDTA, layered over 50% glycerol, and centrifuged for 30 min. at 6000×g. The pellet is resuspended in standard phosphate buffered saline solution (PBS) free of $Mg^{++}$ and $Ca^{++}$. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If the GST/PYY analog polypeptide fusion protein is produced in bacteria as a soluble protein, it may be purified using the GST Purification Module (Pharmacia Biotech).

The fusion protein may be subjected to digestion to cleave the GST from the PPF hybrid polypeptide. The digestion reaction (20-40 μg fusion protein, 20-30 units human thrombin (4000 U/mg (Sigma) in 0.5 mL PBS) is incubated 16-48 hrs. at room temperature and loaded on a denaturing SDS-PAGE gel to fractionate the reaction products. The gel is soaked in 0.4 M KCl to visualize the protein bands. The identity of the protein band corresponding to the expected molecular weight of the hybrid polypeptide may be confirmed by partial amino acid sequence analysis using an automated sequencer (Applied Biosystems Model 473A, Foster City, Calif.).

In a particularly preferred method of recombinant expression of the hybrid polypeptides of the present invention, 293 cells may be co-transfected with plasmids containing the hybrid polypeptide cDNA in the pCMV vector (5' CMV promoter, 3' HGH poly A sequence) and pSV2neo (containing the neo resistance gene) by the calcium phosphate method. Preferably, the vectors should be linearized with ScaI prior to transfection. Similarly, an alternative construct using a similar pCMV vector with the neo gene incorporated can be used. Stable cell lines are selected from single cell clones by limiting dilution in growth media containing 0.5 mg/mL G418 (neomycin-like antibiotic) for 10-14 days. Cell lines are screened for hybrid polypeptide expression by ELISA or Western blot, and high-expressing cell lines are expanded for large scale growth.

It is preferable that the transformed cells are used for long-term, high-yield protein production and as such stable expression is desirable. Once such cells are transformed with vectors that contain selectable markers along with the desired expression cassette, the cells may be allowed to grow for 1-2 days in an enriched media before they are switched to selective media. The selectable marker is designed to confer resistance to selection, and its presence allows growth and recovery of cells that successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk–, hgprt– or aprt– cells, respectively. Also, anti-metabolite resistance can be used as the basis of selection for dhfr, that confers resistance to methotrexate; gpt, that confers resistance to mycophenolic acid; neo, that confers resistance to the aminoglycoside, G418; also, that confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, β-glucuronidase and its substrate, GUS, and luciferase and its substrate, luciferin.

Many of the hybrid polypeptides of the present invention may be produced using a combination of both automated peptide synthesis and recombinant techniques. For example, a hybrid polypeptide of the present invention may contain a combination of modifications including deletion, substitution, and insertion by PEGylation. Such a hybrid polypeptide may be produced in stages. In the first stage, an intermediate polypeptide containing the modifications of deletion, substitution, insertion, and any combination thereof, may be produced by recombinant techniques as described. Then after an optional purification step as described herein, the intermediate polypeptide is PEGylated through chemical modification with an appropriate PEGylating reagent (e.g., from Nektar Therapeutics, San Carlos, Calif.) to yield the desired hybrid polypeptide. One skilled in the art will appreciate that the above-described procedure may be generalized to apply to a hybrid polypeptide containing a combination of modifications selected from deletion, substitution, insertion, derivation, and other means of modification well known in the art and contemplated by the present invention.

It may be desirable to purify the hybrid polypeptides generated by the present invention. Peptide purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography, polyacrylamide gel electrophoresis, and isoelectric focusing. A particularly efficient method of purifying peptides is reverse phase HPLC, followed by characterization of purified product by liquid chromatography/mass spectrometry (LC/MS) and Matrix-Assisted Laser Desorption Ionization (MALDI) mass spectrometry. Additional confirmation of purity is obtained by determining amino acid analysis.

Certain aspects of the present invention concern the purification, and in particular embodiments, the substantial purification, of an encoded protein or peptide. The term "purified peptide" as used herein, is intended to refer to a composition, isolatable from other components, wherein the peptide is purified to any degree relative to its naturally obtainable state. A purified peptide therefore also refers to a peptide, free from the environment in which it may naturally occur.

Generally, "purified" will refer to a peptide composition that has been subjected to fractionation to remove various other components, and which composition substantially retains its expressed biological activity. Where the term "substantially purified" is used, this designation will refer to a composition in which the peptide forms the major component of the composition, such as constituting about 50%, about 60%, about 70%, about 80%, about 90%, about 95% or more of the peptides in the composition.

Various techniques suitable for use in peptide purification will be well known to those of skill in the art. These include, for example, precipitation with ammonium sulphate, PEG, antibodies, and the like; heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the peptides always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed, utilizing an HPLC apparatus, will generally result in a greater "-fold" purification than the same technique utilizing a low pressure chromatography system. Methods exhibiting a lower degree of relative purification may have advantages in total recovery of protein product, or in maintaining the activity of an expressed protein.

One may optionally purify and isolate such hybrid polypeptides from other components obtained in the process. Methods for purifying a polypeptide can be found in U.S. Pat. No. 5,849,883. These documents describe specific exemplary methods for the isolation and purification of G-CSF compositions that may be useful in isolating and purifying the hybrid polypeptides of the present invention. Given the disclosure of these patents, it is evident that one of skill in the art would be well aware of numerous purification techniques that may be used to purify hybrid polypeptides from a given source.

Also it is contemplated that a combination of anion exchange and immunoaffinity chromatography may be employed to produce purified hybrid polypeptide compositions of the present invention.

Pharmaceutical Compositions

The present invention also relates to pharmaceutical compositions comprising a therapeutically or prophylactically effective amount of at least one hybrid polypeptide of the invention, or a pharmaceutically acceptable salt thereof, together with pharmaceutically acceptable diluents, preservatives, solubilizers, emulsifiers, adjuvants and/or carriers useful in the delivery of the hybrid polypeptides. Such compositions may include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., thimersol, benzyl alcohol), and bulking substances (e.g., lactose, mannitol); incorporation of the material into particulate preparations of polymeric compounds, such as polylactic acid, polyglycolic acid, etc., or in association with liposomes. Such compositions will influence the physical state, stability, rate of in vivo release, and rate of in vivo clearance of the present hybrid polypeptides. See, e.g., Remington's Pharmaceutical Sciences 1435-712, 18th ed., Mack Publishing Co., Easton, Pa. (1990).

In general, the present hybrid polypeptides will be useful in the same way that the individual component polypeptides are useful in view of their pharmacological properties. One preferred use is to peripherally administer such hybrid polypeptides for the treatment or prevention of metabolic conditions and disorders. In particular, the compounds of the invention possess activity as agents to reduce nutrient availability, reduce food intake, suppress appetite, and effect weight loss. In another embodiment, a preferred use is to administer such hybrid polypeptides for the treatment of diabetes or diabetes related conditions and disorders.

The present hybrid polypeptides may be formulated for peripheral administration, including formulation for injection, oral administration, nasal administration, pulmonary administration, topical administration, or other types of administration as one skilled in the art will recognize. More particularly, administration of the pharmaceutical compositions according to the present invention may be via any common route so long as the target tissue is available via that route. In a preferred embodiment, the pharmaceutical compositions may be introduced into the subject by any conventional peripheral method, e.g., by intravenous, intradermal, intramusclar, intramammary, intraperitoneal, intrathecal, retrobulbar, intrapulmonary (e.g., term release); by oral, sublingual, nasal, anal, vaginal, or transdermal delivery, or by surgical implantation at a particular site. The treatment may consist of a single dose or a plurality of doses over a period of time. Controlled continual release of the compositions of the present invention is also contemplated.

The formulation may be liquid or may be solid, such as lyophilized, for reconstitution. Aqueous compositions of the present invention comprise an effective amount of the hybrid polypeptide, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients also can be incorporated into the compositions. In some cases, it will be convenient to provide a hybrid polypeptide of the invention and another food-intake-reducing, diabetes treating, plasma glucose-lowering, or plasma lipid-altering agent, such as an amylin, an amylin agonist analog, a CCK or CCK agonist, or a leptin or leptin agonist, or an exendin or exendin agonist analog, in a single composition or solution for administration together. In other cases, it may be more advantageous to administer the additional agent separately from said hybrid polypeptide.

The hybrid polypeptide of the invention may be prepared for administration as solutions of free base, or pharmacologically acceptable salts in water suitably mixed with a surfactant, such as hydroxypropylcellulose. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like. Such products are readily prepared by procedures well known to those skilled in the art. Dispersions also can be prepared in glycerol, liquid polyethylene glycols, and mixtures thereof and in oils. Under ordinary conditions of storage and use, these preparations contain a preservative to prevent the growth of microorganisms.

In one embodiment, the pharmaceutical compositions of the present invention are formulated so as to be suitable for parenteral administration, e.g., via injection or infusion. Preferably, the hybrid polypeptide is suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. A form of repository or "depot" slow release preparation may be used so that therapeutically effective amounts of the preparation are delivered into the bloodstream over many hours or days following transdermal injection or delivery.

The pharmaceutical compositions suitable for injectable use include sterile aqueous solutions or dispersions and sterile powders for the extemporaneous preparation of sterile injectable solutions or dispersions. In all cases, the form should be sterile and should be fluid to the extent that easy syringability exists. It is also desirable for the hybrid polypeptide of the invention to be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents (for example, sugars or sodium chloride). Prolonged absorption of the injectable compositions can be brought about by the use in the compositions of agents delaying absorption (for example, aluminum monostearate and gelatin).

Sterile injectable solutions may be prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques that yield a powder of the active ingredient plus any additional desired ingredient from a previously sterile-filtered solution thereof.

Generally, a therapeutically or prophylactically effective amount of the present hybrid polypeptides will be determined by the age, weight, and condition or severity of the diseases, conditions or disorders of the recipient. See, e.g., Remington's Pharmaceutical Sciences 697-773. See also Wang and Hanson, Parenteral Formulations of Proteins and Peptides:

Stability and Stabilizers, *Journal of Parenteral Science and Technology*, Technical Report No. 10, Supp. 42:2 S (1988). Typically, a dosage of between about 0.001 μg/kg body weight/day to about 1000 μg/kg body weight/day, may be used, but more or less, as a skilled practitioner will recognize, may be used. Dosing may be one or more times daily, or less frequently, and may be in conjunction with other compositions as described herein. It should be noted that the present invention is not limited to the dosages recited herein.

Appropriate dosages may be ascertained through the use of established assays for determining level of metabolic conditions or disorders in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

An effective dose will typically be in the range of about 1 to 30 μg to about 5 mg/day, preferably about 10 to 30 μg to about 2 mg/day and more preferably about 5 to 100 μg to about 1 mg/day, most preferably about 5 μg to about 500 μg/day, for a 50 kg patient, administered in a single or divided doses. Preferably, dosages are between about 0.01 to about 100 μg/kg/dose. The exact dose to be administered may be determined by one of skill in the art and is dependent upon the potency of the particular compound, as well as upon the age, weight and condition of the individual. Administration should begin whenever, e.g., suppression of nutrient availability, food intake, weight, blood glucose or plasma lipid modulation is desired, for example, at the first sign of symptoms or shortly after diagnosis of obesity, diabetes mellitus, or insulin-resistance syndrome. Administration may be by any route, e.g., injection, preferably subcutaneous or intramuscular, oral, nasal, transdermal, etc. Dosages for certain routes, for example oral administration, may be increased to account for decreased bioavailablity, for example, by about 5-100 fold.

Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. See, e.g., Remington's Pharmaceutical Sciences, supra, pages 1435-1712. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

It will be appreciated that the pharmaceutical compositions and treatment methods of the invention may be useful in fields of human medicine and veterinary medicine. Thus the subject to be treated may be a mammal, preferably human or other animal. For veterinary purposes, subjects include for example, farm animals including cows, sheep, pigs, horses and goats, companion animals such as dogs and cats, exotic and/or zoo animals, laboratory animals including mice, rats, rabbits, guinea pigs and hamsters; and poultry such as chickens, turkeys, ducks and geese.

In addition, the present invention contemplates a kit comprising a hybrid polypeptide of the invention, components suitable for preparing said hybrid polypeptide of the invention for pharmaceutical application, and instructions for using said hybrid polypeptide and components for pharmaceutical application.

To assist in understanding the present invention, the following examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. The examples illustrate the preparation of the present hybrid polypeptides, and the testing of these hybrid polypeptides of the invention in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

Example 1

Preparation of Hybrid Polypeptides

Peptides of the invention may be assembled on a Symphony peptide synthesizer (Protein Technologies, Inc.) using Rink amide resin (Novabiochem) with a loading of 0.43-0.49 mmol/g at 0.050-0.100 mmol or a pre-loaded Wang Resin (Fmoc-Tyr(tBu)-Wang resin) 0.63 mmol/g (Novabiochem). Fmoc amino acid (5.0 eq, 0.250-0.500 mmol) residues are dissolved at a concentration of 0.10 M in 1-methyl-2-pyrrolidinone. All other reagents (HBTU, 1-Hydroxybenzotriazole hydrate and N,N-Diisopropylethylamine) are prepared as 0.55 M Dimethylformamide solutions. The Fmoc protected amino acids are then coupled to the resin-bound amino acid using, HBTU (2.0 eq, 0.100-0.200 mmol), 1-Hydroxybenzotriazole hydrate (1.8 eq, 0.090-0.18 mmol), N,N-Diisopropylethylamine (2.4 eq, 0.120-0.240 mmol) for 2 hours. Following the last amino acid coupling, the peptide is deprotected using 20% (v/v) piperidine in dimethylformamide for 1 hour. Once peptide sequence is complete, the Symphony peptide synthesizer is programmed to cleave the resin. Trifluoroacetic acid (TFA) cleavage of the peptide from resin is carried out using 93% TFA, 3% phenol, 3% water and 1% triisopropylsilane for 1 hour. The cleaved peptide is precipitated using tert-butyl methyl ether, pelleted by centrifugation and lyophilized. The pellet is re-dissolved in water (10-15 mL), filtered and purified via reverse phase HPLC using a C18 column and an acetonitrile/water gradient containing 0.1% TFA.

A general procedure for N-capping the peptides of the invention with fatty acids (e.g., octanoic and stearic acids) is as follows: Peptide on rink amide resin (0.1 mmol) is suspended in NMP (5 mL). In a separate vial, HBTU (0.3 mmol), HOBt (0.3 mmol) is dissolved in DMF (5 mL) followed by the addition of DIEA (0.6 mmol). This solution is added to the resin and this suspension is shaken for 2 hrs. The solvent is filtered and washed thoroughly with NMP (5 mL×4) and $CH_2Cl_2$ (20 mL), dried and is subjected to the TFA cleavage for 1 hr. The yield of the desired peptide is ca. 40 mg after cleavage and purification.

PEG modification may be carried out in solution on a free epsilon-amino group of lysine or a terminal amino group of a purified peptide using commercially available activated PEG esters. The resulting PEGylated derivatives are purified to homogeneity by reverse phase HPLC and the purity is confirmed by LC/MS and MALDI-MS.

Certain exemplary hybrid polypeptides of the invention are shown in Table 1-1. Various modifications to the embodied compounds are envisioned, such as chemical modifications such as glycosylation, PEG modifications, etc.; amino acid modifications such as substitutions, insertions and deletions, etc. Further, even though represented as C-terminally amidated, it is understood that the hybrid polypeptides of the invention may alternatively be in the free acid form.

TABLE 1-1

Certain Exemplary Hybrid Compounds of the Invention

| SEQ ID: | |
|---|---|
| 1 | HGEGTFTSDLSKQMEEEAVRLFIEWLKNGGPSSGAPPPS-ASLRHYLNLVTRQRY-$NH_2$ |
| 2 | HGEGTFTSDLSKQMEEEAVRLFIEWLKNGGPSSGAPPPS-RHYLNLVTRQRY-$NH_2$ |
| 3 | HGEGTFTSDLSKQMEEEAVRLFIEWLKNGGPSSGAPPPS-NRYYASLRHYLNLVTRQRY-$NH_2$ |
| 4 | HGEGTFTSDLSKQMEEEAVRLFIEWLKNGGPSSGAPPPS-βAla-βAla-ASLRHYLNLVTRQRY-$NH_2$ |
| 5 | HGEGTFTSDLSKQMEEEAVRLFIEWLKNGGPSSGAPPPS-βAla-βAla-RHYLNLVTRQRY-$NH_2$ |
| 6 | HGEGTFTSDLSKQMEEEAVRLFIEWLKNGGPSSGAPPPS-βAla-βAla-VTRQRY-$NH_2$ |
| 7 | HGEGTFTSDLSKQMEEEAVRLFIEWLKN-ASLRHYLNLVTRQRY-$NH_2$ |
| 8 | HGEGTFTSDLSKQMEEEAVRLFIEWLKN-RHYLNLVTRQRY-$NH_2$ |
| 9 | HGEGTFTSDLSKQMEEEAVRLFIEWLKN-NRYYASLRHYLNLVTRQRY-$NH_2$ |
| 10 | HGEGTFTSDLSKQMEEEAVRLFIEWLKN-βAla-βAla-ASLRHYLNLVTRQRY-$NH_2$ |
| 11 | HGEGTFTSDLSKQMEEEAVRLFIEWLKN-βAla-βAla-RHYLNLVTRQRY-$NH_2$ |
| 12 | HGEGTFTSDLSKQMEEEAVRLFIEWLKN-βAla-βAla-VTRQRY-$NH_2$ |
| 13 | HGEGAFTSDLSKQLEEEAVRLFIEFLKNNRYYASLRHYLNLVTRQRY-$NH_2$ |
| 14 | HGEGAFTSDLSKQLEEEAVRLFIEFLKNASLRHYLNLVTRQRY-$NH_2$ |
| 15 | HGEGAFTSDLSKQLEEEAVRLFIEFLKNRHYLNLVTRQRY-$NH_2$ |
| 16 | HGEGAFTSDLSKQLEEENRYYASLRHYLNLVTRQRY-$NH_2$ |
| 17 | HGEGAFTSDLSKQLEEEAVRLFIEFLKN-βAla-βAla-ASLRHYLNLVTRQRY-$NH_2$ |
| 18 | HGEGAFTSDLSKQLEEEAVRLFIEFLKN-βAla-βAla-RHYLNLVTRQRY-$NH_2$ |
| 19 | HGEGAFTSDLSKQLEEEAVRLFIEFLKN-βAla-βAla-VTRQRY-N $NH_2$ |
| 20 | HGEGTFTSDLSKQMEEEAVRLFIEWLKNGGPSSGAPPPS-DY($SO_3$)MGWMDF-$NH_2$ |
| 21 | HGEGTFTSDLSKQMEEEAVRLFIEWLKN-DY($SO_3$)MGWMDF-$NH_2$ |
| 22 | HGEGTFTSDLSKQMEEEAVRLFIEWLKN-DF($CH_2SO_3$)MGWMDF-$NH_2$ |
| 23 | HGEGTFTSDLSKQMEEEAVRLFIEWLKN-[8-amino-3,6-dioxaoctanoyl]-DY($SO_3$)MGWMDF-$NH_2$ |
| 24 | HGEGTFTSDLSKQMEEEAVRLFIEWLKN-[8-amino-3,6-dioxactoanoyl]-DF($CH_2SO_3$)MGWMDF-$NH_2$ |
| 25 | HGEGTFTSDLSKQMEEEAVRLFIEWLKKCNTATCVLGRLSQELHRLQTYPRTNTGSNTY-$NH_2$ |
| 26 | HGEGTFTSDLSKQMEEEAVRLFIEWLKKANTATAVLG-$NH_2$ |
| 27 | HGEGTFTSDLSKQMEEEAVRLFIEWLKN-12-Ado-KCNTATCVLGRLSQELHRLQTYPRTNTGSNTY-$NH_2$ |
| 28 | HGEGTFTSDLSKQMEEEAVRLFIEWLKN-12-Ado-CNTATCVLGRLSQELHRLQTYPRTNTGSNTY-$NH_2$ |
| 29 | HGEGTFTSDLSKQMEEEAVRLFIEWLKN-3,6-dioxaoctanoyl-KCNTATCVLGRLSQELHRLQTYPRTNTGSNTY-$NH_2$ |
| 30 | HGEGTFTSDLSKQMEEEAVRLFIEWLKN-3,6-dioxaoctanoyl-CNTATCVLGRLSQELHRLQTYPRTNTGSNTY-$NH_2$ |
| 31 | HGEGTFTSDLSKQMEEEAVRLFIEWLKN-5-Apa-KCNTATCVLGRLSQELHRLQTYPRTNTGSNTY-$NH_2$ |
| 32 | HGEGTFTSDLSKQMEEEAVRLFIEWLKN-5-Apa-CNTATCVLGRLSQELHRLQTYPRTNTGSNTY-$NH_2$ |
| 33 | HGEGTFTSDLSKQMEEEAVRLFIEWLKN-βAla-βAla-KCNTATCVLGRLSQELHRLQTYPRTNTGSNTY-$NH_2$ |
| 34 | HGEGTFTSDLSKQMEEEAVRLFIEWLKN-βAla-βAla-CNTATCVLGRLSQELHRLQTYPRTNTGSNTY-$NH_2$ |
| 35 | HGEGTFTSDLSKQMEEEAVRLFIEWLKN-4,7,10-trioxa-13-tridecanamine succinimidyl-KCNTATCVLGRLSQELHRLQTYPRTNTGSNTY-$NH_2$ |
| 36 | HGEGTFTSDLSKQMEEEAVRLFIEWLKN-4,7,10-trioxa-13-tridecanamine succinimidyl-CNTATCVLGRLSQELHRLQTYPRTNTGSNTY-$NH_2$ |

TABLE 1-1-continued
Certain Exemplary Hybrid Compounds of the Invention
| SEQ ID: | |
|---|---|
| 203 | DF(CH2SO3)MGWMDF-*GKR*-KCNTATCATQRLANELVRLQTYPRTNVGSNTY-NH2 |
| 38 | KCNTATCATQRLANFLVR-RYYASLRHYLNLVTRQRY-NH2 |
| 39 | isocaproyl-STAVL-(Aib)-K(formyl)-LSQEL-(Aib)-K(formyl)-LQT-NRYYASLRHYLNLVTRQRY-NH$_2$ |
| 40 | isocaproyl-STAVL-(Aib)-K(formyl)-LSQEL-(Aib)-K(formyl)-L-ELNRYYASLRHYLNLVTRQRY-NH$_2$ |
41
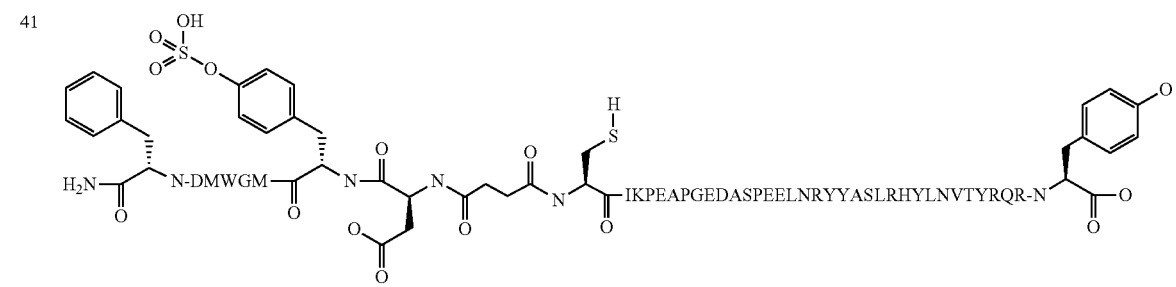
42
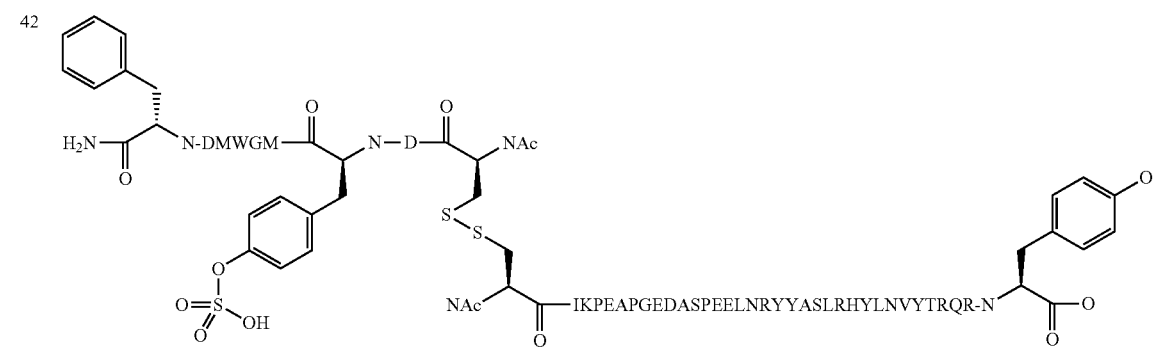
43
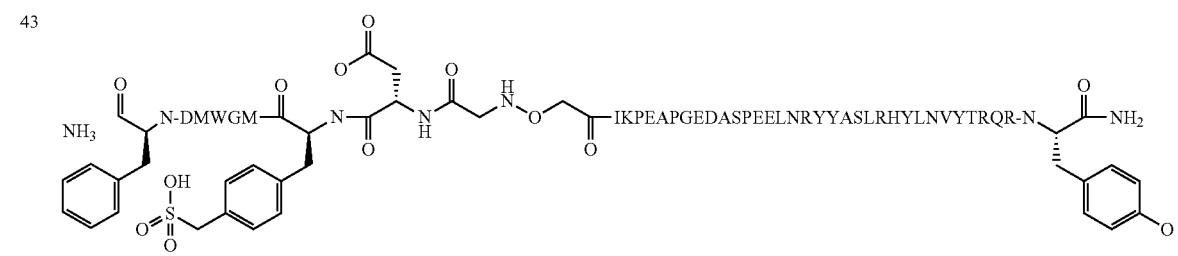
309
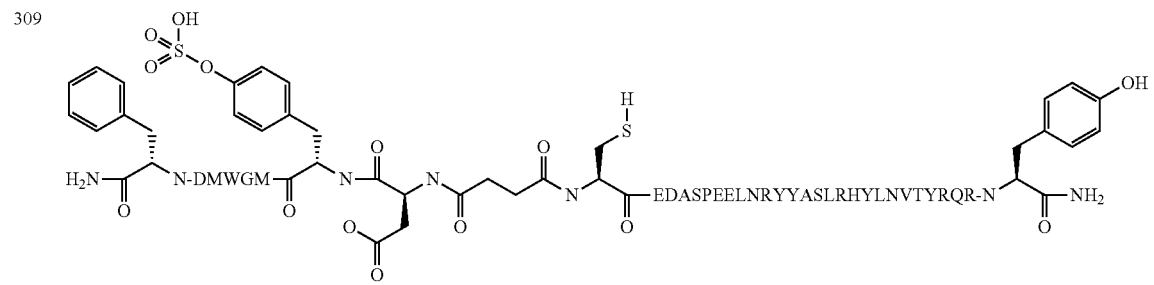

TABLE 1-1-continued

Certain Exemplary Hybrid Compounds of the Invention

SEQ ID:

310

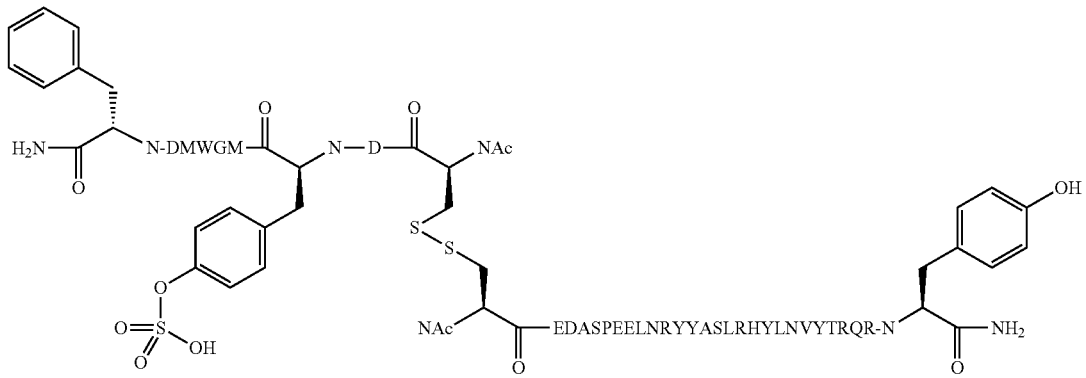

311

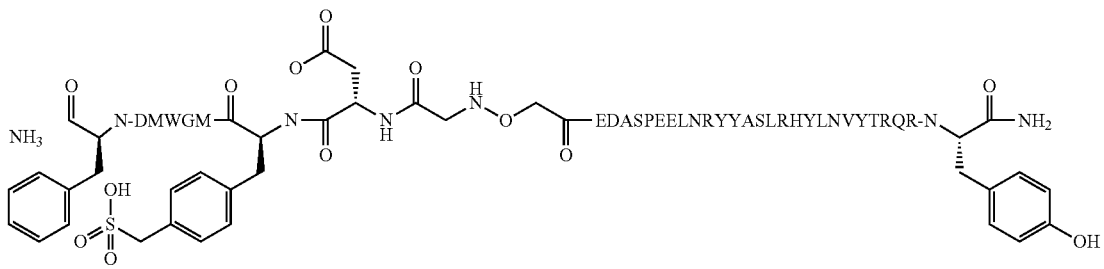

| | |
|---|---|
| 27 | [29]12 Ado-Exendin(1-28)-hAmylin(1-7)-[11,18]Arg-sCt(8-27)-hAmylin(33-37) |
| 28 | [29]12 Ado-Exendin(1-28)-[1]des-Lys-hAmylin(1-7)-[11,18]Arg-sCt(8-27)-hAmylin(33-37) |
| 29 | [29]3,6-dioxaoctanoyl-Exendin(1-28)-hAmylin(1-7)-[11,18]Arg-sCt(8-27)-hAmylin(33-37) |
| 30 | [29]3,6-dioxaoctanoyl-Exendin(1-28)-[1]des-Lys-hAmylin(1-7),[11,18]Arg-sCt(8-27)-hAmylin(33-37) |
| 31 | [29]5 Apa-Exendin(1-28)-hAmylin(1-7)-[11,18]Arg-sCt(8-27)-hAmylin(33-37) |
| 32 | [29]5 Apa-Exendin(1-28)-[1]des-Lys-hAmylin(1-7)-[11,18]Arg-sCt(8-27)-hAmylin(33-37) |
| 33 | [29]betaAla-betaAla-Exendin(1-28),hAmylin(1-7)-[11,18]Arg-sCt(8-27)-hAmylin(33-37) |
| 34 | [29]betaAla-betaAla-Exendin(1-28)-[1]des-Lys-hAmylin(1-7)-[11,18]Arg-sCt(27)-hAmylin(33-37) |
| 35 | [29]4,7,10-trioxa-13-tridecanamine succinimidyl-Exendin(1-28)-hAmylin(1-7)[11,18]Arg-sCt(8-27)-hAmylin(33-37) |
| 36 | [29]4,7,10-trioxa-13-tridecanamine succinimidyl-Exendin(1-28)-[1]des-Lys-hAmylin(1-7)-[11,18]Arg-sCt(8-27)-hAmylin(33-37) |
| 312 | [29](Gly-Gly-Gly)-Exendin(1-28),hAmylin(1-7)-[11,18]Arg-sCt(8-27)-hAmylin(33-37) |
| 313 | [29](Gly-Gly-Gly)-Exendin(1-28)-[1]des-Lys-hAmylin(1-7)-[11,18]Arg-sCt(27)-hAmylin(33-37) |

Example 2

Binding Assays

The hybrid polypeptides of the invention may be tested in a variety of receptor binding assays using binding assay methodologies generally known to those skilled in the art. Such assays include those described herein.

Amylin binding assay: Evaluation of the binding of some exemplary compounds of the invention to amylin receptors may be carried out as follows in nucluues accumbens membranes prepared from rat brain. Male Sprague-Dawley® rats (200-250) grams are sacrificed by decapitation. Brains are removed and place in cold phosphate-buffered saline (PBS). From the ventral surface, cuts are made rostral to the hypothalamus, bounded laterally by the olfactory tracts and extending at a 45° angle medially from these tracts. This basal forebrain tissue, containing the nucleus accumbens and surrounding regions, is weighed and homogenized in ice-cold 20 mM HEPES buffer (20 mM HEPES acid, pH adjusted to 7.4 with NaOH at 23° C.). Membranes are washed three times in fresh buffer by centrifugation for 15 minutes at 48,000×g. The final membrane pellet is resuspended in 20 mM HEPES buffer containing 0.2 mM phenylmethylsulfonyl fluoride (PMSF).

To measure $^{125}$I-amylin binding (see, Beaumont K et al. Can J Physiol Pharmacol. 1995 July; 73(7):1025-9), membranes from 4 mg original wet weight of tissue are incubated with $^{125}$I-amylin at 12-16 μM in 20 mM HEPES buffer containing 0.5 mg/ml bacitracin, 0.5 mg/ml bovine serum albumin, and 0.2 mM PMSF. Solutions are incubated for 60 minutes at 2° C. Incubations are terminated by filtration through GF/B glass fiber filters (Whatman Inc., Clifton, N.J.) that are presoaked for 4 hours in 0.3% poylethyleneimine in order to reduce nonspecific binding of radiolabeled peptides. Filters are washed immediately before filtration with 5 ml cold PBS, and immediately after filtration with 15 ml cold PBS. Filters are removed and radioactivity assessed in a gamma-counter at a counting efficiency of 77%. Competition curves are generated by measuring binding in the presence of $10^{-12}$ to $10^{-6}$ M unlabeled test compound and are analyzed by nonlinear regression using a 4-parameter logistic equation (Inplot program; GraphPAD Software, San Diego).

CGRP receptor binding assay: Evaluation of the binding of compounds of the invention to CGRP receptors are essentially as described for amylin except using membranes prepared from SK-N-MC cells, known to express CGRP receptors (Muff, R. et. al., Ann NY Acad. Sci. 1992: 657, 106-16). Binding assays are performed as described for amylin except using 13,500 cpm 125I-hCGRP/well or 21.7 µM/well (Amersham).

Adrenomedullin binding assay: Binding to the adrenomedullin receptor may be investigated using HUVECs that contain the adrenomedullin receptor (Kato J et. al., *Eur J Pharmacol.* 1995, 289:383-5) using the Perkin Elmer AlphaScreen™ assay for cyclic AMP using an optimum of 25-30,000 cells per well. Elevation of cAMP levels is not large for HUVEC compared to CHO cells. As such, CHO cells may be chosen as a negative control since they do not express the adrenomedullin receptor if desired.

Calcitonin receptor binding assay: Binding to the calcitonin receptor may be investigated using CHO cells or T47D cells, which also express the calcitonin receptor (Muff R. et. al, *Ann NY Acad. Sci.* 1992, 657:106-16 and Kuestner R. E. et. al. *Mol. Pharmacol.* 1994, 46:246-55), as known in the art.

Leptin binding assay: Two in vitro bioassays are routinely used to assess leptin binding and receptor activation (see e.g., White, et al., 1997. *Proc. Natl. Acad. Sci. U.S.A.* 94: 10657-10662). An alkaline phosphatase ("AP")-leptin ("OB") fusion protein ("AP-OB") may be used to measure inhibition of leptin binding in the absence or presence of recombinant mouse leptin (positive control) or peptide, by COS-7 cells transfected with the long (signaling) form of the mouse OB receptor ("OB-RL"). Signal transduction assays may be done in GT1-7 cells cotransfected with AP reporter and OB-RL constructs. Secreted alkaline phosphatase ("SEAP") activity in response to stimulation with mouse leptin or peptide may be measured by chemiluminescence.

Y1 receptor binding assay: Membranes are prepared from confluent cultures of SK-N-MC cells that endogenously expresses the neuropeptide Y1 receptors. Membranes are incubated with 60 pM [$^{125}$I]-human Peptide YY (2200 Ci/mmol, PerkinElmer Life Sciences), and with unlabeled active compound for 60 minutes at ambient temperature in a 96 well polystyrene plate. Then well contents are harvested onto a 96 well glass fiber plate using a Perkin Elmer plate harvestor. Dried glass fiber plates are combined with scintillant and counted on a Perkin Elmer scintillation counter.

Y2 receptor binding assay: Membranes are prepared from confluent cultures of SK-N-BE cells that endogenously expresses the neuropeptide Y2 receptors. Membranes are incubated with 30 pM [$^{125}$I]-human Peptide YY (2200 Ci/mmol, PerkinElmer Life Sciences), and with unlabeled active compound for 60 minutes at ambient temperature in a 96 well polystyrene plate. Then well contents are harvested onto a 96 well glass fiber plate using a Perkin Elmer plate harvestor. Dried glass fiber plates are combined with scintillant and counted on a Perkin Elmer scintillation counter.

Y4 receptor binding assay: CHO-K1 cells are transiently transfected with cDNA encoding neuropeptide Y4 gene, and then forty-eight hours later membranes are prepared from confluent cell cultures. Membranes are incubated with 18 pM [$^{125}$I]-human Pancreatic Polypeptide (2200 Ci/mmol, PerkinElmer Life Sciences), and with unlabeled active compound for 60 minutes at ambient temperature in a 96 well polystyrene plate. Then well contents are harvested onto a 96 well glass fiber plate using a Perkin Elmer plate harvestor. Dried glass fiber plates are combined with scintillant and counted on a Perkin Elmer scintillation counter.

Y5 receptor binding assay: CHO-K1 cells are transiently transfected with cDNA encoding neuropeptide Y5 gene, and then forty-eight hours later membranes are prepared from confluent cell cultures. Membranes are incubated with 44 pM [$^{125}$I]-human Peptide YY (2200 Ci/mmol, PerkinElmer Life Sciences), and with active compound for 60 minutes at ambient temperature in a 96 well polystyrene plate. Then well contents are harvested onto a 96 well glass fiber plate using a Perkin Elmer plate harvestor. Dried glass fiber plates are combined with scintillant and counted on a Perkin Elmer scintillation counter.

GLP-1 receptor binding assay: GLP-1 receptor binding activity and affinity may be measured using a binding displacement assay in which the receptor source is RINmSF cell membranes, and the ligand is [$^{125}$I]GLP-1. Homogenized RINm5F cell membranes are incubated in 20 mM HEPES buffer with 40,000 cpm [$^{125}$I]GLP-1 tracer, and varying concentrations of test compound for 2 hours at 23° C. with constant mixing. Reaction mixtures are filtered through glass filter pads presoaked with 0.3% PEI solution and rinsed with ice-cold phosphate buffered saline. Bound counts are determined using a scintillation counter. Binding affinities are calculated using GraphPad Prism software (GraphPad Software, Inc., San Diego, Calif.).

Example 3

Mouse Food Intake Assay

The hybrid polypeptides of the invention may be tested for appetite suppression in the mouse food intake assay and for their effect on body weight gain in diet-induced obesity (DIO) mice. The experimental protocols for the screens are described below. Female NIH/Swiss mice (8-24 weeks old) are group housed with a 12:12 hour light:dark cycle with lights on at 0600. Water and a standard pelleted mouse chow diet are available ad libitum, except as noted. Animals are fasted starting at approximately 1500 hrs, 1 day prior to experiment. The morning of the experiment, animals are divided into experimental groups. In a typical study, n=4 cages with 3 mice/cage.

At time=0 min, all animals are given an intraperitoneal injection of vehicle or compound, typically in an amount ranging from about 10 nmol/kg to 75 nmol/kg, and immediately given a pre-weighed amount (10-15 g) of the standard chow. Food is removed and weighed at various times, typically 30, 60, and 120 minutes, to determine the amount of food consumed (Morley, Flood et al., *Am. J. Physiol.* 267: R178-R184, 1994). Food intake is calculated by subtracting the weight of the food remaining at the e.g., 30, 60, 120, 180 and/or 240 minute time point, from the weight of the food provided initially at time=O, Significant treatment effects are identified by ANOVA (p<0.05). Where a significant difference exists, test means are compared to the control mean using Dunnett's test (Prism v. 2.01, GraphPad Software Inc., San Diego, Calif.).

Activity in the food intake assay and sequence of parent molecules used for the synthesis of hybrids herein are:

| Description | mpd # | 60 min ED50 (nmol/kg) | Sequence | Mouse Food Intake, % basal | | | | Dose |
|---|---|---|---|---|---|---|---|---|
| | | | | 30 min | 60 min | 120 min | 180 min | |
| PYY(3-36) | 1 | 3 | IKPEAPGEDASPEELN RYYASLRHYLNLVTR QRY-NH2 (SEQ ID NO: 58) | -31 | -38 | -40 | -26 | 10 nmol/Kg |
| Exendin-4 | | 5 | HGEGTFTSDLSKQME EEAVRLFIEWLKNGG PSSGAPPPS-NH2 (SEQ ID NO: 66) | -41 | -60 | -61 | -60 | 4.8 nmol/Kg |
| Exendin-4 (1-28) | 11 | 0.3 | HGEGTFTSDLSKQME EEAVRLFIEWLKN-NH2 (SEQ ID NO: 237) | -50 | -62 | -49 | -49 | 16.3 nmol/Kg |
| Exendin-4 (1-28) [Ala5, Leu14, Phe25] | 12 | 13 | HGEGAFTSDLSKQLE EEAVRLFIEFLKN-NH2 (SEQ ID NO: 240) | -53 | -61 | -50 | -53 | 16.7 nmol Kg |
| Rat Amylin | | 9 | KCNTATCATQRLANF LVRSSNNLGPVLPPTN VGSNTY-NH2 (SEQ ID NO: 44) | -58 | -40 | -36.5 | -35.5 | 25 nmol/Kg |
| hAmylin(1-7)-11,18Arg-sCT(8-27)-Amylin(33-37) | 10 | 26 | KCNTATCVLGRLSQE LHRLQTYPRTNTGSN TY-NH2 (SEQ ID NO: 396) | -60 | -47 | -42.5 | -32 | 25 nmol/Kg |
| CCK-8 | | 26 | DY(SO3) MGWMDF-NH2 (SEQ ID NO: 55) | -92 | -56 | -27 | | 10 nmol/Kg |

Example 4

Body Weight Gain in Fattened C57B1/6 (Diet-Induced-Obesity, or DIO) Mice

Male C57BL/6 mice (4 weeks old at start of study) are fed high fat (HF, 58% of dietary kcal as fat) or low fat (LF, 11% of dietary kcal as fat) chow. After 4 weeks on chow, each mouse is implanted with an osmotic pump (Alzet #2002) that subcutaneously delivers a predetermined dose of hybrid polypeptide continuously for two weeks. Body weight and food intake are measured weekly (Surwit et al., *Metabolism—Clinical and Experimental*, 44: 645-51, 1995). Effects of the test compound are expressed as the mean+/-sd of % body weight change (i.e., % change from starting weight) of at least 14 mice per treatment group (p<0.05 ANOVA, Dunnett's test, Prism v. 2.01, GraphPad Software Inc., San Diego, Calif.).

Exendin/PYY Hybrids. Exemplary hybrid polypeptides of the invention were synthesized using a C-terminally truncated exendins (e.g., exendin-4(1-28) or $^5$Ala, $^{14}$Leu, $^{25}$Phe-exendin-4(1-28)) and an N-terminally truncated PYY spanning the 18-36 to 31-36 regions. As such, the exemplary hybrid polypeptides generally comprise two modules, wherein the first module is a fragment of an exendin-4 analog and the second module is a peptidic enhancer selected from PYY truncations. For comparison, a β-alanine dipeptide spacers were also incorporated between the peptide building blocks in several variants (see Table 4-1).

TABLE 4-1

Exendin/PYY Hybrids, Receptor Binding Data, and Their Effects in the Food Intake Assay

| Description | Cmpd # | Receptor Binding (IC50) nM | | Mouse Food Intake % basal | | | |
|---|---|---|---|---|---|---|---|
| | | Y2 | GLP1R | 30 min | 60 min | 120 min | Dose |
| PYY(3-36) (SEQ ID NO: 58) | | 0.04 | — | -31 | -38 | -40 | -26 |
| $^5$Ala, $^{14}$Leu, $^{25}$Phe-exendin-4(1-28) (SEQ ID NO: 240) | | — | 1.9 | -50 | -62 | -49 | -49 |
| $^5$Ala, $^{14}$Leu, $^{25}$Phe-exendin-4(1-17)-PYY(18-36) (SEQ ID NO: 16) | | 1.7 | 1000 | -4 | -11 | -10 | 10 nmol/Kg |
| $^5$Ala, $^{14}$Leu, $^{25}$Phe-exendin-4(1-28)-PYY(22-36) (SEQ ID NO: 14) | | 17 | 2.1 | 21 | 9 | -4 | 10 nmol/Kg |
| $^5$Ala, $^{14}$Leu, $^{25}$Phe-exendin-4(1-28)-βAla-βAla-PYY(22-36) (SEQ ID NO: 17) | | 9 | 0.81 | -3 | -5 | -22 | 10 nmol/Kg |

TABLE 4-1-continued

Exendin/PYY Hybrids, Receptor Binding Data, and Their Effects in the Food Intake Assay

| Description | Cmpd # | Receptor Binding (IC50) nM | | Mouse Food Intake % basal | | | Dose |
|---|---|---|---|---|---|---|---|
| | | Y2 | GLP1R | 30 min | 60 min | 120 min | |
| 5Ala, 14Leu, 25Phe-exendin-4(1-28)-PYY(25-36) (SEQ ID NO: 15) | 2 | nd | nd | 8 | −13 | −30 | 10 nmol/Kg |
| 5Ala, 14Leu, 25Phe-exendin-4(1-28)-βAla-βAla-PYY(25-36) (SEQ ID NO: 18) | 3 | 13 | 0.22 | −9 | −25 | −42 | 10 nmol/Kg |
| 5Ala, 14Leu, 25Phe-exendin-4(1-28)-βAla-βAla-PYY(31-36) (SEQ ID NO: 19) | 4 | 1000 | 0.25 | −14 | −36 | −52 | 10 nmol/Kg |
| exendin-4(1-28)-PYY(25-36) (SEQ ID NO: 8) | — | 16 | 0.29 | −30 | −37 | −45 | 10 nmol/Kg |
| exendin-4(1-28)-βAla-βAla-PYY(25-36) (SEQ ID NO: 5) | — | 7.8 | 0.16 | −24 | −40 | −52 | 10 nmol/Kg |
| exendin-4(1-28)-βAla-βAla-PYY(31-36) (SEQ ID NO: 6) | — | 1000 | 0.19 | −49 | −56 | −61 | 10 nmol/Kg |

As shown in Table 4-1, certain exemplary compounds of the invention showed efficacy in the food intake assay. Certain peptides were also tested at 75 nmol/kg in the DIO assay and proved to be more efficacious than PYY (FIG. 1). As observed for other hybrids herein, hybrids can retain binding to one, two or more receptors that recognize the parent molecules. Hybrids were designed that recognize at least one receptor from each parent or from only one parent, as desired. As observed for other hybrids herein, use of a linker (which can act as a spacer between each adjacent hormone portion) can provide increased activity, including receptor(s) binding and in vitro and in vivo activity, such as weight loss. The results herein indicate that a C-terminal portion of PYY can modulate activity.

Exendin/Amylin Hybrids. Further exemplary hybrid polypeptides of the invention were prepared from C-terminally truncated exendin (1-27) (SEQ ID NO: 236), C-terminally truncated amylin peptides (e.g., amylin(1-7) (SEQ ID NO: 217), 2,7Ala-Amylin(1-7) (SEQ ID NO: 285), and Amylin(33-27) (SEQ ID NO: 243), and optional sCT fragments (e.g., sCT(8-10), 11,18Arg-sCT(8-27) (SEQ ID NO: 289) and 14Glu,11,18Arg-sCT(8-27) (SEQ ID NO: 286). Whereas both hybrid polypeptides were very active in appetite suppression (see Table 4-2), superior to the same dose of rat amylin, the onset of action differed from the activity profiles of the parent molecules (data not shown). At a dose of 1 nmol/kg, Compound 5 was as effective as rat amylin.

TABLE 4-2

Exendin/Amylin Hybrids and Their Effect in the FI Assay

| Description | Cmpd# | Receptor Binding Assay | | | | Mouse Food Intake % basal | | | Dose |
|---|---|---|---|---|---|---|---|---|---|
| | | GLP-1 | Amylin | CGRP | CT | 30 min | 60 min | 120 min | |
| Exendin-4(1-27)-Amylin(1-7)-11,18Arg-sCT(8-27)-Amylin(33-37) | 5 (SEQ ID No. 25) | | | | | −24 | −40 | −48 | 25 nmol/Kg |
| Exendin-4(1-27)-2,7Ala-Amylin(1-7)-sCT(8-10) | 6 (SEQ ID NO. 26) | | | | | −40 | −59 | −66 | 25 nmol/Kg |
| Exendin-4(1-28)-betaAla-betaAla-Amylin(1-7)-11,18Arg-sCT(8-27)-Amylin(33-37) | 14 (SEQ ID NO: 33) | 0.3 | 0.2 | 113 | 0.1 | −5 | −30 | −51 | 3 nmol/Kg |
| Exendin-4(1-28)-Gly-Gly-Gly-Amylin(1-7)-11,18Arg-sCT(8-27)-Amylin(33-37) | 15 (SEQ ID NO: 312) | 0.4 | 0.2 | 63 | 0.03 | −8 | −36 | −51 | 3 nmol/Kg |
| Exendin-4(1-27)-Amylin(1-7)-11,18Arg-sCT(8-27)-Amylin(33-37) | 5 (SEQ ID NO: 25) | 1.7 | 0.6 | 178 | 0.5 | −20 | −10 | −26 | 3 nmol/Kg |

Both compounds also showed excellent efficacy when screened in the DIO assay (FIG. 2).

Further exemplary compounds were assayed for effect on blood glucose levels and in a food intake assay. These tests included compounds 14 and 15. Compound 14, which includes a betaAla linker, is $^{29}$βAla-βAla-Exendin(1-28), hAmylin(1-7)-$^{11,18}$Arg-sCt(8-27)-hAmylin(33-37) (SEQ ID NO: 33), (alternatively written as Exendin(1-28)-βAla-βAla-hAmylin(1-7)-$^{11,18}$Arg-sCt(8-27)-hAmylin(33-37), while Compound 15 contains a Gly linker: $^{29}$GlyGlyGly-Exendin(1-28),hAmylin(1-7)-$^{11,18}$Arg-sCt(8-27)-hAmylin(33-37) (SEQ ID NO: 312). The longer exendin(1-28) provided increased activity compared to exendin(1-27).

A Blood Glucose Assay was performed to test effect on lowering blood glucose levels. Female NIH/Swiss mice (8-20 weeks old) were group housed with a 12:12 hour light:dark cycle with lights on at 0600. Water and a standard pelleted mouse chow diet were available ad libitum, except as noted. The morning of the experiment, animals were divided into experimental groups and fasted starting at approximately 0630 hrs. In a typical study, n=2 cages with 3 mice/cage. At time=0 min, a blood glucose sample was taken and immediately followed by an intraperitoneal injection of vehicle or compound in an amount ranging from about 1 nmol/kg to 25 nmol/kg. Blood glucose was measured at 30, 60, 120, 180, and 240 min. Percent pre-treatment was calculated by dividing the blood glucose at the e.g., 30, 60, 120, 180 and/or 240 minute time point by the blood glucose at time=0 min. Significant treatment effects were identified by ANOVA ($p<0.05$). Where a significant difference exists, test means were compared to the control mean using Dunnett's test (Prism v. 4.01, GraphPad Software Inc., San Diego, Calif.). The results on exemplary compounds are presented in FIG. 5A. Points represent mean±sd. Peptide was injected intraperitoneally (IP) at t=0 immediately following baseline sample into 2-hour fasted NIH/Swiss mice. Samples were taken at t=30, 60, 120, 180 and 240 min. Blood glucose was measured with a OneTouch® Ultra® (LifeScan, Inc., a Johnson & Johnson Company, Milpitas, Calif.). * $p<0.05$ vs. vehicle control; ANOVA, Dunnett's test.

A food intake assay was performed as previously described herein. The results are presented in FIG. 5B. Points represent mean±sd of n=4 cages (3 mice/cage). Peptide was injected intraperitoneally (IP) at t=0 into overnight-fasted NIH/Swiss mice. Food was introduced immediately after injection and amount consumed measured at t=30, 60, and 120 min. * $p<0.05$ vs. vehicle control; ANOVA, Dunnett's test.

Parental Compound 10 and exendin compounds have opposing effects in the Glucose Assay. One would expect that joining them would result in counteracting effects or, at best, a dilution of the effect seen with the more potent parent compound. However, in the Glucose Assay, the exemplary hybrid compounds were just as efficacious as exendin(1-28) and had a longer duration of action.

From the food intake data, the exemplary compounds were anorexigenic. Activity was generally better than the parent compounds dosed individually. Activity was comparable to the parent compounds dosed together but at half the concentration of drug (3 nmol/kg hybrid versus 6 nmol/kg total for co-dosed parent compounds); thus further demonstrating hybrid superiority. The addition of a linker increased activity of the hybrids. The Gly-Gly-Gly linker was more effective than the betaAla-betaAla linker in this case.

Exendin/CCK-8 Hybrids. Yet further exemplary hybrid polypeptides of the invention were prepared from full length or C-terminally truncated exendin-4 attached to the N-terminus of CCK-8 either directly or via a linker, preserving the N-terminal amide of the CCK-8. (Table 4-3). Further, certain hybrids were prepared incorporating the naturally occurring Tyr(SO$_3$), while another hybrid incorporating the more stable Phe(CH$_2$SO$_3$) group was prepared. All the prepared hybrid polypeptides were active in inhibiting food intake (Table 4-3).

TABLE 4-3

Exendin/CCK-8 Hybrids and Their Effect in the Food Intake Assay

| Description | Cmpd# | Receptor Binding (IC50) nM GLP1-R | Mouse Food Intake % basal | | | Dose |
| --- | --- | --- | --- | --- | --- | --- |
| | | | 30 min | 60 min | 120 min | |
| Exendin-4(1-28) amide | 11 (SEQ ID NO: 237) | 0.63 | | | | |
| Exendin-4-CCK-8 | — (SEQ ID NO: 20) | | −12 | −28 | −28 | 10 nmol/Kg |
| Exendin-4(1-28)-CCK-8 | 7 (SEQ ID NO: 21) | 75 | −20 | −36 | −45 | 10 nmol/Kg |
| Exendin-4(1-28)-CCK-8 [Phe(CH$_2$SO$_3$)] | 8 (SEQ ID NO: 22) | 31 | −24 | −47 | −66 | 10 nmol/Kg |
| Exendin-4(1-28)-[8-amino-3,6-dioxaoctanoyl]-CCK-8 | 9 (SEQ ID NO: 23) | | −12 | −28 | −40 | 10 nmol/Kg |

Exemplary exendin/CCK-8 hybrid polypeptides were tested in the DIO assay at 25 nmol/kg (FIGS. 3A and 3B). The data shows an initial weight loss, followed by a rebound effect in all compounds. Interestingly, the rebound effect appears to be diminished in hybrids incorporating the more hydrolytically stable Phe(CH2SO3) residue (compare FIGS. 3A and 3C), as well as hybrids incorporating a linker, for example the linker 8-amino-3,6-dioxaoctanoyl, between the exendin and the CCK residues (compare FIGS. 3A and 3B). A ten-fold greater amount of CCK-8 (250 nmol/kg/day) was needed to produce about a −2.8% change at day 2, which rebounded to the HF diet control level at day 7.

Amylin/PYY Hybrid. An Amylin/PYY hybrid polypeptide was synthesized that contained truncated segments of each peptide. In-vivo activity in the food intake assay is shown in Table 4-4.

TABLE 4-4

Amylin/PYhybrid

| Description | Mouse Food Intake % Basal | | | Dose |
|---|---|---|---|---|
| | 30 min | 60 min | 120 min | |
| Amylin(1-18)-PYY(19-36) (SEQ ID NO. 38) | −13 | −14 | −13 | 25 nmol/Kg |

To ascertain if exemplary hybrid polypeptides of the invention are more potent than their parent component peptide hormones, exemplary compounds were tested in the food intake assay at the minimum efficacious dose of the more active parent molecule. The results are shown in FIGS. 4A and 4B, which also compares the effects of pooled parent peptides (Compounds 1, 11, and 12 are component peptide hormones, analogs or fragments thereof). The data indicate that several peptides are at least as equipotent as the pooled parent peptides. In parallel with the in vivo studies, in vitro receptor binding and functional assays (cyclase activity) have been performed for all the compounds (data not shown).

Amylin-sCT/leptin hybrids. Further exemplary hybrids were made which contained a leptin peptide fragment joined to Compound 10, an amylin-sCT-amylin chimera described herein. Compound 16 is [Ser117, dLeu119]leptin(116-122)-Amylin(1-7)-[11,18Arg]sCT(8-27)-Amylin(33-37) (SEQ ID NO: 397). The compound bound (RBA=receptor binding assay) the amylin and CT receptors, with some binding to the CGRP receptor. The compound was also able to activate the CT receptor (C1A assay).

| Compound | Cmpd# | Assay | IC50 |
|---|---|---|---|
| [Ser117,dLeu119]leptin(116-122)-Amylin(1-7)-[$^{11,18}$Arg]sCT(8-27)-amylin(33-37) (SEQ ID NO: 397) | 16 | amylin RBA | 0.04 nM |
| | 16 | CGRP RBA | 81 nM |
| | 16 | CT CYCLASE(C1A) | 2.2 nM |
| | 16 | CT RBA (C1A) | 0.063 nM |
| | 16 | GLP RBA (RIN) | 1000 nM |

This representative molecule was tested for activity in a food intake assay as described herein. Although leptin was not active in this assay, Compound 16 was anorexigenic at 1 mg/kg. Compound 16 was also superior to rat amylin (at 25 nmol/kg) in its anorexigenic effect. While Compound 10 reduced food intake 91-95% compared to controls, much more effectively; Compound 16 reduced the cumulative intake to 34-38% that of controls. Further exemplary embodiments include a head-to-head joining of the N-terminus of the leptin peptide with that of the Amylin(1-7)-[$^{11,18}$Arg]sCT(8-27)-amylin(33-37) compound.

CCK/Amylin-sCT Hybrids An exemplary hybrid of CCK with an amylin-sCT chimera demonstrated relevant receptor specificity and activation. The exemplary compound having sequence DF(P—CH$_2$SO$_3$)MGWMDFGKR KCNTATCATQRLANELVRLQTYPRTNVGSNTY (SEQ ID NO: 398) demonstrated an IC50 of 0.044 nM in a CT receptor binding assay, 4.4 nM in a CGRP receptor binding assay, 0.083 nM in an amylin receptor binding assay, and 1000 nM in a GLP Receptor cyclase (RIN).

While the present invention has been described in terms of preferred examples and embodiments, it is understood that variations and modifications will occur to those skilled in the art. Therefore, it is intended that the appended claims cover all such equivalent variations which come within the scope of the invention as claimed.

What is claimed is:

1. A hybrid polypeptide comprising a first bio-active peptide hormone covalently linked to a second bio-active peptide hormone; wherein:
the first bio-active peptide hormone comprises a peptide selected from the group consisting of:
exendin-4.
exendin-4 fragments that exhibit at least one hormonal activity of exendin-4;
analogs and derivatives of exendin-4 that exhibit at least one hormonal activity of exendin-4; and
fragments of analogs and derivatives of exendin-4 that exhibit at least one hormonal activity of exendin-4;
the second bio-active peptide hormone comprises a peptide selected from the group consisting of:
amylin;
amylin fragments that exhibit at least one hormonal activity of amylin;
analogs and derivatives of amylin that exhibit at least one hormonal activity of amylin; and
fragments of analogs and derivatives of amylin that exhibit at least one hormonal activity of amylin.

2. The hybrid polypeptide of claim 1, wherein the first bio-active peptide hormone is located at the C-terminal end of the hybrid polypeptide.

3. The hybrid polypeptide of claim 1, wherein the first bio-active peptide hormone is located at the N-terminal end of the hybrid polypeptide.

4. The hybrid polypeptide of claim 3, wherein the component peptide hormone of the first bio-active peptide hormone comprises an exendin-4 and the component peptide hormone of the second bio-active peptide hormone comprises an amylin.

5. The hybrid polypeptide of claim 1, wherein the hybrid polypeptide comprises bio-active peptide hormone combinations selected from the group consisting of: exendin/amylin and amylin/exendin bio-active peptide hormones.

6. The hybrid polypeptide of claim 1, wherein the first bioactive peptide hormone exhibits stimulating insulin secretion activity and the second bioactive peptide hormone exhibits reducing body weight activity.

7. The hybrid polypeptide of claim 1, wherein the first bioactive peptide hormone comprises exendin-4, a bio-active analog of exendin-4 or a bioactive fragment of exendin-4.

8. The hybrid polypeptide of claim 7, wherein the first bioactive peptide hormone has at least 60% amino acid sequence identity to exendin-4.

9. The hybrid polypeptide of claim 8, wherein the first bioactive peptide hormone comprises a peptide selected from the group consisting of exendin-4, $^{14}$Leu $^{25}$Phe-exendin-4, $^{5}$Ala $^{14}$Leu $^{25}$Phe-exendin-4, $^{14}$Leu $^{22}$Ala $^{25}$Phe-exendin-4, exendin(7-15), $^{2}$Ser-exendin(7-15), exendin-4(1-27), exendin(1-28), exendin-4(1-29), exendin-4(1-30), $^{14}$Leu$^{25}$Phe-exendin-4(1-27),$^{5}$Ala $^{14}$Leu $^{25}$Phe-exendin-4(1-27), $^{14}$Leu $^{22}$Ala $^{25}$Phe-exendin-4(1-27), $^{14}$Leu $^{25}$Phe-exendin-4(1-28); $^{5}$Ala $^{14}$Leu $^{25}$Phe-exendin-4(1-28), and $^{14}$Leu-exendin-(1-28).

10. The hybrid polypeptide of claim 1, wherein the second bio-active peptide hormone comprises amylin, a bio-active analog of amylin or a bioactive fragment of amylin.

11. The hybrid polypeptide of claim 10, wherein the second bio-active peptide hormone has at least 60% amino acid sequence identity to human amylin.

12. The hybrid polypeptide of claim 11, wherein the second bio-active peptide hormone comprises a peptide selected from the group consisting of amylin, $^{25,28,29}$Pro-h-amylin, amylin(1-7), $^{2,7}$Ala-amylin(1-7), sCT(8-10), sCT(8-27), $^{11,18}$Arg-sCT(8-27), hAmylin(1-7)-$^{11,18}$Arg-sCT(8-27)-Amylin(33-37), $^{14}$Glu $^{11,18}$Arg-sCT(8-27), des-$^{1}$Lys-h-amylin, $^{25}$Pro $^{26}$Val $^{28,29}$Pro-h-amylin, $^{18}$Arg $^{25,28}$Pro-h-amylin, des-$^{1}$Lys $^{18}$Arg $^{25,28}$Pro-h-amylin, $^{18}$Arg $^{25,28,29}$Pro-h-amylin, des-$^{1}$Lys $^{18}$Arg $^{25,28,29}$Pro-h-amylin, des-$^{1}$Lys $^{25,28,29}$Pro-h-amylin, $^{25}$Pro $^{26}$Val $^{28,29}$Pro-h-amylin, $^{28}$Pro-h-amylin, $^{2-37}$h-amylin, $^{1}$Ala-h-amylin, Ala-h-amylin, $^{2,7}$Ala-h-amylin, $^{1}$Ser-h-amylin, $^{29}$Pro-h-amylin, $^{25,28}$Pro-h-amylin, des-$^{1}$L $^{25,28}$Pro-h-amylin, $^{23}$Leu $^{25}$Pro $^{26}$Val $^{28,29}$Pro-h-amylin, $^{23}$Leu $^{25}$Pro $^{26}$Val $^{28}$Pro-h-amylin, des-$^{1}$Lys $^{23}$Leu $^{25}$Pro $^{26}$Val $^{28}$Pro-h-amylin, $^{18}$Arg $^{23}$Leu $^{25}$Pro $^{26}$Val $^{28}$Pro-h-amylin, $^{18}$Arg $^{23}$Leu $^{25,28,29}$Pro-h-amylin, $^{18}$Arg $^{23}$Leu $^{25,28}$Pro-h-amylin, $^{17}$Ile $^{23}$Leu $^{25,28,29}$Pro-h-amylin, $^{17}$Ile $^{25,28,29}$Pro-h-amylin, des-$^{1}$Lys $^{17}$Ile $^{23}$Leu $^{25,28,29}$Pro-h-amylin, $^{17}$Ile $^{18}$Arg $^{23}$Leu-h-amylin, $^{17}$Ile $^{18}$Arg $^{23}$Leu $^{26}$Val $^{29}$Pro-h-amylin, $^{17}$Ile $^{18}$Arg $^{23}$Leu $^{25}$Pro $^{26}$Val $^{28,29}$Pro-h-amylin, $^{13}$Thr $^{21}$His $^{23}$Leu $^{26}$Ala $^{28}$Leu $^{29}$Pro $^{31}$Asp-h-amylin, $^{13}$Thr $^{21}$His $^{23}$Leu $^{26}$Ala $^{29}$Pro $^{31}$Asp-h-amylin, des-$^{1}$Lys $^{13}$Thr $^{21}$His $^{23}$Leu $^{26}$Ala $^{28}$Pro $^{31}$Asp-h-amylin, $^{13}$Thr $^{18}$Arg $^{21}$His $^{23}$Leu $^{26}$Ala $^{29}$Pro $^{31}$Asp-h-amylin, $^{13}$Thr $^{18}$Arg $^{21}$His $^{23}$Leu $^{28,29}$Pro $^{31}$Asp-h-amylin, and $^{13}$Thr $^{18}$Arg $^{21}$His $^{23}$Leu $^{25}$Pro $^{26}$Ala $^{28,29}$Pro $^{31}$Asp-h-amylin.

13. The hybrid polypeptide of claim 1, wherein the C-terminus is amidated.

14. The hybrid polypeptide of claim 1, wherein the first peptide hormone is covalently linked through a linker to the second peptide hormone.

15. The hybrid polypeptide of claim 14, wherein the linker is chemically stable.

16. The hybrid polypeptide of claim 15, wherein the linker comprises a moiety selected from the group consisting of an alkyl, a PEG, an amino acid, a polyaminoacid, a bifunctional linker, an aminocaproyl, a beta-alanyl, an 8-amino-3,6-dioxaoctanoyl, Lys, Glu, Gly, and Cys.

17. The hybrid polypeptide of claim 16, wherein the linker comprises a moiety selected from the group consisting of poly-his, poly-arg, poly-lys, poly-ala, beta-alanyl beta-alanyl, Gly-Gly-Gly, or Gly-Lys-Arg.

18. The hybrid polypeptide of claim 16, wherein the linker is 1 to 30 residues long, is 2 to 30 residues, or is 3 to 30 residues long.

19. The hybrid polypeptide of claim 18, wherein the linker is 2, 3, 4, 5, 6, 7, 8, 9 or 10 residues long.

20. The hybrid polypeptide of claim 1, wherein the hybrid polypeptide is produced recombinantly.

* * * * *